US007045685B2

(12) United States Patent
Christian et al.

(10) Patent No.: US 7,045,685 B2
(45) Date of Patent: May 16, 2006

(54) INSECT VIRUSES AND THEIR USES IN PROTECTING PLANTS

(75) Inventors: Peter Daniel Christian, Lyneham (AU); Karl Hienrich Julius Gordon, Weston (AU); Terry Nelson Hanzlik, Chapman (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 353 days.

(21) Appl. No.: 09/991,262

(22) Filed: Nov. 20, 2001

(65) Prior Publication Data

US 2003/0041349 A1 Feb. 27, 2003
US 2005/0172357 A9 Feb. 27, 2003

Related U.S. Application Data

(63) Continuation of application No. 09/234,238, filed on Jan. 20, 1999, now abandoned, which is a continuation of application No. 08/440,522, filed on May 12, 1995, now abandoned, which is a continuation-in-part of application No. 08/089,372, filed on Jul. 8, 1993, now abandoned.

(30) Foreign Application Priority Data

Aug. 14, 1992 (AU) .......................................... PL4081/92

(51) Int. Cl.
  C12N 15/82 (2006.01)
  C12N 5/10 (2006.01)
  C12N 15/33 (2006.01)
  C12N 15/90 (2006.01)
  A01H 5/00 (2006.01)

(52) U.S. Cl. .................... 800/302; 435/320.1; 435/419; 536/23.72; 800/279

(58) Field of Classification Search .............. 435/320.1, 435/410, 419, 468; 536/23.72; 800/278, 279, 800/302
See application file for complete search history.

(56) References Cited

U.S. PATENT DOCUMENTS 5,135,917 A    8/1992  Burch ......................... 514/44
5,254,678 A   10/1993  Haseloff et al. ........... 536/23.2
5,508,186 A    4/1996  Young et al. ............... 435/235

OTHER PUBLICATIONS

Gordon et al., Virology, 2001, vol. 288, pp. 36–50.*
Agrawal et al., "Assembly of the T = 4 Nudaurelia capensis ω Virus Capsid Protein, Post–Translational Cleavage, and Specific Encapsidation of Its mRNA in a Baculovirus Expression System," Virology, 207(1):89–97 (1995).
Hanzlik, et al., "A novel small RNA virus isolated from the cotton bollworm, Helicoverpa armigera," Journal of General Virology, 74:1805–1810 (1993).

Agrawal et al., "Sequence and Analysis of the Capsid Protein of Nudaurelia Capensis ω Virus, an Insect Virus with T = 4 Icosahedral Symmetry," Virology, 190:806–814 (1992).
Rubinstein et al., "Short Communications: The Nucleic Acids of Viruses Infecting Heliothis armigera," Virology, 69:323–326 (1976).
Dasmahapatra et al., "Infectious RNA derived by transcription from cloned cDNA copies of the genomic RNA of an insect virus," Proc. Natl. Acad. Sci. USA,83:63–66 (1986).
Hahn et al., "Infectious Sindbis virus transient expression vectors for studying antigen processing and presentation," Proc. Natl. Acad. Sci. USA, 89:2679–2683 (1992).
McCutchen et al., "Development of a Recombinant Baculovirus Expressing an Insect–Selective Neurotoxin: Potential for Pest Control," Bio/Technology, 9:848–852 (1991).
Scotti et al., "The Biology and Ecology of Strains of an Insect Small RNA Virus Complex," Advances in Virus Research, 26:117–143 (1981).
Meinke et al., "Unusual Sequence Organization in CenB, an Inverting Endoglucanase from Cellulomonas fimi," J. Bacterio., 173(1):308–314 (1991).
Cavarelli, et al., "Crystallization and Preliminary Structure Analysis of an Insect Virus with T = 4 Quasi–Symmetry: Nudaurelia capensis ω Virus," Acta. Cryst, B47, 23–29 (1991).
Christian et al., "Insect Viruses: New Strategies for Pest Control," Chapter 4 of Molecular Approaches to Fundamental and Applied Entomology, (J. Oakeshott, M. Whitten, Ed.) New York: Springer–Verlag: 128–123 (1995).
Green et al., "Systematic Generation of Sequence–Tagged Sites for Physical Mapping of Human Chromosomes: Application to the Mapping of Human Chromosome 7 Using Yeast Artificial Chromosomes," Genomics, 11:548–564 (1991).
Gillies et al., "Antigen binding and biological activities of engineered mutant chimeric antibodies with human tumor specifities," Human Antibodies and Hybridomas., 1(1):47–54 (1990).
Capon et al., "Two distinct families of human and bovine interferon–α genes are coordinately expressed and encoded functional Polypeptides," Molecular and Cellular Biology, 5(4):768–779 (1985).
O'Conner et al., "An extra copy of nimEcyclinB elevates pre–MPF levels and partially suppresses mutation of numTcdc25 in Aspergillus nidulans," The EMBO Journal, 11(6):2139–2149 (1992).

(Continued)

*Primary Examiner*—Ashwin Mehta
(74) *Attorney, Agent, or Firm*—Dorsey & Whitney LLP; Richard F. Trecartin

(57) ABSTRACT

The present invention relates to an isolated small RNA virus capable of infecting insect species including Heliothis species, and to the nucleotide sequences and proteins encoded thereby. The invention contemplates uses of the virus in controlling insect attack in plants.

10 Claims, 52 Drawing Sheets

OTHER PUBLICATIONS

Burgess et al., "Possible Dissociation of the Heparin–binding and Mitogenic Activities of Heparin–binding (Acidic Fibroblast) Growth Factor–1 from its Receptor–binding Activities by Site–directed Mutagenesis of a Single Lysine Residue," J. Cell Biol., 11:2129–2138 (1990).

Lazar et al., "Transforming Growth Factor α: Mutation of Aspartic Acid 47 and Leucine 48 results in Different Biological Activities," Molecular and Cellular Biology, 8(#):1247–1252 (1988).

Tao et al., "Studies of Aglycosylated Chimeric Mouse–Human IgG. Role of Carbohydrate in the Structure and Effector Functions Mediated by the Human IgG Constant Region," The Journal of Immunology, 143(8):2595–2601 (1989).

Vaeck et al., "Transgenic plants protected from insect attack," Nature, 328:33–37 (1987).

Fischhoff et al., "Insect Tolerant Transgenic Tomato plants," Bio/Technology, 5:807–813 (1987).

Tiong et al., "Microbial Control of an Outbreak of Darna trima (Moore) and oil palm (*Elaeis guineensis* Jacq.) in Sarawak (Malaysian Borneo)." Proc. Malays. Int. Agric. Oil. Conf., 624–639 (1976).

Garzon et al., "Nodaviridae," Atlas of Invertebrates Virus, (Eds. J.R. Adam and J.R. Bonami), CRC Press, 351–593 (1991).

Hendry et al., "Nodaviridae of Invertebrates," Viruses of Invertebrates, (Ed. E. Kurtak) 227–275.

Desmier et al., "Use of Microbial Pesticides for field crops, the case of viruses to control oil palm and coconut leaf–eating caterpillars," Proceedings to the Biotechnology for Tropical Plant Protection Conference, Abstract, Kuala Lumpur, Aug. 1992, Malaysian Plant Protection Society.

Bawden et al., "The Specificity of *Helicoverpa armigera* Stunt Virus Infectivity," Journal of Invertebrate Pathology, 74:156–163 (1999).

Rubinstein et al., "A nonoccluded Virus of the American Bollworm, Heliothis Armigera (HUBN)," Phytophylactica, 11:179–180 (1979).

Tam et al., "Hepatitis E Virus (HEV): Molecular cloning and Sequencing og the Full Length Viral Genome," Virology, 185:120–131 (1991).

Moore, N.F., "The Nudaurelia Beta Family of Insect Viruses," Viruses of Invertebrates. Marcel Dekker: New York. Ed: E. Kurstak, 277–299 (1991).

\* cited by examiner

Map of HaSV RNA 1 clones

```
5'                                                              3'
        E3      1 kb       2 kb        3 kb      4 kb      5 kb
        ┬┬┬┬ ┬ ┬  ┬┬ ┬┬  ┬    ┬    ┬     ┬ ┬      ┬   ┬┬
        X S Sc  S    K X   Sm        X S         Sc H3
              Sc       Sc
```

```
        ─────────────  ─────────────
            B11U            B35

───────────────────
                    B110
```

H3=Hind3, K=Kpn1, Sc=Sac1, S=Sal1, Sm=Sma1, X=Xho1

FIG. 1a

Map of HaSV RNA 2 clones

```
        5'                                        3'
                        1k              2k
                        |               |
RNA     ──────────────────────────────────────
         | |      |  |       |  |     |  |
         X S     E  S        S  P     P  N hr236   ──────────────────────── hr247              ────────────────── hr249                        ─────────────
```

E=EcoR1, N=Not1, P=Pst1, S=Sal1, X=Xho1

FIG. 1b

```
         10                  30                    50
GTTCTGCCTCCCCCGGACGGTAAATATAGGGGAACAATGTACGCGAAAGCGACAGACGTG
----+----|----+----|----+----|----+----|----+----|----+----|
                                         M  Y  A  K  A  T  D  V
                                         replicase start
         70                  90                   110
GCGCGTGTCTACGCCGCGGCAGATGTCGCCTACGCGAACGTACTGCAGCAGAGAGCAGTC
----+----|----+----|----+----|----+----|----+----|----+----|
 A  R  V  Y  A  A  A  D  V  A  Y  A  N  V  L  Q  Q  R  A  V
        130                 150                   170
AAGTTGGACTTCGCCCCGCCACTGAAGGCACTAGAAACCCTCCACAGACTGTACTATCCG
----+----|----+----|----+----|----+----|----+----|----+----|
 K  L  D  F  A  P  P  L  K  A  L  E  T  L  H  R  L  Y  Y  P
        190                 210                   230
CTGCGCTTCAAAGGGGGCACTTTTACCCCCGACACAACACCCGATCCTGGCCGGGCACCAA
----+----|----+----|----+----|----+----|----+----|----+----|
 L  R  F  K  G  G  T  L  P  P  T  Q  H  P  I  L  A  G  H  Q
        250                 270                   290
CGTGTCGCAGAAGAGGTTCTGCACAATTTCGCCAGGGGACGTAGCACAGTGCTCGAGATA
----+----|----+----|----+----|----+----|----+----|----+----|
 R  V  A  E  E  V  L  H  N  F  A  R  G  R  S  T  V  L  E  I
```

FIG. 2

```
          310                 330                 350
GGGCCGTCTCTGCACAGCGCACTTAAGCTACATGGGCACCGAACGCCCCGTCGCAGAC
---------+---------+---------+---------+---------+---------+
 G  P  S  L  H  S  A  L  K  L  H  G  A  P  N  A  P  V  A  D 370                 390                 410
TATCACGGGTGCACCAAGTACGGCACCCGCGACGGCTCGCGACACATTACGGCCTTAGAG
---------+---------+---------+---------+---------+---------+
 Y  H  G  C  T  K  Y  G  T  R  D  G  S  R  H  I  T  A  L  E 430                 450                 470
TCTAGATCCGTCGCCACAGGCCCGGAGTTCAAGGCCGACGCCTCACTGCTCGCCAAC
---------+---------+---------+---------+---------+---------+
 S  R  S  V  A  T  G  R  P  E  F  K  A  D  A  S  L  L  A  N 490                 510                 530
GGCATTGCCTCCCGCACCTTCTGCGTCGACGGAGTCGGCTCTTGCGCGTTCAAATCGCGC
---------+---------+---------+---------+---------+---------+
 G  I  A  S  R  T  F  C  V  D  G  V  G  S  C  A  F  K  S  R 550                 570                 590
GTTGGAATTGCCAATCACTCCCTCTATGACGTGACCCTAGAGGAGCTGGCCAATGCGTTT
---------+---------+---------+---------+---------+---------+
 V  G  I  A  N  H  S  L  Y  D  V  T  L  E  E  L  A  N  A  F
```

FIG. 2 Cont'd

```
        610             630            650
GAGAACCACGGACTTCACATGGTCCGCGCGTTCATGCACATGCCAGAAGAGCTGCTCTAC
---+----|----+----|----+----|----+----|----+----|----+----|
 E  N  H  G  L  H  M  V  R  A  F  M  H  M  P  E  E  L  L  Y 670             690            710
ATGGACAACGTGGTTAATGCCGAGCTCGGCTACCGCTTCCACGTTATTGAAGAGCCTATG
---+----|----+----|----+----|----+----|----+----|----+----|
 M  D  N  V  V  N  A  E  L  G  Y  R  F  H  V  I  E  E  P  M 730             750            770
GCTGTGAAGGACTGCGCATTCCAGGGGGGACCTCCGTCTCCACTTCCCTGAGTTGGAC
---+----|----+----|----+----|----+----|----+----|----+----|
 A  V  K  D  C  A  F  Q  G  G  D  L  R  L  H  F  P  E  L  D 790             810            830
TTCATCAACGAGAGCCAAGAGAGGCGCATCGAGAGGCTGGCCGCCCGCTCCTACTCC
---+----|----+----|----+----|----+----|----+----|----+----|
 F  I  N  E  S  Q  E  R  R  I  E  R  L  A  A  R  G  S  Y  S 850             870            890
AGACGCGCCGTCATTTTCTCCGGCGACGACGACTGGGGTGATGCGTACTTACACGACTTC
---+----|----+----|----+----|----+----|----+----|----+----|
 R  R  A  V  I  F  S  G  D  D  D  W  G  D  A  Y  L  H  D  F
```

FIG. 2 Cont'd

```
        910                                        950
CACACATGGCTCGCCTACCTACTGGTGAGGAACTACCCCACTCCGTTTGGTTTCTCACTC
  H  T  W  L  A  Y  L  L  V  R  N  Y  P  T  P  F  G  F  S  L 970                                        1010
CATATAGAAGTCCAGAGGCGCCACGGCTCCAGCATTGAGCTGCGCATCACTCGGCGCCA
  H  I  E  V  Q  R  R  H  G  S  S  I  E  L  R  I  T  R  A  P 1030                                       1070
CCTGGAGACCGCATGCTGGCCGTCGTGCCCAGGACGTCCCAAGGCCTCTGCAGAATCCCA
  P  G  D  R  M  L  A  V  V  P  R  T  S  Q  G  L  C  R  I  P 1090                                       1130
AACATCTTTTATTACGCCGACGCGTCGGGCACTGAGCATAAGACCATCCTTACGTCACAG
  N  I  F  Y  Y  A  D  A  S  G  T  E  H  K  T  I  L  T  S  Q 1150                                       1190
CACAAAGTCAACATGCTGCTCAATTTTATGCAAACGCGTCCTGAGAAGGAACTAGTCGAC
  H  K  V  N  M  L  L  N  F  M  Q  T  R  P  E  K  E  L  V  D
```

FIG. 2 Cont'd

```
                1210              1230              1250
       ATGACCGTCTTGATGTCGTTCGCGCGCTAGGCTGCGCGGATCGTGGTCGCCTCAGAA
         -----+----+----+----+----+----+----+----+----+----+
         M  T  V  L  M  S  F  A  R  A  R  L  R  A  I  V  V  A  S  E 1270              1290              1310
       GTCACCGAGAGCTCCTGGAACATCTCACCGGCTGACCTGGTCCGCACTGTCGTGTCTCTT
         -----+----+----+----+----+----+----+----+----+----+
         V  T  E  S  S  W  N  I  S  P  A  D  L  V  R  T  V  V  S  L 1330              1350              1370
       TACGTCCTCCACATCATCGAGCGCCGAAGGGCTGCGGTCGCTGTCAAGACCGCCAAGGAC
         -----+----+----+----+----+----+----+----+----+----+
         Y  V  L  H  I  I  E  R  R  R  A  A  V  A  V  K  T  A  K  D 1390              1410              1430
       GACGTCTTTGGAGAGACTTCGTTCTGGGAGAGTCTCAAGCACGTCTTGGGCTCCTGTTGC
         -----+----+----+----+----+----+----+----+----+----+
         D  V  F  G  E  T  S  F  W  E  S  L  K  H  V  L  G  S  C  C 1450              1470              1490
       GGTCTGCGCAACCTCAAAGGCACCGACGTCGTCTTTACTAAGCGCGTCGATAAGTAC
         -----+----+----+----+----+----+----+----+----+----+
         G  L  R  N  L  K  G  T  D  V  V  F  T  K  R  V  D  K  Y
```

FIG. 2 Cont'd

```
                                    1530                     1550
        1510                          |                        |
CGAGTCCACTCGCTCGGAGACATAATCTGCGACGTCCGCCTGTCCCCTGAAACAGGTCGGC
------+---------+---------+---------+---------+---------+----
   R  V  H  S  L  G  D  I  I  C  D  V  R  L  S  P  E  Q  V  G 1590                     1610
        1570                          |                        |
TTCCTGCCGTCCCGCGTACCACCTGCCCGGCGTCTTTCACGACAGGGAAGAGCTTGAGGTC
------+---------+---------+---------+---------+---------+----
   F  L  P  S  R  V  P  P  A  R  V  F  H  D  R  E  E  L  E  V 1650                     1670
        1630                          |                        |
CTTCGCGAAGCTGGCTGCTACAACGAACGTCCGGGTACCTTCCACTCCCTGTGGAGGAG
------+---------+---------+---------+---------+---------+----
   L  R  E  A  G  C  Y  N  E  R  P  V  P  S  T  P  P  V  E  E 1710                     1730
        1690                          |                        |
CCCCAAGGTTTCGACGCCGACTTGTGGCACGCCGACTTGTGGCACGCCGACTACCGC
------+---------+---------+---------+---------+---------+----
   P  Q  G  F  D  A  D  L  W  H  A  T  A  A  S  L  P  E  Y  R 1770                     1790
        1750                          |                        |
GCCACCTTGCAGGCAGGTCTCAACACCGACGTCAAGCAGCTCAAGATCACCCTCGAGAAC
------+---------+---------+---------+---------+---------+----
   A  T  L  Q  A  G  L  N  T  D  V  K  Q  L  K  I  T  L  E  N
```

FIG. 2 Cont'd

```
              1810                1830                1850
GCCCTCAAGACCATCGACGGGCTCACCCTCTCCCCAGTCAGAGGGCCTCGAGATGTACGAG
  ----+----|----+----|----+----|----+----|----+----|----+----|
  A   L   K   T   I   D   G   L   T   L   S   P   V   R   G   L   E   M   Y   E 1870                1890                1910
GGCCCGCCAGGCAGCGGCAAGACGGGCACCCTCATCGCCGCCCTTGAGGCCGGGGCGGT
  ----+----|----+----|----+----|----+----|----+----|----+----|
  G   P   P   G   S   G   K   T   G   T   L   I   A   A   L   E   A   A   G   G 1930                1950                1970
AAAGCACTTTACGTGGCACCCACCAGAGAACTGAGAGAGGCTATGGACCGGCGGATCAAA
  ----+----|----+----|----+----|----+----|----+----|----+----|
  K   A   L   Y   V   A   P   T   R   E   L   R   E   A   M   D   R   R   I   K 1990                2010                2030
CCGCCGTCCGCCCTCGGCCTACGCCAACATGTCGCCCTTGCGATTCTCCGTGCCACCGCC
  ----+----|----+----|----+----|----+----|----+----|----+----|
  P   P   S   A   S   A   T   Q   H   V   A   L   A   I   L   R   R   A   T   A 2050                2070                2090
GAGGGCGCCCCCTTTCGCTACCGTGGTTATCGACGAGTGCTTCATGTTCCCGCTCGTGTAC
  ----+----|----+----|----+----|----+----|----+----|----+----|
  E   G   A   P   F   A   T   V   V   I   D   E   C   F   M   F   P   L   V   Y
```

FIG. 2 Cont'd

```
        2110              2130              2150
GTCGGGATCGTGCACGCCCTTGTCCCCGAGCTCACGAATAGTCCTTGTAGGGACGTCCAC
---+----+----+----+----+----+----+----+----+----+----+----+
 V  A  I  V  H  A  L  S  P  S  S  R  I  V  L  V  G  D  V  H 2170              2190              2210
CAAATCGGGTTTATAGACTTCCAAGGCACACAAGCGCGAACATGCCGCTCGTTCGACGTC
---+----+----+----+----+----+----+----+----+----+----+----+
 Q  I  G  F  I  D  F  Q  G  T  S  A  N  M  P  L  V  R  D  V 2230              2250              2270
GTTAAGCAGTGCCGCCGTCGGGCGCACTTTCAAACCAAGCGCTGTCCGGCCGACGTCGTT
---+----+----+----+----+----+----+----+----+----+----+----+
 V  K  Q  C  R  R  R  T  F  N  Q  T  K  R  C  P  A  D  V  V 2290              2310              2330
GCCACCACGTTTTTCCAGAGCTTGTACCCCGGGTGCACAACCACCTCAGGGTGCGTCGCA
---+----+----+----+----+----+----+----+----+----+----+----+
 A  T  F  F  Q  S  L  Y  P  G  C  T  T  T  S  G  C  V  A 2350              2370              2390
TCCATCAGCCACGTCGCCCCAGACTACCGCAACAGCCAAGGCGCAAACGCTCTGCTTCACG
---+----+----+----+----+----+----+----+----+----+----+----+
 S  I  S  H  V  A  P  D  Y  R  N  S  Q  A  Q  T  L  C  F  T
```

FIG. 2 Cont'd

```
         2410              2430              2450
CAGGAGGAAAAGTCGCGCCACGGGGCTGAGGGCGCGATGACTGTGCACGAAGCGCAGGA
-----+----+----+----+----+----+----+----+----+----+----+----+
 Q  E  E  K  S  R  H  G  A  E  G  A  M  T  V  H  E  A  Q  G 2470              2490              2510
CGCACTTTTGCGTCTGTCATTCTGCATTACAACGGCTCCACAGCAGAGAAGCTCCTC
-----+----+----+----+----+----+----+----+----+----+----+----+
 R  T  F  A  S  V  I  L  H  Y  N  G  S  T  A  E  Q  K  L  L 2530              2550              2570
GCTGAGAAGTCGCACCTTCTAGTCGGCATCACGCGCCACCAACCACCTGTACATCCGC
-----+----+----+----+----+----+----+----+----+----+----+----+
 A  E  K  S  H  L  L  V  G  I  T  R  H  T  N  H  L  Y  I  R 2590              2610              2630
GACCCGACAGGTGACATTGAGAGACAACTCAACCATAGCGCGAAAGCCGAGGTGTTTACA
-----+----+----+----+----+----+----+----+----+----+----+----+
 D  P  T  G  D  I  E  R  Q  L  N  H  S  A  K  A  E  V  F  T 2650              2670              2690
GACATCCCTGCACCCCTGGAGATCACGACTGTCAAACCGAGTGAAGAGGTGCAGCGCAAC
-----+----+----+----+----+----+----+----+----+----+----+----+
 D  I  P  A  P  L  E  I  T  T  V  K  P  S  E  E  V  Q  R  N
```

FIG. 2 Cont'd

```
2710                         2730                         2750
GAAGTGATGGCAACGATACCCCCGCAGAGTGCCACGCCCGCACGGAGCAATCCATCTGCTC
 E  V  M  A  T  I  P  P  Q  S  A  T  P  H  G  A  I  H  L  L 2770                         2790                         2810
CGCAAGAACTTCGGGGACCAACCCGACTGTGGCTGTGTCGCTTTGGCGAAGACCGGCTAC
 R  K  N  F  G  D  Q  P  D  C  G  C  V  A  L  A  K  T  G  Y 2830                         2850                         2870
GAGGTGTTTGGCGGTCGTGCCAAAATCAACGTAGAGCTTGCCGAACCCGACGCGGACCCCG
 E  V  F  G  G  R  A  K  I  N  V  E  L  A  E  P  D  A  T  P 2890                         2910                         2930
AAGCCGCATAGGGCCGTTCCAGGAAGGGGTACAGTGGGTCAAGGTCACCAACGCGTCTAAC
 K  P  H  R  A  F  Q  E  G  V  Q  W  V  K  V  T  N  A  S  N 2950                         2970                         2990
AAACACCAGGCGCTCCAGACGCTGTTGTCCCGCTACACCAAGCGAAGCGCTGACCTGCCG
 K  H  Q  A  L  Q  T  L  L  S  R  Y  T  K  R  S  A  D  L  P
```

FIG. 2 Cont'd

```
                 3010                       3030                       3050
CTACACGAAGCTAAGGAGGACGTCAAACGCATGCTAAACTCGCTTGACCGACATTGGGAC
--------+---------+---------+---------+---------+---------+
  L  H  E  A  K  E  D  V  K  R  M  L  N  S  L  D  R  H  W  D 3070                       3090                       3110
TGGACTGTCACTGAAGACGCCCGTGACCGAGCTGTCTTCGAGACCCAGCTCAAGTTCACC
--------+---------+---------+---------+---------+---------+
  W  T  V  T  E  D  A  R  D  R  A  V  F  E  T  Q  L  K  F  T 3130                       3150                       3170
CAACGCGGCGGCACCGTCGAAGACCTGCTGGAGCCAGACGACCCCTACATCCGTGACATA
--------+---------+---------+---------+---------+---------+
  Q  R  G  G  T  V  E  D  L  L  E  P  D  D  P  Y  I  R  D  I 3190                       3210                       3230
GACTTCCTTATGAAGACTCAGCAGAAAGTGTCGCCCAAGCCGATCAATACGGGCAAGGTC
--------+---------+---------+---------+---------+---------+
  D  F  L  M  K  T  Q  Q  K  V  S  P  K  P  I  N  T  G  K  V 3250                       3270                       3290
GGGCAGGGGGATCGCGCCGCTCACTCAAAGTCTCTCAACTTCGTCCTCGCTTGGATACGC
--------+---------+---------+---------+---------+---------+
  G  Q  G  D  R  A  A  H  S  K  S  L  N  F  V  L  A  A  W  I  R
```

FIG. 2 Cont'd

```
             3310                        3330                         3350
    ATACTCGAGGAGATACTCCGTACCGGGAGCCGCACGGTCCGGTACAGCAACGGTCTCCCC
    ----+----|----+----|----+----|----+----|----+----|----+----|
     I  L  E  E  I  L  R  T  G  S  R  T  V  R  Y  S  N  G  L  P 3370                        3390                         3410
    GACGAAGAAGAGGCCATGCTGCTCGAAGCGAAGATCAATCAAGTCCCACACGCCACGTTC
    ----+----|----+----|----+----|----+----|----+----|----+----|
     D  E  E  E  A  M  L  L  E  A  K  I  N  Q  V  P  H  A  T  F 3430                        3450                         3470
    GTCTCGGGCGGACTGGACCGAGTTTGACACCGCCCACAATAACACGAGTGAGCTGCTCTTC
    ----+----|----+----|----+----|----+----|----+----|----+----|
     V  S  A  D  W  T  E  F  D  T  A  H  N  N  T  S  E  L  L  F 3490                        3510                         3530
    GCCGCCCTTTTAGAGCGCATCGGCACGCCTGCAGCTGCCGTTAATCTATTCAGAGAACGG
    ----+----|----+----|----+----|----+----|----+----|----+----|
     A  A  L  L  E  R  I  G  T  P  A  A  A  V  N  L  F  R  E  R 3550                        3570                         3590
    TGTGGGAAACGCACCTTGCGAGCGAAAGGGTCTAGGCTCCCGTTGAAGTCGACGGTCTGCTC
    ----+----|----+----|----+----|----+----|----+----|----+----|
     C  G  K  R  T  L  R  A  K  G  L  G  S  V  E  V  D  G  L  L
```

FIG. 2 Cont'd

```
         3610              3630              3650
GACTCCGGGCGCAGCTTGGACGCCTTGCCGCAACACCATCTTCTCTGCCGCCGTCATGCTC
 D  S  G  A  A  W  T  P  C  R  N  T  I  F  S  A  A  V  M  L 3670              3690              3710
ACGCTCTTCCGCGGCGTCAAGTTCGCAGCTTTCAAAGGCGACGACTCGCTCCTCTGTGGT
 T  L  F  R  G  V  K  F  A  A  F  K  G  D  D  S  L  L  C  G 3730              3750              3770
AGCCATTACCTCCGTTTCGACGCTAGCCGCCTTCACATGGGCGAACGTTACAAGACCAAA
 S  H  Y  L  R  F  D  A  S  R  L  H  M  G  E  R  Y  K  T  K 3790              3810              3830
CATTTGAAGGTGGAGGTGCAGAAAATCGTGCCGTACATCGGACTCCTCGTCTCCGCTGAG
 H  L  K  V  E  V  Q  K  I  V  P  Y  I  G  L  L  V  S  A  E 3850              3870              3890
CAGGTCGTCCTCGACCCCGTCAGGAGCGCTCTCAAGATATTTGGGCGCTGCTACACAAGC
 Q  V  V  L  D  P  V  R  S  A  L  K  I  F  G  R  C  Y  T  S
```

FIG. 2 Cont'd

```
        3910                3930                3950
GAACTCCTTTACTCCAAGTACGTGGAGGCTGTGAGAGACATCACCAAGGGCTGGAGTGAC
  E  L  Y  S  K  Y  V  E  A  V  R  D  I  T  K  G  W  S  D 3970                3990                4010
GCCCGCTACCACAGCCTCCTGTGCCACATGTCAGCATGCTACTACAATTACGCGCCGGAG
  A  R  Y  H  S  L  L  C  H  M  S  A  C  Y  Y  N  Y  A  P  E 4030                4050                4070
TCTGCGGGCGTACATCATCGACGCTGTTGTTCGCTTTGGGCGCGGACTTCCCGTTTGAA
  S  A  A  Y  I  I  D  A  V  V  R  F  G  R  G  D  F  P  F  E 4090                4110                4130
CAACTGCGCGTGGTGCGTGCCCATGTGCAGGCACCCGACGCTTACAGCAGCACGTATCCG
  Q  L  R  V  V  R  A  H  V  Q  A  P  D  A  Y  S  S  T  Y  P 4150                4170                4190
GCTAACGTGCGCGCATCGTGCCTTGACCACGTCTTCGAGCCCCGCCAGGCCGCCCCG
  A  N  V  R  A  S  C  L  D  H  V  F  E  P  R  Q  A  A  A  P
```

FIG. 2 Cont'd

```
                    4210                    4230                    4250
GCAGGTTTCGTTGCGACATGTGCGAAGCCTTCTTCACTTACCGCGAAAGCT
---+---------+---------+---------+---------+---------+
 A  G  F  V  A  T  C  A  K  P  E  T  P  S  S  L  T  A  K  A
                                                         M  C  E  A  G  N  A  F  F  T  Y  R  E  S  W
                                                         P11a start 4270                    4290                    4310
GGTGTGTTTCTGCGACTACAAGCCACGTTGCGACTGGGACTGCGCCCCGGAGTCTCCATGG
---+---------+---------+---------+---------+---------+
 G  V  S  A  T  T  S  H  V  A  T  G  T  A  P  P  E  S  P  W
    C  F  C  D  Y  K  P  R  C  D  W  D  C  A  P  G  V  S  M  G 4330                    4350                    4370
GATGCACCTGCAGCCAACAGCTTTTCGGAGTTATTGACACCGGAGACCCCGTCCACATCA
---+---------+---------+---------+---------+---------+
 D  A  P  A  A  N  S  F  S  E  L  L  T  P  E  T  P  S  T  S
    C  T  C  S  Q  Q  L  F  G  V  I  D  T  G  D  P  V  H  I 4390                    4410                    4430
TCCCTCGCCGTCATCGTCTTCATCGGACTCCTCTACATCGTGTGGAAGGTCGCTCAGTGGT
---+---------+---------+---------+---------+---------+
 S  S  P  S  S  S  S  D  S  S  T  S  C  G  R  S  L  S  G
 L  A  V  I  V  F  I  G  L  L  Y  I  V  W  K  V  A  Q  W  W
```

FIG. 2 Cont'd

```
                    4450                          4470                          4490
GGAGACACCGCAAGGACCACCAGAGAAGACTTGAACAGCAGAAAGCCGCCTTCGCAAGACAGG
--------+---------+---------+---------+---------+---------+
 G  D  T  A  R  T  T  E  D  L  N  S  R  K  P  P  S  Q  D  R
 R  H  R  K  D  H  H  R  R  L  E  Q  Q  K  A  A  F  A  R  Q  A 4510                          4530                          4550
CAATCACGCTCGTCTGAATGTCTGGACAGAAGCGGAGAAAGGACAGGCAGTTCGTTAACT
--------+---------+---------+---------+---------+---------+
 Q  S  R  S  S  E  C  L  D  R  S  G  E  R  T  G  S  S  L  T
 I  T  L  V  *  M  S  G  Q  K  R  R  K  D  R  Q  F  V  N  C
                   P11b start 4570                          4590                          4610
GCCCCCACTGCTCCGAGCCCCTCATTCTCTCATTTTTCGGAAAGAGCTCGACTGGCGACCCGGG
--------+---------+---------+---------+---------+---------+
 A  P  T  A  P  S  P  S  F  S  F  S  E  R  A  R  L  A  T  G
 P  H  C  S  E  P  L  I  L  I  F  G  K  S  S  T  G  D  R  A 4630                          4650                          4670
CCGACTGTGCCGCTGCGACATCACCTTCGGCAACCCCATCCTGCGCCACGGACCAGGTT
--------+---------+---------+---------+---------+---------+
 P  T  V  A  A  T  S  P  S  A  T  P  S  C  A  T  D  Q  V
 D  C  R  R  C  D  I  T  F  G  N  P  I  L  R  H  G  P  G  C
```

FIG. 2 Cont'd

```
         4690        4710        4730
GCCGCGAGGACCACGCCGGACTTTGCGCCTTTCCTGGGTTCCCAGTCTGCCGTGCTGTC
-----+----+----+----+----+----+----+----+----+----+----+---+
 A  A  R  T  P  D  F  A  P  F  L  G  S  Q  S  A  R  A  V
   R  E  D  H  A  G  L  C  A  F  P  G  F  P  V  C  P  C  C  L 4750        4770        4790
TCGAAGCCGTACCGGCCCCCCACGACTGCCCGTTGGAAAGAATCACCCGCTCCACGCG
-----+----+----+----+----+----+----+----+----+----+----+---+
 S  K  P  Y  R  P  P  T  T  A  R  W  K  E  V  T  P  L  H  A
   E  A  V  P  A  P  H  D  C  P  L  E  R  S  H  P  A  P  R  V 4810        4830        4850
TGGAAGGGCGTGACCGGAGACCGGAAGTCAGGGAGGAGACCCGGAGACAGCGGCGGTC
-----+----+----+----+----+----+----+----+----+----+----+---+
 W  K  G  V  T  G  D  R  P  E  V  R  E  D  P  E  T  A  A  V
   E  G  R  D  R  R  P  T  G  S  Q  G  G  P  G  D  S  G  G  R 4870        4890        4910
GTCCAGGCTCTGATCAGCGGCCGTTATCCTCAGAAGACGAAGTTTCCTCCGACGCATCC
-----+----+----+----+----+----+----+----+----+----+----+---+
 V  Q  A  L  I  S  G  R  Y  P  Q  K  T  K  L  S  S  D  A  S
   P  G  S  D  Q  R  P  L  S  S  E  D  E  A  F  L  R  R  I  Q
```

```
             4930              4950              4970
AAAGGCTACTCAAGAACTAAGGGATGCTCACAATCCACCTCTTTTCCTGCCCCGAGTGCG
    ---+----+----+----+----+----+----+----+----+----+----+----+
 K  G  Y  S  R  T  K    G  C  S  Q  S  T  S  F  P  A  P  S  A
 R  L  L  K  N  *     M  L  T  I  H  L  F  S  C  P  E  C  G
                      P14 start
             4990              5010              5030
GATTACCAGGCCCGCGACTGCCAGACAGTCCGAGTCTGCCGCGCCGCTGCAGAGATGGCG
    ---+----+----+----+----+----+----+----+----+----+----+----+
 D  Y  Q  A  R  D  C  Q  T  V  R  V  C  R  A  A  A  E  M  A
 L  P  G  P  R  L  P  D  S  P  S  L  P  R  R  C  R  D  G  A 5050              5070              5090
CGCTCATGTATTCACGAGCCGTTGGCTTCATCTGCCGCCAGTGCCGACTTGAAGCGCATA
    ---+----+----+----+----+----+----+----+----+----+----+----+
 R  S  C  I  H  E  P  L  A  S  S  A  A  S  A  D  L  K  R  I
 L  M  Y  S  R  A  V  G  F  I  C  R  Q  C  R  L  E  A  H  T 5110              5130              5150
CGCTCTACCTCGGACTCTGTTCCCGATGTAAAGATCAGCAAGAGCGCATGAAGGAACAAA
    ---+----+----+----+----+----+----+----+----+----+----+----+
 R  S  T  S  D  S  V  P  D  V  K  I  S  K  S  A  *
 L  Y  L  G  L  C  S  R  C  K  D  Q  Q  E  R  M  K  E  Q  N
```

```
                    5170                        5190                       5210
ATTAGTTTCCTTGTTCGTAAACAAGGTGTCCCTCCCATTGAGGTAAAGACTCTGGTGAG
    ----+----|----+----|----+----|----+----|----+----|----+----|
        *
                    5230                        5250                       5270
TCCTCAACGTTACTCGTTGAGTCTGCTGCGGTTCGATTCCATTCCCAAGCAGCAAAGGGT
    ----+----|----+----|----+----|----+----|----+----|----+----|
                    5290                        5310
GCGCAACTAGTACGGCGCCCCCCTGGGATACCA
    ----+----|----+----|----+----|
```

FIG. 2 Cont'd

```
          10                        30                        50
GTTTTCTTTCTTTACCAAGTGTGGTAAAATTTAAACAAAGAAGAAACCAGGACCCGTAA
----+----+----+----+----+----+----+----+----+----+----+----+

70                        90                       110
CCCGGCCCTTACACACCCTCGAGTCCGGTGACCACCCGGATTATACGTCGCCACCACACGGC
----+----+----+----+----+----+----+----+----+----+----+----+

130                       150                       170
GCCTTTCCGACCACTCTCGAGAGTCGTTGGGAGTTCGTCCGTGACCACCCGGTTGGCA
----+----+----+----+----+----+----+----+----+----+----+----+

190                       210                       230
GTCGACAGAGACGCTTCCGGACCACTAGAACCCTCCTCGAGCGACGCACACAGCACACACA
----+----+----+----+----+----+----+----+----+----+----+----+

250                       270                       290
CCGCCCTTAGCTGCACCTACGGCAGCGGTTGATAGCGCGGATTTATGAGCGAGCACCATC
----+----+----+----+----+----+----+----+----+----+----+----+
                                          M  S  E  H  T  I
                                          P17 start
         310                       330                       350
GCCCACTCCATCACACATTACCACCCGGTTACACCCTTGCCCTAATACCCCCTGAACCTGAA
----+----+----+----+----+----+----+----+----+----+----+----+
 A  H  S  I  T  L  P  P  G  Y  T  L  A  L  I  P  P  E  P  P  E
```

FIG. 3a

```
                                      370                                390                                 410
                        GCAGGATGGGGAGATGCTGGAGTGGCTGGAGCGTCACAGCGACCTCACAACCGTCGCGGAACCCGTA
                        ----------+---------+---------+---------+---------+---------+
                        A  G  W  E  M  L  E  W  R  H  S  D  L  T  T  V  A  E  P  V
                                           M  G  D  A  G  V  A  S  Q  R  P  H  N  R  R  G  T  R  N
                                           P71 start
                                      430                                450                                 470
                        ACGTTCGGGTCAGCGGCCAACACCGTCACCGTCAATGGTAGAAGAAACCAACGGCGTCGGA
                        ----------+---------+---------+---------+---------+---------+
                        T  F  G  S  A  P  T  P  S  S  M  V  E  E  T  N  G  V  G
                        V  R  V  S  A  N  T  V  T  V  N  G  R  R  N  Q  R  R  R  T
                                      490                                510                                 530
                        CCGGAAGGCAAGTTTCTCCCCCTGACAATTTCACCGCTGCTGCACAAGACCTCGCGCAAA
                        ----------+---------+---------+---------+---------+---------+
                        P  E  G  K  F  L  P  L  T  I  S  P  L  L  H  K  T  S  R  K
                        G  R  Q  V  S  P  P  D  N  F  T  A  A  A  Q  D  L  A  Q  S
                                      550                                570                                 590
                        GCCTTGACGCCAACACCGTCACTTTCCCCGCTAACATCTCTAGCATGCCCGAATTCCGGA
                        ----------+---------+---------+---------+---------+---------+
                        A  L  T  P  T  P  S  L  S  P  L  T  S  L  A  C  P  N  S  G
                        L  D  A  N  T  V  T  F  P  A  N  I  S  S  M  P  E  F  R  N
```

FIG. 3a Cont'd

```
                    610                    630                    650
ATTGGGCCAAGGGAAAGATCGACCTCGACTTCCATCGGCTTCCGATTCCATCGGCTGGTACTTCAAGTACC
---+---------+---------+---------+---------+---------+---------+
 I  G  P  R  E  R  S  T  S  T  P  I  P  S  A  G  T  S  S  T
   W  A  K  G  K  I  D  L  D  S  D  S  I  G  W  Y  F  K  Y  L 670                    690                    710
TTGACCCAGAGTCTGCTACAGAGTCTGCGCGCCGTCGGCCGAGTACTCGAAGATCCCTG
---+---------+---------+---------+---------+---------+---------+
 L  T  Q  R  V  L  Q  S  L  R  A  P  S  A  S  T  R  R  S  L
   D  P  A  G  A  T  E  S  A  R  A  V  G  E  Y  S  K  I  P  D 730                    750                    770
ACGGCCTCGTCAAGTTCTCCGTCGACGCAGAGATAAGAGAGATCTATAACGAGGAGTGCC
---+---------+---------+---------+---------+---------+---------+
 T  A  S  S  S  S  P  S  T  Q  R  *
   G  L  V  K  F  S  V  D  A  E  I  R  E  I  Y  N  E  E  C  P 790                    810                    830
CCGTCGTCACTGACGTGTCCGTCCCCCTCGACGGCCGCCAGTGGAGCCTCTCGATTTCT
---+---------+---------+---------+---------+---------+---------+
   V  V  T  D  V  S  V  P  L  D  G  R  Q  W  S  L  S  I  F  S
```

FIG. 3a Cont'd

```
       850           870           890
CCTTTCCGATGTTCAGAAACCGCCTACGTCGCCGTAGCGAACGTCGAGAACAAGGAGATGT
 F  P  M  F  R  T  A  Y  V  A  V  A  N  V  E  N  K  E  M  S 910           930           950
CGCTCGACGTTGTCAACGACCTCATCGAGTGGCTCAACAATCTCGCCGACTGGCGTTATG
 L  D  V  V  N  D  L  I  E  W  L  N  N  L  A  D  W  R  Y  V 970           990          1010
TCGTTGACTCTCGAACAGTGGATTAACTTCACCAATGACACCACGTACTACGTCCGCATCC
 V  D  S  E  Q  W  I  N  F  T  N  D  T  T  Y  Y  V  R  I  R 1030          1050          1070
GCGTTCTACGTCCAACCTACGACGTTCCAGAGACCCCACAGAGGGCCTTGTTCGCACAGTCT
 V  L  R  P  T  Y  D  V  P  D  P  T  E  G  L  V  R  T  V  S 1090          1110          1130
CAGACTACCGCCTCACTTATAAGGCCGATAACATGTGAAGCCAACATGCCAACACTCGTCG
 D  Y  R  L  T  Y  K  A  I  T  C  E  A  N  M  P  T  L  V  D
```

FIG. 3a Cont'd

```
                              1150                           1170                           1190
ACCAAGGCTTTTGGATCGGGGGCCAGTACGCTCTCACCCCGACTAGCCTACCGCAGTACG
----+----|----+----|----+----|----+----|----+----|----+----|
 Q  G  F  W  I  G  G  Q  Y  A  L  T  P  T  S  L  P  Q  Y  D 1210                           1230                           1250
ACGTCAGCGAGGCCTACGCTCTGCACACTTTGACCTTCGCCAGACCATCCAGCGCCGCTG
----+----|----+----|----+----|----+----|----+----|----+----|
 V  S  E  A  Y  A  L  H  T  L  T  F  A  R  P  S  S  A  A  A 1270                           1290                           1310
CACTCGCCGTTGTGTGGGCAGGTTTGCCACAGGGTGGCACTGCGCCTGCAGGCACTCCAG
----+----|----+----|----+----|----+----|----+----|----+----|
 L  A  F  V  W  A  G  L  P  Q  G  G  T  A  P  A  G  T  P  A 1330                           1350                           1370
CCTGGGAGCAGGCATCCTCGGGTGGCTACCTCACCTGGCGCCACAACGGTACTACTTCC
----+----|----+----|----+----|----+----|----+----|----+----|
 W  E  Q  A  S  S  G  G  Y  L  T  W  R  H  N  G  T  T  F  P 1390                           1410                           1430
CAGCTGGCTCCGTTAGCTACGTTCTCCCTGAGGGTTTCGCCCTTGAGCGCTACGACCCGA
----+----|----+----|----+----|----+----|----+----|----+----|
 A  G  S  V  S  Y  V  L  P  E  G  F  A  L  E  R  Y  D  P  N
```

FIG. 3a Cont'd

```
         1450                    1470                    1490
ACGACGGCTCTTGGACCGACTTCGCTTCCGCAGGAGACACCGTCACTTTCCGGCAGGTCG
----+----|----+----|----+----|----+----|----+----|----+----|
 D   G   S   W   T   D   F   A   S   A   G   D   T   V   T   F   R   Q   V   A 1510                    1530                    1550
CCGTCGACGAGGTCGTTGTGACCAACAACCCCGCCGGCGGCGGCAGCGCCCCCACCTTCA
----+----|----+----|----+----|----+----|----+----|----+----|
 V   D   E   V   V   V   T   N   N   P   A   G   G   G   S   A   P   T   F   T 1570                    1590                    1610
CCGTGAGAGTGCCCCCCTTCAAACGCTTACACCAACACCGTGTTTAGGAACACGCTCTTAG
----+----|----+----|----+----|----+----|----+----|----+----|
 V   R   V   P   P   S   N   A   Y   T   N   T   V   F   R   N   T   L   L   E 1630                    1650                    1670
AGACTCGACCCTCCTCCTCGTAGGCTCGAACTCCCTATGCCACCTGCTGACTTTGGACAGA
----+----|----+----|----+----|----+----|----+----|----+----|
 T   R   P   S   S   R   R   L   E   L   P   M   P   P   A   D   F   G   Q   T 1690                    1710                    1730
CGGTCGCCAACAACCCGAAGATCGAGCAGTCGCTTCTTAAAGAAACACTTGGCTGCTATT
----+----|----+----|----+----|----+----|----+----|----+----|
 V   A   N   N   P   K   I   E   Q   S   L   L   K   E   T   L   G   C   Y   L
```

FIG. 3.a Cont'd

```
                1750                       1770                      1790
TGGTCCACTCCAAAATGCGAAACCCCGTTTTCCAGCTCACGCCAGCTCCTTGGCG
----+----|----+----|----+----|----+----|----+----|----+----
 V  H  S  K  M  R  N  P  V  F  Q  L  T  P  A  S  S  F  G  A 1810                       1830                      1850
CCGTTTCCTTCAACAATCCGGGTTATGAGCGCACACGCGACCTCCCGGACTACACTGGCA
----+----|----+----|----+----|----+----|----+----|----+----
 V  S  F  N  N  P  G  Y  E  R  T  R  D  L  P  D  Y  T  G  I 1870                       1890                      1910
TCCGTGACTCATTCGACCAGAACATGTCCACCGCTGTGGCCCACTTCCGCTCACTCTCCC
----+----|----+----|----+----|----+----|----+----|----+----
 R  D  S  F  D  Q  N  M  S  T  A  V  A  H  F  R  S  L  S  H 1930                       1950                      1970
ACTCCTGCAGTATCGTCACTAAGACCTACCAGGGTTGGGAAGGCGTCACGAACGTCAACA
----+----|----+----|----+----|----+----|----+----|----+----
 S  C  S  I  V  T  K  T  Y  Q  G  W  E  G  V  T  N  V  N  T 1990                       2010                      2030
CGCCTTTCGGCCAATTCGCGCACGCGGGCCTCCTCAAGAATGAGGAGATCCTCTGCCTCG
----+----|----+----|----+----|----+----|----+----|----+----
 P  F  G  Q  F  A  H  A  G  L  L  K  N  E  E  I  L  C  L  A
```

FIG. 3a Cont'd

```
2050                    2070                    2090
CCGACGACCTGGCCACCCGTCTCACAGGTGTCTACCCCGCCACTGACAACTTCGCGGCCG
-----+---------+---------+---------+---------+---------+
 D  D  L  A  T  R  L  T  G  V  Y  P  A  T  D  N  F  A  A  A 2110                    2130                    2150
CCGTTTCTGCCTTCGCCGCGAACATGCTGTCCTCCGTGCTGAAGTCGGAGGCAACGTCCT
-----+---------+---------+---------+---------+---------+
 V  S  A  F  A  A  N  M  L  S  S  V  L  K  S  E  A  T  S  S 2170                    2190                    2210
CCATCATCAAGTCCGTTGGCGAGACTGCCGTCGGCGCTCAGTCCGGCCTCGCGAAGC
-----+---------+---------+---------+---------+---------+
 I  I  K  S  V  G  E  T  A  V  G  A  A  Q  S  G  L  A  K  L 2230                    2250                    2270
TACCCGGGACTGCTAATGAGTGTACCAGGGAAGATTGCCGCCGTGTCCGGCGCGCCGAG
-----+---------+---------+---------+---------+---------+
 P  G  L  L  M  S  V  P  G  K  I  A  A  R  V  R  A  R  R  A 2290                    2310                    2330
CGCGCCGCCGCGGCCGCTCGTGCCAATTAGTTTGCTCGTCCTGTTTCGCCGTTTCGTAAA
-----+---------+---------+---------+---------+---------+
 R  R  R  A  A  R  A  A  N  *
```

FIG. 3a Cont'd

```
          2350                2370              2390
ACGGGCGTGGTCCCGCACATTACGCGTACCCTAAAGACTCTGGTGAGTCCCCGTCGTTACA
----------+---------+---------+---------+---------+---------+

2410                2430              2450
CGACGGGTCTGCCCGGTTCGATTCCATTCCCAAGCGGCAAGAAGGACGTAGTTAGCTCT
----------+---------+---------+---------+---------+---------+

2470
GCGTCCCTCGGGATACCA
----------+-------
```

FIG. 3a Cont'd

```
                     10                             30                              50
GTTTTCTTTCTTTACCAAGTGTGGTAAAATTTAAACAAAGAAGAAAACCAGGACCGTAA
------+---------+---------+---------+---------+---------+

70                             90                            110
CCCGGCCCTTACACACCTCGAGTCCGTGACCACCGGATTATACGTCGCCCACCACACGGC
------+---------+---------+---------+---------+---------+

130                            150                            170
GCCTTTTCCGACCACTCTCGAGAGTCGTTGGGAGTTTCGTCCGTGACCACCCGGTTGGCA
------+---------+---------+---------+---------+---------+

190                            210                            230
GTCGACAGACGCTTCCGGACCACTAGAACCTCCTCGAGCGACGCACACAGCACACACA
------+---------+---------+---------+---------+---------+

250                            270                            290
CCGCCTTAGCTGCACCTACGGCAGCGTTGATAGCGCGGATTTATGAGCCGAGCACACCATC
------+---------+---------+---------+---------+---------+
                                               M  S  E  H  T  I
                                               "P70" fusion protein start
           310                            330                            350
GCCCACTCCATCACATTACCACCCGGTTACACCCCTTGCCCTAATACCCCCTGAACCTGAA
------+---------+---------+---------+---------+---------+
 A  H  S  I  T  L  P  P  G  Y  T  L  A  L  I  P  P  E  P  P  E
```

Fig. 3b

```
              370              390              410
     GCAGGATGGGAGATGCTGGAGTGGCGTCACAGCGACCTCACAACCGTCGCGGAACCCGTA
     ---------+---------+---------+---------+---------+---------+
      A  G  W  E  M  L  E  W  R  H  S  D  L  T  T  V  A  E  P  V 430              450              470
     ACGTTCGGGTCAGCGCCAACACCGTCACCGTCAATGGTAGAAGAAACCAACGGGTCGGA
     ---------+---------+---------+---------+---------+---------+
      T  F  G  S  A  P  T  P  S  P  S  M  V  E  E  T  N  G  V  G 490              510              530
     CCGGAAGGCAAGTTTCTCCCCCTGACAATTTCACCGCTGCACAAGACCTCGCGCAAA
     ---------+---------+---------+---------+---------+---------+
      P  E  G  K  F  L  P  L  T  I  S  P  L  H  K  T  S  R  K 550              570              590
     GCCTTGACGCCAACACCGTCACTTTCCCCGCTAACATCTCTAGCATGCCCGAATTCCGG
     ---------+---------+---------+---------+---------+---------+
      A  L  T  P  T  P  S  L  S  P  A  N  I  S  S  M  P  E  F  R 610              630              650
     AATTGGGCCAAGGGAAAGATCGACCTCGACTCCGATTCCATCGGCTGGTACTTCAAGTAC
     ---------+---------+---------+---------+---------+---------+
      N  W  A  K  G  K  I  D  L  D  S  D  S  I  G  W  Y  F  K  Y
```

Fig. 3b (cont'd)

```
                    670                         690                        710
CTTGACCCAGCCGGGTGCTACAGAGTCTGCGCGCCGTCGGCGAGTACTCGAAGATCCCT
---------+---------+---------+---------+---------+---------+
 L  D  P  A  G  A  T  E  S  A  R  A  V  G  E  Y  S  K  I  P 730                         750                        770
GACGGGCCTCGTCAAGTTCTCCGTCGACGCAGAGAGATAAGAGAGATCTATAACGAGGAGTGC
---------+---------+---------+---------+---------+---------+
 D  G  L  V  K  F  S  V  D  A  E  I  R  E  I  Y  N  E  E  C 790                         810                        830
CCCGTCGTCACTGACGTGTCCGTCCCCCTCGACGGCCGCCAGTGGAGCCTCTCGATTTTC
---------+---------+---------+---------+---------+---------+
 P  V  V  T  D  V  S  V  P  L  D  G  R  Q  W  S  L  S  I  F 850                         870                        890
TCCTTTCCGATGTTCAGAACCGCCTACGTCGCCGTAGCGAACGTCGAGAACAAGGAGATG
---------+---------+---------+---------+---------+---------+
 S  F  P  M  F  R  T  A  Y  V  A  V  A  N  V  E  N  K  E  M 910                         930                        950
TCGCTCGACGTTGTCAACGACCTCATCGAGTGGCTCAACAATCTCGCCGACTGGCGTTAT
---------+---------+---------+---------+---------+---------+
 S  L  D  V  V  N  D  L  I  E  W  L  N  N  L  A  D  W  R  Y
```

Fig. 3b(cont'd)

```
              970                     990                    1010
     GTCGTTGACTCTGAACAGTGGATTAACTTCACCAATGACACCACGTACTACGTCCGCATC
     ----+----|----+----|----+----|----+----|----+----|----+----|
      V  V  D  S  E  Q  W  I  N  F  T  N  D  T  T  Y  Y  V  R  I 1030                    1050                    1070
     CGCGTTCTCTACGTCCAACCTACGACGTTCCAGACCCCACAGAGGGCCTTGTTCGCACAGTC
     ----+----|----+----|----+----|----+----|----+----|----+----|
      R  V  L  R  P  T  Y  D  V  P  D  P  T  E  G  L  V  R  T  V 1090                    1110                    1130
     TCAGACTACCGCCTCACTTATAAGGCGATAACATGTGAAGCCAACATGCCAACACTCGTC
     ----+----|----+----|----+----|----+----|----+----|----+----|
      S  D  Y  R  L  T  Y  K  A  I  T  C  E  A  N  M  P  T  L  V 1150                    1170                    1190
     GACCAAGGCTTTTGGATCGGGCGGCCAGTACGCTCTCACCCCGACTAGCCTACCGCAGTAC
     ----+----|----+----|----+----|----+----|----+----|----+----|
      D  Q  G  F  W  I  G  G  Q  Y  A  L  T  P  T  S  L  P  Q  Y 1210                    1230                    1250
     GACGTCAGCGAGGCCTACGCTCTGCACACTTTGACCTTCGCCAGAACCATCCAGCGCCGCT
     ----+----|----+----|----+----|----+----|----+----|----+----|
      D  V  S  E  A  Y  A  L  H  T  L  T  F  A  R  P  S  S  A  A
```

Fig. 3b(cont'd)

```
            1270                          1290                         1310
GCACTCGCGTTGTGTGGGCAGGTTTGCCACAGGGTGGCACTGCGCCTGCAGGCACTCCA
-----+----|----+----|----+----|----+----|----+----|----+----|
 A   L   A   F   V   W   A   G   L   P   Q   G   G   T   A   P   A   G   T   P 1330                         1350                         1370
GCCTGGGAGCAGGCATCCTCGGGTGGCTACCTCACCTGGCGCCACAACGGTACTACTTTC
-----+----|----+----|----+----|----+----|----+----|----+----|
 A   W   E   Q   A   S   S   G   G   Y   L   T   W   R   H   N   G   T   T   F 1390                         1410                         1430
CCAGCTGGCTCCGTTAGCTACGTTCTCCCCTGAGGGTTTCGCCCTTGAGCGCTACGACCCG
-----+----|----+----|----+----|----+----|----+----|----+----|
 P   A   G   S   V   S   Y   V   L   P   E   G   F   A   L   E   R   Y   D   P 1450                         1470                         1490
AACGACGGCTCTCTTGGACCGACTTCGCTTCCGCAGGAGACACCGTCACTTTCCGGCAGGTC
-----+----|----+----|----+----|----+----|----+----|----+----|
 N   D   G   S   W   T   D   F   A   S   A   G   D   T   V   T   F   R   Q   V 1510                         1530                         1550
GCCGTCGACGAGGTCGTTGTGACCAACAACCCCGCCGGCGGCAGCGCCCCCACCTTC
-----+----|----+----|----+----|----+----|----+----|----+----|
 A   V   D   E   V   V   V   T   N   N   P   A   G   G   S   A   P   T   F
```

Fig. 3b (cont'd)

```
              1570                1590                1610
     ACCGTGAGAGTGCCCCCTTCAAACGCTTACACCAACACCGTGTTTAGGAACACGCTCTTA
      T  V  R  V  P  P  S  N  A  Y  T  N  T  V  F  R  N  T  L  L 1630                1650                1670
     GAGACTCGACCCTCCTCTCGTAGGCTCGAACTCCCTATGCCACCTGCTGACTTTGGACAG
      E  T  R  P  S  S  R  R  L  E  L  P  M  P  P  A  D  F  G  Q 1690                1710                1730
     ACGGTCGCCAACAACCCGAAGATCGAGCAGTCGCTTCTTAAAGAAACACTTGGCTGCTAT
      T  V  A  N  N  P  K  I  E  Q  S  L  L  K  E  T  L  G  C  Y 1750                1770                1790
     TTGGTCCACTCCAAAATGCGAAACCCCGTTTTTCCAGCTCACGCCAGCTCCTTTGGC
      L  V  H  S  K  M  R  N  P  V  F  Q  L  T  P  A  S  S  F  G 1810                1830                1850
     GCCGTTTCCTTCAACAATCCGGGTTATGAGCGCACACGGCGACCTCCCGGACTACACTGGC
      A  V  S  F  N  N  P  G  Y  E  R  T  R  D  L  P  D  Y  T  G
```

Fig. 3b (cont'd)

```
                    1870                          1890                           1910
ATCCGTGACTCATTCGACCAGAACATGTCCACCGCTGTGGCCCACTTCCGCTCACTCTCC
 I  R  D  S  F  D  Q  N  M  S  T  A  V  A  H  F  R  S  L  S 1930                          1950                           1970
CACTCCTGCAGTATCGTCACTAAGACCTACCAGGGTTGGGAAGGCGTCACGAACGTCAAC
 H  S  C  S  I  V  T  K  T  Y  Q  G  W  E  G  V  T  N  V  N 1990                          2010                           2030
ACGCCTTTCGGCCAATTCGCGCACGCGGCCTCCTCAAGAATGAGGAGATCCTCTGCCTC
 T  P  F  G  Q  F  A  H  A  G  L  L  K  N  E  E  I  L  C  L 2050                          2070                           2090
GCCGACGACCTGGCCACCCGTCTCACAGGTGTCTACCCCGCCACTGACAACTTCGCGGCC
 A  D  D  L  A  T  R  L  T  G  V  Y  P  A  T  D  N  F  A  A 2110                          2130                           2150
GCCGTTTCTGCCTTCGCCGCGAACATGCTCCTCCGTGCTGAAGTCGGAGGCAACGTCC
 A  V  S  A  F  A  A  N  M  L  S  S  V  L  K  S  E  A  T  S
```

Fig. 3b (cont'd)

```
                           2190                        2210
       TCCATCATCAAGTCCGTGTGGCCGAGACTGCCGTCGGCGCGCTCAGTCCGGCCTCGGCGAAG
2170   ----+----|----+----|----+----|----+----|----+----|----+----|
        S  I  I  K  S  V  G  E  T  A  V  G  A  A  A  Q  S  G  L  A  K 2250                        2270
       CTACCCGGAACTGCTAATGAGTGTACCAGGAAGATTGCCGGCGTGTCCGGCGCGCGCCGA
2230   ----+----|----+----|----+----|----+----|----+----|----+----|
        L  P  G  L  L  M  S  V  P  G  K  I  A  A  R  V  R  A  R  R 2310                        2330
       GCGCGCCGCGCCGCGCCGCTCGTGCCAATTAGTTTGCTCGCTCCTGTTTCGCCGTTTCGTAA
2290   ----+----|----+----|----+----|----+----|----+----|----+----|
        A  R  R  R  A  A  R  A  N  *

2370                        2390
       AACGGGCGTGGTCCCCGCACATTACGCGTACCCTAAAGACTCTGGTGAGTCCCCGTCGTTAC
2350   ----+----|----+----|----+----|----+----|----+----|----+----|

2430                        2450
       ACGACGGGTCTGCCGCGGTTCGATTCCATTCCCAAGCGGCAAGAAGGACGTAGTTAGCTC
2410   ----+----|----+----|----+----|----+----|----+----|----+----|

TGCGTCCCTCGGGATACCA
2470   ----+----|---------
```

Fig. 3b (cont'd)

FIG. 4
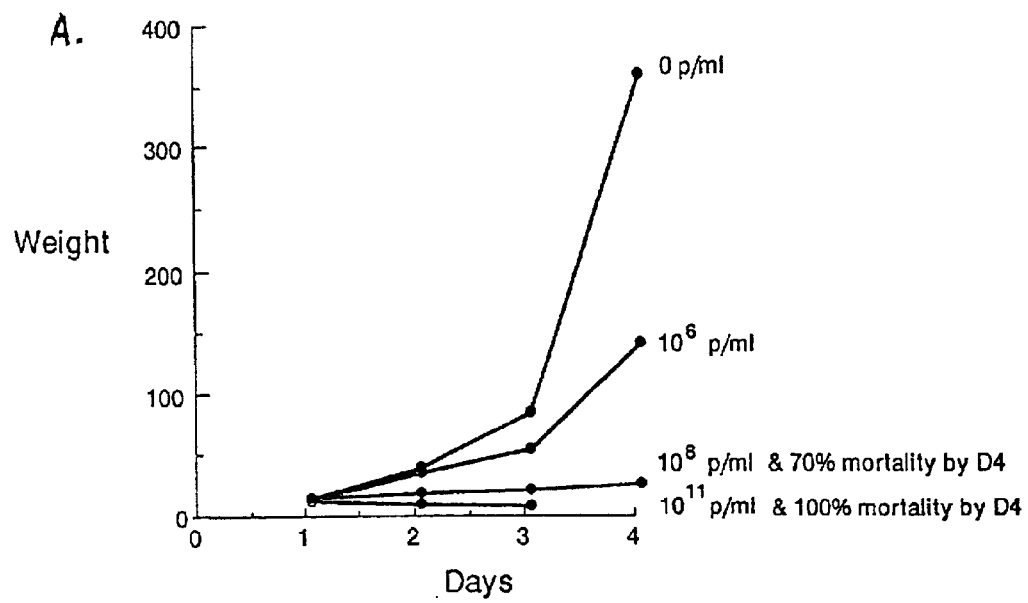
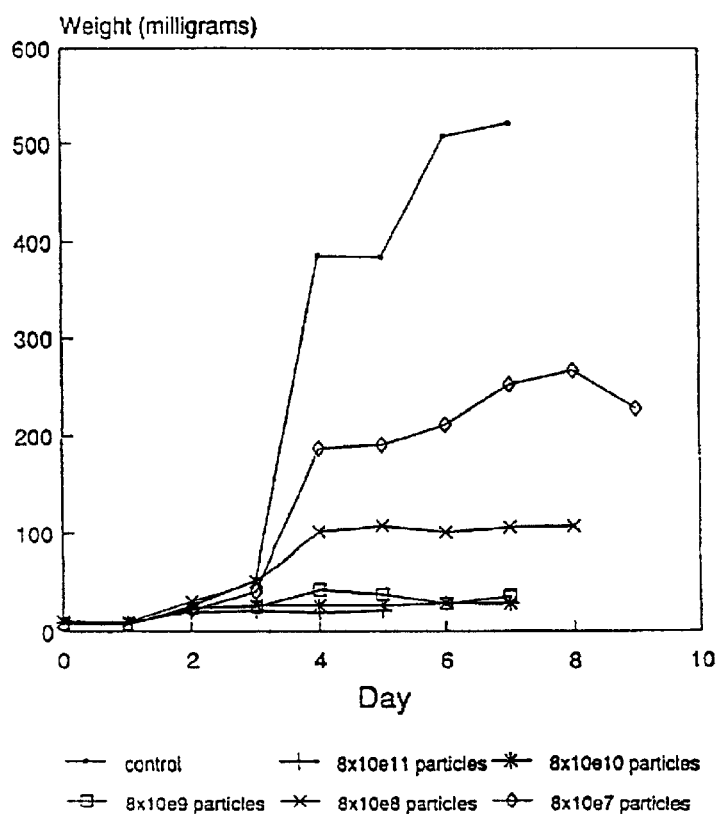

FIG. 10

FIG. 11
WESTERN BLOTS OF HaSV CAPSID PROTEIN
A.  HaSV ANTISERUM
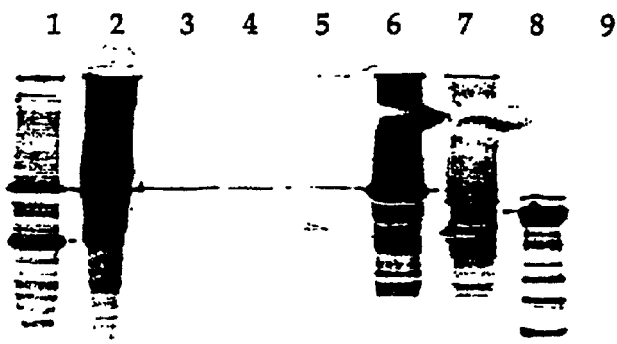
B  HaSV ANTISERUM            C.  Bt ANTISERUM
          

FIG. 12

DOT-BLOT DETECTION OF HaSV IN FIELD-COLLECTED

HELICOVERPA LARVAE transgenic plant genome:

| P71 capsid protein | capsotoxin fusion |

FIG. 14a

Virus capsoid strategy: capsotoxin encapsulation proteins: P71 capsoids assembled:

capsotoxin fusion proteins cleaved upon assembly capsoids enter feeding larvae and disassembled:

releasing active, insect-specific toxin

HaSV RNA 1 — replicase
HaSV RNA 2 — P17, capsid protein transgenic plant genome: replicase | (a/s?) toxin | capsid protein transcripts: replicase | (a/s?) toxin

FIG. 14b proteins: P71 capsoids assembled:

Virus capsoid strategy: toxin message encapsulation and amplification replicase
(a/s?) toxin capsoids enter and infect feeding larvae capsoids disassembled: replicase | (a/s?) toxin mRNA amplification and expression and secretion of toxin

Virus expression in plants: the one-way vector

FIG. 14c

HaSV RNA 1 — replicase
HaSV RNA 2 — P17, capsid protein transgenic plant genome: replicase ... capsid protein transcripts: replicase proteins: P71 capsoids assembled:

capsoids enter and infect feeding larvae capsoids disassembled:

replicase

RNA 1 replicates and causes anti-feeding effect

---

HaSV RNA 1 — replicase
HaSV RNA 2 — P17, capsid protein

FIG. 14d transgenic plant genome: replicase | P17, defective cp | capsid protein transcripts: replicase | P17, defective cp proteins: P71 capsoids assembled: replicase, P17, defective cp capsoids enter and infect feeding larvae capsoids disassembled: replicase, P17, defective cp viral RNA replicates and causes anti-feeding effect

INSECT VIRUSES AND THEIR USES IN PROTECTING PLANTS

This application is a continuation of U.S. Ser. No. 09/234,238 filed Jan. 20, 1999, now abandoned, which is a continuation of U.S. Ser. No. 08/440,522, filed May 12, 1995, now abandoned, which is a continuation-in-part of U.S. Ser. No. 08/089,372, filed Jul. 8, 1993, now abandoned, which claims the benefit of the filing date of Australian Provisional Application Serial Number PL 4801 filed on Aug. 14, 1992.

FIELD OF THE INVENTION

The present invention relates to insect viruses useful in control of insect attack on plants. It particularly relates to biological insecticides, especially those comprised of insect viruses. In particular applications, the invention also provides recombinant viruses and transgenic plants.

BACKGROUND OF THE INVENTION

There is increasing awareness of the desirability of insect pest control by biological agents. Considerable effort in recent years has been devoted to the identification and exploitation of DNA viruses with large genomes, especially the baculoviruses. These viruses generally require extensive genetic manipulation to become effective insecticides, and the first such modified viruses are only now being evaluated.

In contrast, very little effort has been devoted to the study and use of small viruses with RNA genomes.

Four main groups of small RNA viruses have been isolated from insects. These include members of the Picornaviridae, the Nodaviridae, the Tetraviridae and the unclassified viruses. Descriptions of these groups can be found in the Atlas of Invertebrate Viruses (eds J. R. Adams and J. R. Bonami) (CRC Press, Boca Raton, 1991) and Viruses of Invertebrates (ed. E. Kurstak) (Marcel Dekker, New York, 1991). These disclosures relating to these viruses concern their pathology and biology, not their use in biological control.

Further information regarding small RNA viruses of insects an be found in P. D. Scotti et al (1981) "The biology and ecology of strains of an insect small RNA virus complex" *Advances in Virus Research* 26, 117–143. This review describes the insect picornaviruses cricket paralysis virus and *Drosophila* C virus (diameters estimated at 27–30 nm with one RNA component of 7.5–8.5 kb). N. F. Moore & T. W. Tinsley (1982) The small RNA viruses of insects. Brief review *Archives of Virology* 72, 229–245. This review included viruses of the following families:

Nodaviridae (diameter 29–30 nm, 2 RNA components totalling 4.5 kb)

Picornaviridae (diameter 27–30 nm, one RNA component of 7.5–8.5 kb)

*Nudaurelia* β family (now called Tetraviridae) (diameter around 35 mn, either one RNA of 5.5 kb or two totalling 8 kb)

N. F. Moore, B. Reavy & L. A. King (1985) General characteristics, gene organisation and expression of small RNA viruses of insects. *Journal of general Virology* 66, 647–659. This reference defines small RNA viruses of insects as being those less than 40 nm in diameter. The review covers Picornaviridae, Nodaviridae and the *Nudaurelia* β family (now called Tetraviridae).

D. Hendry, V. Hodgson, R Clark and J Newman (1985) Small RNA viruses co-infecting the pine emperor moth (*Nudaurela cytherea capensis*). *Journal of general Virology* 66, 627–632 described viruses with mean diameters of 40 nm and 38 nm and one or two RNA components up to 5.5 kb in length.

Most recently, the term insect small RNA viruses has been used by one of the present inventors to cover three main recognised toxic groups: the Picornaviridae, the Tetraviridae and the Nodaviridae (P. Scotti & P. Christian (1994) The promises and potential problems of using small RNA insect viruses for insect control. *Sains Malaysiana* 23, 9–18).

These references illustrate a long standing usage of the term in this field of the term "small RNA virus" for viruses with certain characteristics as listed above. Another important characteristic of these virus groups is that they are not occluded, in contrast to many large viruses like the cytoplasmic polyhydrosis (RNA) viruses or the DNA baculoviruses, granulosis viruses and entomopox viruses. The term would also be applied to viruses not members of the three families listed above, as long as they satisfied the definition of being up to 40 nm in size. There are reports of such unclassified viruses (eg in Hendry et al. 1985). Moreover, the taxonomic status of some members of the Tetraviridae still requires clarification and it might even be possible for this family to be split, with HaSV and other members with two RNA components in their genome being separated from those with only one component, like the type member *Nudaurelia* β virus, which has not yet been sequenced. The above definition of "small RNA virus" would still cover all members of such virus families.

SUMMARY OF THE INVENTION

In a first aspect of the present invention there is provided an isolated small RNA virus wherein the virus is up to 40 nm in size, is not occluded and infects insect species including Heliothis species.

In one particular embodiment, the present invention provides an isolated preparation of *Heliothis armigera* stunt virus referred to as "HaSV" herein.

In a further aspect of the present invention there is provided an isolated nucleic acid molecule comprising a nucleic acid sequence hybridizable with RNA 1 (SEQ ID No: 39) or RNA 2 (SEQ ID No: 47) described herein under low stringency conditions.

In still a further aspect the invention provides a vector comprising a nucleic acid molecule, the sequence of which is hybridizable with RNA 1 (SEQ ID No: 39) or RNA 2 (SEQ ID No: 47) as described herein. These vectors include expression and transfer vectors for use in animals including insect, plant and bacterial cells.

In a further aspect the invention provides an isolated protein or polypeptide preparation of the proteins or polypeptides derivable from the isolated virus of the present invention. The invention also extends to antibodies specific for the protein and polypeptide preparations.

In a yet further aspect the invention provides a recombinant insect virus vector incorporating all or a part of the isolated virus of the present invention.

In a still further aspect of the present invention there is provided a method of controlling insect attack in a plant comprising genetically manipulating said plant so that it is capable of producing HaSV or mutants, derivatives or variants thereof or an insecticidally effective portion of HaSV, mutants, variants or derivatives thereof such that insects feeding on the plants are deleteriously effected. The present invention also provides a transgenic plant so manipulated.

BRIEF DESCRIPTION OF FIGURES

FIG. 1a is a restriction map of RNA 1 (SEQ ID No. 39) clones.

FIG. 1b is a restriction map of RNA 2 (SEQ ID No. 47) clones.

FIG. 2 is the complete sequence of RNA 1 (SEQ ID No: 39) and of major encoded polypeptides, namely replicase (SEQ ID No: 40), 11a (SEQ ID NO: 42), 11b (SEQ ID NO: 44) and P14 (SEQ ID NO: 46).

FIG. 3a is the complete sequence of RNA 2 (SEQ ID No. 47) in the authentic version, and its encoded polypeptides, namely P17 (SEQ ID No: 48) and P71 (SEQ ID No: 50).

FIG. 3b is the sequence of RNA 2 variant (a 5C version) (SEQ ID No: 51) and its major encoded polypeptide(s), namely P70 (SEQ ID No: 52).

FIGS. 4a and 4b illustrate bioassay data showing HaSV induced stunting of larvae.

Figure 10:
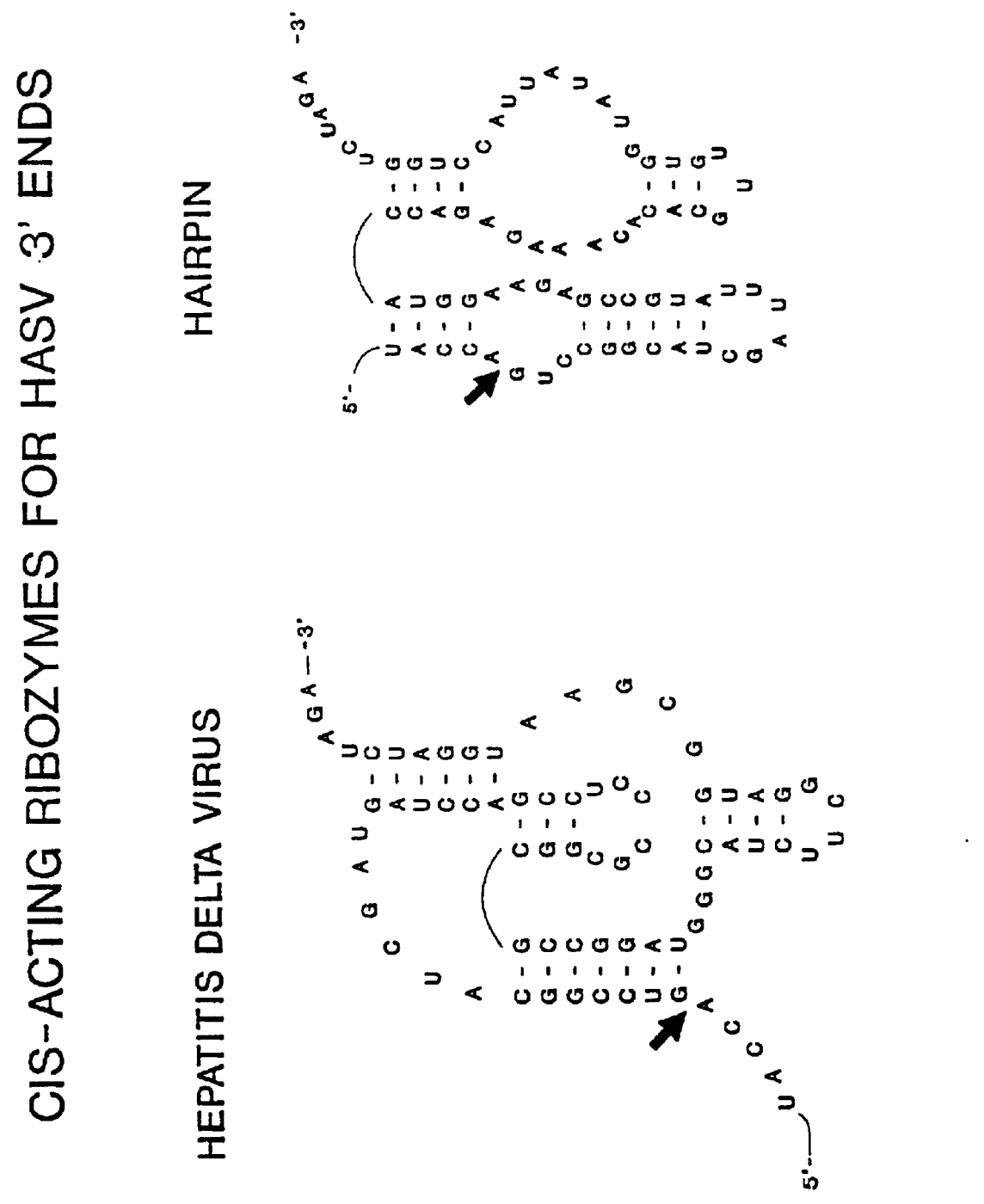

FIG. 10 Ribozymes to yield correct 3' ends. The sequences of ribozymes inserted as short cDNA fragments into HaSV cDNA clones are shown. The ribozyme fragments were assembled and cloned as described in the text. Designed self-cleavage points are indicated by bold arrows.

FIG. 11 Immunoblots to map epitopes on HaSV. A. Detected with HaSV antiserum. Lane 1: pTP70del SP; lane 2: pTP70; lane 3: pTP17; lane 4: control; lane 5: pTP70del N; lane 6: pTP70; lane 7: pTP71; lane 8: HaSV virions; lane 9; molecular weight markers. B. Detected with HaSV antiserum. Lane 1: pTP70del N; lane 2: pTP70del SPN; lane 3: pTP70. C. Detected with an antiserum to the Bt toxin (CryIA(c)). lane 1: pTP70; lane 2: HaSV virions; lane 3: control extract.

FIG. 12 New field isolates of HaSV. The genomic organization of RNA 2 is shown at the top of the Figure. PCR using appropriate primers with BamHI restriction sites and in some cases altered context sequences of the AUG initiating translation of the P17 (SEQ ID No. 48) or P71 (SEQ ID No. 50) genes were used to make fragments for cloning into the BamHI sites of the expression vectors. Constructs 17E71 (SEQ ID No. 35) and P71 (SEQ ID No. 50) have altered context sequences of the AUG initiating translation of the P17 (SEQ ID No. 48) and P71 (SEQ ID No. 50) genes respectively; these alterations correspond to the context derived from the JHE gene (see text). All context sequences are given on the right of the figure. R2 is a clone of the complete RNA sequence as a BamHI fragment in the vector.

FIGS. 14a to f Various strategies utilizing the present invention.

DETAILED DESCRIPTION OF PREFERRED EMBODIMENTS

Figure 5:
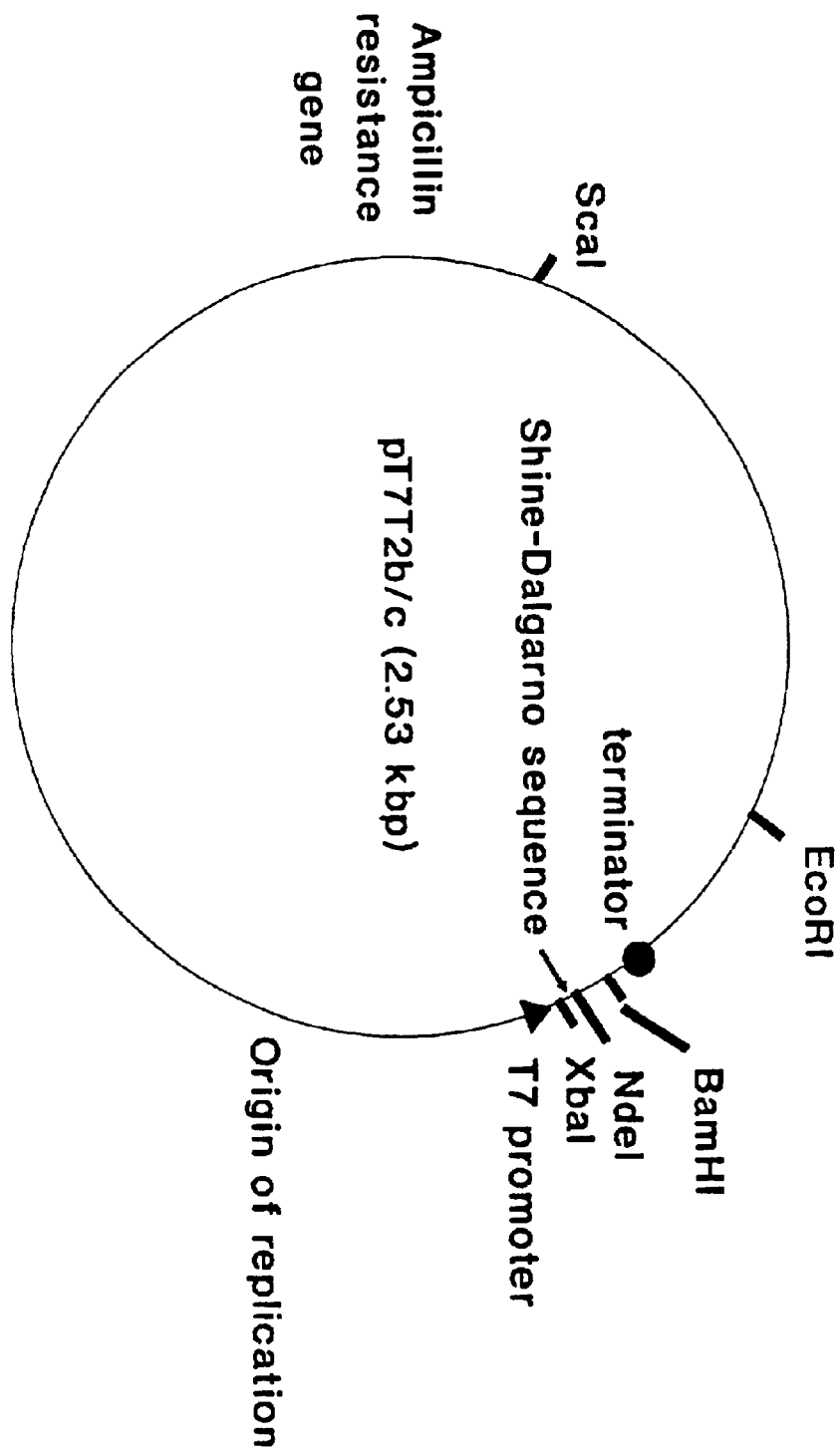
FIG. 5 is a map of Vector plasmid pT7T2b and pT7T2c.
Figure 6:
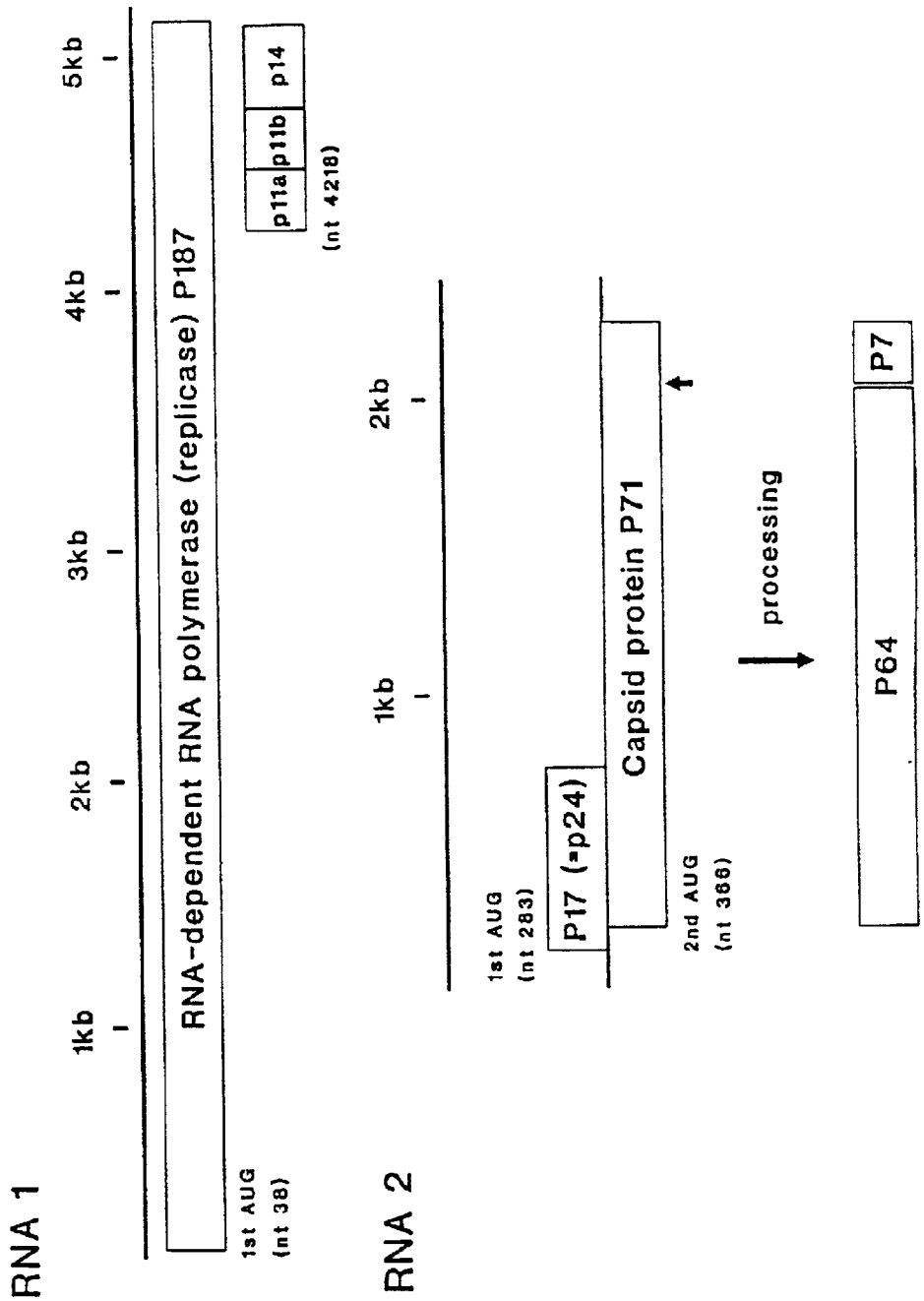
FIG. 6 is a schematic representation of the proteins encoded by RNA 1 (SEQ ID No. 39) and RNA 2 (SEQ ID No. 47).
Figure 7:
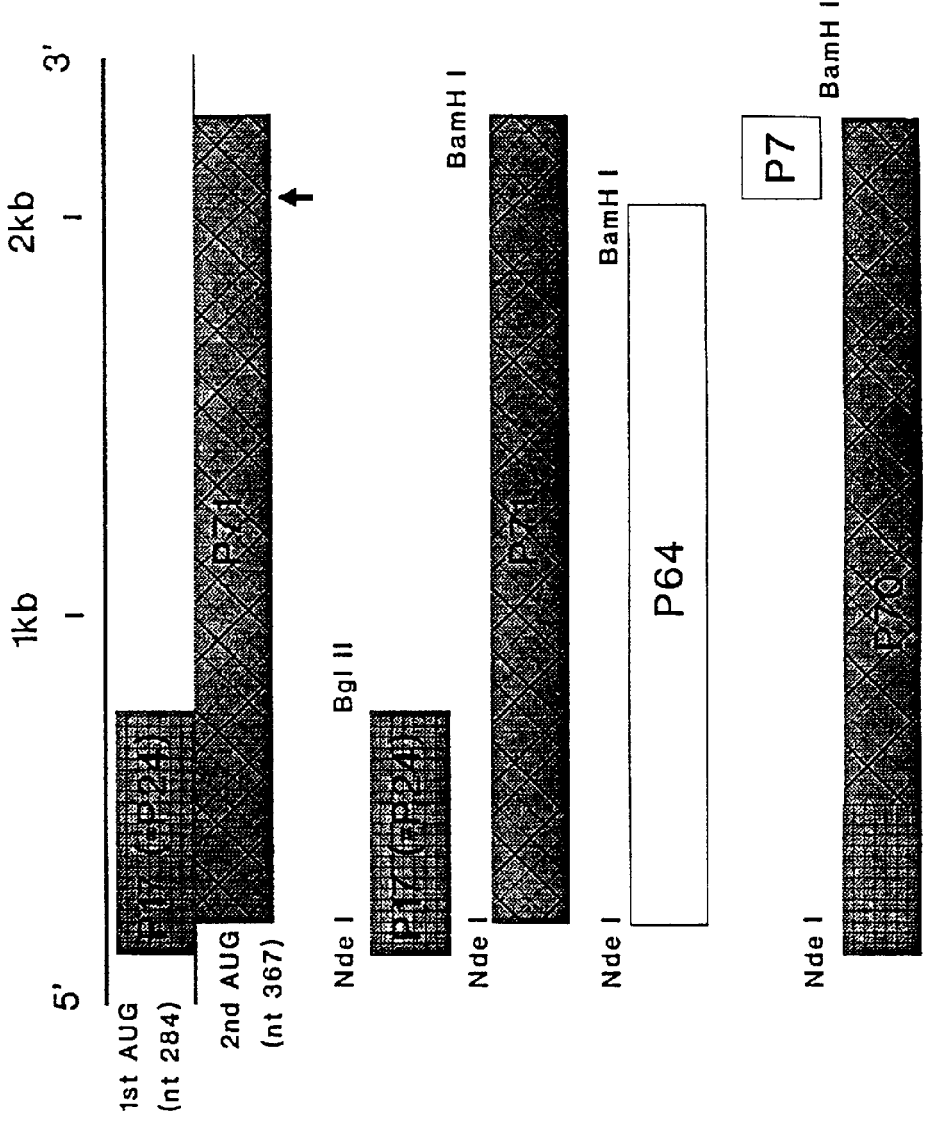
FIG. 7 is a schematic representation of the proteins expressed by RNA 2 (SEQ ID No. 47) in bacteria DNA fragments encoding P17 (SEQ Id No. 48), P71 (SEQ ID No. 50), P64, P7 and the fusion protein P70 (SEQ ID No. 52) were synthesized by PCR. The flanking NdeI and BamHI sites used in cloning are indicated. (Note that P17 is followed by BglII site, whose cohesive ends are compatible with those of BamHI).

A first aspect of the invention contemplates use of small RNA viruses for biological control of insects. In particular, in accordance with the first aspect of this invention there is provided an isolated small RNA virus, particularly *H. armigera* stunt virus or mutants, variants or derivatives thereof capable of infecting insects, in particular the insect species such as *Helicoverpa armigera*. The small RNA virus isolate of the instant invention is insecticidal and in particular stunts the growth of insect larvae, for example *Helicoverpa armigera* larvae and inhibits or prevents development into the adult stage.

The small RNA viruses of the instant invention have insecticidal, anti-feeding, gut-binding or any synergistic property or other activity useful for insect control.

In particular, *Helicoverpa armigera* stunt virus (HaSV) particles are isometric and approximately 36 nm in diameter with a buoyant density on CsCl gradients of 1.36 g/ml. The virus is composed of two major capsid proteins of approximately 64 and 7 KDa in size as determined on SDS-PAGE. The HaSV genome is much later than the largest known nodavirus (another class of RNA viruses) and comprises two ss (+) RNA molecules of approximately 5.3 and 2.4 kb. The genome appears to lack a blockage of unknown structure at the 3' termini that is found in Nodaviridae. The HaSV genome however shares a capped structure and non-polyadenylation with Nodaviridae. HaSV differs significantly from Nodaviridae and *Nudaurelia* w virus in terms of its immunological properties. In particular the large capsid protein has different antigenic determinants. Other properties of HaSV are described in the Examples.

The host range of HaSV includes Lepidopterans such as from the subfamily Heliothinae. Species known to be hosts are *Helicoverpa* (*Heliothis*) *armigera, H. punctigera, H. zea, Heliothis virescens* and other such noctuides as *Spodoptera exigua, H. armigera* which is known by the common names corn ear worm, cotton ball worm, tomato grub and tobacco bud worm is a pest of economic significance in most countries. *H. punctigera,* the native bud worm, is a pests of the great economic significance in Australia. Members of the Heliothinae, which include Helicoverpa and Heliothis, and especially *H. armigera* are among the most important and widespread pests in the world. In the U.S. *Heliothis virescens* and *Helicoverpa zea* are particularly important pests.

The first aspect of the invention provides an isolated small RNA virus capable of infecting insects including Heliothis species. In a particularly preferred form the invention relates to mutants, variants and derivatives of HaSV. The terms "mutant", "variant" and "derivative" include all naturally occurring and artificially created viruses or viral components which differ from the HaSV isolate as herein described in nucleotide content or sequence, amino acid content or sequence, immunological reactivity, non-glycosylation or glycosylation pattern and/or infectivity but generally retain insecticidal activity. Specifically the terms "mutant", "variant" and "derivative" of HaSV covers small RNA viruses which have one or more functional characteristic of HaSV described herein. Examples of mutants, variants or derivatives of HaSV include small RNA viruses that have different nucleic or amino acid sequences from HaSV but retain one of more functional features of HaSV. These may include strains with genetically silent substitutions, strains carrying replication and encapsidation sequences and signals that are functionally related to HaSV, or strains that carry functionally related protein domains.

In a preferred aspect the invention relates to mutants, variants or derivatives 2 of HaSV which encode replication or encapsidation sequences, structures or signals with 60%, preferably 70%, more preferably 80%, still more preferably 90% and even more preferably 95% nucleotide sequence identity to the nucleotide sequences HaSV.

In another preferred aspect the invention relates to mutants, variants or derivatives of HaSV which encode proteins with at least 50%, preferably 60%, preferably 70%, more preferably 80%, still more preferably 90% and even more preferably 95% amino acid sequence identity to proteins or polypeptides of HaSV.

In another preferred aspect the invention relates to mutants, variants or derivatives of HaSV with 50%, more preferably 60%, still more preferably 70%, more preferably 80%, still more preferably 90 or 95% nucleotide sequence identity to the following biologically active domains encoded by the HaSV genome:

RNA 1 (SEQ ID No: 39)—amino acid residues 401 to 600 or the other domains in the replicase RNA 2 (SEQ ID No: 47) (in the capsid protein)
  amino acid residues 273 to 435
  amino acid residues 50 to 272
  amino acid residues 436 to the COOH terminus Preferably the viral isolate of the present invention is biologically pure which means a preparation of the virus comprising at least 20% relative to other components as determined by weight, viral activity or any other convenient means. More preferably the isolates are 50% pure, still more preferably it is 60%, even more preferably it is 70% pure, still more preferably it is 80% pure and even more preferably it is 90% or more, pure.

In a second aspect the present invention relates to a nucleotide sequence or sequences hybridizable with those of HaSV. The term nucleotide sequence used herein includes RNA, DNA, cDNA and nucleotide sequences complementary thereto. Such nucleotide sequences also include single or double stranded nucleic acid molecules and linear and covalently closed circular molecules. The nucleic acid sequences may be the same as the HaSV sequences as herein described or may contain single or multiple nucleotide substitutions and/or deletions and/or additions thereto. The term nucleotide sequence also includes sequences with sufficient homology to hybridize with the nucleotide sequence under low, preferably medium and most preferably high stringency conditions (Sambrook J, Fritsch, E. F. & Maniatis T. (1989) Molecular Cloning: A Laboratory Manual, 2nd Edition, Cold Spring Harbour Laboratories Press) and to nucleotide sequences encoding functionally equivalent sequences. In still a more preferred embodiment the invention comprises the nucleotide sequences of genome components 1 and 2 (SEQ ID Nos: 39 and 47) as represented by FIGS. 1 and 2 hereinafter or parts thereof, or mutants, variants, or derivatives thereof The terms "mutants", "variants" or "derivatives" of nucleotide genome components 1 and 2 (SEQ ID Nos: 39 and 47) has the same meaning, when applied to nucleotide sequences as that given above and includes parts of genome components 1 and 2 (SEQ ID Nos: 39 and 47).

The second aspect of the invention also relates to nucleotide signals, sequences or structures which enable the nucleic acid on which they are present to be replicated by HaSV replicase. Furthermore the invention relates to the nucleotide signals, sequences or structures which enable nucleic acids on which they are present to be encapsidated.

In a particularly preferred embodiment of the second aspect, the invention comprises nucleotide sequences which are mutants of the capsid gene having the following sequences:

```
ATG GGC GAT GCC GGC GTC GCGT TCA CAG  (SEQ ID No: 2)

ATG GAG GAT GCT GGA GTG GCG TCA CAG   (SEQ ID No: 3)

ATG AGC GAG GCC GGC GTC GCG TCA CAG   (SEQ ID No: 4)
```

In a preferred aspect the invention relates to nucleotide sequences of HaSV encoding insecticidal activity including the capsid protein gene and P17 (SEQ ID No: 48) and mutants, variants and derivatives thereof.

In another preferred aspect the invention comprises nucleotide sequences including the following ribozyme oligonucleotides:

```
5'CCATCGATGCCGGACTGGTATCCCAGGGGG          (called "HVR1C1a" herein)   (SEQ ID No: 5)
```

-continued

| | | |
|---|---|---|
| 5'CCATCGATGCCGGACTGGTATCCCGAGGGAC | (called "5'HVR2Cla" herein) | (SEQ ID No: 6) |
| 5'CCATCGATGATCCAGCCTCCTCGCGGCGCCGGATGGGCA | (called "RZHDV1" herein) | (SEQ ID No: 7) |
| 5'GCTCTAGATCCATTCGCCATCCGAAGATGCCCATCCGGC | (called "RZHDV2" herein) | (SEQ ID No: 8) |
| 5'CCATCGATTTATGCCGAGAAGGTAACCAGAGAAACACAC | (called "RZHC1" herein) | (SEQ ID No: 9) |
| 5'GCTCTAGACCAGGTAATATACCACAACGTGTGTTTCTCT | (called "RZHC2" herein) | (SEQ ID No: 10) |

Ribozyme sequences are useful for obtaining translation, replication and encapsidation of the transcript. It is therefore desirable to cleave the transcript downstream of its t-RNA-like structure or poly A tail prior to translation, replication or encapsidation of the transcript.

The present invention also further extends to oligonucleotide primers for the above sequences, antisense sequences and nucleotide probes for the above sequences and homologues and analogues of said primers, antisense sequences and probes. Such primers and probes are useful in the identification, isolation and/or cloning of genes encoding insecticidally effective proteins or proteins required for viral activity, from HaSV or another virus (whether related or unrelated) carrying a similar gene or similar RNA sequence. They are also useful in screening for HaSV or other viruses in the field or in identifying HaSV or other viruses in insects, especially in order to identify related viruses capable of causing pathogenecity similar to HaSV.

Any pair of oligonucleotide primers derived from either RNA 1 or RNA 2 (SEQ ID Nos: 39 and 47) and located between ca 300 and 1500 bp apart can be used as primers. The following pairs of primer sequences exemplify particularly preferred embodiments of the present invention: Specifically for RNA 1 (SEQ ID No: 39):
1. HVR1B5' (SEQ ID No: 38) (described below) and the primer complementary to nucleotides 1192–1212 of FIG. 1.
2. The primer corresponding to nucleotides 4084 and 4100 of FIG. 13 and the primer HVR13p (SEQ ID No: 12) described below Specifically for RNA 2 (SEQ ID No: 47):
1. The primer corresponding to nucleotides 459 to 476 of FIG. 2 and the primer complementary to nucleotides 1653 to 1669 of FIG. 2 (this would include the central variable domain)
2. R2cdha5 and the primer complementary to nucleotides 1156 to 1172 of FIG. 2
3. The primer corresponding to nucleotides 1178 to 1194 and the primer complementary to nucleotides 2072 to 2091 (of FIG. 2).

Other combinations giving shorter fragments are also possible.

Further preferred primers include:

| | | |
|---|---|---|
| 5'GGGGGGAATTCATTTAGGTGACACTATAGTTCTGCCTCCCCGGAC | (called "HvR1SP5p" herein) | (SEQ ID No: 11) |
| 5'GGGGGGATCCTGGTATCCCAGGGGGC | (called "HvR13p" herein) | (SEQ ID No: 12) |
| 5'CCGGAAGCTTGTTTTTCTTTCTTTACCA | (called "Hr2cdna5" herein) | (SEQ ID No: 13) |
| 5'GGGGGATCCGATGGTATCCCGAGGGACGCTCAGCAGGTGGCATAGG | (called "HvR23p" herein) | (SEQ ID No: 14) |
| AAATAATTTTGTTACTTTAGAAGGAGATATACATATGAGCGAGCGAGCACAC | (called "HVPET65N" herein) | (SEQ ID No: 15) |
| AAATAATTTTGTTTAACCTTAAGAAGGAGATCTACATATGCTGGAGTGGCGTCAC | (called "HVPET63N" herein) | (SEQ ID No: 16) |
| GGAGATCTACATATGGGAGATGCTGGAGTG | (called "HVPET64N" herein) | (SEQ ID No: 17) |
| GTAGCGAACGTCGAGAA | (called "HVRNA2F3" herein) | (SEQ ID No: 18) |
| GGGGGATCCTCAGTTGTCAGTGGCGGGGTAG | (called "HVP65C" herein) | (SEQ ID No: 19) |
| GGGGATCCCTAATTGGCACGAGCGGCGC | (called "HVP6C2" herein) | (SEQ ID No: 20) |
| AATTACATATGGCGGCCGCCGTTTCTGCC | (called "HVP6MA" herein) | (SEQ ID No: 21) |
| AATTACATATGTTCGCGGCCGCCGTTTCT | (called "HVP6MF" herein) | (SEQ ID No: 22) |

The invention also relates to vectors encoding the nucleotide sequence described above and to host cells including the same. Preferably these vectors are capable of expression in animal, plant or bacterial cell or are capable of transferring the sequences of the present invention to the genome of other organisms such as plants. More preferably they are capable of expression in insect and crop plant cells.

In a preferred aspect the invention relates to the vectors pDHVR1, pDHVR1RZ, pDHVR2, pDHVR2RZ, p17V71, p17E71, pPH, pV71, p17V64, p17E64, pP64, pBacHVR1, pBacHVR1RZ, pBacHUR2, pBacHVR2RZ, pHSPR1, pHSPR1RZ, pHSPR2, pHSPR2RZ, pSR1(E3)A, pSR1(E3) B, pSR2A, pSR2B, pSX2P70, pSXR2P70, pSRP2B, pBHVR1B, pBHVR2B, pT7T2P64, pSR2P70, pT7T2P65, pT7T2P70, pT7T2-P71, pBSKSE3, pBSR15, pBSR25p, pSR25, phr236P70, phr235P65, pGemP63N, pGemP64N, pGemP65N, pP64N, pP65H, pTP6MA, pTP6MF, pTP17, pTP17delBB, pP656 or p70G as described hereinafter.

In a third aspect the invention relates to polypeptides or proteins encoded by HaSV and to homologues and analogues thereof This aspect of the invention also relates to derivatives and variants of the polypeptides and proteins of HaSV. Such derivatives and variants include substitutions and/or deletions of one or more amino acids, and amino and carboxy terminal fusions with other polypeptides or proteins. In a preferred aspect the invention relates to the proteins P7, P16, P17 (SEQ ID No: 48), P64, P70 (SEQ ID No: 52), P71 (SEQ ID No: 50), P1 la (SEQ ID No: 42), P11b (SEQ ID No: 44), P14 (SEQ ID No: 46) and P187 (SEQ ID No: 40) described herein and to homologues and analogues thereof, including fusion proteins particularly of P71 (SEQ ID No: 50) such as P70 (SEQ ID No: 52) described herein. In a most preferred aspect the invention relates to polypeptides or proteins from HaSV which have insecticidal activity themselves or provide target specificity for insecticidal agents. In particular the invention relates to polypeptides or fragments thereof with insect gut binding specificity, particularly to the variable domains thereof as herein described. In addition, homologues and analogues with said insecticidal activity of the polypeptides and proteins are also included within the scope of the invention. In addition the invention also relates to antibodies (such as monoclonal or polyclonal antibodies or chimeric antibodies including phage antibodies produced in bacteria) specific for said polypeptide and protein sequences. Such antibodies are useful in detecting HaSV and related viruses or the protein products thereof.

In a fourth aspect the invention provides an infectious, recombinant insect virus including a vector, an expressible nucleic acid sequence comprising all of, or a portion of the HaSV genome, including an insecticidally effective portion of the genome and optionally, material derived from another insect virus species or isolate(s).

Insect virus vectors suitable for the invention according to this aspect, include baculoviruses, entomopoxviruses and cytoplasmic polyhedrosis viruses. Most preferably, the insect virus vector is selected from the group comprising the baculovirus genera of nuclear polyhedrosis viruses (NPV's) and granulosis viruses (GV's). In this aspect of the invention the vector acts as a carrier for the HaSV genes encoding insecticidal activity. The recombinant insect virus vector may be grown by either established procedures Shieh, (1989), Vlak (in press) or any other suitable procedure and the virus disseminated as needed. The insect virus vectors may be those described in copending International application No. PCT/AU92/00413.

The nucleic acid sequence or sequences incorporated into the recombinant vector may be a cDNA, DNA or DNA sequence and may comprise the genome or portion thereof of a DNA or RNA of HaSV or another species. The term "material derived from another insect virus species or isolate" includes any nucleic acid sequence, or protein sequence or parts thereof which are useful in exerting an insecticidal effect when incorporated in the recombinant vector of the invention. Suitable nucleic acid sequences for incorporation into the recombinant vector include insecticidally effective agents such as a neurotoxin from the mite *Pyemotes tritici* (Tomalski, M. D. & Miller, L. K. Nature 352, 82–85 (1991) a toxin component of the venom of the North African scorpion *Androctonus australia* Maeda, S. et al. Virology 184-777–780 (1991) Stewart, L. M. D. et al., Nature 352, 85–88 (1991), Conotoxins from the venom of *Conus* spp. (Olivera B. M. et al., Science 249, 257–263 (1990); Woodward S. R. et al., EMBO J. 9, 1015–1020 (1990); Olivera B. M. et al., Eur. J. Biochem. 202, 589–595 (1991).

The exogenous nucleic acid sequence may be operably placed into the insect virus vector between a viral or cellular promoter and a polyadenylation signal. Upon infection of an insect cell, the vector virus will cause the production of either infectious virus genomic RNA or infectious encapsidated viral particles.

The promoters may be constitutively expressed or inducible. These include tissue specific promoters, temperature sensitive promoters or promoters which are activated when the insect feeds on a metabolite in the plant that it is desired to protect.

Recombinant insect virus vectors according to the present invention may include nucleic acid sequences comprising all or an infectious or insecticidally effective portion of genome the HaSV and optionally another insect virus species or isolate.

In a particularly preferred embodiment of the present invention there is provided assembled capsids comprising one or more of the capsid proteins of the present invention, or derivatives or variants thereof as contemplated or described herein. These assembled virus capsids are useful as vectors for insecticidal agents. As such the assembled viral capsids may be used to administer insecticidal agents such as various nucleotide sequences with insecticidal activity or various toxins to an insect. Nucleotide sequences in the form of RNA or DNA which can be used include those of the HaSV genome or other insect viruses. Toxins which can be used advantageously include those which are active intracellularly and may also include neurotoxins with an appropriate transportation mechanism to reach the insect neurones.

The efficacy or insecticidal activity of infectious genomic RNA or viral particles produced by insect cells infected with insect vectors according to this aspect of the invention, may be enhanced as described below. Moreover the virus vector itself may include within a non-essential region(s), one or more nucleic acid sequences encoding substances that are deleterious to insects such as the insecticidally effective agents described above. Alternatively an extra genome component may be added to the HaSV genome either by insertion into one of the HaSV genes or by adding it to the ends of the genome.

In a particularly preferred embodiment there is provided a recombinant baculovirus vector comprising HaSV or part thereof having insecticidal properties.

Other modifications which may be made to the infectious recombinant insect virus according to the fourth aspect include:

i) splitting the exogenous HaSV nucleic acid molecules comprising the genome and cloning the fragments into the insect vector so that they cannot rejoin. One component, preferably the virus RNA replicase, could be expressed from a separately-transcribed fragment, the transcripts of which would not be replicated by the replicase they encode. The remainder of the genome (having insecticidal activity or encoding the capsid protein or a separate toxin m-RNA) could be encoded by, for example, a second separately-transcribed fragment, the transcripts of which are capable of being amplified by the replicase. Consequently, whilst the transcripts from the second or other fragment would effect their insecticidal activity upon the infected insect cell, they would not be able to infect another insect cell, (even if encapsidated) because the replicase or replicase-encoding transcripts would be absent;

This modification would allow an inherent biological containment to be built into the insecticidal vectors, which, when used in conjunction with the use of non-persistent DNA virus vectors such as those described in the above mentioned copending application, would allow a new level of environmental safety greatly extending earlier approaches based on baculovirus vectors.

ii) Manipulation of encapsidation signals or sequences essential for replicase binding or production of sub-genomic mRNA's including expression of exogeneous insect control factors as RNAs dependent on the virus for replication. This involves determination of RNA sequences and signals important for replication and encapsidation of virus RNAs, such as by analysis of replication of deletion mutants carrying reporter genes in appropriate cells, followed by studies on the transmission of the reporter gene to larvae by feeding of virus. These deletion mutants can be used to carry genes for insect control factors/toxins to larvae after replacing the reporter gene by a suitable toxin gene such as shown in FIG. 12;

iii) using an insect promoter responsive to virus infection and, for example, placing copies of the viral replicase gene under the control of two promoters, one which is constitutive or expressed at early stages of vector infection, and the other being a cellular promoter turned on by the ensuing RNA viral infection. This system would then make more copies of the replicase mRNA available as the amount of its template increased. Such a promoter may be isolated using techniques analogous to enhancer trapping, that is, transforming insect cells with a suitable reporter gene and looking for induction of the reporter upon virus infection of a population of transformed cells.

In a fifth aspect the invention relates to a method of controlling insect attack in plants by genetically manipulating plants to express HaSV or parts thereof which can confer insecticidal activity optionally in combination with other insecticidally effective agents. Such plants are referred to as transgenic plants.

The term "express" should be understood as referring to the process of transcribing the genome or portion thereof into RNA or, alternatively, the process of transcribing the genome or portion thereof into RNA and then, in turn, translating the RNA into a protein or peptide.

In a sixth aspect the invention relates to the transgenic plants per se as described above. Transgenic plants according to the invention may be prepared for example by introducing a DNA construct including a cDNA or DNA fragment encoding all or a desired infectious portion of HaSV, into the genome of a plant. The cDNA or DNA fragment may, preferably, be operably placed between a plant promoter and a polyadenylation signal. Promoters may cause constitutive or inducible expression of the sequences under their control. Furthermore they may be specific to certain tissues, such as the leaves of a plant where insect attack occurs but not to other parts of the plant such as that used for food. The inducible promoters may be induced by stimuli such as disturbance of wind or insect movement on the plant's tissues, or may be specifically turned on by insect damage to plant tissues. Heat may also be a stimulus for promoter induction such as in spring where temperatures increase and likelihood of insect attack also increases. Other stimuli such as spraying by a chemical (for instances a harmless chemical) may induce the promoter.

The cDNA or DNA fragment may encode all or a desired infectious portion of the wild-type, recombinant or otherwise mutated HaSV. For example, deletion mutants could be used which lack segments of the viral genome which are non-essential for replication or perhaps pathogenicity.

The nucleotide sequences of the invention can be inserted into a plant genome by already established techniques, for example by an Agrobacterium transfer system or by electroporation.

Plants which may be used in this aspect of the invention include plants of both economic and scientific interest. Such plants may be those in general which need protection against the insect pests discussed herein and in particular include tomato, potato, corn, cotton, field pea and tobacco.

To enhance the efficacy of infectious genomic RNA or viral particles expressed by transgenic plants according to the invention, the DNA construct introduced into the plants' genome may be engineered to include one or more exogenous nucleic acid sequences encoding substances that are deleterious to insects. Such substances include, for example, *Bacillits thuringiensis* d-toxin, insect neurohormones, insecticidal compounds form wasp or scorpion venom or of heterologous origin, or factors designed to attack and kill infected cells in such a way so as to cause pathogenesis in the infected tissue (for example, a ribozyme targeted against an essential cellular function).

DNA constructs may also be provided which include;

i) mechanisms for regulating pathogen expression (for example, mechanisms which restrict the expression of ribozymes to the insect cells) by tying for example, expression to abundant virus replication, production of minus-strand RNA or sub-genomic mRNA's; and/or ii) mechanisms similar to, or analogous to, those described in copending International patent application number PCT/AU92/00413 so as to achieve a limited-spread system (such as control of replication).

Transgenic plants according to the present invention may also be capable of expressing all or an infectious or insecticidal portion of genomes from HaSV and one or more species or isolates of insect viruses.

In a seventh aspect of the invention HaSV, or insecticidally effective parts thereof, or the infectious recombinant virus vectors of the fourth aspect of the present invention may be applied directly to the plant to control insect attack. HaSV or the recombinant virus vectors may be produced either in whole or in part in either whole insects or in culture cells of insects or in bacteria or in yeast or in some other expression system. HaSV or the recombinant virus forms may be applied in a crude form, semi purified or purified form optionally in admixture with agriculturally acceptable carrier to the crop in need of protection. HaSV may also be applied as a facilitator of infection where existing insect populations already infected with another agent, such as one or more other viruses whereby HaSV is able to act synergistically to bring about an insecticidal effect. Alternatively HaSV and another agent such as one or more viruses may be applied together to plants to control insects feeding thereon.

A deposit of HaSV No. 18.4 was made on Aug. 5th 1992 at the Australian Government Analytical Laboratories. The deposit was given accession No. N92/35575.

EXAMPLE 1

Taxanomic, Physiochemical and Biochemical Characterisation of an Insect Virus: HaSV Materials and Methods A Animals and virus production. *H. Armigara* larvae were raised as described in Teakle R. E. and Jensen J. M. (1985) *Heliothis punctiger* in Singh P and Moore R. F. (eds) Handbook of Insect Rearing Vol. 2., Elsevier, Amsterdam pp 313–322. Larvae were infected for virus production by feeding five day old larvae on 10 mg pieces of diet to which 0.064 $OD_{260}$ units of HaSV had been applied. After 24 hours the larvae were then transferred to covered 12-well plates (BioScientific, Sydney, Australia) that contained sufficient diet and grown for eight days after which they were collected and frozen at −80° C. until further processed. Frozen larvae were weighed to 10 g, placed into 200 ml of 50 mM Tris buffer (pH 7.4), homogenized, and filtered through four layers of muslin. This homogenate was centrifuged in a Sorvall SS-34 rotor at 10,000×g for 30 minutes whereupon the supernatant was transferred to fresh tubes and recentrifuged in Beckman SW-28 rotor at 100K×g for 3 hours. The resultant band was collected and repelleted in 50 mM pH 7.2 Tris buffer in a Beckman SW-28 tube by centrifugation at 100K×g for 3 hours. The pelleted virus was resuspended overnight in 1 ml of buffer at 4° C. then layered onto a discontinuous CsCl gradient containing equal volumes of 60% and 30% CsCl (w/v) in a Beckman SW-41 tube and centrifuged at 12 h at 200×g. The resultant pellet was suspended in 100 ml of buffer and frozen for further use.

B Particle Characterization

Staining with acridine orange was as described in Mayor H. D. and Hill N. O. (1961) Virology 14: p 264. Buoyant density was estimated in CsCl gradients according to Scotti P. D., Longworth J. F., Plus N, Crozier G. and Reignanum C. (1981) Advances in Virus Research 26: 117–143.

C Immunological Procedure

Rabbit anti-sera to HaSV was produced by standard immunological procedures. Rabbit antisera to the *Nudaurelia* o virus in addition to the virus itself was provided by Don Hendry (Rhodes University, Grahamstown, South Africa). Rabbit antisera to the *Nudaurelia* b virus was supplied by the late Carl Reinganum (Plant Research Institute, Burnley, Vic, Australia). The immunological relationship to the *Nudaurelia* w virus was determined by the standard reciprocal double diffusion technique. Immunoblotting was performed according to Towbin H., Staeheln T. and Gordon J. (1979) PNAS. Antibodies monospecific for the major 65 kDa capsid protein were prepared by incubating polyclonal antisera with sections of nitrocellulose blotted with the 65 kDa protein. After extensive washing in Tris buffered saline, the bound antibodies were eluted in 50 mM citric buffer, pH 8.0 after a 5 minute incubation.

D Protein Characterization

Polyacrylamide gel electrophoresis in the presence of SDS followed the procedure of Laemmli U K 1970 Nature 227: 680–685 and was done with 12.5% gels unless otherwise noted with low and high molecular weight standards from BioRad. Staining was done with a colloidal preparation of Coomassie Blue G-250 (Gradipore Ltd, Pyrmont, New South Wales, Australia). Determination of the $M_r$ of the smallest protein was done with a 16% gel and standards of 3.4 kDa, 12.5 kDa and 21.5 kDa (Boehringer Mannheim). Glycosylation of the viral proteins was determined by a general glycan staining procedure with reagents supplied by Boehringer Mannheim; the positive control was fetuin. N-termini of proteins were sequenced using procedures described by Matsudairia (1989) Purification of Proteins and Peptides by SDS-PAGE in A Practical Guide to Protein and Peptide Purification for Microsequencing ed Matsudaira P. T. Academic Press, San Diego pp 52–72 on an Applied Biosystems 477A gas phase sequencer.

E Nucleic Acid Characterization

RNA was removed from capsids by twice vortexing a virus suspension with equal volumes of neutralized phenol then with phenol/chloroform (50:50). RNA was then precipitated from the aqueous phase in the presence of 300 mM sodium acetate and 2.5 volumes of ethanol. Digestions of the HaSV nucleic acid with RNAse A and DNAse I (Boehringer Mannheim) were done with pBSSK(−) phagemid ssDNA and dsDNA (Stratagene) and RNA controls (BRL). Denaturing agarose gel electrophoresis in the presence of formaldehyde was performed according to Sambrook et al (1989). The state of polyandenylation of the viral RNA was determined by two methods. The first method was to compare the binding of identical amounts (20 mg) of viral RNA and poly(A)-selected RNA from *Helicoveipa virescens* to a 1 ml slurry of 5 mg of oligo-d(T) cellulose (Pharmacia) in a binding buffer consisting of 20 mM Tris pH 7.8, 500 mM NaCl, 1 mM EDTA and 0.04% SDS. The second method was to observe specific priming of viral RNA and viral RNA polyadenylated with poly(A) polymerase (Pharmacia) with $d(T)_{16}$A/C/G primers in RNA sequencing reactions using reverse transcriptase (U.S. Biochemical) and a protocol provided by the supplier. The 5' cap structure of the genomic RNA and HaSV was determined by observing the ability of polynucleotide kinase to phosphorylate viral RNA with and without preincubation with tobacco acid pyrophosphatase and alkaline phosphatase (Promega) under conditions described by the supplier.

F In Vitro Translation of HaSV RNA

In vitro translation of HaSV RNA was performed with lysates of both rabbit reticulocytes and wheat germ (Promega) as directed by the supplier. Reactions were conducted in 10 ml volumes with 1.0 mg of RNA in the presence of five u Ci $^{35}$S-methionine. The labelled proteins were resolved on 10% and 14% SDS-PAGE gels as described above then visualised by autoradiography of the dried gels. The two viral RNAs were separated by a “freeze and squeeze” method after resolution on nondenaturing low-melting-point agarose gels in TAE (Sambrook, et al. 1989). Briefly, agarose slices containing the RNA were melted at 65° C. in a volume of TAE buffer equal to six times the agarose volume. The solution was allowed to gel on ice before freezing at −80° C. for 30 minutes. The frozen solution was thawed on ice then centrifuged at 14,500×g for 10 minutes after which the supernatant was withdrawn and precipitated by the addition of ethanol.

G Bioassay of Virus-Induced Pathogenisis

Known amounts of virus isolate, as shown in FIG. 3, were fed to larvae at the growth stages indicated by admixture to standard diet. At the time points shown, the larvae were weighed and the mean and SD calculated. Growth of infected larvae was compared to those of uninfected control populations from the same hatching batch in every experiment.

Results i) Characteristics and Taxonomy of HaSV

The virus particles are isometric and are approximately 36–38 nm in diameter. They are composed of two major capsid proteins, of 65 kDa and 6 kD is size. The virons contain two single-stranded (+) RNA species of 5.3 kb and 2.4 kb length. The virus bears a similarity in these respects to the *Nudaurelia* w virus, which has been tentatively regarded as a member of the Tetraviridae; these two viruses differ however, in the above respects from other viruses in this group and are likely to form a new virus family, sharing chiefly their capsid structure (T=4) with the Tetraviridae.

ii) Particle Characterization and Serology

The buoyant density of HaSV was calculated to be 1.296 g/ml in CsCl at pH 7.2. The $A_{260}/A_{280}$ ratio of HaSV viral particles was 1.22 indicating a nucleic acid content of approximately 7% (Gibbs and Harrison, (1976) Plant Virology: The Principles London: Edward Arnold. Reciprocal immuno-double diffusion comparisons between HaSV and the *Nudaurelia* w virus showed no serological relationship. The more sensitive technique of immunoblotting also showed a complete lack of any antigenic relationship. In addition, HaSV did not react with antisera to the *Nudaurelia* b virus in a immuno-diffusion test or when immunoblotted. However, no *Nudaurelia* b virus was available as a positive control in these latter two immunological experiments. When HaSV was stained with acridine orange then irradiated with 310 nm UV light, the particles fluoresced red which indicated a single stranded genome.

iii) Protein Characterization

Examination of the capsid proteins of HaSV with polyacrylamide gel electrophoresis in the presence of SDS showed variable results depending on the quantity of protein present. At low protein loadings, two. proteins in major abundance were evident that had $M_r$'s of 65,000 and 6,000 along with a protein in minor abundance with Mr of 72,000 (data not shown). When more protein was present on the gels, however, at least 12 more distinct bands with Mr's ranging between 15,000 and 62,000 became evident. Probing the resolved and blotted proteins with antibodies monospecific for the major 65 kDa capsid protein showed all but two of the proteins shared common antigens with the major 65 kDa protein. The major 6 kDa capsid protein and a minor band migrating at $M_r=16,000$ failed to react with both the monospecific antibodies and untreated antisera.

The capsid proteins were shown to be non-glycosylated as they failed to react with a hydrazine analog after oxidation with periodic acid. The N-terminus of the 65 kDa protein appeared to be blocked in some manner as two efforts to conduct an Edman degradation failed. After the second attempt, the sample was treated with n-chlorosuccinimide and shown to be in a quantity normally adequate for sequencing. The N-terminus of the 6 kDa protein, however, was not blocked as an unambiguous 16-residue sequence was readily obtained. The sequence of the N-terminus of the 6 kDa capsid protein and those of a cyanogen bromide cleaved fragment of the 65 kDa protein are as follows:

be labelled with polynucleotide kinase unless pretreated with tobacco acid pyrophosphatase and alkaline phosphatase.

v) In Vitro Translation

In vitro translation of the viral RNA yielded different results in the two translation systems used (data not shown). The 5.5 kb RNA translated very poorly in the reticulocyte system whereas it produced in the wheatgerm system more than 20 proteins ranging in size from $M_r=195,000$ to $M_r=12,000$. The 2.4 kb viral RNA strand yielded a major protein with an $M_r=24,000$ in both systems in addition to a minor protein at $M_r=70$ kDa. A time course of the translation reaction with the 5.5 kb RNA strand showed all labelled proteins were produced at similar rates indicating that the smaller products did not arise through processing of the larger ones. However when a time course experiment was done with translation of the smaller 2.4 kb RNA strand, the 24 kDa protein appeared before the 70 kDa protein.

vi) Presence of Another Form of HaSV

Frequently, during purification of HaSV virions, a minor band appeared in varying amounts on the CsCl gradient that had a buoyant density of 1.3 g/ml. On four occasions, when particles from this minor band were used to infect *H. armigera* larvae that were then processed as before for purification of HaSV virions, the HaSV band with a density of 1.296 g/ml was again recovered in vast excess to a varying minor amount of the more dense band. No virions of either type were recovered from uninfected control larvae. Proteins extracted from the more dense particles appeared identical to those from the less dense particles when examined by SDS-PAGE and immunoblotting with antibodies specific for the 65 kDa capsid protein of HaSV. Extraction

```
6 kDa protein:
PheAlaAlaAlaValSerAlaPheAlaAlaAsnMetLeuSerSerValLeuLysSer    (SEQ ID No: 23)

65 kDa protein:
ProThrLeuValAspGlnGlyPheTrpIleGlyGlyGlnTyrAlaLeuThrProThrSer (SEQ ID No: 24)
```

Detailed sequence analysis of the RNA genome carried out in Example 3 showed that RNA 1 (SEQ ID No: 39) encodes a protein of molecular weight 186,980 hereinafter referred to as P187 (SEQ ID No: 40) and RNA 2 (SEQ ID No: 47) encodes proteins with molecular weight 16, 522 (called P17 (SEQ ID No: 48)) and 70,670 (called P71 (SEQ ID No: 50)). P71 (SEQ ID No: 50) is processed into two proteins of molecular weight 63,378 (called P64) and 7,309 (called P7).

iv) Nucleic Acid Characterization

The extracted nucleic acid from HaSV was readily hydrolysed by RNAse A but not by DNAse I. Denaturing agarose gel electrophoresis of the extracted RNA genome of HaSV indicated two strands that migrated at 5.5 kb and 2.4 kb. The RNA strands were shown not to have extensive regions of polyadenylation as only 24% of the viral RNA bound to the oligo-d(T) cellulose matrix as opposed to 82% of poly(A)-selected RNA. Further evidence for the non-polyadenylation of the viral genome was provided by the observation that the oligo primer, $d(T)_{16}G$, gave a clear sequencing ladder using reverse transcriptase only after in vitro polyadenylation of the viral strands with poly(A)-polymerase.

The demonstration that the strands could be modified with poly(A)-polymerase also showed the lack of any 3' modification. The 5' termini of the viral strands were shown to be capped, most likely with $m^7G(5')ppp(5')G$, as they could not and examination of the RNA genome with denaturing agarose gel electrophoresis also showed the same 5.5 and 2.4 kb bands. When particles from the more dense band were examined by electron microscopy as before, they appeared to have a larger diameter 45 nm but otherwise highly similar to the 38 nm particles.

The molar ratio of the two RNA strands was determined by quantitative densitometry of fluorograms of the resolved strands. The ratio derived from an average of four measurements of various loadings on denaturing gels proved to be 1.7:1 (5.5 kb strand: 2.4 kb strand) which is somewhat lower than the expected ratio of 2.3:1 for equimolar amounts of each strand.

The genome of HaSV has major differences that make it distinct from those of the nodaviruses, the only other group of bipartite small RNA viruses pathogenic to animals. Although HaSV shares the characteristic of a bipartite genome with the only animal viruses having such a divided genome, the nodaviridae, it differs in virtually every other aspect from this group. Both segments of its genome are considerably larger than the corresponding nodaviral RNAs (Hendry D. A., (1991) Nodaviridae of Invertebrates. in (ed. E. Kurstak) Viruses of Invertebrates. Marcel Dekker, New York, pp. 227–276). However, the division of genetic labour is similar with the larger component carrying the replicase gene and the smaller one encoding the capsid proteins. Direct comparison of the sequences shows little homology between these viruses, at either RNA or protein level. The Nodaviruses, have the already mentioned unusual 3' blockage (probably a protein), whereas the HaSV RNAs terminate in a distinctive secondary structure resembling a tRNA.

vii) Bioassays of Virus Isolates on Larvae

The original constructs made to express the capsid proteins (precursor and processed forms) in E. coli for bioassay started at the first AUG (nts 284 to 286). Production of full-length, immuno-reactive protein from these was due to these clones being the 5C sequence version with the extra C residue. Bioassays of these proteins have been difficult due to problems with obtaining suitable Heliothis larvae for the tests.

Purified native HaSV was used to conduct bioassays in non-noctuid insect species. The native HaSV was orally administered, the larvae scored for symptoms of infection and growth was measured. Dot blotting for HaSV RNA was also conducted. Based on these experiments native HaSV does not appear to infect the following larvae.

| Species | Order | Family |
|---|---|---|
| *Galleria mellonella* | Lepidoptera | Pyradidae |
| *Tineola bissellia* | Lepidoptera | Tineidae |
| *Epiphyas postvittana* | Lepidoptera | Tortricidae |
| *Lucilia cuprina* | Diptera | Calliphoridae |
| *Dacus tyronii* | Diptera | Tephritidae |
| *Antitrogus parvulus* | Coleoptera | Scarabaediae |
| *Lepidiota picticollis* | Coleoptera | Scarabaediae |
| *Sericesthis germinata* | Coleoptera | Scarabaediae |

The above experiment conducted with the larvae of *Spodoptera exigita* and *S. litura* showed that native HaSV infects these species but not to the same degree as seen in *Heliothis arniigera.*

EXAMPLE 2

Other Virus Isolates

Materials and Methods

A Virus Isolation

Apparently infected (viz diseased) larvae of Helicoverpa sp were collected in February 1993 at Mullaley (NSW), Narrabri (NSW) and Toowoomba (QLD) (Australia). Referring to FIG. 10 the samples in wells 2A–2D were from parasitised *H. armigera* larvae collected from sorghum at Mullaley; the sample in 6C was collected from sunflower at Toowoomba; the sample in 7D was collected from cotton at the Narrabri Research Station. The latter two larvae may have been either *H. armigera* or *H. punctigera,* which are both easily infected with HaSV.

B Virus RNA Extraction

Larvae collected were ground up and RNA extracted. RNA extraction and purification were as per Example 1.

C Dot-Blot Northern Hybridization

Extracts of viral RNA was analysed by Northern dot-blot hybridisation using a probe made from cloned HaSV sequences derived from 3'-terminal 1000 units of RNA 1 and RNA 2 by random priming in a Boehringer Mannheim kit according to the supplier's instructions were employed. RNA extracts were transferred to Zeta-Probe (BioRad) for probing. Hybridization under high stringency washing conditions were as specified by BioRad. Hybridizations were carried out in the following solution:

1 mM EDTA, 500 mM $HaH_2PO_4$, pH 7.2, 7% SDS, at 65° C. in a rotating Hybaid hybridization chamber. After completion of hybridization and removal of the solution containing the probe, the filters were washed twice in 1 mM EDTA, 40 mM $HaH_2PO_4$ pH 7.2, 5% SDS, at 65° C. (1 h each), followed by 2 washes in 1 mM EDTA, 40 mM $HaH_2PO_4$, pH 7.2 1% SDS, at 65° C. (1 h each), before autoradiography.

Results

Referring to FIG. 10, samples 9A, 9B, 10A, 10B and 10C contain HaSV infected positive control lab-raised larvae; 9C–H contain healthy (HaSV-free) negative control lab-raised larvae; All other wells (beginning 1–8) contain extract from field-collected larvae. Numbers 2A–D, 6C and 7D gave positive signals indicating that these isolates are either the same as HaSV or derivatives or variants thereof. Election microscopy employing (−) staining confirmed that the samples which gave positive signals contained abundant icosohedral virus particles of approximately 36mm in size.

The presence of HaSV in larvae which had tested positive in the Northern hybridization dot-blot was confirmed by Western blotting of crude extracts from such infected larvae, using the polyclonal antibody to the HaSV capsid protein. For routine screening of such extracts in order to identify further isolates of HaSV or to confirm the presence of the virus, use of a monoclonal antibody or its equivalent is preferable, in order to achieve (i) higher sensitivity of detection and (ii) greater specificity of detection.

EXAMPLE 3

Identification, Isolation and Characterisation of Insect Virus Genes

Materials and Methods

A Animals and Virus Production

*H. armigera* larvae were raised as described in Example 1.

B Protein Characterization

Was conducted as described in Example 1.

C Nucleic Acid Characterization

Was conducted as in Example 1.

D Fractionation of Virus RNA

The two viral RNAs were separated by a "freeze and squeeze" method after resolution on nondenaturing low melting point agarose gels in TAE (Sambrook, et al, 1989). Briefly, agarose slices containing the RNA were melted at 65° C. in a volume of TAE buffer equal to six times the agarose volume. The solution was allowed to gel on ice before freezing it at −80° C. for 30 minutes. The frozen solution was thawed on ice then centrifuged at 14,500 g for 10 minutes after which the supernatent was withdrawn and precipitated by the addition of ethanol.

E In Vitro Translation of HaSV RNA

Was as in Example 1.

F cDNA Synthesis and Cloning of Virus Genome

The virus RNAs were reverse transcribed into cDNA using the Superscript RTase (a modified form of the Moloney murine leukaemia virus (MMLV) RTase, produced by Life Technologies Inc). Oligo(dT) was used as a primer on RNA which had been polyadenylated iii vitro. After size selection of DNA fragments over 1 kbp in length, the cDNA was then blunt-end ligated using T4 DNA ligase (Boehringer Mannheim or Promega, under conditions described by the suppliers) into vector pBSSK(−) (Stratagene) which had been cut with EcoRV and dephosphorylated with calf intestinal alkaline phosphatase (Boehringer Mannheim). *E. coli* strain JM109 or JPA101 were electroporated with the ligation mixture and white colonies selected on colour-indicator plates Sambrook et al, 1989.

For some clones of RNA2 (SEQ ID No: 47), cDNA was synthesised using the RTase of AMV (Promega) and a specific primer complementary to nucleotide sequence 2285–2301 of RNA 2 (SEQ ID No: 47). The same buffer and conditions were used for the Superscript RTase (above). The AMV RTase was found not to make cDNA form a primer annealing to the terminal 18 nucleotide sequence (see below), nor to be able to reach the 5'-end of the RNA with the primer here described.

G Sequencing of DNA and RNA

The cDNA clones were separated as single-stranded or double-stranded DNA, using the deaza-dGTP and deaza-dITP nucleotide analogues (Pharmacia) in the deaza T7 sequencing kit as recommended by this. supplier. Synthetic oligonucleotides were used as primers. The 5' terminal sequences of the two RNAs were determined using reverse transcriptase to sequence the RNA template directly, from specific oligonucleotide primers located about 200 nucleotides downstream from the termini. Such RNA sequencing was performed using the reverse transcriptase sequencing kit from Promega, under the conditions described by the manufacturer.

The sequence of the 20 or so nucleotides at the 5' terminus of each RNA was checked using direct RNase digestion of 5'-labelled RNA under conditions designed to confer sequence-specificity. Direct RNA sequence using RNases was performed with the RNase sequencing kit from US Biochemicals, following the protocols provided by the manufacturer. This also confirmed that the sequence of the most abundant RNA is consistent with that of the RNA analysed using the specific primer and RTase.

All transcription of plasmids linearized as described were performed as recommended by the suppliers of SP6 RNA polymerase, in the presence of IImM cap analogue, 0.2 mM GTP, and 0.5 mM of the other NTPs.

H Subcloning and Expression

PCR Amplification

The polymerase chain reaction (PCR) was used to obtain sequences covering virus genes in a form suitable for cloning into expression vectors. The reaction was performed with Taq DNA polymerase (Promega) as described by the supplier, in a rapid cycling thermal sequencer manufactured by Corbett Research (Sydney, Australia). A typical reaction involved 1 cycle of 1 min at 90° C., 25 cycles of 95° C. (10 sec), 50° C. (20 sec), 72° C. (1.5 min), followed by one cycle of 72° C. for 5 min. Templates were generally cDNA or cDNA clones derived from HaSV RNAs, made as described below. Primers were as described below for the relevant constructs.

Upon termination of the PCR reaction, the product's ends were made blunt by treatment with E. coli DNA polymerase I (Klenow fragment) at ambient temperature for 15 minutes. After heating at 65° C. for 10 minutes, the reaction was cooled on ice and the reaction mix made 1 mM in ATP. The product then 5'-phosphorylated using 5 units of T4 polynucleotide kinase at 37° C. for 30 minutes. After heating at 65° C. for 10 minutes, the product was run on a 1% low-melting agarose gel and purified as described for RNA in section E above.

ligations: Vectors and restriction fragments cut with the enzymes described were run on 1% low-melting-point agarose gels and excised as slices. These slices were then melted at 65° C. for 5 minutes, before cooling to 37° C. Fragment and vectors were then ligated in 10 ul total volume at 14° C. overnight using T4DNA ligase (BRL, Boehringer Mannheim or Promega), in the buffers supplied by the manufacturers.

expression: Expression plasmids containing viral genes (e.g. for the capsid protein) were transformed into E. coli strain BL21 (DE3) or HMS174 (DE3) (supplied by Novagen). After growth as specified by the supplier, protein expression was induced by the addition of isopropyl b-D-thiogalactopyranoside (IPTG), at 0.4 nM to the growing culture for a period of 3 h. Expressed proteins were analysed by SDS-polyacrylamide gel electrophoresis of bacterial extracts (Laemmli, 1970).

Results i) Mapping cDNA Clones of HaSV

The template for cDNA synthesis was virus RNA which had been polyadenylated in vitro. Oligo(dT) was used as a primer for the Superscript reverse transcriptase (RTase; a modified form of the Moloney murine leukaemia virus (MMLV) RTase, produced by Life Technologies Inc). The cDNA was cloned into vector pBSSK(−) as described earlier. The larger clones were selected for further analysis by restriction mapping and Northern hybridization. All the probes tested hybridized either to RNA 1 or to RNA 2, suggesting that there are no regions of extensive sequence homology between the two RNA's. Furthermore, screening of a number of other clones excluded the theoretical possibility that either RNA band may actually contain more than one species.

ii) RNA 1 (SEQ ID No: 39) Clones

Three large RNA 1 (SEQ ID No: 39) clones (B11U, B11O and B35) obtained for the first round of clones were further analysed by restriction mapping and shown to form an overlap spanning over 3 kbp (this was later confirmed by sequencing). The second round of cloning then yielded E3 of 5.3 kbp, representing 99.7% of RNA 1 (SEQ ID No: 39). A complete restriction map of clone E3 showed it to align with that previously determined for three overlapping clones. On the basis of this alignment, the 5' end of the insert in B11U was placed about 300 nucleotides downstream from the 5' end of the RNA.

Once clones covering a contiguous block had been identified, the orientation 3 relative to the RNA was determined.

iii) RNA 2 (SEQ ID No: 47) Clones

Three significant cDNA clones were isolated for RNA 2 (SEQ ID No: 47) (FIG. 2). One, hr 236, contains about 88% of RNA 2 (SEQ ID No: 47) (2470 bp total length), and runs from the 3' end to 240 bp from the 5' end. The other clones, hr247 and hr 249 are 3' coterminal subgenomic fragments of 1520 bp and 760 bp, respectively. Orientation of clone hr236 was determined by strand specific hybridization. While a much stronger signal was seen with a probe for one orientation, the probe specific for the other orientation also yielded a signal, indicating that there are extensive regions of reverse complementarity within the positive strand sequence. Such sequences are likely to form extensive short and long-range secondary structure.

The clones contain the 3' sequence of HaSV RNA 2 (SEQ ID No: 47) as they all have the same 3' sequence adjacent to the poly (A) stretch added in vitro before cDNA priming. The remaining 5' sequence of RNA 2 has been obtained by direct RNA sequencing using two reverse transcriptases as described above.

iv) Sequencing of Virus Genome

The clones mapped in section (i) were selected for further analysis by sequencing.

The cDNA clones were completely sequenced as single-stranded DNA in both orientations, using the deaza-dGTP and deaza-dITP nucleotide analogues (Pharmacia) and synthetic oligonucleotides as primers.

v) Sequence of Genome Component 1 (SEQ ID No: 39) (see FIG. 1)

The 5310 nucleotides of RNA 1 (SEQ ID No: 39) encode a protein of molecular weight 187,000 which is regarded as the RNA-dependent RNA polymerase (replicase) in view of its amino acid sequence similarity in certain limited regions to replicases of other RNA viruses. The apparent molecular weight of this protein upon ill vitro translation of virus RNA and SDS-PAGE is 195,000.

Sequence analysis of RNA 1 (SEQ ID No: 39) was concentrated on clone E3 which extends from the 3' end of RNA 1 to 18 nucleotides form the 5' end (FIG. 1). The complete sequence has been confirmed by sequencing in both directions. An ORF of 1750 amino acids and spanning virtually the complete RNA (5310 nucleotides in length) has been detected. This ORF begins with the first AUG on the sequence at position 34 and terminates at nucleotide 5290 and is thought to encode the RNA-dependent RNA polymerase (replicase)(referred to as P187 (SEQ ID No: 40) in FIG. 1) required for virus replication, since it contains the Gly-Asp-Asp conserved triplet and surrounding sequences identified in these enzymes, which are usually large (over 100 kDa), in addition to further homology with the polymerase encoded by tobacco mosaic virus and other plus-stranded RNA viruses.

Referring to FIG. 1 the sequence is presented as the upper strand of the cDNA sequence. This strand is therefore in the same sense as the viral (positive-sense) RNA. The sequence of the protein encoded by the major open reading frame, encoding the putative RNA-dependent RNA replicase, is shown, as are those of the small open reading frames at the 3' end, corresponding to the proteins P11a (SEQ ID No: 42), P11b (SEQ ID No: 44) and P14 (SEQ ID No: 46).

Clone E3 was inserted downstream of the SP6 promoter for in vitro transcription. As mentioned above, the transcript of this clone can be translated in the wheat germ system to yield the 195 kDa protein observed upon translation of fractionated RNA 1 (SEQ ID No: 39) from the virus. The latter yields more lower molecular weight products, presumably due to being contaminated with nicked and degraded RNA. The products derived from the in vitro transcript can therefore be regarded as defining the coding capacity of the complete RNA 1 (SEQ ID No: 39) of HaSV.

vi) Sequence of Genome Component 2 (see FIG. 2)

The 2470 nucleotides encode a protein of molecular weight 71,000 which contains the peptide sequences corresponding to those determined from the two virus capsid proteins. This protein is therefore the precursor of these capsid proteins. The protein is a major product of in vitro translation of this RNA obtained either from virus particles or by in vitro transcription of a full-length cDNA clone; in addition, another major translation product of apparent molecular weight 24,000 is obtained. This protein is derived from a molecular weight 17,000 reading frame overlappling the slab of the capsid protein gene.

Clones hr236 and hr247 were completely sequenced as the first step in RNA 2 sequencing. These sequences were then extensively compared to that obtained by direct RNA sequencing using AMV reverse transcriptase.

Comparison of the cloned sequence with that by direct RNA sequencing showed both clones lacked 50 nucleotide present in the RNA (at around nucleotide 1500). The sequence of this stretch was obtained by direct RNA sequencing using the AMV RTase. The MMLV "Superscript" RTase, which was used to make all the cDNA clones, was found to simply by-pass this region in sequencing reactions. These 50 nucleotides contain a very stable GC-rich hairpin flanked by a 6 bp direct repeat, and the MMLV RTase skips from the first repeat to the second.

The sequence of RNA 2 (SEQ ID No: 47) was then completed using plasmids pSR2A and pSR2P70 constructed as described below. The plasmids contain a segment of cDNA derived for the AMV RTase, as well as the sequence corresponding to the 5' 240 nucleotides of RNA 2 (SEQ ID No: 47) which are not present on phr236 (FIG. 2). The sequence of RNA in FIG. 2 is presented as the upper strand of the cDNA sequence. This strand is therefore in the same sense as the viral (positive-sense) RNA. The sequences of the proteins encoded by the major open reading frames, encoding the capsid protein precursor P71 (SEQ ID No: 50), and P17 (SEQ ID No: 48).

The sequence of RNA 2 (SEQ ID No: 47) encodes a major ORF running from a methionine initiation codon at nucleotides 366 to 368 to a termination codon at nucleotides 2307 to 2309. This protein encoded by this ORF has a theoretical molecular weight of 71,000 (SEQ ID No: 50). This initiation codon is in a good context (AGGatgG), suggesting that it will be well recognized by scanning ribosomes. The size of the product is close to that of the residual putative precursor protein identified in purified virus, and to the size of the in vitro translation product obtained from RNA 2 (SEQ ID No: 47).

The approach adopted to identify the gene encoding the capsid protein was to obtain amino acid sequence information from the two abundant capsid proteins and then locate these on the protein encoded by the sequence of the virus RNA's. CNBr cleaved products of the capsid protein were therefore sequenced. These fragments gave a clear and unambiguous sequence shown in Example 1. These sequences determined were then located on the large ORF of RNA 2 (SEQ ID No: 47). (FIG. 2)

In the case of the small capsid protein, the clear and unambiguous sequence, obtained is located near the carboxy terminus of the major ORF on RNA 2 (SEQ ID No: 47). Starting at the point corresponding to the amino-terminal residue of the sequence determined for the 6 kDa protein, and continuing to the carboxy-terminus of the complete reading frame, the protein encoded by the sequence 7.2 kDa and has a hydrophobic N-terminal region and an arginine rich (basic) C-terminal region. It is an extremely basic protein with a pI of 12.6.

The two abundant capsid proteins are derived from a single precursor, which is processed at a specific site. This is presumably immediately amino-terminal to the sequence FAAAVS . . . (SEQ ID No: 25)

RNA 2 (SEQ ID No: 47) appears to be a bicistronic mRNA (see FIGS. 2 and 5). The first methionine codon is encoded on the sequence of RNA at nucleotides 283 to 285. This ATG is in a poor context (TTTatgA), making it a weaker initiation codon. It initiates a reading frame of 157 amino acids, encoding a protein of molecular weight 17,000 (SEQ ID No: 48). (The second AUG [nts 366 to 368] initiates the 71 kDa (SEQ ID No: 50) precursor of the capsid protein). Since the first AUG is in a poor context, abundant expression of the capsid precursor would be expected. In fact, in vitro translation of a full length RNA 2 (SEQ ID No: 47) transcribed from a reconstructed cDNA clone yields two major protein products of relative mobility 71,000 (SEQ ID No: 50) and 24,000, similar to those already observed upon translation of viral RNA 2 (SEQ ID No: 47). The protein of Mr 24,000 appears to correspond to the 157 amino acid protein, despite the significant anomaly in apparent size. The 24,000 Mr product was also observed upon translation of an in vitro transcript covering only nucleotides 220 to 1200 of RNA 2 (SEQ ID No: 47). This region contains no open reading frame other than those already mentioned and cannot encode a protein longer than 157 amino acids.

The protein of Mr 24,000 seen upon in vitro translation appears to correspond to P17 (SEQ ID No: 48), with the anomaly in apparent size probably being due to the high content of proline (P), glutamate (E), serine (S) and threonine (T). These amino acids cause the protein run more slowly on a gel thereby giving it an apparent size of Mr 24,000.

The Mr 24,000 protein (hereinafter referred to as P17 (SEQ ID No: 48)) may have a function in modifying or manipulating the growth characteristics or cell cycle of HaSV-infected cells. Although a protein of 16 kDa (identified in Example 1) is found in small amounts in the capsid, it does not react with antiserum against the virus particles this is unlikely to correspond to P17 (SEQ ID No: 48), since a preparation of the latter proteins migrates with a molecular weight of 24,000 on SDS gels.

Sequence analysis of the Region from nucleotide 500 to 600 of RNA 2 (SEQ ID No: 47) showed that it has the sequence shown in FIG. 2, as do the plasmids pSR2A, pSR2P70, pSR2B and pSXR2P70. However, plasmids pT7T72P65 and pT7T2P70 have an extra C residue at nucleotide 570. The RNA sequence from which they are derived from is shown in FIG. 2 (the "5C" version). In this sequence the first ATG (nucleotides 283 to 285) is in the same reading frame as most of the capsid protein gene. The resultant fusion protein is called "P70" (SEQ ID No: 52) and its carboxyterminal-truncated version (a variant of the native P64) is "P65". In view of these clones it was considered important to resolve whether any virus RNA carrying the extra C residue was present in the viral RNA population first isolated for investigation.

Direct sequencing of the virus RNA using reverse transcriptase confirmed that the 4C version lacking the extra residue was the abundant form of the RNA. In order to exclude the possibility of a small amount of the RNA having the extra residue, a sensitive PCR assay was designed. This showed that the extra C residue was not present on any RNA in the viral population, and had been introduced into some clones as a PCR artefact. These clones were however retained and used in bacterial expression experiments (below) because of the high level expression obtained of the P65 and P70 (SEQ ID No: 52) fusion proteins.

vii) Comparison with the Sequence of the *Nudaurelia* w Capsid Gene

The sequence of most of the RNA2 of the *Nudaurelia* w virus has recently been published by Agrawal D. K. and Johnson J. E. (Virology 190 806–814, 1992). From the published sequence it has been determined that this sequence shows 63% homology to that of HaSV RNA2 (SEQ ID No: 47) at the nucleotide level and 66% at the overall amino acid level. A detailed comparison of the capsid proteins of these two viruses shows the amino-terminal 45 residues to be variable, the next 220 residues to be highly conserved, the next 180 residues to be variable and the c-terminal 200 residues covering the small protein P7 to be highly conserved. A more detailed comparison is discussed below.

The published report did not find a complete reading frame corresponding to the 157 amino acid protein (P17 (SEQ ID No: 48)) gene reported above. The AUG is however present, as is a reading frame—starting upstream of the start of the capsid gene—showing considerable amino acid homology to P17 (SEQ ID No: 48) of HaSV. In vitro translation of purified *Nudaurelia* w virus RNA 2 and a re-examination of the nucleotide sequencing data for this RNA may help to resolve the question of whether the *Nudaurelia* w virus also encodes a protein homologous to the HaSV P17.

More interestingly, antisera against these two viruses, which are similar at a nucleotide sequence level, do not show any cross-reactivity.

viii) Construction of Full-Length Clones

RNA 1 (SEQ ID No: 39)

cDNA clone E3, described above contains all but the 5'–18 nucleotides of RNA 1 (SEQ ID No: 39) and included the complete ORF present on the sequence. The first full-length clone of RNA 1 (SEQ ID No: 39) is therefore based on E3. The 4.9 kbp XbaI-ClaI fragment from clone E3 was recloned into pBSKS(−) (Stratagene) cut with XbaI and ClaI, giving pBSKSE3.

The full-length clone of RNA 1 (SEQ ID No: 39) was completed using PCR. The primer defining the 5' end of the RNA carried an EcoRI site, the promoter for the SP6 RNA polymerase and a sequence corresponding to the 5' 17 nucleotides of RNA 1, as shown in FIG. 1. The sequence of this primer was:

HvR1SP5p:

5'-GGGGGGAATTCATTTAGGTGACACTATAGTTCTGCCTCCCCGGAC (SEQ ID No: 11) (The G which initiates transcription is underlined)

Using an oligonucleotide complementary to nucleotides 1192–1212, a PCR product of 1240 bp was efficiently made. The template was cDNA synthesised using the MMLV RTase and the same oligonucleotide complementary to nucleotides 1192–1212 was the primer. Upon termination of the PCR reaction, the product's ends were made blunt and then 5'-phophorylated as described below. The purified PCR fragment was then cleaved with restriction endonuclease XbaI and the 450 bp subfragment corresponding to the 5' end of RNA 1 (SEQ ID No: 39) cloned into the plasmid pBSSK(−)(Stragene) cut with EcoRV and XbaI, to give pBSR15.

To assemble the full-length of RNA 1 (SEQ ID No: 39), pBSKSE3 (above) was cut with XbaI and ScaI giving fragments of 1.2 kbp and 6.8 kbp. pBSR15 was cut with the same enzymes, giving fragments of 2 and 1.8 kbp. Ligation of the 6.8 kbp fragment for pBSKSE3 and the 1.8 kbp fragment for mpBSR15 yielded pSR1(E3)A. Upon linearization at ClaI and in vitro transcription with the SP6 RNA polymerase, and RNA corresponding to RNA 1 (SEQ ID No: 39), and terminating in a poly(A) stretch of about 50 nucleotides, is obtained.

Since the natural RNA 1 (SEQ ID No: 39) does not have a poly (A) tail, an alternative plasmid was constructed which carries a BamHII restriction site immediately downstream of the 3'end of RNA 1 (SEQ ID No: 39). Again this terminal fragment was made using PCR as above. The sequence of the primer was as follows: HvR13p: 5'-GGGGGGATCCTGGTATCCCAGGGGCGC (SEQ ID No: 12) (the nucleotide complementary to that which was determined as the 3' one, based on its adjacency to the poly(A) stretch, is underlined; RNA terminating at the BamHI site will have the sequence GCGCCCCCUGGGAUACCaggauc (SEQ ID No: 26)).

The template was clone E3 and an oligonucleotide corresponding to nucleotides 4084–4100 was the other primer. The 1220 bp product was blunt-ended, kinased and gel-purified as described above, before cleavage with HindIII. The resulting 420 bp subfragment corresponding to the 3' end of RNA 1 (SEQ ID No: 39) cloned into plasmid pSR1(E3)A cut with ClaI, end-filled with Klenow and then cut with HindIII. The resulting plasmid is pSR1(E3)B. Upon linearization at BamHI and in vitro transcription with the SP6 RNA polymerase, and RNA corresponding to RNA 1 (SEQ ID No: 39), and terminating as described immediately above is obtained.

ix) RNA 2 (SEQ ID No: 47)

In constructing the full-length cDNA clone to enable in vitro transcription of this RNA hr236 described above was used as a basis. Two separate PCR products, one corresponding to the 5' portion of RNA 2 (SEQ ID No: 47), which is missing from this clone altogether, and another covering the region where clone hr236 lacks the hairpin-forming sequence described above, were required.

The primer defining the 5' end of the RNA carried a HindIII site and a sequence corresponding to the 5' 18 nucleotides of RNA 2 (SEQ ID No: 47), as shown in FIG. 2. The sequence of this primer was:

Hr2cdna5: 5'-CCGGAAGCTTGTTTTTCTTTCTTTACCA (SEQ ID No: 13)

(The nucleotide underlined corresponds to that identified as the first nucleotide of RNA 2. (SEQ ID No: 47))

Using an oligonucleotide complementary to nucleotides 1653–1669, a PCR product of 1.67 kbp was made. The template was cDNA synthesised using the MMLV RTase and an oligonucleotide complementary to the 18 nucleotides at the 3' end of RNA 2 (SEQ ID No: 47) as the primer. Upon termination of the PCR reaction, the product was blunt-ended, kinased and gel-purified as described above, before cleavage with PstI. The resulting 1.3 kbp subfragment corresponding to the 5' half of RNA 2 (SEQ ID No: 47) was cloned into plasmid pBSSK(-) (Stragene) cut with EcoRV and PstI, giving plasmid pBSR25p. In order to place this subfragment corresponding to the 5' half of RNA 2 (SEQ ID No: 47) downstream of the SP6 promoter for in vitro transcription, a 1.3 kbp HindIII-BamHI fragment was excised from pBSR25p and ligated into HindIII-BamHI cut pGEM-1 (Promega), giving plasmid pSR25.

The second PCR product, covering the region where clone hr236 lacks the hairpin-forming sequence described above, was synthesised using as primers oligonucleotides corresponding to nucleotide sequence 873 to 889 of RNA 2 (SEQ ID No: 47) and to the complement of nucleotide sequence 2290–2309. Upon termination of the PCR reaction, the product was blunt-ended, kinased and gel-purified as described above, before cleavage with AatII. The resulting 1.1 kbp subfragment covering the required region was cloned into plasmid phr236 cut with HindIII, end-filled with Klenow and cut with AatII, giving plasmid phr236P70.

The two segments were joined covering the first 230 nucleotides of RNA 2 (SEQ ID No: 47) together. Plasmid phr236P70 was cut at the SacI site in the vector adjacent to the 5' end of the insert and this made blunt-ended using Klenow in the absence of dNTPs. After heat-inactivation of the Klenow, the plasmid was cut with EcoRI, yielding fragments of 4.5 kbp and 380 bp. Plasmid pSR25 was cut with NheI, blunt-ended by end-filling with Klenow and cut with EcoRI, yielding fragments of 2.8 kbp, 900 bp and 750 bp. The 4.5 kbp fragment of phr236P70 and the 900 bp fragment of pSR25 were ligated to give pSR2P70. This clone covers all of RNA 2 (SEQ ID No: 47) except for the 3' 169 nucleotides.

To complete the full-length clone of RNA 2 (SEQ ID No: 47), it was necessary to insert a fragment covering the 3' end. As with RNA 1 (SEQ ID No: 39), two versions were made. One, called pSR2A, used the 3' end as present in phr236, together with the poly(A) tail present in this version. The other pSR2B, used a PCR fragment carrying a BamHI site immediately downstream of the 3' nucleotide, as in pSR1 (E3)B above. To construct pSR2A, a 350 bp NotI-ClaI fragment was excised from phr236 and cloned into pSR2P70 cut with the same endonucleases. Linearization at the unique ClaI site allows in vitro transcription of the complete RNA 2 (SEQ ID No: 47) and a poly(A) tail of about 50 nucleotides in length.

To make pSR2B, an appropriate PCR product was made using as primers an oligonucleotide corresponding to nucleotide sequence 1178 to 1194 and to the 3' terminal 18 nucleotides of RNA 2 (SEQ ID No: 47). The latter primer carried a BamHII site attached, giving it the sequence:

H v R 2 3 p :

5'-GGGGGATCCGATGGTATCCCGAGGGACGC (SEQ ID No: 14)

The template used was a plasmid phr236. Upon termination of the PCR reaction, the product was blunt-ended, kinased and gel-purified as described above, before cleavage with NotI. The resulting 400 bp subfragment covering the required region was cloned into plasmid pSR2P70 cut with ClaI, end-filled with Klenow and cut with NotI, giving plasmid pSRP2B. Linearization at the unique BamHI site allows in vitro transcription of the complete RNA 2 (SEQ ID No: 47), terminating with the sequence ACCaggatc.

x) Construction of pSXR2P70

This plasmid was made to determine where p24 starts. A 2.1 kbp XhoI-BamHI fragment was cut from clone pSR2P70 and ligated into the vector pGEM-1 (Promega) which had been cut with SalI and BamHI. In vitro transcription of the resulting plasmid after linearization at the unique BamHI site yielded an RNA covering about 70 nucleotides upstream of the first ATG at nucleotides 283 to 286, plus a short sequence derived from the vector.

In vitro translation of the RNA from pSXR2P70 yielded both proteins (P70 (SEQ ID No: 52) +P24).

xi) Description of Virus-Induced Pathology

The virus induces a rapid anti-feeding effect in Helicoverpa larvae as determined by experiments with larvae the results of which are shown in FIG. 3. FIG. 3 shows: A. neonate larvae (less than 24 h old) were fed the designated concentrations of isolated virus (in particles per ml [of diet] added to solid diet). They were weighed on following days and the mean of a statistically significant number (24) of larvae shown. Where necessary, mortality was recorded for the higher concentrations. The vertical axis shows the fold-increase in weight from the hatching weight of 0.1 mg per larvae. This scale therefore also corresponds to weight in units of 0.1 mg (ie 300 is equivalent to 30 mg). B. As for A, but the larvae were 5 days old at the start of the virus feeding. The vertical scale is in mg weight.

No weight gain at all was detectable with neonates which had been fed the doses of virus over $10^8$ particles per ml (virus added to diet). In addition, 100% mortality was evident after four days at the highest doses. Virus doses as low as $10^6$ particles per ml (virus added to diet) still cause significant stunting. The five day old larvae showed a cessation of feeding after 48 hours and significant stunting at 4 dpi, but no mortality at comparable virus doses (FIG. 3). Neonates are therefore very sensitive indeed to this virus. Virus particles accumulate specifically in the midgut. This potent anti-feeding effect may be due to the capsid protein or another protein encoded by the virus, or to the effect of any combination of such proteins.

xii) Expression of Virtus-Encoded Proteins in Bacteria

The Vectors

The expression system used initially was derived from the pET-11 system (Novagen). Trimmed down versions of pET- 11b and c were constructed and used to compare expression of the capsid proteins. However, due to difficulties experienced with this system substantial modification of the original vectors was carried out in order to achieve much higher yields. These results are described in xiii-b) below.

The initial trimmed-down vectors discussed above were made as follows: pGEM-2 (Promega) which carries T7 promoter adjacent to a poly-linker sequence, but has no sequences corresponding to the lac operon, was cut at the unique XbaI (34) and ScaI (1651) sites, giving fragments of 1.61 and 1.25 kbp. The plasmids pET-11b and c were cut with the same enzymes, giving fragments of 4.77 and 0.91 kbp. The 1.61 kbp fragment of pGEM-2, carrying the c-terminal portion of the ampicillin-resistance gene, the origin of replication and the T7 promoter, was then ligated to the 0.91 kbp fragment of the pET vector, which carries a sequence covering the Shine-Dalgarno sequence, the ATG (in a NdeI site), the terminator for the T7 polymerase and the N-terminal portion of the ampicillin-resistance gene. The resulting plasmids of approximately 2.53 kbp, called pT7T2-b and c, therefore carry a complete T7 transcription unit, which may be used as an expression system in a manner similar to the original pET-11 plasmids, but are repressor-neutral within the cell; they neither titrate away repressor by carrying a binding site, nor do they carry the gene producing the repressor. They were found to grow very well in *E. coli* strains JM109 and BL21 (DE3), and to be very efficient expression vectors. The repressor present in the cells was found to be sufficient to keep the genomic T7 polymerase gene uninduced and therefore the foreign gene unexpressed in the absence of IPTG.

xiii-a) Construction of Plasmids for Expression of Capsid Proteins

In this section, all proteins expressed from segments of HaSV RNA 2 (SEQ ID No: 47) are referred to by the size of their gene, as defined in FIG. 4 and in section vi) of this example. The following plasmids were constructed by PCR, using the abovementioned full-length clone of RNA 2 (SEQ ID No: 47), plasmid pSR2A as the template, except where mentioned otherwise.

Groups of plasmids expressed protein starting at each of the first three methionine initiation codons found on the sequence of HaSV RNA 2 (SEQ ID No: 47). For those proteins initiating at the first methionine initiation codon found on the sequence of HaSV RNA 2 (SEQ ID No: 47) (which initiates the P17 (SEQ ID No: 48) gene; oligonucleotide primer HVPET65N (SEQ ID No: 15)), an extra group of plasmids was made by PCR using as a template the version of the RNA 2 sequence carrying an extra C residue inserted at residue 570 (SEQ ID No: 51) (as depicted in FIG. 2). Expression constructs initiating at the third methionine initiation codon found on the sequence of HaSV RNA 2 (which is located within the P17 gene; oligonucleotide primer HVPET63N (SEQ ID No: 16)) were made by PCR using as a template only the version of the RNA 2 sequence carrying an extra C residue inserted at residue 570 (SEQ ID No: 51). For these latter expression constructs, as well as those designed to initiate expression from the second methionine initiation codon found on the sequence of HaSV RNA 2 (SEQ ID No: 47) (which initiates the P71 gene; oligonucleotide primer HVPET64N (SEQ ID No: 17)), two versions were constructed.

One version terminated at a point corresponding to the c-terminus of the processed (P64) form of the capsid protein and was made using oligonucleotide primer HVP65C (SEQ ID No: 19). The other version terminated at a point corresponding to the c-terminus of the precursor (P71 (SEQ ID No: 50)) form of the capsid protein and was made using oligonucleotide primer HVP6C2 (SEQ ID No: 20).

The sequence encoding P64 (or the precursor, P71 (SEQ ID No: 50)) was synthesised in two segments using PCR. The amino-terminal half of the gene was obtained using as primers oligonucleotides incorporating one of the three ATG possible initiation codons for the ORF, in addition to an oligonucleotide with the sequence TCAGCAGGTGGCAT-AGG (SEQ ID No: 27); complementary to nucleotides 1653 to 1669 of the sequence shown in FIG. 2. The forward primers were as follows:

HVPET65N:
AAATAATTTTGTTTACTTTAGAAG-GAGATATACATATGAGCGAGCGAGCAC AC (SEQ ID No: 15)
(the underlined sequence corresponds to nucleotides 283 to 296 of the sequence shown in FIG. 2)

HVPET63N
AAATAATTTTGTTTAACCTTAAGAAG-GAGATCTACATATGCTGGAGTGGCG TCAC (SEQ ID No: 16)
(the underlined sequence corresponds to nucleotides 373 to 390 of the sequence shown in FIG. 2; the AflII (CTTAAG) and BglII (AGATCT) sites introduced into the sequence by single nucleotide changes (shown in italics) in the oligonucleotide are shown in bold).

HVPET64N
GGAGATCTACATATGGGAGATGCTGGAGTG (SEQ ID No: 17)
(the underlined sequence corresponds to nucleotides 366 to 383 of the sequence shown in FIG. 2; the BglII site introduced into the sequence by a single nucleotide change in the oligonucleotide is shown in bold).

The PCR products obtained from each combination of one of these primers with the abovementioned one were treated with the Klenow fragment of *E. coli* DNA polymerase, and then with T4 polynucleotide kinase in the presence of 1 mM ATP, before purification by agarose gel electrophoresis as described above. Each product was then cleaved with AatII to yield fragments of 0.95 and 0.4 kbp, and each resulting fragment of about 0.95 kbp cloned intro vector pGEM-2 (Promega) cut with HincII and AatII, giving plasmids pGEMP63N (in which the insert commenced with oligonucleotide HVPET63N (SEQ ID No: 16)), pGEMP64N (in which the insert commenced with oligonucleotide HVPET64N (SEQ ID No: 17)) and pGemP65N (in which the insert commenced with oligonucleotide HYPET65N (SEQ ID No; 15)). The fragment covering portion of the HaSV capsid gene was then excised with enzymes AatII and XbaI.

Two versions of plasmid pGemP65N were made, using different templates as described above. pGemP65N was derived from the sequence of the viral RNA, as in plasmid pSF2A; plasmid pGemP65Nc was derived from the sequence carrying an extra C residue, as shown in FIG. 2 (see "5C version").

In parallel, the carboxy-terminal halves of the major capsid protein variant, whether terminating as for P64 or for P71 (SEQ ID No: 50), were also produced using PCR. An oligonucleotide primer, HVRNA2F3, with the sequence GTAGCGAACGTCGAGAA (SEQ ID No: 18) (corresponding to nucleotides 873 to 889 of the sequence shown in FIG. 2) was used in conjunction with each of the two primers following:

HVP65C
GGGGGATCCTCAGTTGTCAGTGGCGGGGTAG (SEQ ID No: 19) (the underlined sequence is complementary to nucleotides 2072 to 2091 of the sequence shown in FIG. 2).

HVP6C2
GGGGATCCCTAATTGGCACGAGCGGCGC (SEQ ID No: 20)
(the underlined sequence is complementary to nucleotides 2290 to 2309 of the sequence shown in FIG. 2).

The PCR products obtained from each combination of one of these primers with the above mentioned one (HvRNA2F3 (SEQ ID No: 18)) were treated with the Klenow fragment of E coli DNA polymerase, and then with T4 polynucleotide kinase in the presence of 1 mM ATP, before purification by agarose gel electrophoresis as described above. Each product was then cleaved with AatII to yield fragments of 0.9 kbp (in the case of HVP65C (SEQ ID No: 19)) or 1.1 kbp (in the case of HVP6C2 (SEQ ID No: 20)) and 0.4 kbp, and each resulting fragment of about 0.9 or 1.1 kbp cloned into plasmid phr236 cut with HindlIl, treated with Klenow and AatII, giving plasmids phr236P65C and phr236P70 (which has already been described above), respectively. The fragment covering the c-terminus of the capsid protein gene was then excised with enzymes AatII and BamHI.

To assemble plasmids for expression in suitable strains of E. coli, the excised XbaI-AatII fragments of 0.95 kbp covering the amino-terminal half of the gene and the excised AatII-BamHl fragments of 0.9 or 1.1 kbp covering the carboxy-terminal half of the gene were simultaneously ligated into the vector pT7T2 cut with XbaI and BamHI. Initial transformation was of E. coli strain JM109. Recombinant plasmids carrying the correct insert were then transformed into strain BL21(DE3) for expression as described above.

The plasmid obtained by ligating the aminoterminal fragment commencing with oligonucleotide primer HVPET63N (SEQ ID No: 16) to the c-terminal fragment ending at oligonucleotide primer HVP65C (SEQ ID No: 19) in the epxression vector pT7T2b was called pP65G.

In the case of plasmid pP64N, containing an insert from HVPET64N (SEQ ID No: 17) to HVP65C (SEQ ID No: 19), the fragment covering the amino-terminal half of the oligonucleotide was excised by BglII and ScaI from the plasmid pGemP64N and the fragment covering the remainder of the gene was excised with ScaI and EcoRI from plasmid pT7T2-P65. These two fragments were then ligated simultaneously into pP65G which had been cut with BglII sand EcoRI.

The resulting construct carrying the complete P71 (SEQ ID No: 50) precursor gene was called pT7T2-P71 and that carrying the P64 form of the gen was called pT7T2-P64. In the case of plasmids derived from pGemP65N and pGemnP65Nc, carrying inserts commencing as defined by primer HVPET65N, the expression plasmid derived from pGemP65N which is based on PCR products made using as the template the sequence of the viral RNA, as in plasmid pSR2A, was called pTP17; a truncated form of this plasmid, which expresses P17 (SEQ ID No: 48), Was made by cutting at the unique BglII and BamHI sites, removing the intervening fragment (which corresponds to the c-terminal part of the insert) and religating the compatible cohesive ends, to give pTP17delBB. The expression plasmids derived from plasmid pGemP65Nc (which was derived from the sequence carrying an extra C residue, were called pT7T2-P65 (carrying an insert terminating at the primer HVP65C (SEQ ID No: 19)) and pT7T2-P70 (carrying an insert terminating at the primer HVP6C2 (SEQ ID No: 20)).

Expression of P6

Two forms of this protein, which arises through processing of the large capsid protein variant precursor P70 (SEQ ID No: 52) and therefore lacks its own initiation codon, were made. One form (protein MA) replaced the phenylalanine at the start of this protein with methionine, giving it the amino-terminal sequence MAA . . . ; the other carries an additional methionine residue, giving it the amino-terminal sequence MFAA . . . The oligonucleotides used for PCR-amplified products covering the p6 coding sequence carried a NdeI site (bold) at the ATG codon, for direct ligation into the pET-11 vectors. The primers used were:

```
                                          (SEQ ID No: 21)
HVP6MA:  AATTACATATGGCGGCCGCCGTTTCTGCC (SEQ ID No: 22)
HVP6MF:  AATTACATATGTTCGCGGCCGCCGTTTCT
```

Each of these primers was used in conjunction with primer HVP6C2 (SEQ ID No: 20) to generate a PCR product of 0.2 kbp. These products were blunt-end ligated into vector pBSSK(−) which had been cut with EcoRV and dephosphorylated. The insert corresponding to the p6 gene was excised with NdeI and BamHI (using the BamHI site in the primer HVP6C2 (SEQ ID No: 20)) and ligated into the expression vector pET-1Ib, which had been cut with the same enzymes. For expression at higher levels, the insert was transferred to PT7T2 as a XbaI-BamHI fragment, yielding plasmids pTP6MA and pTP6MF.

IPTG induction of bacteria containing plasmids pTP6MA or pTP6MF were used produce p6 for bioassay.

xiii-b) Expression of Viral Genes in E. coli and Bioassay in Larvae

Expression of P64

IPTG induction of bacteria containing plasmid pT7T2-P65, which contains an insert running from the location of primer HVPET65N (SEQ ID No: 15) to that of primer HVP65C (SEQ ID No: 19), yielded a protein of molecular weight 68 000. This was 3 000 molecular weight greater than the size of the authentic coat protein, as expected. Expression of pP65G, which contains an insert running from HVPET63N (SEQ ID No: 16) to HVP65C (SEQ ID No: 19), yielded a protein of 65 000 molecular weight.

The authentic capsid protein (P64) was expressed poorly from plasmid pT7T2-P64. Recloning this insert as a NdeI-BamHI fragment back into the other form of the vector (PT7T2b) did not alter this.

Expression of P70

IPTG induction of bacteria containing plasmid pT7T2-P70, which contains an insert running from the location of primer HVPET65N (SEQ ID No: 15) to that of primer HVP6C2 (SEQ ID No: 20), yielded a protein of molecular weight 73 000. This was 3 000 molecular weight larger than the size of the precursor of the coat protein, as expected.

The authentic capsid protein precursor (P71 (SEQ ID No: 50)) was expressed poorly from plasmid pT7T2-P71. Recloning this insert as a Ndel-BamHI fragment back into the other form of the vector (pT7T2b) did not alter this.

Due to the observation mentioned in vi) above, plasmids designed to express all forms of the capsid proteins from several possible ATG's at the start of the open reading frame were constructed.

It was found that both authentic P64 and P71 (SEQ ID No: 50) were expressed poorly in bacteria. In contrast, P17 (SEQ ID No: 48) and the forms of the capsid protein commencing at the P17 ATG were expressed very well. The extra C residue present in the latter two constructs resulted in a fusion protein being made from these expression plasmid. The sequence of the fusion proteins can be derived from FIG. 2 by including an extra C at position 570. The fusion caused the first 67 residues of the HaSV capsid protein to be replaced by the first 95 residues of P17 (SEQ ID No: 48).

Good expression of the large capsid precursor and protein was achieved, but the size of these proteins were above 3 kDa larger than the authentic forms. Notwithstanding this the expression products of the vectors containing the 5C variant of RNA 2 (SEQ ID No: 51) are still useful because the resulting product, a P70 (SEQ ID No: 52) variant, is only modified at the NH2 terminus. Since this terminus is thought to be embedded in the capsid structure and therefore not to participate in the initial interaction with the larval midgut cell, the variant is still useful.

In order to produce constructs which ensure that the expressed proteins possessed the native amino terminus, new plasmids carrying the correct sequence were then cloned into the expression vector (pT7T2). It was found these plasmids to express proteins of the correct size.

The P6 has not yet been to expressed from the new constructs. No evidence has been found for processing of P70 to yield the mature proteins in bacteria, nor upon in vitro translation of synthetic full-length RNA 2 (SEQ ID No: 47).

The P17 (SEQ ID No: 48) gene has also been cloned into the same vectors for expression and bio-assay. This protein accumulates well in bacteria upon induction, and electron microscopy analysis has shown it form spectacular honeycomb-like structures under the bacterial cell wall, completely surrounding the cell interior (results not shown). The properties of this protein including its amino acid composition and ability to form tube-like structures when expressed in bacteria suggest that it may be an homolog of a gap junction protein. The latter is involved in forming the channels linking the cytoplasms of adjacent epithelial cells in the insect gut. P17 could then play a role in enlarging or forming these channels, thereby enabling cell-to-cell movement of the virus in the insect gut, analogous to the movement or spreading proteins encoded by plant RNA viruses.

In order to ensure that the expressed proteins carried the native amino terminus the correct sequence has also been cloned into the expression vector (pT7T2). The vector had been very slightly modified to that described above to introduce two novel restriction sited (for AflIII and BgIII) flanking the Shine-Dalgarno sequence. The resulting constructs have been found to be poor producers of the capsid proteins. The complete coding regions (which have been completely checked by re-sequencing) have therefore been recloned into the more satisfactory vectors. Results using these constructs suggest that the amino-terminus of the capsid protein presents inherent difficulties in expression. These difficulties may be imposed by either the nucleotide sequence encoding the amino terminus, or the actual amino acid sequence itself. To discriminate between these possibilities, two types of mutants were made in the sequence encoding the amino terminal 5 residues of the HaSV capsid protein. These amino-terminal mutants are as follows:

EXAMPLE 4

Expression in Baculovirus Vectors and Bioassay on Larvae

Materials and Methods

A(i) Cloninig of HaSV Capsid Protein Gene

The capsid protein gene was amplified by PCR using the following primers:

5' primers:

HV17V71:                                           (SEQ ID No: 34)
5'GGGGGATCCCGCGGATTT<u>ATG</u>AGCGAG

HV17E71:                                           (SEQ ID No: 35)
5'GGGGGATCCCGCGGAGAC<u>ATG</u>AGCGAGCACAC

HVP71:                                             (SEQ ID No: 36)
5'GGGGGATCCAGCGAC<u>ATG</u>AGAGATGCTGGAGTGG

HVV71:                                             (SEQ ID No: 37)
5'GGGGGATCCAGCGAC<u>ATG</u>AGAGATGCTGGAGTGG

The ATG triplets initiating P17 (SEQ ID No: 48) (in HV17V71 (SEQ ID No: 34) and HV17E71 (SEQ ID No: 35)) or P71 (SEQ ID No: 50) (in HVP71 and HVV71) are underlined)

3' Primers

Primers HVP65C (SEQ ID No: 19) and HVP6C2 (SEQ ID No: 20), described in Example 3. Results section Xiiia, were used. These constructs were made using one of the four 5' primers and HVP6C2 (SEQ ID No: 20). Plasmids constructed from PCR products made using one of the four 5'-primers and HVP65C (SEQ ID No: 19) are called 17V64 (made using 5' primer 17E71 (SEQ ID No: 35)), P64 (made using 5' primer P71 (SEQ ID No: 36)) and V64 (made using 5' primer V71 (SEQ ID No: 37)). These plasmids allow expression of P64.

A(ii) Cloning a Full Length cDNA of HaSV RNA 1 (SEQ ID No: 39)

For expression of an RNA transcript corresponding to full length HaSV RNA 1 (SEQ ID No: 39), in insect cells by baculovirus infection or plasmid transfection, PCR was used to generate a fragment of cDNA linking the 5' end of RNA 1 (SEQ ID No: 39) to a Bam HI site.

The primers were:

HVR1B5'

5' GGGGGATCCGTTCTGCCTCCCCGGAC (SEQ ID No: 38)

(where the underlined nucleotide represents the start of natural RNA 1 (SEQ ID No: 39)), and an oligonucleotide complementary to nucleotides 1192=1212 of RNA 1 (SEQ ID No: 39).

The template was plasmid pSR1(E3)B described in Example 3 above.

```
HVP71GLY
CCCATATG GGC GAT GCC GGC GTC GCG TCA CAG    (SEQ ID No: 28)
         Met Gly Asp Ala Gly Val Ala Ser GLn (SEQ ID No: 29)

HVP71SER:
CCCATATG AGC GAG GCC GGC GTC GCG TCA CAG    (SEQ ID No: 30)
         Met Ser Glu Ala Gly Val Ala Ser Gln (SEQ ID No: 31)

Native HaSV seq:
   ATG GGA GAT GCT GGA GTG GCG TCA CAG       (SEQ ID No: 32)
   Met Gly Asp Ala Gly Val Ala Ser Gln       (SEQ ID No: 33)
```

A segment of the 1240 bp PCR fragment corresponding to the 5' 320 nucleotides of RNA 1 (SEQ ID No: 39) was excised with Bam HI and ASC II and cloned into the Bam HI site of pBSSK(−)[Stratagene] together with the 5 kbp ASCII-Bam HI fragment of pSRl(E3)B, giving plasmid pBHVR1B, which carries the complete cDNA to HaSV RNA 1 (SEQ ID No: 39), flanked by Bam HI sites.

A(iii) Cloning a Full Length CDNA of HaSV RNA 2 (SEQ ID No: 47)

For expression of an RNA transcript corresponding to full length RNA 2 (SEQ ID No: 47) in insect cells by baculovirus infection or plasmid transfection, plasmid pB+NR2B was made by inserting a fragment carrying Hind III and Bam HI sites from the multiple cloning site of vector pBSSK(−) [Stratagene] into plasmid pSR2B described above. The resulting plasmid, called pBHVR2B, carried the cDNA corresponding to full length HaSV RNA 2 (SEQ ID No: 47), flanked by Bam HI sites.

A(iv) Baculovirus Transfer Plasmids

Bam HI fragments of 5.3 and 2.5 kbp corresponding to HaSV RNA's 1 and 2 (SEQ ID Nos: 39 and 47) respectively, were excised from pBHVR1B and pBHVR2B respectively and inserted into the baculovirus transfer vectors described below, which had been linearised with Bam HI.

B. Baculovirus Expression of Proteins

Baculovirus transfer vectors and engineered AcMNPV virus were transfected into *Spodoptera frugiperda* (SF9) cells as described by the supplier (Clontech) and as described in the following references:

Vlak, J. M. & Kens, R. J. A. (1990) in "Viral Vaccines", Wiley-Liss Inc., NY, pp. 92–128;

Kitts, P. A. et al (1990) Nucleic Acids Research 18: 5667–5672; Kitts, P. A. and Possee, R. P. (in preparation); Possee, R. D. (1986) Virus Research, 5: 43–59.

C. Western Blotting

As in Example 1

D. Oligonucleotides

The following Ribozyme Oligonucleotides were produced according to standard methods.

```
HVR1Cla                                      (SEQ ID No: 5)
5'CCATCGATGCCGGACTGGTATCCCAGGGGG

5'HVR2Cla                                    (SEQ ID No: 6)
5'CCATCGATGCCGGACTGGTATCCCGAGGGAC

RZHDV1                                       (SEQ ID No: 7)
5'CCATCGATGATCCAGCCTCCTCGCGGCGCCGGATGGGCA

RZHDV2                                       (SEQ ID No: 8)
5'GCTCTAGATCCATTCGCCATCCGAAGATGCCCATCCGC

RZHC1                                        (SEQ ID No: 9)
5'CCATCGATTTATGCCGAGAAGGTAACCAGAGAAACACAC

RZHC2                                        (SEQ ID No: 10)
5'GCTCTAGACCAGGTAATATACCACAACGTGTGTTTCTCT
```

Results

A series of recombinant baculoviruses has been constructed, based on the pVL941 transfer vector (PharMingen) or pBakPak8 (Clontech) and the AcMNPV. These are designed to express the correct forms of the precursor and processed HaSV capsid proteins (P64 and P71 (SEQ ID No: 50)) as well as the smaller capsid protein P6, and P17 (SEQ ID No: 48). In all systems where replicatable RNA encoding the nucleotide sequences of the present invention are to be used, such as eukaryotic systems, in order to get efficient replication, translation or encapsidation of the RNA it is necessary to excise structures downstream of the t-RNA like structure such as the 3' extension or poly A tail on the RNA. In order to carry out such an excision, ribozymes or other suitable mechanisms may be employed. This self cleavage activity of the ribozyme containing transcript should proceed at such a rate that most of the transcript is transported into the cytoplasm of the cell before the regeneration of a replicatable 3' end occurs. Such ribozyme systems are more fully explained in Examples 7 and 9. In the results presented here highly efficient production of P64 and P71 (SEQ ID No: 50) has been achieved. Electron microscopy and density gradient analysis have confirmed that empty particles ("capsoids") are being produced in infected cells that efficiently express the P71 precursor gene. P17 (SEQ ID No: 48) placed in the context of the *H. virescens* juvenile hormone esterase (JHE) gene (Hanzlik T. N., et al, J. Biol. Chem. 264, 12419–25 (1989)) is produced, but not in large amounts. The latter construct results in a reduction of expression of the capsid protein from the same recombinant, presumably due to a reduction in the number of ribosomes reaching the AUG for the capsid gene.

SF9 cells infected with recombinant baculovirus have been shown to contain large amounts of icosahedral virus particles by electron microscopy (data not shown). These particles contained no RNA, and were empty inside. This observation shows that signals on the viral RNA required for encapsidation of RNA must be located in either the 5' 270 nucleotides or the 3' 170 nucleotides, or both, since these sequences were missing from the RNA transcripts made using recombinant baculovirus. Expression of HaSV proteins was confirmed by Western blotting of total protein extracts from infected insect cells.

In addition, the pAcUW31 vector (Clontech), which carries two promoters, is being used to simultaneously express p6 and p64 as separate proteins. In order to bioassay the capsid protein produced in baculovirus infected cells, it is first necessary to purify it from the baculovirus expression vector. Preliminary attempts have made use of density gradients, based on the observation that empty virus particles ("assembled capsids") are in fact produced in infected cells.

Figure 13:
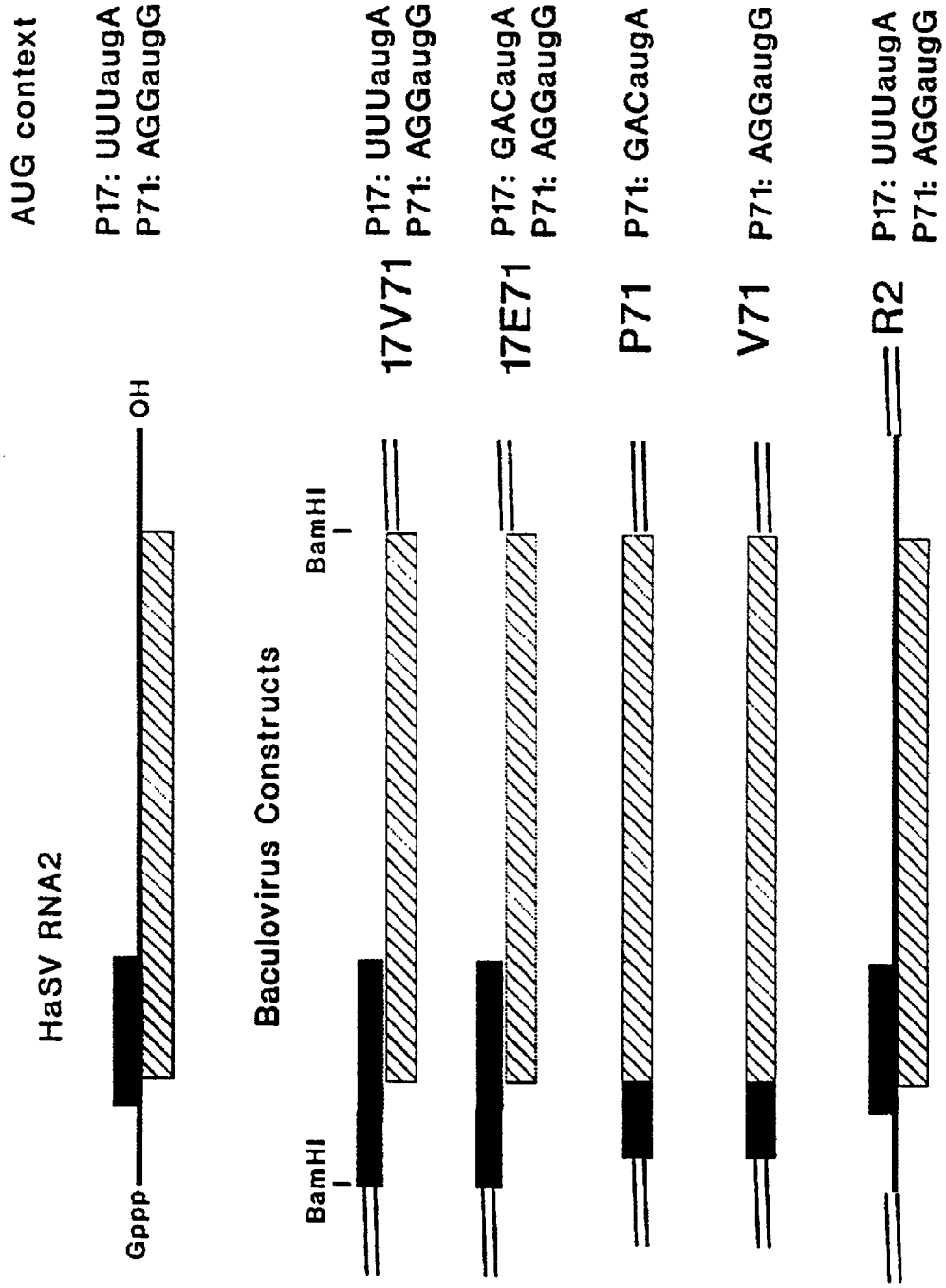
FIG. 13 Maps of the expression constructs in baculovirus vectors.
Figure 14E:
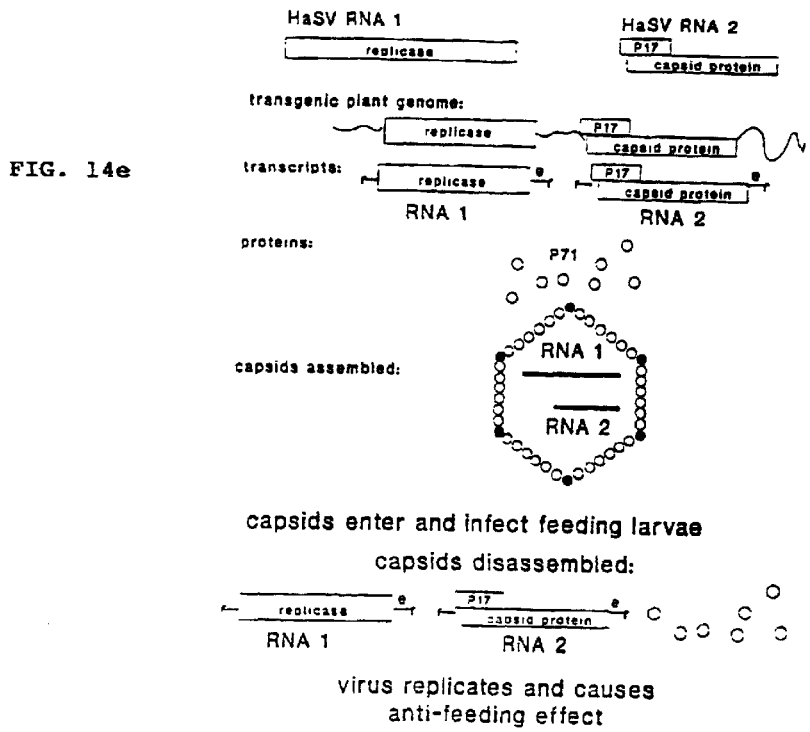
Figure 14F:
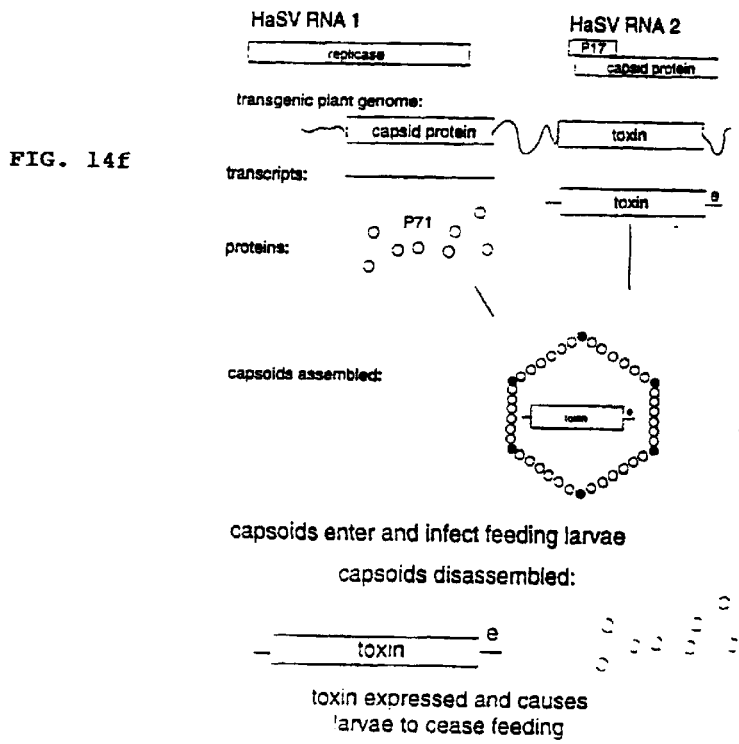
Figure 15:
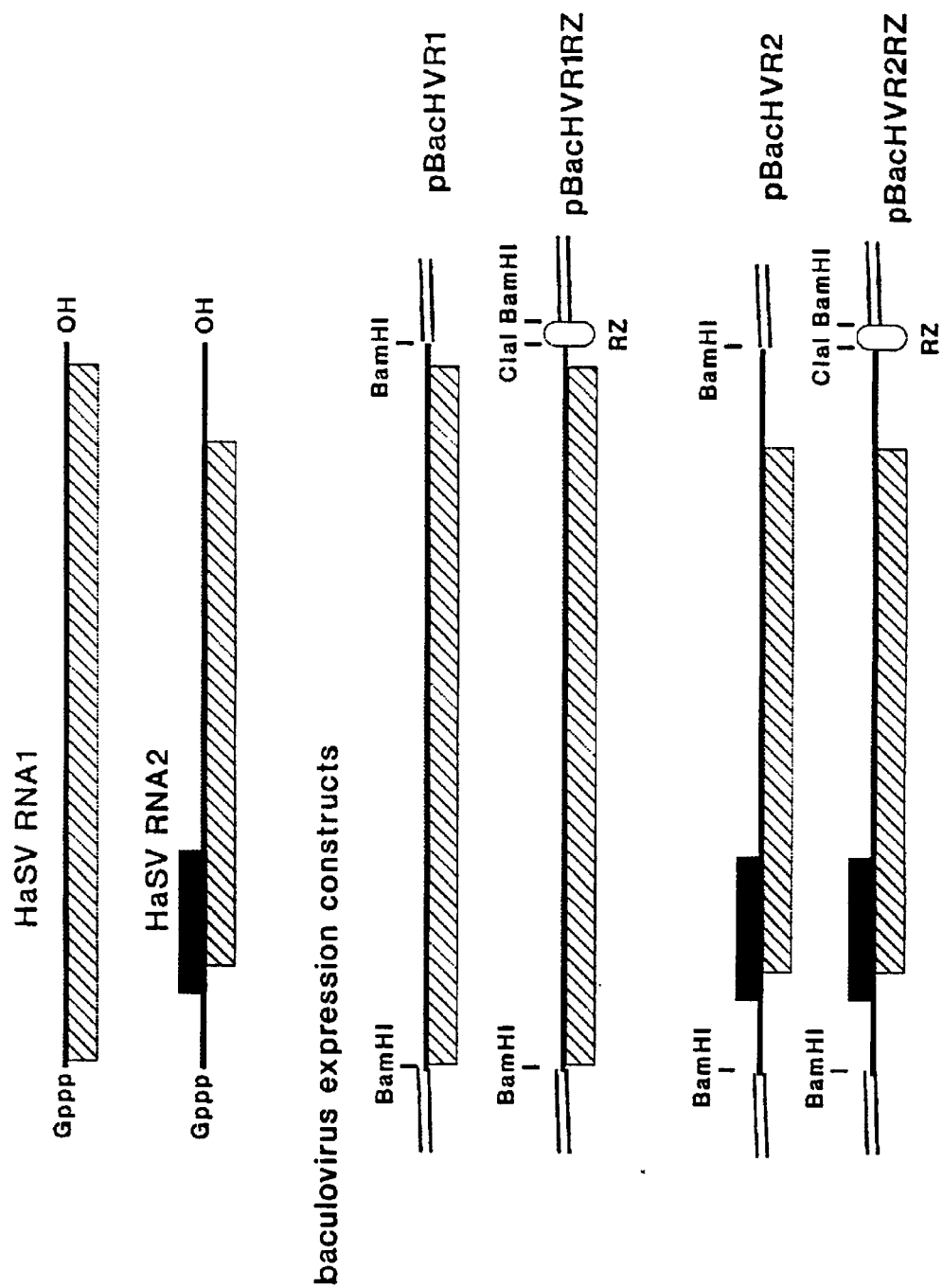
FIG. 15 Expression of RNAs 1 and 2 (SEQ ID Nos. 39 & 47) from baculovirus vectors. The full-length cDNA clone of HaSV RNA 1 or 2 (SEQ ID Nos. 39 & 47) was inserted as a BamHI fragment into the baculoexpression vectors. PCR was used to add BamHI sites immediately adjacent to the 5' and 3' termini of the RNA 1 sequence; sequences of the primers are given in the text. Constructs R1RZ and R2RZ carry cis-acting ribozymes immediately adjacent to the 3' end of the sequence of RNA 1 and 2 (SEQ ID Nos. 39 & 47) respectively.
Figure 16:
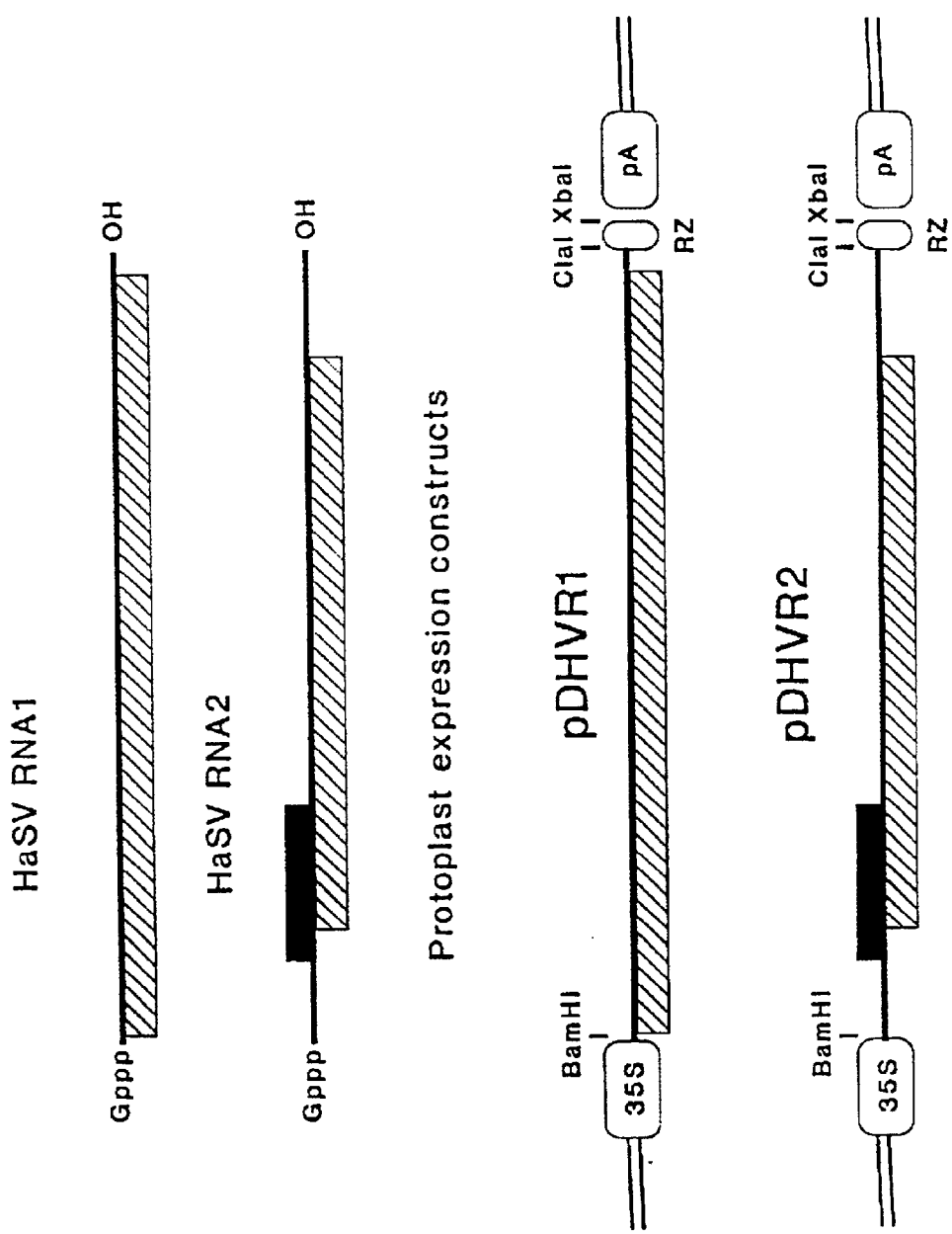
FIG. 16 Expression strategies for HaSV cDNAs in plant cells. The upper part of the Figure shows the genome organization of RNAs 1 and 2 (SEQ ID Nos. 39 & 47). The lower part shows insertion of cDNAs corresponding to these RNAs into a plasmid vector, between 35S promoter of cauliflower mosaic virus and the polyadenylation (pA) signal on plasmid pDH51 (Pietrzak et al, 1986). The cDNAs were obtained by PCR using suitable primers, with a BamHI site inserted by PCR immediately upstream of the start of each cDNA. The cDNAs are terminated by ClaI sites, allowing direct linkage to ribozyme sequences as described in the text.

As outlined earlier, the HaSV genome or portion thereof is a particularly effective insecticidal agent for insertion into baculovirus vectors. Such a vector is constructed by insertion of the complete virus genome or portion thereof (preferably the replicase gene) into the baculovirus genome as shown in FIG. 13. Preferably the virus genome or replicase is transcribed from a promoter active constitutively in insect cells or active at early stages upon baculovirus infection. An example of such a promoter is the heat shock promoter described in Example 7. Heat shock promoters are also activated in stressed cells, for example cells stressed by baculovirus infection. An even more preferable use of such a baculovirus construct is to use the HSP promoter to drive the HaSV replicase and another gene for a toxin (as exemplified elsewhere in the specification) where the RNA expressing the toxin gene is capable of being replicated by the HaSV replicase. Such recombinant baculoviruses carrying the HaSV genome or portions thereof for expression in larvae at early or other stages of the baculovirus infection cycle are particularly effective biological insecticides.

EXAMPLE 5

Effect of HaSV Genes and their Products on Plants
Materials and Methods

A. Electroporation of Protoplasts

Protoplasts of *Nicotiana tobacum, N. phumbaginifolia* and *Triticum aesticum* and oats were produced and electroporated with either HaSV or HaSV RNA as described in Matsunaga et al (1992) J.Gen. Virol. 73: 763–766.

B. Northern Blot Analysis—RNA Extraction from Protoplasts after Harvest

The protoplasts are subjected to 3 cycles of freezing and thawing, and then an equal volume of 2x extraction buffer (100 mM Tris-HCI, pH 7.5, 25 mM EDTA, 1% SDS, made in DEPC treated water) is added, followed by 1 volume of phenol (equilibrated in 10 mM Tris-HCl pH 8.0) heated to 65° C. The samples are mixed by vortexing and incubated at 65° C. for 15 min, vortexing every 5 min. After phase separation by centrifugation at room temperature for 5 min, the aqueous phase is re-extracted with phenol, re separated by centrifugation and re-extracted with chloroform/isoamyl alcohol. To the aqueous phase are then added 0.1 volume of DEPC-treated sodium acetate (pH 5.0) and 2 volumes of ethanol. The RNA is recovered by precipitation at −70° C., followed by centrifigation at 4° C. for 15 min. The samples were then analysed by agarose gel electrophoresis as described in example 1.

After blotting to Zeta-Probe membrane (BioRad), the hybridization protocols were as above for Example 2.

C. Total Protein from HaSV—Electroporated Protoplasts

Protoplasts were analysed by SDS-polyacrylamide gel electrophoresis and Western blotting as described in Example 1.

Results i) Use of Complete (Replication-Competent) RNA Virus Genome in Protoplasts a) HaSV Replication in Protoplasts The nodavirus FHV has previously been shown to replicate in barley protoplasts (Selling N. H., Allison, R. F. and Kaesberg P. Proc. Natl. Acad. Sci. USA 87,434–8 (1990). To determine whether HaSV virus RNA can replicate in plants protoplasts, when introduced by electroporation, experiments using protoplasts from *Nicotiana plumbaginifoli* and wheat have been conducted. (These are all species for which protoplasts are regularly available in the Division of Plant industry). Assays for replication including RNA (Northern) blots using probes derived from cloned fragments of cDNA to RNAs 1 and 2 (SEQ ID Nos: 39 and 47), and Western blots, using the antiserum to purified HaSV particles. Initial experiments showed that both HaSV virus and RNA electroporated into protoplasts of *N. plumbaginifolia* resulted in HaSV replication as studied using and verified by northern blots and ELISA. As a positive control TMV RNA was electroporated and was replication observed.

b) Bioassays

Protoplasts into which HaSV RNA had been introduced by electroporation were harvested after 6 or 7 days post electroporation and used in bioassays on neonate larvae by addition to normal diet. The results showed significant stunting of test larvae in comparison to control larvae (see Table 1 below). Protoplasts lacking HaSV RNAs had no effect on the larvae, confirming the result of control experiments. This result confirms that HaSV RNA, when expressed or replicated in plant cells, is able to cause the formation of infectious virus particles able to control insect larvae feeding on the plant material. Northern blotting has been used to confirm that RNA electroporation into protoplasts leads to RNA replication.

TABLE 1

Results of Bioassay from a typical experiment with Nicotiana and oat protoplasts (oat results are shown in brackets) [see over]

| Treatment | Number | Escapes | Number stunted |
|---|---|---|---|
| 1. diet only | 12 (12) | 2 (3) | 0/10 (0/9) |
| 2. diet + protoplasts | 12 (12) | 0 (1) | 0/12 (0/11) |
| 3. HaSV + diet | 12 (12) | 0 (1) | 12/12 (11/11) |
| 4. diet + HaSV/protoplasts | 12 (n.d.) | 0 (n.d.) | 12/12 (n.d.) |
| 5. diet + RNA/protoplasts | 12 (12) | 0 (0) | 11/12 (10*/12) |

*HaSv replication in the larvae was confirmed except for two larvae which were dead. The letters "n.d." mean the experiment was not done.

The above results demonstrate assembly of HaSV particles from electroporated RNA in protoplasts of both moncot and dicot plant species.

c) Plasmids to Test Replication of Cloned and Engineered Forms of HaSV (1) Plasmids allowing in vitro transcription of HaSV RNAs 1 and 2 (SEQ ID Nos: 39 and 47) for electroporation into protoplasts have already been described above. (2) Plasmids for transient expression of individual HaSV RNAs (1 or 2) (SEQ ID Nos: 39 and 47) in protoplastg. Full-length cDNAs for the two viral RNAs have been inserted into expression plasmids pDH51 (with the CaMV 35 S promoter. Pietrzak M., et al (9186) Nucl. Acids Res. 14, 5857–68) for dicots and pActI.cas (with the rice actin promoter) for monocots (McElroy et al (1990) The Plant Cell 2: 163–171). As with the vectors for expression in insect cells, these expression plasmids are being modified to include a cis-acting ribozyme for generation of authentic ends. The non-ribozyme plasmids gave no virus replication.

ii) Expression of Capsid Protein in Plants

In view of the present inventors' observation that empty particles ("assembled capsids") are being produced in baculovirus-infected cells that efficiently express the P71 precursor gene, expression of the coding region for the capsid protein in tobacco plants was investigated. The vector chosen for this purpose is based on pDH51 which carries the CaMV 35S promoter and polyadenylation signal. If necessary for improved expression, this vector can be modified by the addition of a translation enhancer sequence from e.g. TMV. Although certain groups have constructed transgenic plants expressing the capsid proteins of plant viruses, there has been only one recent report of assembly of empty capsids in such plants (Bertioli et al.,(1991) J. gen. Virol. 72: 1801–9). Bertioli et al point out that the protein-protein interactions in most icosohedral plant RNA viruses may be too weak to allow assembly of such capsids. In addition to the present inventors' observation of empty HaSV capsids, it has been found these capsids are very tough, showing great resilience to e.g. repeated cycles of freezing and thawing, so that it is expected to see assembly of empty HaSV capsids ("assembled capsids") in transgenic plants.

Construction of Capsid Protein Expression Plasmid

Vector used was pDH51; linearised with BamHI and phosphatased.

Insert was PCR product made using following 2 primers:
CAPPLANT:
5' GGGGATCC ACA ATG GGA GAT GCT GGA GTC-3' (BamHI)
(i.e. A BamHI site followed by plant consensus context for ATG of capsid protein gene and 15 further nucleotides of this gene-nts 366–383 of HaSV RNA2).

HVP6C2 (Example 3)

The PCR product was made with VENT polymer (New England Biolabs). After gel purification, it was cut with BamHI and cloned into the vector. Orientation screened with EcoRI to identify insert in same direction as promoter giving plasmid pDHVCAPB. Expression was verified by Western blotting using anti-HaSV antiserum. Both precursor P71 and processed P64 capsid protein were detected in protoplasts following transfection with pDHVCAPB, showing assembly of virus-like particles.

EXAMPLE 6

Identification of Midgut Binding Domains

Materials & Methods

A. Plasmid Construction

Was as described in Examples 3 and 4.

B. Western Blotting

Was as described in Examples 1 and 3.

C. Invitro Translation

In vitro transcripts of cloned CDNA of HaSV RNA's was translated in vitro as in Examples 1 and 3.

D. Preparation of Brush Border Membrane Vesicles

Brush Border Membrane Vesicles were prepared from freshly isolated larvae midguts of *H. Armigera* by the method of M. Wolfersberger et al (1987) Comp. Biochem. Physiol. 86A: 301–308, as modified by S. F. Garczyuski et.al. (1991) Applied Environ. Micro-biol 57: 1816–2820. Brush Border Membrane Vesicles binding assays using invitro labelled protein or $^{125}$I-labelled protein were as described in Garczynski et.al. (1991) or in H. M. Horton and Burand, J. P. (1993) J. Virol. 67: 1860–1868.

Results i) Determination of Epitopes on the Capsid Surface

Comparison of the recently published sequence of the *Nudaurelia ω virus* (NwV) cap sid protein with that of HaSV shown that these proteins are closely related and fall into four distinct domains, which are alternatively variable and highly conserved. These domains are summarised as follows:

| Residues: | HaSV | 1–49 | 50–272 | 273–435 | 437–647 |
|---|---|---|---|---|---|
| | NωV | 1–46 | 47–269 | 270–430 | 431–645 |
| % identity: | | 37 | 81 | 34 | 81 |

Comparison of this observation with the alignment by Agrawal and Johnson (1992) between the NwV and the nodavirus BBV (whose crystal structure is known: Hosur et al (1987) Proteins: Structure, Function & Genetics 2: 167–176) showed that the variable region coincided with a region forming the most prominent surface protrusion on the BBV capsid. Both HaSV and NwV carry large insertions at this point relative to BBV, and these insertions are largely different in sequence. Assuming that the alignment by Agrawal and Johnson (1992) is correct, then this means that HaSV and NwV have a more prominent pyramid-like structures as a surface protrusion than do the nodaviruses, and the pyramid-like structures are different. As already noted, there is no immunological cross-reactivity between the two viruses, despite the high degree of identity. There is thus a strong implication of the variable domain as a surface protrusion which functions as the sole antigenic region.

To confirm this a 400 bp NarI fragment spanning the variable region was deleted from the capsid gene in the expression vector. With end-filling of these sites the deletion is in-frame, so that a truncated protein of ca. 57 KDa is produced in bacteria upon induction. This protein was recognized only poorly on Western blots by the antiserum against intact HaSV particles made in rabbits. The central variable domain was recognized well by the antiserum when expressed in isolation from the rest of the capsid gene.

As shown in the table above the region of HaSV capsid protein comprising residues 273–439 shows great divergence form the corresponding region of the NwV capsid protein, compared to its immediate flanking regions. Within this region an especially divergent domain is found from residue 351 to residue 411, which shows only 25% identity to the corresponding region of the NwV capsid protein. This region is flanked by the sequences corresponding to the b-sheet structural features b-E(residues 339–349) and b-F (residues 424–431) of the HaSV capsid protein, based on the alignment the NwV and nodavirus capsid proteins by Agrawal and Johnson (1992), and is therefore likely to form the loop of the most prominent surface protrusion on the HaSV capsid. This is based on comparison and correspondence to the nodavirus capsid protein structure and capsid structure as described by Wery J. -P. and Johnson, J. E. (1989) Analytical Chemistry 61, 1341A–1350A and Kaesberg, P., et al. (1990) J. Mol. Biol. 214, 423–435. This loop is thought to contain important epitopes. It is significant that this exterior loop on the nodavirus capsid protein is one of the most variable regions when capsid proteins sequences from a number of nodaviruses are compared (Kaesberg et al. 1990).

Finally, the present inventors have observed a significant level of immunological cross-reaction on Western blots, between antisera against the CryIA(c) Bt toxin and HaSV capsid protein, whether obtained from virus or expressed in bacteria. Initial data from the NarI deletion mutant described above suggest that this binding is not to the central variable domain, but to other regions of the capsid protein. The only other region of the proteins which shows extensive sequence variability, the amino terminus, cannot be responsible for the binding, since both authentic capsid protein and the protein with an altered amino terminus expressed in bacteria are recognized by the anti Bt antisera.

ii) In-Vitro Binding Assays

The full-length clones for in vitro translation yielding highly 35S or $^3$H labelled proteins were constructed by replacing the bacterial translation interaction signal in the T7 plasmids above by the more active eucaryotic context sequence from the JHE gene. The labelled capsid protein made by in vitro translation of the in vitro transcripts may be tested for binding to brush border membrane vesicles (BBMV's). Conditions are optimised by testing different procedures. The deletion mutant lacking approximately 125 amino acids in the central region, and containing the variable domain, as well as others derived from it are also tested.

iii) Fusion Proteins Comprising Virus Capsid Midgut Binding Domains and Other Proteins The idea behind these tests is to fuse the binding domain from the HaSV capsid protein to either large proteins (preferably indigestible, causing protein to aggregate in or on the midgut cells) or toxin domains from other proteins with suitable properties but normally different binding specificities (e.g. Bt). In initial experiments, the gene for the complete capsid protein has been fused to the GUS gene, as has a deletion mutant containing essentially only the central portion of the capsid gene. The resulting fusion proteins are being expressed in bacteria and tested for GUS activity, and makes them sensitive probes for binding experiments on midgut tissue.

iv) Mapping Binding Sites Using Bt/HaSV Fusion Proteins

Analysis of deletion mutants of the CryIA(c) Bt toxin has identified domains which may be involved in determining the host-specificity of this Bt by acting as receptor-binding sites (Schnepf et al (1990) J. Biol. Chem. 265: 20923–20930; Li et al (1991), Nature 353: 815–21. The present inventors have obtained a clone of this toxin gene. Deletion mutants corresponding to those identified by Schnepf et al are constructed. Segments of the HaSV capsid protein gene can then be inserted into these mutants, the protein expressed in bacteria and their insecticidal function assayed.

EXAMPLE 7

Viral Growth in Cell Culture

Materials & Methods

A. Cell Lines

The following cultured insect cell lines were tested for infection by HaSV: *Drosophila melanogaster, Helicoverpa* (ovarian derived), *Heliothis zea* (ovarian derived), *Plutella xylostella, Spodoptera frigiperda* (SF9).

All lines were grown under standard conditions. Upon reaching confluence, the culture medium was removed and all mono-layers covered with 1.5 ml of cell culture medium into which HaSV had been diluted; the average multiplicity of infection (M.O.I.) was $10^4$. After adsorption at 26° C. for 2 h, the inoculum was removed, the cells carefully washed twice with phosphate buffered saline (pH 7.0) and incubation continued with 5 ml of 10%. Foetal calf serum in TC199 culture medium (Cyto Systems).

B. Northern Blotting Analysis

Virus replication in all the above cell lines was confirmed by northern blotting analysis. Total RNA was extracted from infected cells by the method of Chomczynski and Sacchi (1987). Anal. Biochem. 162: 156–159. The cells were lysed in 1 ml of lysis solution (4M guanidinium thiocyanate, 25 mM sodium citrate, pH 7, 0.5% sarcosyl, 0.1M 2-mercaptoethanol). In order, 0.1 ml of 2M sodium acetate, pH 4, 1 ml of phenol (0.2M sodium acetate equilibrated), and 0.2 ml of chloroform-isoamyl alcohol mixture (49:1) were added with thorough mixing between reagents. This was then vortexed for 10 s and cooled on ice for 15 min. Tubes were centrifuged in an Eppendorf centrifuge at 14 k for 15 min at 4° C. for at least 15 min to allow RNA precipitation. RNA was pelleted by centriflugation at 14 k for 15 min, washed with 0.6 ml of ice-cold 70% ethanol, pelleted once again (10K, 10 min), air dried at room temperature and resuspended in DEPC (Sigma) treated millipore water. RNA was subject to denaturing agarose gel electrophoresis in the presence of formaldehyde according to Sambrook et.al. (1989). The gel was Northern transferred to a zeta-probe membrane (Biorad) as described by Sambrook et.al. (1989). The probe was prepared by random-priming the 3' sequences of the HaSV genome using DNA and cDNA clones pSHVR15GB and pT7T2p71SR-1 as per manufacturer's instructions (Boehringer-Mannheim). Hybridization was carried out as described for the standard DNA probe protocol contained within the literature for the zeta-probe membrane (Biorad).

C. Vectors

Vectors as described below.

Results

It has been found that HaSV will replicate in several continuous cell lines, of which the best is the *Spodoptera frugiperda* line SF9. Time course assays by Northern blotting in SF9 cells have shown that RNA 1 (SEQ ID No: 39) replication is clearly detectable within a few hours of infection. RNA 2 (SEQ ID No: 47) is present only in very small amounts early in infection and accumulates much more slowly than RNA 1 (SEQ ID No: 39) does. This observation is consistent with one made earlier in HaSV-infected larvae, where RNA 2 (SEQ ID No: 47) replication was not observed until 3 days after infection.

Some apparent replication was also observed in *Drosophila* cells (DL2), but with the difference that more RNA 2 (SEQ ID No: 47) replication was observed at the early time points compared to the lepidopteran cell lines above.

Plasmids that express the HaSV genome as RNA transcripts from full length cDNA clones have been constructed and tested. These clones, constructed by PCR and carefully checked, have restriction sited immediately adjacent to the ends of the sequence. Transcription is driven from a specially-re-engineered *Drosophila* HSP70 promoter.

i) Constructs for Expression in Insect Cells

The constructs are based on vectors carrying the *Drosophila* HSP 70 or actin promoters and suitable polyadenylation signals from Drosphila (Corces & Pellicer (1984) J. Biol. Chem. 259: 14812–14817) or SV40 (Angelichio et al (1991) Nucl. Acids. Res. 18: 5037–5043). Since transcription from such plasmids generates viral RNAs carrying long 3' terminal extensions derived from sequences in the poladenylation signal fragment, it is necessary to achieve cleavage of the transcript immediately after the 3' sequence of the viral RNA. These plasmids gave no virus replication, presumably because of the 3' terminal extension. The method of choice for obtaining authentic 3' termini is based on introduction of DNA sequences encoding a cis-acting ribozyme into the constructs. With suitable engineering, such a ribozyme will cleave immediately 3' to the viral sequences within the transcript. Suitable ribozymes, based on the hepatitis delta virus (Been M. D., Perrotta, A. T. & Rosenstein, S. P. Biochemistry 31, 11843–52 (1992) or the hairpin cassette ribozyme (Altschuler, M, Tritz R. & Hampel, A. Gene 122, 85–90 (1992) have been designed (see Example 4). This involves synthesis of overlapping oligonucleotides, which are then annealed and end-filled with the Klenow fragment of DNA polymerase, to create short DNA fragments encoding the desired ribozyme. These fragments carry restriction sites at their termini allowing them to be ligated into plasmids between the viral RNA cDNA (which has a 3' restriction site added by PCR) and the restriction fragment carrying the poladenylation signal. Ribozyme function has been verified (Example 9).

The *Drosophila* HSP70 promoter was joined to the HaSV RNA 1 sequence as follows. A BamHI restriction site was introduced into the promoter sequence as described on p. 5 of this specification. Oligonucleotide HVRlB5P described in Example 8 was used to prime PCR of RNA 1 to yield a cDNA copy of the RNA carrying a BamHI restriction site 5' to the RNA 1 sequence and separated from it by the nucleotides ACA which end the HSP70 promoter just before the start of transcription. This common BamHI site was used to link the HSP70 promoter and the HaSV RNA 1 sequence. The resulting plasmid was completed by adding either the hairpin cassette ribozyme (giving plasmid pHSPR1HC) or the HDV ribozyme (giving plasmid pHSPR1HDV) plus the SV40 late polyadenylation sequence.

A similar approach was used to obtain plasmids for RNA 2 i.e. pHSPR2HC and pHSPR2HDV.

An alternative approach is to link the promoter and the HaSV cDNAs using blunt end ligation of a DNA fragment and carrying the promoter and terminating at the last nucleotide before the start of transcription (the underlined residue in ACA) and the cDNA fragments corresponding to either HASV RNA 1 or 2, as described for the plant expression plasmids in Example 9.

The latter approach was used to join the sarcoma virus (RSV) long terminal repeat (LTR) promoter to the HaSV cDNAs for expression in insect cells. The RSV LTR promoter is active in many animal cells (Cullen, B. R. Raymond, K. & Ju, G. (1985) Mol. Cell. Biol. 5,438–447) and also in lepidopteran cell lines (D. Miller personal communication). It was obtained from plasmid pRSVCAT (Gorman, C., Padmanabhan, R. & Howard, B. H., (1983) Science 221, 551–553) as a 495 bp fragment carrying a 5'-XbaI site (added by PCR) and terminating at a blunt end with the sequence AA<u>C</u>, with the underlined residue corresponding to that immediately before the start of transcription. The resulting plasmids, pRSVR1HCLA and pRSVR2HCLA, carry the HaSV RNA 1 and 2 cDNAs, respectively, and are otherwise like pHSPR1HC and pHSPR2HC, respectively. These plasmids carry the SV40 late polyadenylation signal. They allow efficient and precise expression of the HaSV genomic RNAs in insect cells, for example if introduced using a baculovirus vector or by transfection.

EXAMPLE 8

Shedding of Infected Cells

Materials & Methods

A. Confocal Laser Scanning Microscopy. (CLSM)

CLSM enables the visualisation and analysis of three-dimensional cell and tissue structures at the macro and molecular levels. The Leica CLSM used in this example is based on an MC 68020/68881 VME bus (20 MHz) with standard 2 Mbyte framestore and 4 Mbyte RAM and OS9 operating system with programmes written in C code. It incorporates a Leica Diaplan research microscope and using X10/0.45, X25/0.75,X40/1.30 and X63/1.30 Fluotar objectives has a claimed optical efficiency better than 90%. The confocal pinhole is software controlled over the range of 20 to 200 mm. Excitation at 488 and 514 nm is provided by a 2 to 50 mW argon-ion laser.

B. Immunocytochemistry (ICC)

For whole mount ICC, tissues were dissected under saline and fixed in fresh 4% formaldehyde in phosphate buffered saline (PBS) for at least 15 mins. After multiple washes in PBS they were permeablized either by 60 mins incubation in PBT (PLBS with 0.1% Triton X-100 plus 0.2% bovine serum albumin). After 30 mins blocking in PBT+N (5% normal goat serum) tissue was incubated in primary antibody diluted (1:40) in PBT+N for at least 2 hrs at room temperature then at 4° C. overnight. After extensive washing in PBT and 30 mins blocking in PBT+N the FITC conjugated secondary antibody diluted (1:60) in PBT+N was incubated for 2 hrs at room temperature plus overnight at 4° C. After multiple washes in PBT and PBS the tissue was cleared in 70% glycerol and mounted in 0.01%w/v p-phenylenediamine (Sigma#P1519) dissolved in 70% glycerol. All processing was at room temperature unless otherwise stated.

Results

The inventors' current model for the effect of HaSV involves the detection by the insect midgut of infected cells, their identification as infected and their subsequent shedding in numbers sufficient to cause irreparable damage to the insect midgut. The evidence for this is based on the above and on the following direct observation of the fate of infected cells in midgut tissue over 1–3 days post infection. These results in repeat experiments were complicated by the discovery that another unrelated virus was present in the larval population being tested. Preliminary findings indicated that HaSV infection activates or facilitates pathogenesis of the unrelated virus and together these cause severe disruption of the larval gut cells. Thus these two agents appear to act synergistically in causing gut cell disruption.

Midguts from larvae infected with HaSV were treated with the antiserum to purified HaSV particles (above) and examined under the Laser confocal microscope (described above). This established that some midgut cells were sufficiently infected with HaSV to give strong fluorescence signals. Such cells were moreover clearly separating from the surrounding tissue, a sign that they were in the process of being shed.

Similar observation have been made with other insect viruses (Flipsen et al (1992) Society for Invertebrate Pathology Abstract #96) although in these cases the effect is too localised and weak to cause any anti-feeding effect apparently only the small RNA virus of the tetraviridae which are localised to the gut and cause more-or-less severe anti-feeding effects in their hosts (Moore, N. F. in Kurstak E. (Ed) (1991) Viruses of Invertebrates. Marcel Dekker, New York pp 277–285) are capable of such an effect to an extent sufficient for pest control.

Following on from the immune-fluorescence work, in situ hybridization can be carried out to detect RNA replication in infected cells. Furthermore, larvae infected with a recombinant HaSV expressing a foreign gene at early stages (by insertion of that gene into RNA 1 in place of the N-terminal portion of the replicase gene) can be studied. A correlation between virus replication and cell rejection can be confirmed by histochemical analysis of the midgut cells of the infected larvae. Thus the cell-shedding phenomenon offers a direct and rapid assay for early events in HaSV-infected gut tissue. Extracts of baculo-vector infected insect cells carrying empty HaSV particles can be fed to larvae directly and the midgut examined by toluidine blue staining and immune-fluorescence at intervals after infection. This will allow direct determination of whether the particles can bind the brush border membranes in intact gut, and whether such binding can induce the massive disruption evident in normally infected larvae. Control experiments using extracts from cells infected with the baculovector alone can be conducted to observe and distinguish effects due to the vector. The immune-fluorescence assay on midgut tissue allows analysis of binding to midgut brushborder membranes. Once determined for wild-type capsid protein expressed from a baculo-vector, deletion or replacement mutants can be inserted into the baculovectors. Suitable cell extracts from these can be used to infect larvae.

EXAMPLE 9

Engineered Virus and Uses

Materials & Methods
    as indicated in earlier Examples)
i) Engineered Virus as a Vector for Other Toxin Genes This involves placing suitable genes under control of HaSV replication and encapsidation signals. Genes which may be suitable include intracellular insect toxins such as ricin, neurotoxins, gelonin and diphtheria toxins. The toxin gene may be placed in the viral gene such that it is a silent (downstream) cistron on a polycistronic RNA, or in a minus strand orientation, requiring replication by the viral polymerase to be expressed. Standard techniques in molecular biology can be used to engineer these vectors.

A discussion of two recombinant HaSV vectors which have been designed is given below:
for RNA 1 (SEQ ID No: 39)

The reporter gene (or one of the toxin genes mentioned above) is inserted in place of the amino-terminal portion of the putative replicase gene, such that the intiation codon used for the replicase (ie that at nucleotides 37–39 of the sequence) is now used to commence reporter gene translation. The fusion is achieved by the use of artificial NcoI restriction sites common to both sequences.

The short 36 nucleotide 5'-untranslated leader of RNA 1 (SEQ ID No: 39) (shown in upper case) is synthesised as the following sequence:

ggggatccacaGTTCTGCCTCCCCCGGACGGTAAATATA GGGGAACCATG Gtctagagg, (SEQ ID No: 53)

using two overlapping oligonucleotides comprising the first 31 (oligonucleotide HVR1B5P) nucleotides and the complement of the last 40 nucleotides (oligonucleotide HVR1NCO) respectively. These primers are annealed and end-filled by Kienow. The resulting fragment is then cut with BamHI and XbaI (sites underlined) and cloned with plasmid vector pBSIISK(-) to give pBSSKR1NCO.

The GUS gene carrying a NcoI site at the ATG codon was obtained as a NcoI-SacI fragment from plasmid pRAJ275 (Jefferson, RAJ Plant Mol. Biol. Rep 5, 3387–405 (1987)). This Sac site is located just downstream from the coding sequence for the GUS gene.

The 5' leader of HaSV RNA1 is excised as a BamHI-NcoI fragment from the plasmid pBSSKR1NCO, and is ligated together with the NcoI-SacI fragment carrying the GUS gene into plasmid pHSPR1HC or pHSPR1HDV or pDH-StuR1HC carrying the full-length cDNA insert of RNA 1 (see above) which has been cut with BamHI and SacI. The resulting plasmid then carries a complete form of RNA 1 (SEQ ID No: 39) but with the amino-terminal portion of the replicase gene substituted by the GUS gene. It is desirable to produce a construct with approximately the same size as RNA 1 (SEQ ID No: 39) for encapsidation purposes.

Similar approaches are adopted for RNA 2 (SEQ ID No: 47), with the foreign, reporter or toxin gene fused to the initiation codon of either P17 or P71. In either case the context sequence of the introduced gene is modified to give the necessary expression level of that protein. The foreign gene is introduced into plasmids pHSPR2HC or pHSPR2HDV or pDHStuR2HC.

The above recombinants have been described specifically as insertions of a reporter gene (GUS). The toxin genes to be inserted are described on page 14 of the specification. These preferably further require a signal peptide sequence added at the amino-terminus of the protein.

ii) Capsid Technology

Identification of encapsidation (and replication) signals on virus RNA allows design of RNAs which can be encapsidated in HaSV particles during assembly of virus in a suitable production system. The virus cap sids then carry the RNA of choice into the insects midgut cells where the RNA can perform its intended function. Examples of RNAs which may be encapsidated in this manner include RNAs for specific toxins such as intracellular toxins, such as ricin, gelonin, diptheria toxins or neurotoxins. This strategy is based on the resistance of the virus particle to the harsh gut environment.

Other Uses of the Capsid Particle

The capsid particles can be used as vectors for protein toxins. Knowledge of icosahedral particle structure elucidated by the inventors suggests that the amino and especially the C-termini are present within the capsid interior. It is possible to replace or modify the amino acid sequence corresponding to P7 such that it encodes a suitable protein toxin which is cleaved off the bulk of the capsid protein during capsid maturation. As with toxin-encoding mRNAs, the HaSV capsid delivers it to the midgut cell of the feeding insect, where it exerts the desired toxic effect.

iv) Use of HaSV in Plants

The use of HaSV in the production of insect-resistant transgenic plants are shown in FIG. 12. These inventions are based on the use of either the complete HaSV genome, or of the replicase gene as a tool for the amplification of suitable amplifiable mRNAs (e.g. encoding toxin) or of the capsid protein as a means to deliver insecticidal agents. These strategies are now described in some detail.

a) Use of the Complete HaSV Genome

Fragments of cDNA corresponding to the full-length HaSV genome components RNAs 1 and 2 (SEQ ID Nos: 39 and 47) are placed in a suitable vector for plant transformation under the control of either a constitutive plant promoter (e.g. the CaMV 35S promoter mentioned above) or an inducible promoter or a tissue specific (e.g. leaf-specific) promoter. The cDNAs are followed by a cis-cleaving ribozyme and a suitable plant polyadenylation signal. Transcription and translation of these genes in transgenic plant tissues and cells leads to assembly of fully infectious virus particles to infect and kill feeding larvae.

The following experiments were conducted. The plasmids for expression used the CaMV 35S promoter to generate transcripts commencing at the first nucleotide of the HaSV RNAs 1 and 2 (SEQ ID Nos: 39 and 47). The vector pDH51 (M. Pietrzak, R. Shilito, T. Hohn and I. Potrykus (1986). Nucleic Acids Research 14, 5857) which carries the CaMV 35S promoter followed by a multiple cloning site and the CaMV polyadenylation fragment was modified to make a suitable vector, pDH51 Stu, carrying a StuI site at the immediate 3' end of the CaMV 35S promoter. The promoter thereby terminates in the sequence GAGAGGCCT, with the underlined residue being that at which transcription would start. (Similar vectors have been described by Mori et al., J. General Virology 72, 243–246 (1991) and Dessens and Lomonossoff, ibid 74, 889–892 (1993).) The StuI site (AGG/CCT) is followed by a BamHI site (GGATCC). Cleavage of this vector with StuI and BamHI generates a vector DNA molecule with one blunt end (from StuI cleavage) and one sticky BamHI end. This allows ligation of cDNA molecules corresponding to the full-length HaSV genomic RNAs, and carrying a blunt end at the 5' end of the full-length cDNA and a BamHI site after the 3'-end of the full-length cDNA.

Figure 8:
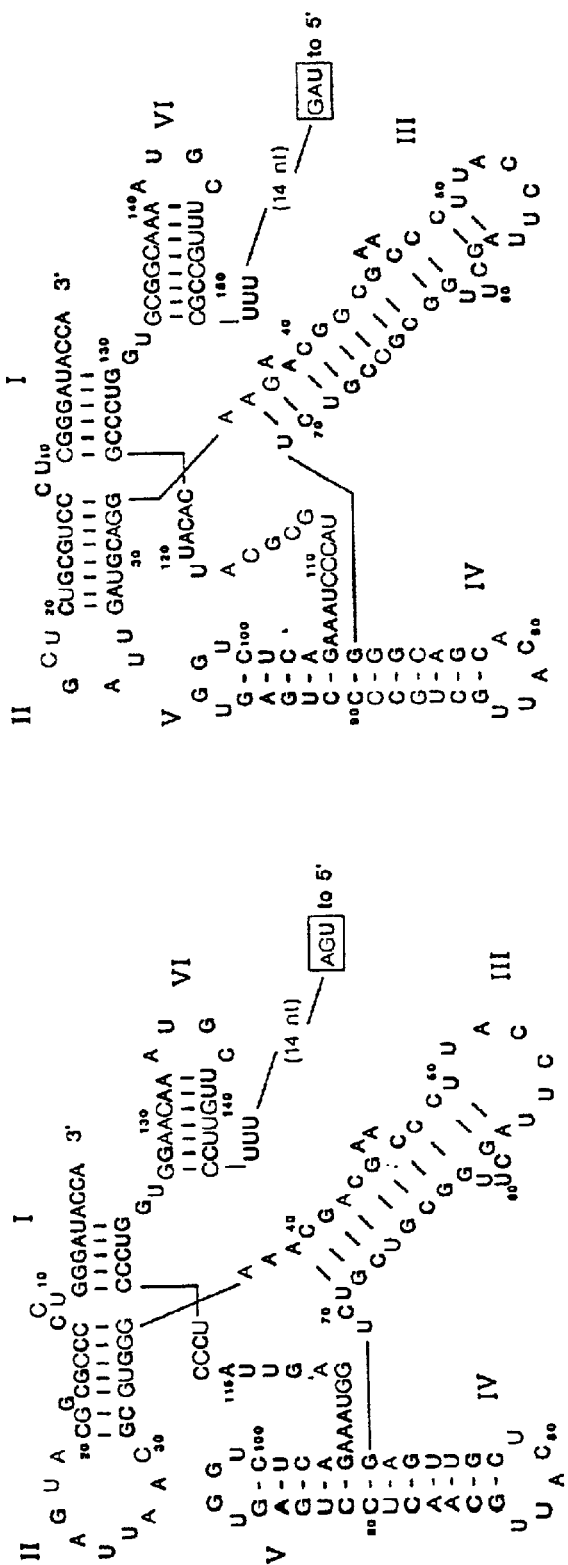
FIG. 8 illustrates the 3'-terminal secondary structure of HaSV RNAs. The tRNA-like structures at the 3' ends of RNAs 1 and 2 (SEQ ID Nos. 39 & 47) are shown. Residues in bold are common to both sequences.
Figure 9:
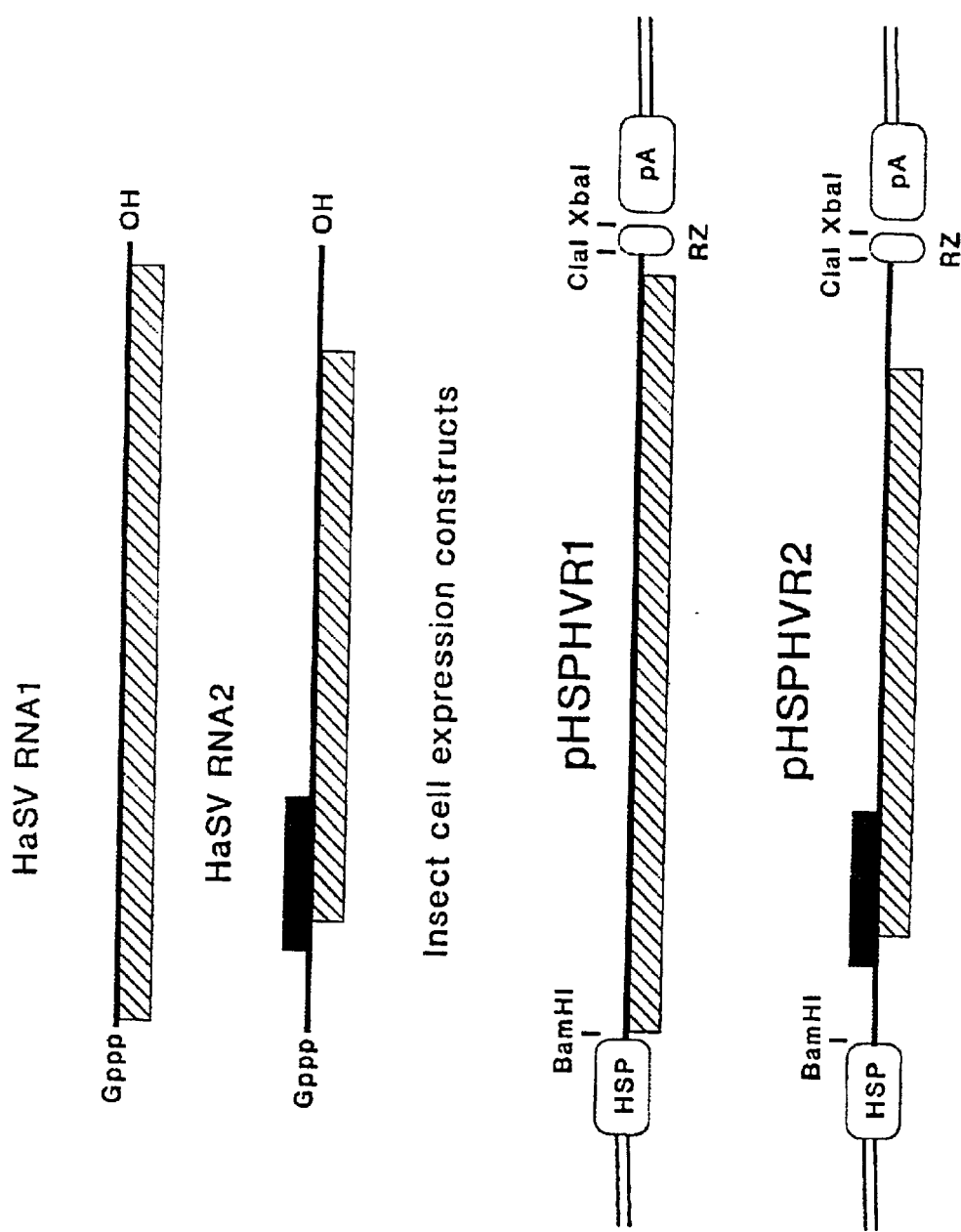
FIG. 9 Expression strategies for HaSV cDNAs in insect cells. The upper part of the figure shows the genome organization of RNAs 1 and 2 (SEQ ID Nos. 39 & 47). The lower part shows insertion of cDNAs corresponding to these RNAs into a plasmid vector, between the heat shock protein (HSP70) promoter of *Drosophila* and a suitable polyadenylation (pA) signal. The HSP promoter was obtained by PCR using suitable primers, with a BamHI site inserted by PCR immediately upstream of the start of transcription, giving the following sequence: GGATCCACAGnnn (SEQ ID No. 1), where the underlined residue is the transcription start site for either RNA. The cDNAs are termed by ClaI sites, allowing direct linkage to ribozyme sequences as described in the text.

Suitable cDNA fragments carrying a blunt end corresponding to the 5'-terminal nucleotide of either RNA 1 or 2 (SEQ ID Nos: 39 and 47) were generated using PCR and an oligonucleotide primer corresponding to the 5'-terminal first 18 nucleotides of the sequence of either RNA 1 (SEQ ID No: 39) or RNA 2 (SEQ ID No: 47). The cDNA sequence corresponding to the 3' terminal sequences of either RNA 1 (SEQ ID No. 39) or RNA 2 (SEQ ID No 47) were followed on these DNA fragments by sequences corresponding to one of the ribozymes whose sequences are shown in FIG. 8 and whose construction is described in Example 7. The 3'-terminal sequence corresponding to an XbaI site (TCTAGA) shown in these ribozyme sequences was followed on the suitable DNA fragments by a BamHI site, which upon cleavage with this enzyme yielded a sticky end capable of being ligated into the BamHI end of the vector cleaved as described above. There were therefore a total of four suitable DNA fragments for insertion into the vector:

RNA 1 (SEQ ID No: 39) followed by the hairpin cassette (HC) ribozyme

RNA 1 (SEQ ID No: 39) followed by the hepatitis delta virus (HDV) ribozyme

RNA 2 (SEQ ID No: 47) followed by the hairpin (HC) ribozyme
RNA 2 (SEQ ID No: 47) followed by the hepatitis delta virus (HDV) ribozyme.

These four fragments were individually ligated into the vector pDH51 Stu cleaved with StuI and BamHI to generate four distinct plasmids as follows:
pDHStuR1HC
pDHStuR1HDV
pDHStuR2HC
pDHStuR2HDV Transcription from the 35S promoter in these plasmids results in RNAs commencing at the first nucleotide of either the RNA 1 sequence (SEQ ID No; 39) or RNA 2 sequence (SEQ ID No: 47) and terminating in the CaMV polyadenylation fragment. Self-cleavage at the locations shown in FIG. 8 by the cis-acting ribozymes obtained within these transcripts generates RNA molecules with the 3'-termini corresponding to the natural virus termini.

After amplification and purification on CsCl gradients, thirty mg of each of these four plasmids was transfected by electroporation into aliquots of two million *N. plumbaginifolia* protoplasts (as described in Example 5) either individually or in the combinations listed below:
pDHStuR1HC+pDHStuR2HC
pDHStuR1HDV+pDHStuR2HDV The production of infectious HaSV particles within transfected protoplasts was then demonstrated by bioassay on heliothis larvae. After incubation at 25° C. for 3–5 days, the protoplasts were recovered by low speed centrifugation and applied directly to standard heliothis diet as surface contamination for bioassay as described in Example 1. Stunting was only observed when plasmids expressing HaSV RNA I (SEQ ID No: 39) and RNA 2 (SEQ ID No: 47) were co-transfected, and then only in the case of those carrying the hairpin ribozyme to generate the viral 3' ends (see Table 2). In contrast, constructs carrying the HDV ribozyme at the 3' end were not infectious. The reasons for this have not been determined. As expected, expression of RNA 1 or 2 (SEQ ID Nos: 39 and 47) alone in protoplasts did not lead to the assembly of infectious particles. Western blot analysis of protoplasts transfected with the RNA 2 (SEQ ID No: 47) constructs did show production of limited amounts of the capsid protein.

Suitable control experiments confirmed that larval stunting was due to HaSV particles generated de novo in the protoplasts. As shown in the Table 2, neither the protoplasts alone nor protoplasts mixed with plasmid DNA were capable of initiating stunting.

TABLE 2

| Treatment | | No. of larvae | Escapes | No. stunted |
|---|---|---|---|---|
| 1. | diet alone | 24 | 0 | 0 |
| 2. | diet + HaSV | 24 | 0 | 24 |
| 3. | diet + protoplasts | 24 | 0 | 0 |
| 4. | diet + pDHStuR1HC | 24 | 0 | 0 |
| 5. | diet + pDHStuR1HDV | 24 | 0 | 0 |
| 6. | diet + pDHStuR2HC | 24 | 0 | 0 |
| 7. | diet + pDHStuR2HDV | 24 | 0 | 0 |
| 8. | diet + pDHStuR1HC + pDHStuR2HC* | 24 | 0 | 22 |
| 9. | diet + pDHStuR1HDV + pDHStuR2HDV* | 24 | 0 | 0 |
| 10. | pDHStuR1HC + pDHStuR2HC (but mixed with protoplasts) | 24 | 0 | 0 |

*these plasmids were co-transfected with pDHVCAPB (see Example 5)

HaSV infection of stunted larvae was confirmed by dot-blotting of RNA using HaSV specific probes. After weighing, larva were sacrificed and total RNA extracted as follows. Each larva was homogenised in the presence of 260 ml deionised water, 24 ml 2M sodium acetate pH 4.0 and 200 ml phenol equilibrated with 2M sodium acetate pH 4.0. After centrifugation at 14 000 rpm for 15 min at 4° C., the supernatant (about 200 ml) was removed and extracted once with an equal volume of chloroform. After centrifugation, the supernatant (about 200 ml) was mixed with 20 ml of sodium acetate and 400 ml of absolute ethanol. The precipitate after centrifugation was vacuum dried and redissolved in 5–10 ml of sterile, DEPC-treated water. For dot-blotting, the RNA was mixed with 70 ml of DEPC-treated water and 30 ml of 10 mM EDTA, 30 mM NaOH. HaSV RNA was determined and quantified by dot blotting (as described in Example 2) using a probe random primed DNA from clones corresponding to the terminal 1000 nucleotides of RNA 1 and 2. All larvae recorded as stunted in the bioassays were found to carry HaSV and give signals comparable to those of the larvae fed purified HaSV particles (Table 2). To confirm that the larvae were infected with HaSV, ten aliquots of protoplasts were electroporated with plasmids pDHStuR1HC+pDHStuR2HC and the protoplasts fed (after incubation) to 150 heliothis larvae. The larvae were allowed to grow for one week, upon which significant stunting was observed in 50% of the larvae, and virus was then purified from these stunted larvae as described in Example 1. Analysis on CsCI gradients showed the production of distinct bands characteristic of HaSV; analysis of the virus particles found in these bands by SDS-PAGE and Western blotting with HaSV antiserum confirmed their identity as authentic HaSV.

These results have therefore demonstrated that DNA plasmids capable of expressing the HaSV genome in plant cells have been constructed. Once introduced into the cells, the plasmids are transcribed to yield HaSV genomic RNA which can drive the assembly of particles able to infect heliothis larvae by the normal oral route. These constructs have therefore been shown to be suitable for use in engineering transgenic plants expressing HaSV.

A variation on this strategy is to remove from the cDNA for RNA 2 (SEQ ID No: 47) the fragments encoding RNA encapsidation and/or replication signals. This results in either the assembly in the plant cells of HaSV particles carrying only RNA 1 (SEQ ID No: 39), or of HaSV particles carrying RNA 1 (SEQ ID No: 39) and a form of RNA 2 (SEQ ID No: 47) which cannot be replicated in the infected insect cell.

A further variation on this strategy is to modify the plant transgene encoding RNA 2 (SEQ ID No: 47) so that it is still replicatable and encapsidatable, but no longer express functional capsid protein. HaSV capsids made in such plant cells will then be capable of making both the replicase and P17 (SEQ ID No: 48) in infected insect cells, but not of assembling progeny virus particles therein (such as shown in FIG. 12(*d*)). These measures confer inherent biological safety in the form of containment on the use of such transgenic plant material.

(b) Use of Portions of HaSV Genome to Deliver Toxins to Insect Cells

This approach makes use of any of the systems described in (a) above. Plant cells contain an additional transgene encoding a suitable insect-specific, intracellular toxin (as described above). Such a toxin gene is expressed by plant RNA polymerase in either a positive or a negative sense (the latter is preferred) and in such a form that the RNA can be encapsidated by HaSV capsid protein and/or replicated by the HaSV replicase in infected insect cells (see FIGS. 12*a* and 12*b*)

Transgenic plants would contain two different transgenes, making either unmodified capsid protein precursor or a modified form in which most of the carboxyterminal protein P7 is replaced by a suitable insect-specific toxin or one which is inactive as part of a fusion protein. (Gelonin or other ribosome-inactivating proteins, insect gut toxins or neurotoxins may be suitable here.) Expression from these two transgenes would be regulated so that only the required amounts of the modified and unmodified forms are made in the plant cell, and assembled in such proportions into the capsoids. One way to modulate the production of capsotixin fusion proteins is to make translation of the carboxyterminal toxin reading frame dependent on a translational frameshift or read-through of a termination codon. With an appropriate low frequency of frame-shifting (eg 0.1–2%), it could even be sufficient to use a single transgene, if it were possible to synthesise the P7 portion and the toxin portion as overlapping genes. Upon assembly (which we have demonstrated in insect cells using the baculovirus vectors) and maturation, the protein precursors are cleaved and release the mature P7 and the toxin, which remain within the capsoids. These proteins are not released until capsoid disassembly occurs in insect gut cells. The processed form of the toxin is then able to kill the pest.

(c) HaSV Particles Devoid of Nucleic Acid Carrying One or More Suitable Protein Toxins and/or Their mRNA A protein toxin (or toxins) is expressed as a fusion with the capsid protein. The fusion protein then assembles into capsid carrying the toxin(s). These capsids present in the plant tissue exert an antifeeding effect on insects attaching the plant.

EXAMPLE 10

Expression of HaSV in Other Delivery Vectors

Materials & Methods (as indicated in earlier Examples)

Constructs similar to those for plant expression are introduced into yeast or bacteria by standard techniques. Virus particles are assembled for either fully infectious virus or any of the modified or biologically contained forms described in Example 9. Microbes produced in suitable fermentation or culture facilities and carrying such forms of the virus are then delivered to the crop by spraying. The microbial cell wall provides extra protection for the virus particles produced within the microbe.

Well established techniques exist for culture and transformation of yeast (Ausubel, F. M. et al. (eds) Current Protocols in Molecular Biology. J. Wiley & Sons, NY, 1989). An example of a yeast expression vector is pBM272, which contains the URA3 selectable marker (Johnston, M. & Davies, R. W. Mol. Cell. Biol. 4, 1440–8, (1984); Stone, D. & Craig, E. Mol. Cell. Biol. 10, 1622–32 (1990). Another example of an expression vector is pRJ28, carrying the Trp1 and Leu2 selectable markers.

Yeast has recently been shown to support replication of RNA replicons derived from a plant RNA virus, brome mosaic virus (Janda, M. & Ahlquist, P. Cell 72, 961–70 (1993). Since the BMV replicase is distantly related to that of HaSV, and the two viruses are likely to replicate by similar strategies within cells, yeast cells probably contain all the cellular factors required for HaSV to generate infectious virus.

For bacteria, suitable expression vectors have been described above.

EXAMPLE 11

The Transvirus Approach for Insect Pest Control: Making Transgenic Plants Expressing HASV 1. Vector Construction A special binary vector was constructed for transforming plants with the HaSV genome. This vector is based on pART27 (A. Gleave (1992) Plant Mol. Biol.20, 1203–1207), which was modified to (1) carry an alternative origin of replication for the host *Agrobacterium tumefaciens* and (2) incorporate restriction sites in the multiple cloning site for restriction enzymes Asc I and Pac I which recognise rare (8 bp) sequences.

For engineering the multiple cloning site, pART27 was cut with SpeI and NotI. Ten picomoles of each of the two oligos whose sequence follows (TOP and BOTTOM) were annealed in 10 microlitres of water (heated to 80° C. for 2 min and allowed to cool slowly to room temperature). The sticky ends on these annealed oligonucleotides allowed the insert to be cloned into pART27 (giving pART27mod) as described in Example No. 3 and 9.

Sequence of oligonucleotide:

(SEQ ID NO: 54)
TOP:     5'-GGCCGCTTAATTAAGGATCCGGCGCGCCA-3'

(SEQ ID NO: 55)
BOTTOM: 3'-CGAATTAATTCCTAGGCCGCGCGGTGATC-5

(The PacI recognition sequence is TTAATTAA, SEQ ID NO: 56 and that for AscI is GGCGCGCC, SEQ ID NO: 57). A 4 kbp SalI fragment from plasmid pART27mod (containing the right border, Iacz marker (+multiple cloning site)nptII gene for kanamycin resistance under control of the nos promoter and polyadenylation signal and the left border) was cloned into the 13 kbp vector pKT231 linearised with XhoI. Plasmid pKT231 carries the IncQ origin of replication for the host *Agrobacterium tumefaciens* and a resistance (marker) gene for streptomycin/spectinomycin. (Bagdasarian, M. & Timmis, K. N. (1982) Curr. Topics Microbiol. Immunol. 96, 46–67). These two fragments were ligated using standard protocols (eg in Example No 3) and transformed into *E. coli* strain DH5α using standard protocols (eg in Example No 3). The resultant plasmid was named pJDML1.

2. Cloning HaSV Genes into Transfer Plasmid

Construction of Transfer Vectors with HaSV Genes

Before the HaSV gene cassettes could be cloned into binary transfer vectors pART27 mod or pJDML1, they were re-cloned into the vector plasmid pBJ33 to provide flanking AscI and PacI sites. Plasmid pBJ33 (provided by Bart Janssen) is based on pBC SK(+) supplied by Stratagene), but with a multiple cloning site modified to contain the following sites:

SacI/PacI/AscI/SacII/XbaI/SpeI/BamHI/PstI/EcoRI/EcoRV/HindIII/ClaI/SalI/XhoI/Ap aI/PacI/AscI/KpnI.

The cDNA fragment corresponding to complete HaSV RNA 1 behind the 35S promoter and terminating in the hairpin cassette ribozyme and the CaMV polyadenylation signal fragment (approx 6 kpb in total) was excised from plasmid pDHStuR1HC (Example 9) with EcoRI and cloned into EcoRI-cut vector pBJ33 to give plasmid pBJ33R1HC. Similarly, the cDNA fragment corresponding to complete HaSV RNA 2 behind the 35S promoter and terminating in the hairpin cassette ribozyme and the CaMV polyadenylation signal fragment (approx 3.3 kbp in total) was excised from plasmid pDHStuR2HC (Example 9) as two fragments, one (covering the 35S promoter and the first 500 bp of the RNA 2 sequence) of about 1kbp with EcoRI and R5rII and the second (covering the remainder of the RNA 2 sequence, the ribozyme and the polyadenylation signal) of about 2.3 kbp with RerII and HindIII. These two fragments were simultaneously ligated into EcoRI and HindIII-cut vector pBJ33 to give plasmid pBJ33R2HC.

A 1.9 kbp fragment comprising the 5' 1.7 kbp of the HaSV capsid gene, together with the polyadenylation fragment, were excised from expression plasmid pDHVCAPB (described in Example 5) as a Eco RI-KpnI fragment and cloned into pTZ19U (pharmacia) cut with EcoRI and KpnI, giving pTZ19UEVCAPB., This portion of the HaSV capsid gene expression cassette was then re-excised as a HindIII-EcoRI fragment and cloned into PBJ33 cut with these enzymes. This plasmid (pBJ33EVCAPB) was then linearized with EcoRI and the ca. 800 bp EcoRI fragment from pDHVCAPB carrying the 35S promoter and the 5' 250 bp of the capsid gene inserted, followed by screening for orientation. The resulting plasmid carrying the reassembled complete capsid gene expression cassette was named pBJ33VCAPB.

Assembling Binary Plasmids

The RNA 1 expression cassette was excised from plasmid pBJ33R1HC with Asci and Paci and cloned into pART27 mod cut with AscI and Paci to give pMLR1. The RNA 2 expression cassette was also cloned as an AscI-PacI fragment into pJDML1 cut with AscI and PacI to give pJDMLR2.

The capsid protein gene cassette was excised from pBJ33 VCAPB with PacI and cloned into plasmid pMLR1 cut with PacI. Resulting plasmids were screened for orientation and the plasmid with the capsid gene and RNA1 in the same orientation was named pMLR1V. The complete fragment carrying the HaSV capsid gene and RNA 1 expression cassettes in pMLR1V was excised with AscI and cloned into pJDMLR2 linearised with AscI to give pHaSV1 (29 kpb). This plasmid carries the HaSV capsid gene expression cassette and the HaSV RNA 1 and RNA 2 expression cassettes in this order and all in the same orientation. The kanamycin resistance gene is located upstream of the capsid gene and in the opposite orientation.

kanamycin. After transfer of regenerating shoots for further selection on kanamycin medium, kanamycin-resistant roots were selected and then tissue from these plants used to verify HaSV gene expression. The numbers of plants selected are shown in the table above for each of the constructs.

4. Western, Northern and Southern Blotting on Transgenic Plants

For western blots: A small amount (0.1 g) of fresh leaf material from each plant was extracted by grinding in 0.2 ml of plant extraction buffer (0.2M NaCl, 0.1M Tes, pH 7.65, 1 mM PMSF, 2% b-mercaptoethanol, 1 mM EDTA). After centrifugation to pellet plant debris the supernatant was collected and 10 µl aliquots run on a SDS-gel for blotting and immuno-analysis with antibody against HaSV as described in Example 1. The results for the first plants assayed are given in Table 3.

For Northern blots: Total leaf RNA was extracted from 0.15 g of fresh leaf material. The leaf material was ground under liquid nitrogen to a powder and then extracted by further grinding in 0.45 ml NTES buffer (0.1M NaCl, 10 mM Tris-HCl pH 8.0, 1 mM EDTA, 0.1% SDS) plus 0.45 ml Tris pH8.0-saturated phenol/chloroform. The slurry was vortexed, centrifuged for 3 min and the aqueous phase mixed with 1 volume of isopropanol to precipitate RNA and DNA. After resuspending the pellet in 0.1 ml water, 1 volume of 4M LiCl was added and the mix stood on ice overnight before centrifugation to pellet RNA. The RNA was then analysed by gel electrophoresis according to the methods in Examples 1 and 2. HaSV specific RNAs were detected by Northern blottings as described in Example 2 and by using riboprobes made to detect the 3'-terminal 1000 nucleotides of each of RNA 1 and 2, made using the Promega Riboprobe kit and used as specified by the supplier.

For Southern blots: to detect HaSV genes in plant genomic DNA.

To recover plant genomic DNA, the supernatant from LiCl precipitation (above) was mixed with 2 volumes of ethanol. The pellet was redissolved and the DNA cut with BamHI before analysis on agarose gels and transfer to nylon membrane as described by Sambrook et al (1989) and by the manufacturer (Zetaprobe/BioRad). HaSV-specific bands were detected described above.

Table of constructs generated:

| Vector | Insert(s) | Name | # Plants (independent transformants) | Comments |
|---|---|---|---|---|
| pART27mod | RNA 1 | pMLR1 | 15 | control |
| pJDML1 | R1 + R2 + CAP | pHaSV1 | 30 | complete virus |
| pART27mod | R1 + CAP | pMLR1V | 15 | subvirus |
| pJDML1 | R1 + CAP | pJDMLR1V | 30 | subvirus |
| pART27mod | RNA2 | pMLR2 | 15 | control |
| pJDML1 | RNA2 | pJDMLR2 | 15 | control |
| pART27mod | CAP | pMLVF | 15 | control |

(CAP = HaSV capsid gene)

3. Plant Transformation and Regeneration

Binary transfer vectors (above) were transformed into *Agrobacterium tumefaciens* strain LBA4404 by electroporation (Lin, J. J. (1994) FOCUS 16,18–19; Lin, J. J. (1994) Plant Science 101, 11–15). Leaf discs from *Nicotiana tabacum* grown under sterile conditions were transformed using cocultivation with transformed *A. tumefaciens* (Horsch, R. B. et al. (1984) Science 23, 496–498; Horsch, R. B. et al. (1988) Plant Molecular Biology Manual A5;1–9; as modified by Lisa Molvig (pers. comm.)) and grown on 5. Bioassays on Leaf Material Two small leaves (2–3 cm in length) were selected from each transformed plant selected, and placed in petri dishes containing 1.5% agarose in water. Three to 8 neonate larvae were placed in each petri dish and observed for 3 days. At the end of this time, larvae were weighed and then total RNA extracted as described in Example 1. The extent of leaf damage was quantified by measuring the area of leaf consumed by each group of larvae over the three days of the assay (see Table 3).

TABLE 3

Preliminary bioassay of HaSV transgenic plants
Three to 8 larvae were placed on a small leaf (from a newly regenerated plant) in a petri dish with no provision of fresh food, after 3 days, larvae were sacrificed and northern blotted; also, protein extracted from leaves of the plants were western blotted using anti-HaSV antisera.

| Plant | Transformation Plasmid | Western Blot for HaSV capsid protein in plant (+/−) | Northern blot for HaSV RNA in plant | Larval Weight (mg) | Damage ($mm^2$ consumed/ larvae) |
|---|---|---|---|---|---|
| Negative Controls | | − | — | 2.1 − 2.7 ± 0.8* | 61 |
| 1.1 (subvirus) (RNA1 = p 71) | pJDMLR1V | + | | 1.1 ± 0.2 | 29 |
| 3.2 (whole virus) | pHaSV1 | + | | 1.0 ± 0.4 | 38 |
| 3.4 (whole virus) | pHaSV1 | + | | 1.2 ± 0.4 | 32 |

*Diet was limiting (ran out of food) in some cases

TABLE 4

Further bioassay of HaSV transgenic plants
Four - 6 individual larvae were fed leaf disc (50 $mm^2$) from control or transgenic plants at one disc each per day for 4 days, before transferred to artificial diet for a further 3 days. RNA was then extracted from the larvae and Northern blotting with HaSV-specific probes used to verify the presence of HaSV in the larvae.

| Plant | Transformed with | Western blot for HaSV capsid protein in plants (+/−) | Mean larval weight (mg) |
|---|---|---|---|
| negative control | | − | 12.4 |
| positive control (leaf + HaSV) | | − | 0.1 |
| 3.2 | pHaSV1 | + | 0.9 |
| 3.10 | pHaSV1 | + | 4.8 |
| 3.11 | pHaSV1 | + | 8.2 |

Efficacy of HaSV as Atransvirus in Plants

Factors affecting the efficacy of HaSV are the viral dose required, the expression levels achieved in plants and the leaf damage observed. These need to be considered separately at this stage due to uncertainty about the efficiency of HaSV assembly in plants and because larvae will continue feeding for about one day after receiving a toxic dose of HaSV.

I. Dose of Virus

Infection with HaSV requires neonate larvae to eat up to 10 000 particles. Assuming that transgenic plants make only 1 particle per cell, this means the larvae must consume up to 10 000 leaf cells.

Since a small tobacco leaf contains about one million cells, larvae could acquire a toxic dose by consuming just 1% of the leaf This dose would correspond to as little as 0.000 000 5% of the soluble protein in these cells ($330 \times 10^{-13}$ g of HaSV per leaf in $7 \times 10^{-13}$ g soluble plant protein per leaf).

II. Expression Levels

Assuming standard levels of 1% expression and complete incorporation into virus particles, there should be about $10^8$ particles per cell ($7 \times 10^{-9}$ g of protein per cell over $330 \times 10^{-19}$ g per HaSV particle).

However, at present only part of this protein is likely to form infectious virus. If 1% does, then there would be $10^6$ particles per cell, well above the toxic dose.

Initial results from Western blots suggest current expression at least exceed 01.1% of soluble cell protein. Processing of the precursor protein appears to occur to a variable extent, suggesting that particle assembly has also occurred.

The dose of infectious virus delivered by transgenic plants must be quantified by appropriately standardised bioassays.

Optimisation of the infectious virus level will be achieved by improving virus assembly rather than just boosting expression of components—this represents a fundamental difference to the situation with toxins like Bt.

III. Leaf Damage

While as little as 1% of the leaf (and more likely far less) may be sufficient to deliver a toxic dose of HaSV, larvae will keep feeding for a limited period after becoming infected. This makes it necessary to determine the extent of leaf damage empirically.

Our initial observations were that plants making detectable levels of HaSV capsids showed reduced susceptibility to larval feeding; this has not been quantified yet, and the assay was a severe one.

Consumption of leaf material by infected larvae may be estimated indirectly using our data on larval growth and frass production, which are approximately equal. Since neonate frass production is too low to quantify, the data were obtained from 4-day old larvae. These produce 30 mg of frass over 7 days, compared to 400 mg for uninfected controls. Neonate growth and frass production may be estimated at 10% of this figure.

Assuming that 1 mg growth or frass-3 mg leaf material, an infected neonate will consume about 5% of a small tobacco leaf (20 mg of a total fresh weight of 350 mg) over seven days compared to over 60% for an uninfected control (240 mg of 350 g).

Biosafety Considerations

It is believed that the approach of controlling pests by making an insect virus in transgenic plants is not dangerous to the environment. This is despite our very tentative observation that some HaSV replication is observed in protoplasts. There has been widespread debate recently concerning the safety of protecting crops against plant viruses by inserting transgenes expressing viral proteins into the plants. Falk, B. W. and Bruening, G., 1994 (Science 263, 1395–1396) identified 3 possible mechanisms which might result in the appearance of novel viruses. These mechanisms are transencapsidation, phenotypic mixing and heterologous recombination.

Transencapsidation or phenotypic mixing involving HaSV plants are not likely to cause problem because:
   the HaSV capsid gene is not acquired by the transencapsidated plant virus genome.
   such an event would yield a virus only capable of "infecting" heliothis larvae, which are not efficient vectors to enlarge the host range of a plant virus.

Heterologous recombination is not perceived as a problem because
   It requires substantial sequence similarity and has only been observed within plant virus families. The tetraviruses are an insect specific virus family showing minimal sequence homology to any plant RNA virus.

Even if interfamily recombination occurred, this would generate a combination of genes for which there is no precedent in either viruses infecting both plants and insects or plants alone (HaSV would not encounter any other insect-specific virus in transgenic plants); these viruses require functions and genes which it is physiologically impossible to generate from such recombinations.

This is because:
1) the four families of insect-vectored plant viruses which replicate in their vectors are much more complicated than HaSV, both in particle structure and in genome organisation. All these viruses have negative-stranded or double-stranded RNA genomes and at least 4–5 genes.
2) even the four families of insect-vectored plant viruses which circulate in their vectors without replicating are more complicated than HaSV in genome organisation, number of genes and expression strategies; although they have (+)-stranded RNA genomes, they are found in a different virus superfamily, with replicases essentially unrelated to that of HaSV. Their capsids are unrelated to that of HaSV and are not uncoated in the insect vectors.

All the simple, (+) stranded plant viruses which more closely resemble HaSV (which include some passively transmitted by sucking insects, ie without entering the vector).
- must have a plant cell-cell movement protein for which there is no direct functional equivalent in HaSV.
- have replicases specifically adapted to plant cells, and with minimal overall amino acid sequence homology (under 25%) to that of HaSV.
- have capsids specifically adapted for long range movement in plants and vectoring by insects without entering these or being uncoated in them; these capsid genes have no detectable sequence homology to HaSV or other insect capsids.

Sub-Virus
Containment Strategies

Although the expression of HaSV in transgenic plants is not considered to present any environmental hazard, some HaSV constructs we have used to engineer plants contain essentially suicidal versions of both RNA 1 and 2. This has been achieved for RNA 2 by deleting all sequences apart from those directly encoding the capsid protein and demonstrating that effective virus can still be assembled in plant cells. This alone will prevent transmission of progeny virus, since infected larvae respond as though they had ingested normal virus, but are unable to produce infectious progeny virus. The virus produced in plants therefore only infects targets feeding on the crop plant and can neither infect other species nor persist in the environment.

It is also possible to engineer subviral forms of RNA 1 which retain efficacy but do not allow production of viable progeny virus. (For example, remove replication signals from RNA 1).

1) Results

The subvirus approached was tested using the following combination of plasmids transiently expressed in protoplast and followed by bioassay as described above.

| Plasmids | | Bioassays weights (mg) of larvae fed on protoplast extracts | HaSV RNAs 1 & 2 detected by Northern blotting of RNA extracted from larvae |
|---|---|---|---|
| 1. | pDHStuR1HC + pDHVCAPB | 29 ± 15 | + |
| 2. | pDHStuRI HDV + pHV CAPB | 57 ± 25 | (−) |
| 3. | Control: (diet only/diet + protoplasts | 85 ± 15 | − |
| 4. | pDHStuR1 HC + pDHStuR2 HC + pDHVCAPB | 33 ± 28 | + |
| 5. | pDHStuR1 HDV + pDHStuR2 HDV + pDHVCAPB | 64 ± 22 | − | ii) RNA extraction from larvae showed (a) that larvae fed protoplasts transfected with pDHStuR1HC+pDHStuR2HC+DHVCAPB contained both RNA1 and 2 of HaSV in intact form.

(b) that larvae fed protoplasts transfected with pDHStuR1HC+DHV CAPB (subvirus) contained a very small amount of intact HaSV RNA1 and a considerably greater amount of degraded RNA1.

(c) that larvae fed protoplasts transfected with pDHStuR1HDV+pDHStuR2HDV+pDHVCAPB contained no HaSVRNA with one exception.

(d) that larvae fed protoplasts transfected with pDHStuR1 HDV+pDHVCAPB contained no HaSV RNA.

CONCLUSIONS

The HC (HaSV expression) constructs with the hairpin cassette ribozyme give infectious particles with both RNAs; the HDV expression constructs do not under these conditions.

That the subvirus approach results in RNA1 replicating in larvae but this RNA is degraded because it cannot be encapsidated due to missing replicatable RNA2.

That subvirus approach gives stunting as effectively as does the complete virus approach under these conditions.

What is claimed is:

1. An isolated nucleic acid molecule comprising a nucleotide sequence selected from the group consisting of:
   a) the nucleotide sequence set forth in SEQ ID NO:39;
   b) the nucleotide sequence set forth in SEQ ID NO:47;
   c) a nucleotide sequence encoding the amino acid sequence of SEQ ID NO: 40; and
   d) a nucleotide sequence encoding the amino acid sequence of SEQ ID NO: 50.

2. An expression or transfer vector comprising at least one molecule of claim 1.

3. A vector comprising the molecule of claim 1 that replicates, expresses or encapsidates said nucleic acid molecule in a plant cell.

4. A vector comprising the molecule of claim 1 that transfers said nucleic acid molecule to a plant cell.

5. The vector of claim 3 or claim 4 which comprises a ribozyme for facilitating replication, expression or encapsidation of the nucleic acid molecule.

6. The vector of claim 5 wherein said ribozyme has a sequence selected from one of the following sequences:

(SEQ ID No: 5)
5' CCATCGATGCCGGACTGGTATCCCAGGGGG (SEQ ID No: 6)
5' CCATCGATGCCGGACTGGTATCCCGAGGGAC (SEQ ID No: 7)
5' CCATCGATGATCCAGCCTCCTCGCGGCGCCGGATGGGCA (SEQ ID No: 8)
5' GCTCTAGATCCATTCGCCATCCGAAGATGCCCATCCGGC (SEQ ID No: 9)
5' CCATCGATTTATGCCGAGAAGGTAACCAGAGAAACACAC (SEQ ID No: 10)
5' GCTCTAGACCAGGTAATATACCACAACGTGTGTTTCTCT

7. An expression or transfer vector, wherein the vector is selected from the group consisting of: pDHVR1, pDHVr1RZ, pDHVR2, pDHVR2RZ, p17V71, p17E71, pV71, pBacHVR1, pBacHVR1RZ, pBacHUR2, pBacHVR2RZ, pHSPR1, pHSPR1RZ, pHSPR2, pHSPR2rZ, pSR1(E3)A, pSR1(E3)B, pSR2A, pSR2B, pSXR2P70, pBHVR1B, pBHVR2B, pSR2P70, pT7T2P71, pBSKSE3, pBSR15, pBSR25p, pSR25, and phr236P70.

8. A host cell comprising the vector of claim 2, wherein the host cell is a plant cell.

9. A method of controlling insect attack of a plant comprising inserting into the plant a first nucleic acid molecule selected from the group consisting of:
   a) the nucleotide sequence set forth in SEQ ID NO:39; and
   b) a nucleotide sequence encoding the amino acid sequence of SEQ ID NO: 40,
and a second nucleic acid molecule selected from the group consisting of:
   c) the nucleotide sequence set forth in SEQ ID NO:47; and
   d) a nucleotide sequence encoding the amino acid sequence of SEQ ID NO: 50,
wherein said first nucleic acid molecule and said second nucleic acid molecule further comprise a ribozyme for facilitating replication, expression or encapsidation of said nucleic acid molecule and wherein the plant produces HaSV viral particles, and insects feeding on the plant are deleteriously effected.

10. A transgenic plant comprising a first nucleic acid molecule selected from the group consisting of:
   a) the nucleotide sequence set forth in SEQ ID NO:39; and
   b) a nucleotide sequence encoding the amino acid sequence of SEQ ID NO: 40,
and a second nucleic acid molecule selected from the group consisting of:
   c) the nucleotide sequence set forth in SEQ ID NO:47; and
   d) a nucleotide sequence encoding the amino acid sequence of SEQ ID NO: 50,
wherein said first nucleic acid molecule and said second nucleic acid molecule further comprise a ribozyme for facilitating replication, expression or encapsidation of said nucleic acid molecule and wherein the plant produces HaSV viral particles, and insects feeding on the plant are deleteriously effected.

* * * * *

SEQUENCE LISTING (1) GENERAL INFORMATION:

(iii) NUMBER OF SEQUENCES: 57

(2) INFORMATION FOR SEQ ID NO: 1:

(i) SEQUENCE CHARACTERISTICS:
       (A) LENGTH: 13 base pairs
       (B) TYPE: nucleic acid
       (C) STRANDEDNESS: unknown
       (D) TOPOLOGY: unknown (ii) MOLECULE TYPE: DNA (xi) SEQUENCE DESCRIPTION: SEQ ID NO: 1:

GGATCCACAG NNN                                      13

(2) INFORMATION FOR SEQ ID NO: 2:

(i) SEQUENCE CHARACTERISTICS:
       (A) LENGTH: 28 base pairs
       (B) TYPE: nucleic acid
       (C) STRANDEDNESS: unknown
       (D) TOPOLOGY: unknown (ii) MOLECULE TYPE: DNA (xi) SEQUENCE DESCRIPTION: SEQ ID NO: 2:

ATGGGCGATG CCGGCGTCGC GTTCACAG                      28

(2) INFORMATION FOR SEQ ID NO: 3:

(i) SEQUENCE CHARACTERISTICS:
       (A) LENGTH: 27 base pairs
       (B) TYPE: nucleic acid
       (C) STRANDEDNESS: unknown
       (D) TOPOLOGY: unknown (ii) MOLECULE TYPE: DNA (xi) SEQUENCE DESCRIPTION: SEQ ID NO: 3:

ATGGAGGATG CTGGAGTGGC GTCACAG                       27

(2) INFORMATION FOR SEQ ID NO: 4:

(i) SEQUENCE CHARACTERISTICS:
       (A) LENGTH: 27 base pairs
       (B) TYPE: nucleic acid
       (C) STRANDEDNESS: unknown
       (D) TOPOLOGY: unknown (ii) MOLECULE TYPE: DNA (xi) SEQUENCE DESCRIPTION: SEQ ID NO: 4:

ATGAGCGAGG CCGGCGTCGC GTCACAG                       27

(2) INFORMATION FOR SEQ ID NO: 5:

(i) SEQUENCE CHARACTERISTICS:
       (A) LENGTH: 30 base pairs
       (B) TYPE: nucleic acid
       (C) STRANDEDNESS: unknown
       (D) TOPOLOGY: unknown (ii) MOLECULE TYPE: DNA (xi) SEQUENCE DESCRIPTION: SEQ ID NO: 5:

-continued

CCATCGATGC CGGACTGGTA TCCCAGGGGG                          30

(2) INFORMATION FOR SEQ ID NO: 6:

(i) SEQUENCE CHARACTERISTICS:
        (A) LENGTH: 31 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 6:

CCATCGATGC CGGACTGGTA TCCCGAGGGA C                         31

(2) INFORMATION FOR SEQ ID NO: 7:

(i) SEQUENCE CHARACTERISTICS:
        (A) LENGTH: 39 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 7:

CCATCGATGA TCCAGCCTCC TCGCGGCGCC GGATGGGCA                 39

(2) INFORMATION FOR SEQ ID NO: 8:

(i) SEQUENCE CHARACTERISTICS:
        (A) LENGTH: 39 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 8:

GCTCTAGATC CATTCGCCAT CCGAAGATGC CCATCCGGC                 39

(2) INFORMATION FOR SEQ ID NO: 9:

(i) SEQUENCE CHARACTERISTICS:
        (A) LENGTH: 39 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 9:

CCATCGATTT ATGCCGAGAA GGTAACCAGA GAAACACAC                 39

(2) INFORMATION FOR SEQ ID NO: 10:

(i) SEQUENCE CHARACTERISTICS:
        (A) LENGTH: 39 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 10:

GCTCTAGACC AGGTAATATA CCACAACGTG TGTTTCTCT                 39

(2) INFORMATION FOR SEQ ID NO: 11:

(i) SEQUENCE CHARACTERISTICS:
        (A) LENGTH: 45 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 11:

```
GGGGGGAATT CATTTAGGTG ACACTATAGT TCTGCCTCCC CGGAC          45
```

(2) INFORMATION FOR SEQ ID NO: 12:

(i) SEQUENCE CHARACTERISTICS:
        (A) LENGTH: 27 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 12:

```
GGGGGGATCC TGGTATCCCA GGGGGGC                              27
```

(2) INFORMATION FOR SEQ ID NO: 13:

(i) SEQUENCE CHARACTERISTICS:
        (A) LENGTH: 28 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 13:

```
CCGGAAGCTT GTTTTTCTTT CTTTACCA                             28
```

(2) INFORMATION FOR SEQ ID NO: 14:

(i) SEQUENCE CHARACTERISTICS:
        (A) LENGTH: 46 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 14:

```
GGGGGATCCG ATGGTATCCC GAGGGACGCT CAGCAGGTGG CATAGG         46
```

(2) INFORMATION FOR SEQ ID NO: 15:

(i) SEQUENCE CHARACTERISTICS:
        (A) LENGTH: 52 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 15:

```
AAATAATTTT GTTACTTTAG AAGGAGATAT ACATATGAGC GAGCGAGCAC AC  52
```

(2) INFORMATION FOR SEQ ID NO: 16:

(i) SEQUENCE CHARACTERISTICS:
        (A) LENGTH: 55 base pairs

```
            (B) TYPE: nucleic acid
            (C) STRANDEDNESS: unknown
            (D) TOPOLOGY: unknown (ii) MOLECULE TYPE: DNA (xi) SEQUENCE DESCRIPTION: SEQ ID NO: 16:

AAATAATTTT GTTTAACCTT AAGAAGGAGA TCTACATATG CTGGAGTGGC GTCAC            55

(2) INFORMATION FOR SEQ ID NO: 17:

(i) SEQUENCE CHARACTERISTICS:
            (A) LENGTH: 30 base pairs
            (B) TYPE: nucleic acid
            (C) STRANDEDNESS: unknown
            (D) TOPOLOGY: unknown (ii) MOLECULE TYPE: DNA (xi) SEQUENCE DESCRIPTION: SEQ ID NO: 17:

GGAGATCTAC ATATGGGAGA TGCTGGAGTG                                        30

(2) INFORMATION FOR SEQ ID NO: 18:

(i) SEQUENCE CHARACTERISTICS:
            (A) LENGTH: 17 base pairs
            (B) TYPE: nucleic acid
            (C) STRANDEDNESS: unknown
            (D) TOPOLOGY: unknown (ii) MOLECULE TYPE: DNA (xi) SEQUENCE DESCRIPTION: SEQ ID NO: 18:

GTAGCGAACG TCGAGAA                                                      17

(2) INFORMATION FOR SEQ ID NO: 19:

(i) SEQUENCE CHARACTERISTICS:
            (A) LENGTH: 31 base pairs
            (B) TYPE: nucleic acid
            (C) STRANDEDNESS: unknown
            (D) TOPOLOGY: unknown (ii) MOLECULE TYPE: DNA (xi) SEQUENCE DESCRIPTION: SEQ ID NO: 19:

GGGGGATCCT CAGTTGTCAG TGGCGGGGTA G                                      31

(2) INFORMATION FOR SEQ ID NO: 20:

(i) SEQUENCE CHARACTERISTICS:
            (A) LENGTH: 28 base pairs
            (B) TYPE: nucleic acid
            (C) STRANDEDNESS: unknown
            (D) TOPOLOGY: unknown (ii) MOLECULE TYPE: DNA (xi) SEQUENCE DESCRIPTION: SEQ ID NO: 20:

GGGGATCCCT AATTGGCACG AGCGGCGC                                          28

(2) INFORMATION FOR SEQ ID NO: 21:

(i) SEQUENCE CHARACTERISTICS:
            (A) LENGTH: 29 base pairs
            (B) TYPE: nucleic acid
            (C) STRANDEDNESS: unknown
            (D) TOPOLOGY: unknown
```

```
        (ii) MOLECULE TYPE: DNA (xi) SEQUENCE DESCRIPTION: SEQ ID NO: 21:

AATTACATAT GGCGGCCGCC GTTTCTGCC                                  29

(2) INFORMATION FOR SEQ ID NO: 22:

(i) SEQUENCE CHARACTERISTICS:
            (A) LENGTH: 29 base pairs
            (B) TYPE: nucleic acid
            (C) STRANDEDNESS: unknown
            (D) TOPOLOGY: unknown (ii) MOLECULE TYPE: DNA (xi) SEQUENCE DESCRIPTION: SEQ ID NO: 22:

AATTACATAT GTTCGCGGCC GCCGTTTCT                                  29

(2) INFORMATION FOR SEQ ID NO: 23:

(i) SEQUENCE CHARACTERISTICS:
            (A) LENGTH: 19 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO: 23:

Phe Ala Ala Ala Val Ser Ala Phe Ala Ala Asn Met Leu Ser Ser Val
1               5                   10                  15

Leu Lys Ser (2) INFORMATION FOR SEQ ID NO: 24:

(i) SEQUENCE CHARACTERISTICS:
            (A) LENGTH: 20 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO: 24:

Pro Thr Leu Val Asp Gln Gly Phe Trp Ile Gly Gly Gln Tyr Ala Leu
1               5                   10                  15

Thr Pro Thr Ser
            20

(2) INFORMATION FOR SEQ ID NO: 25:

(i) SEQUENCE CHARACTERISTICS:
            (A) LENGTH: 6 amino acids
            (B) TYPE: amino acid
            (C) STRANDEDNESS: unknown
            (D) TOPOLOGY: unknown (ii) MOLECULE TYPE: protein (xi) SEQUENCE DESCRIPTION: SEQ ID NO: 25:

Phe Ala Ala Ala Val Ser
1               5

(2) INFORMATION FOR SEQ ID NO: 26:

(i) SEQUENCE CHARACTERISTICS:
            (A) LENGTH: 23 base pairs
```

```
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 26:

GCGCCCCCUG GGAUACCAGG AUC                                              23

(2) INFORMATION FOR SEQ ID NO: 27:

(i) SEQUENCE CHARACTERISTICS:
        (A) LENGTH: 17 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 27:

TCAGCAGGTG GCATAGG                                                     17

(2) INFORMATION FOR SEQ ID NO: 28:

(i) SEQUENCE CHARACTERISTICS:
        (A) LENGTH: 32 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 6..32

(xi) SEQUENCE DESCRIPTION: SEQ ID NO: 28:

CCCAT ATG GGC GAT GCC GGC GTC GCG TCA CAG                              32
      Met Gly Asp Ala Gly Val Ala Ser Gln
       1               5

(2) INFORMATION FOR SEQ ID NO: 29:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO: 29:

Met Gly Asp Ala Gly Val Ala Ser Gln
 1               5

(2) INFORMATION FOR SEQ ID NO: 30:

(i) SEQUENCE CHARACTERISTICS:
        (A) LENGTH: 32 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 6..32

(xi) SEQUENCE DESCRIPTION: SEQ ID NO: 30:

CCCAT ATG AGC GAG GCC GGC GTC GCG TCA CAG                              32
```

```
        Met Ser Glu Ala Gly Val Ala Ser Gln
          1               5
```

(2) INFORMATION FOR SEQ ID NO: 31:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO: 31:

```
Met Ser Glu Ala Gly Val Ala Ser Gln
  1               5
```

(2) INFORMATION FOR SEQ ID NO: 32:

(i) SEQUENCE CHARACTERISTICS:
        (A) LENGTH: 27 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 1..27

(xi) SEQUENCE DESCRIPTION: SEQ ID NO: 32:

```
ATG GGA GAT GCT GGA GTG GCG TCA CAG                         27
Met Gly Asp Ala Gly Val Ala Ser Gln
  1               5
```

(2) INFORMATION FOR SEQ ID NO: 33:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO: 33:

```
Met Gly Asp Ala Gly Val Ala Ser Gln
  1               5
```

(2) INFORMATION FOR SEQ ID NO: 34:

(i) SEQUENCE CHARACTERISTICS:
        (A) LENGTH: 27 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 34:

```
GGGGGATCCC GCGGATTTAT GAGCGAG                               27
```

(2) INFORMATION FOR SEQ ID NO: 35:

(i) SEQUENCE CHARACTERISTICS:
        (A) LENGTH: 32 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 35:

GGGGGATCCC GCGGAGACAT GAGCGAGCAC AC                                    32

(2) INFORMATION FOR SEQ ID NO: 36:

(i) SEQUENCE CHARACTERISTICS:
        (A) LENGTH: 34 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 36:

GGGGGATCCA GCGACATGAG AGATGCTGGA GTGG                                  34

(2) INFORMATION FOR SEQ ID NO: 37:

(i) SEQUENCE CHARACTERISTICS:
        (A) LENGTH: 34 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 37:

GGGGGATCCA GCGACATGAG AGATGCTGGA GTGG                                  34

(2) INFORMATION FOR SEQ ID NO: 38:

(i) SEQUENCE CHARACTERISTICS:
        (A) LENGTH: 26 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 38:

GGGGGATCCG TTCTGCCTCC CCGGAC                                           26

(2) INFORMATION FOR SEQ ID NO: 39:

(i) SEQUENCE CHARACTERISTICS:
        (A) LENGTH: 5312 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 37..5148

(xi) SEQUENCE DESCRIPTION: SEQ ID NO: 39:

```
GTTCTGCCTC CCCCGGACGG TAAATATAGG GGAACA ATG TAC GCG AAA GCG ACA        54
                                    Met Tyr Ala Lys Ala Thr
                                     1               5

GAC GTG GCG CGT GTC TAC GCC GCG GCA GAT GTC GCC TAC GCG AAC GTA       102
Asp Val Ala Arg Val Tyr Ala Ala Ala Asp Val Ala Tyr Ala Asn Val
             10                  15                  20

CTG CAG CAG AGA GCA GTC AAG TTG GAC TTC GCC CCG CCA CTG AAG GCA       150
Leu Gln Gln Arg Ala Val Lys Leu Asp Phe Ala Pro Pro Leu Lys Ala
         25                  30                  35
```

```
CTA GAA ACC CTC CAC AGA CTG TAC TAT CCG CTG CGC TTC AAA GGG GGC    198
Leu Glu Thr Leu His Arg Leu Tyr Tyr Pro Leu Arg Phe Lys Gly Gly
    40              45                  50

ACT TTA CCC CCG ACA CAA CAC CCG ATC CTG GCC GGG CAC CAA CGT GTC    246
Thr Leu Pro Pro Thr Gln His Pro Ile Leu Ala Gly His Gln Arg Val
55              60                  65                  70

GCA GAA GAG GTT CTG CAC AAT TTC GCC AGG GGA CGT AGC ACA GTG CTC    294
Ala Glu Glu Val Leu His Asn Phe Ala Arg Gly Arg Ser Thr Val Leu
                75                  80                  85

GAG ATA GGG CCG TCT CTG CAC AGC GCA CTT AAG CTA CAT GGG GCA CCG    342
Glu Ile Gly Pro Ser Leu His Ser Ala Leu Lys Leu His Gly Ala Pro
                    90                  95                  100

AAC GCC CCC GTC GCA GAC TAT CAC GGG TGC ACC AAG TAC GGC ACC CGC    390
Asn Ala Pro Val Ala Asp Tyr His Gly Cys Thr Lys Tyr Gly Thr Arg
            105                 110                 115

GAC GGC TCG CGA CAC ATT ACG GCC TTA GAG TCT AGA TCC GTC GCC ACA    438
Asp Gly Ser Arg His Ile Thr Ala Leu Glu Ser Arg Ser Val Ala Thr
120                 125                 130

GGC CGG CCC GAG TTC AAG GCC GAC GCC TCA CTG CTC GCC AAC GGC ATT    486
Gly Arg Pro Glu Phe Lys Ala Asp Ala Ser Leu Leu Ala Asn Gly Ile
135                 140                 145                 150

GCC TCC CGC ACC TTC TGC GTC GAC GGA GTC GGC TCT TGC GCG TTC AAA    534
Ala Ser Arg Thr Phe Cys Val Asp Gly Val Gly Ser Cys Ala Phe Lys
                155                 160                 165

TCG CGC GTT GGA ATT GCC AAT CAC TCC CTC TAT GAC GTG ACC CTA GAG    582
Ser Arg Val Gly Ile Ala Asn His Ser Leu Tyr Asp Val Thr Leu Glu
                    170                 175                 180

GAG CTG GCC AAT GCG TTT GAG AAC CAC GGA CTT CAC ATG GTC CGC GCG    630
Glu Leu Ala Asn Ala Phe Glu Asn His Gly Leu His Met Val Arg Ala
            185                 190                 195

TTC ATG CAC ATG CCA GAA GAG CTG CTC TAC ATG GAC AAC GTG GTT AAT    678
Phe Met His Met Pro Glu Glu Leu Leu Tyr Met Asp Asn Val Val Asn
200                 205                 210

GCC GAG CTC GGC TAC CGC TTC CAC GTT ATT GAA GAG CCT ATG GCT GTG    726
Ala Glu Leu Gly Tyr Arg Phe His Val Ile Glu Glu Pro Met Ala Val
215                 220                 225                 230

AAG GAC TGC GCA TTC CAG GGG GGG GAC CTC CGT CTC CAC TTC CCT GAG    774
Lys Asp Cys Ala Phe Gln Gly Gly Asp Leu Arg Leu His Phe Pro Glu
                235                 240                 245

TTG GAC TTC ATC AAC GAG AGC CAA GAG CGG CGC ATC GAG AGG CTG GCC    822
Leu Asp Phe Ile Asn Glu Ser Gln Glu Arg Arg Ile Glu Arg Leu Ala
                    250                 255                 260

GCC CGC GGC TCC TAC TCC AGA CGC GCC GTC ATT TTC TCC GGC GAC GAC    870
Ala Arg Gly Ser Tyr Ser Arg Arg Ala Val Ile Phe Ser Gly Asp Asp
            265                 270                 275

GAC TGG GGT GAT GCG TAC TTA CAC GAC TTC CAC ACA TGG CTC GCC TAC    918
Asp Trp Gly Asp Ala Tyr Leu His Asp Phe His Thr Trp Leu Ala Tyr
280                 285                 290

CTA CTG GTG AGG AAC TAC CCC ACT CCG TTT GGT TTC TCA CTC CAT ATA    966
Leu Leu Val Arg Asn Tyr Pro Thr Pro Phe Gly Phe Ser Leu His Ile
295                 300                 305                 310

GAA GTC CAG AGG CGC CAC GGC TCC AGC ATT GAG CTG CGC ATC ACT CGC    1014
Glu Val Gln Arg Arg His Gly Ser Ser Ile Glu Leu Arg Ile Thr Arg
                315                 320                 325

GCG CCA CCT GGA GAC CGC ATG CTG GCC GTC GTC CCA AGG ACG TCC CAA    1062
Ala Pro Pro Gly Asp Arg Met Leu Ala Val Val Pro Arg Thr Ser Gln
                    330                 335                 340

GGC CTC TGC AGA ATC CCA AAC ATC TTT TAT TAC GCC GAC GCG TCG GGC    1110
Gly Leu Cys Arg Ile Pro Asn Ile Phe Tyr Tyr Ala Asp Ala Ser Gly
            345                 350                 355
```

-continued

| | |
|---|---|
| ACT GAG CAT AAG ACC ATC CTT ACG TCA CAG CAC AAA GTC AAC ATG CTG<br>Thr Glu His Lys Thr Ile Leu Thr Ser Gln His Lys Val Asn Met Leu<br>360                     365                   370 | 1158 |
| CTC AAT TTT ATG CAA ACG CGT CCT GAG AAG GAA CTA GTC GAC ATG ACC<br>Leu Asn Phe Met Gln Thr Arg Pro Glu Lys Glu Leu Val Asp Met Thr<br>375                  380                385                390 | 1206 |
| GTC TTG ATG TCG TTC GCG CGC GCT AGG CTG CGC GCG ATC GTG GTC GCC<br>Val Leu Met Ser Phe Ala Arg Ala Arg Leu Arg Ala Ile Val Val Ala<br>                  395                400                405 | 1254 |
| TCA GAA GTC ACC GAG AGC TCC TGG AAC ATC TCA CCG GCT GAC CTG GTC<br>Ser Glu Val Thr Glu Ser Ser Trp Asn Ile Ser Pro Ala Asp Leu Val<br>            410                415                420 | 1302 |
| CGC ACT GTC GTG TCT CTT TAC GTC CTC CAC ATC ATC GAG CGC CGA AGG<br>Arg Thr Val Val Ser Leu Tyr Val Leu His Ile Ile Glu Arg Arg Arg<br>        425                430                435 | 1350 |
| GCT GCG GTC GCT GTC AAG ACC GCC AAG GAC GAC GTC TTT GGA GAG ACT<br>Ala Ala Val Ala Val Lys Thr Ala Lys Asp Asp Val Phe Gly Glu Thr<br>440                     445                   450 | 1398 |
| TCG TTC TGG GAG AGT CTC AAG CAC GTC TTG GGC TCC TGT TGC GGT CTG<br>Ser Phe Trp Glu Ser Leu Lys His Val Leu Gly Ser Cys Cys Gly Leu<br>455                     460                465                470 | 1446 |
| CGC AAC CTC AAA GGC ACC GAC GTC GTC TTT ACT AAG CGC GTC GTC GAT<br>Arg Asn Leu Lys Gly Thr Asp Val Val Phe Thr Lys Arg Val Val Asp<br>                  475                480                485 | 1494 |
| AAG TAC CGA GTC CAC TCG CTC GGA GAC ATA ATC TGC GAC GTC CGC CTG<br>Lys Tyr Arg Val His Ser Leu Gly Asp Ile Ile Cys Asp Val Arg Leu<br>            490                495                500 | 1542 |
| TCC CCT GAA CAG GTC GGC TTC CTG CCG TCC CGC GTA CCA CCT GCC CGC<br>Ser Pro Glu Gln Val Gly Phe Leu Pro Ser Arg Val Pro Pro Ala Arg<br>        505                510                515 | 1590 |
| GTC TTT CAC GAC AGG GAA GAG CTT GAG GTC CTT CGC GAA GCT GGC TGC<br>Val Phe His Asp Arg Glu Glu Leu Glu Val Leu Arg Glu Ala Gly Cys<br>520                     525                530 | 1638 |
| TAC AAC GAA CGT CCG GTA CCT TCC ACT CCT CCT GTG GAG GAG CCC CAA<br>Tyr Asn Glu Arg Pro Val Pro Ser Thr Pro Pro Val Glu Glu Pro Gln<br>535                     540                545                550 | 1686 |
| GGT TTC GAC GCC GAC TTG TGG CAC GCG ACC GCG GCC TCA CTC CCC GAG<br>Gly Phe Asp Ala Asp Leu Trp His Ala Thr Ala Ala Ser Leu Pro Glu<br>                  555                560                565 | 1734 |
| TAC CGC GCC ACC TTG CAG GCA GGT CTC AAC ACC GAC GTC AAG CAG CTC<br>Tyr Arg Ala Thr Leu Gln Ala Gly Leu Asn Thr Asp Val Lys Gln Leu<br>            570                575                580 | 1782 |
| AAG ATC ACC CTC GAG AAC GCC CTC AAG ACC ATC GAC GGG CTC ACC CTC<br>Lys Ile Thr Leu Glu Asn Ala Leu Lys Thr Ile Asp Gly Leu Thr Leu<br>        585                590                595 | 1830 |
| TCC CCA GTC AGA GGC CTC GAG ATG TAC GAG GGC CCG CCA GGC AGC GGC<br>Ser Pro Val Arg Gly Leu Glu Met Tyr Glu Gly Pro Pro Gly Ser Gly<br>600                     605                610 | 1878 |
| AAG ACG GGC ACC CTC ATC GCC GCC CTT GAG GCC GCG GGC GGT AAA GCA<br>Lys Thr Gly Thr Leu Ile Ala Ala Leu Glu Ala Ala Gly Gly Lys Ala<br>615                     620                625                630 | 1926 |
| CTT TAC GTG GCA CCC ACC AGA GAA CTG AGA GAG GCT ATG GAC CGG CGG<br>Leu Tyr Val Ala Pro Thr Arg Glu Leu Arg Glu Ala Met Asp Arg Arg<br>                  635                640                645 | 1974 |
| ATC AAA CCG CCG TCC GCC TCG GCT ACG CAA CAT GTC GCC CTT GCG ATT<br>Ile Lys Pro Pro Ser Ala Ser Ala Thr Gln His Val Ala Leu Ala Ile<br>            650                655                660 | 2022 |
| CTC CGT CGT GCC ACC GCC GAG GGC GCC CCT TTC GCT ACC GTG GTT ATC<br>Leu Arg Arg Ala Thr Ala Glu Gly Ala Pro Phe Ala Thr Val Val Ile | 2070 |

-continued

```
            665                 670                 675
GAC GAG TGC TTC ATG TTC CCG CTC GTG TAC GTC GCG ATC GTG CAC GCC      2118
Asp Glu Cys Phe Met Phe Pro Leu Val Tyr Val Ala Ile Val His Ala
        680                 685                 690

TTG TCC CCG AGC TCA CGA ATA GTC CTT GTA GGG GAC GTC CAC CAA ATC      2166
Leu Ser Pro Ser Ser Arg Ile Val Leu Val Gly Asp Val His Gln Ile
695                 700                 705                 710

GGG TTT ATA GAC TTC CAA GGC ACA AGC GCG AAC ATG CCG CTC GTT CGC      2214
Gly Phe Ile Asp Phe Gln Gly Thr Ser Ala Asn Met Pro Leu Val Arg
                715                 720                 725

GAC GTC GTT AAG CAG TGC CGT CGG CGC ACT TTC AAC CAA ACC AAG CGC      2262
Asp Val Val Lys Gln Cys Arg Arg Arg Thr Phe Asn Gln Thr Lys Arg
            730                 735                 740

TGT CCG GCC GAC GTC GTT GCC ACC ACG TTT TTC CAG AGC TTG TAC CCC      2310
Cys Pro Ala Asp Val Val Ala Thr Thr Phe Phe Gln Ser Leu Tyr Pro
                745                 750                 755

GGG TGC ACA ACC ACC TCA GGG TGC GTC GCA TCC ATC AGC CAC GTC GCC      2358
Gly Cys Thr Thr Thr Ser Gly Cys Val Ala Ser Ile Ser His Val Ala
760                 765                 770

CCA GAC TAC CGC AAC AGC CAG GCG CAA ACG CTC TGC TTC ACG CAG GAG      2406
Pro Asp Tyr Arg Asn Ser Gln Ala Gln Thr Leu Cys Phe Thr Gln Glu
775                 780                 785                 790

GAA AAG TCG CGC CAC GGG GCT GAG GGC GCG ATG ACT GTG CAC GAA GCG      2454
Glu Lys Ser Arg His Gly Ala Glu Gly Ala Met Thr Val His Glu Ala
                795                 800                 805

CAG GGA CGC ACT TTT GCG TCT GTC ATT CTG CAT TAC AAC GGC TCC ACA      2502
Gln Gly Arg Thr Phe Ala Ser Val Ile Leu His Tyr Asn Gly Ser Thr
            810                 815                 820

GCA GAG CAG AAG CTC CTC GCT GAG AAG TCG CAC CTT CTA GTC GGC ATC      2550
Ala Glu Gln Lys Leu Leu Ala Glu Lys Ser His Leu Leu Val Gly Ile
                825                 830                 835

ACG CGC CAC ACC AAC CAC CTG TAC ATC CGC GAC CCG ACA GGT GAC ATT      2598
Thr Arg His Thr Asn His Leu Tyr Ile Arg Asp Pro Thr Gly Asp Ile
840                 845                 850

GAG AGA CAA CTC AAC CAT AGC GCG AAA GCC GAG GTG TTT ACA GAC ATC      2646
Glu Arg Gln Leu Asn His Ser Ala Lys Ala Glu Val Phe Thr Asp Ile
855                 860                 865                 870

CCT GCA CCC CTG GAG ATC ACG ACT GTC AAA CCG AGT GAA GAG GTG CAG      2694
Pro Ala Pro Leu Glu Ile Thr Thr Val Lys Pro Ser Glu Glu Val Gln
                875                 880                 885

CGC AAC GAA GTG ATG GCA ACG ATA CCC CCG CAG AGT GCC ACG CCG CAC      2742
Arg Asn Glu Val Met Ala Thr Ile Pro Pro Gln Ser Ala Thr Pro His
            890                 895                 900

GGA GCA ATC CAT CTG CTC CGC AAG AAC TTC GGG GAC CAA CCC GAC TGT      2790
Gly Ala Ile His Leu Leu Arg Lys Asn Phe Gly Asp Gln Pro Asp Cys
                905                 910                 915

GGC TGT GTC GCT TTG GCG AAG ACC GGC TAC GAG GTG TTT GGC GGT CGT      2838
Gly Cys Val Ala Leu Ala Lys Thr Gly Tyr Glu Val Phe Gly Gly Arg
920                 925                 930

GCC AAA ATC AAC GTA GAG CTT GCC GAA CCC GAC GCG ACC CCG AAG CCG      2886
Ala Lys Ile Asn Val Glu Leu Ala Glu Pro Asp Ala Thr Pro Lys Pro
935                 940                 945                 950

CAT AGG GCG TTC CAG GAA GGG GTA CAG TGG GTC AAG GTC ACC AAC GCG      2934
His Arg Ala Phe Gln Glu Gly Val Gln Trp Val Lys Val Thr Asn Ala
                955                 960                 965

TCT AAC AAA CAC CAG GCG CTC CAG ACG CTG TTG TCC CGC TAC ACC AAG      2982
Ser Asn Lys His Gln Ala Leu Gln Thr Leu Leu Ser Arg Tyr Thr Lys
            970                 975                 980

CGA AGC GCT GAC CTG CCG CTA CAC GAA GCT AAG GAG GAC GTC AAA CGC      3030
```

```
                Arg Ser Ala Asp Leu Pro Leu His Glu Ala Lys Glu Asp Val Lys Arg
                        985                 990                 995

ATG CTA AAC TCG CTT GAC CGA CAT TGG GAC TGG ACT GTC ACT GAA GAC                3078
Met Leu Asn Ser Leu Asp Arg His Trp Asp Trp Thr Val Thr Glu Asp
    1000                1005                1010

GCC CGT GAC CGA GCT GTC TTC GAG ACC CAG CTC AAG TTC ACC CAA CGC                3126
Ala Arg Asp Arg Ala Val Phe Glu Thr Gln Leu Lys Phe Thr Gln Arg
1015                1020                1025                1030

GGC GGC ACC GTC GAA GAC CTG CTG GAG CCA GAC GAC CCC TAC ATC CGT                3174
Gly Gly Thr Val Glu Asp Leu Leu Glu Pro Asp Asp Pro Tyr Ile Arg
                1035                1040                1045

GAC ATA GAC TTC CTT ATG AAG ACT CAG CAG AAA GTG TCG CCC AAG CCG                3222
Asp Ile Asp Phe Leu Met Lys Thr Gln Gln Lys Val Ser Pro Lys Pro
            1050                1055                1060

ATC AAT ACG GGC AAG GTC GGG CAG GGG ATC GCC GCT CAC TCA AAG TCT                3270
Ile Asn Thr Gly Lys Val Gly Gln Gly Ile Ala Ala His Ser Lys Ser
        1065                1070                1075

CTC AAC TTC GTC CTC GCC GCT TGG ATA CGC ATA CTC GAG GAG ATA CTC                3318
Leu Asn Phe Val Leu Ala Ala Trp Ile Arg Ile Leu Glu Glu Ile Leu
    1080                1085                1090

CGT ACC GGG AGC CGC ACG GTC CGG TAC AGC AAC GGT CTC CCC GAC GAA                3366
Arg Thr Gly Ser Arg Thr Val Arg Tyr Ser Asn Gly Leu Pro Asp Glu
1095                1100                1105                1110

GAA GAG GCC ATG CTG CTC GAA GCG AAG ATC AAT CAA GTC CCA CAC GCC                3414
Glu Glu Ala Met Leu Leu Glu Ala Lys Ile Asn Gln Val Pro His Ala
                1115                1120                1125

ACG TTC GTC TCG GCG GAC TGG ACC GAG TTT GAC ACC GCC CAC AAT AAC                3462
Thr Phe Val Ser Ala Asp Trp Thr Glu Phe Asp Thr Ala His Asn Asn
            1130                1135                1140

ACG AGT GAG CTG CTC TTC GCC GCC CTT TTA GAG CGC ATC GGC ACG CCT                3510
Thr Ser Glu Leu Leu Phe Ala Ala Leu Leu Glu Arg Ile Gly Thr Pro
        1145                1150                1155

GCA GCT GCC GTT AAT CTA TTC AGA GAA CGG TGT GGG AAA CGC ACC TTG                3558
Ala Ala Ala Val Asn Leu Phe Arg Glu Arg Cys Gly Lys Arg Thr Leu
    1160                1165                1170

CGA GCG AAG GGT CTA GGC TCC GTT GAA GTC GAC GGT CTG CTC GAC TCC                3606
Arg Ala Lys Gly Leu Gly Ser Val Glu Val Asp Gly Leu Leu Asp Ser
1175                1180                1185                1190

GGC GCA GCT TGG ACG CCT TGC CGC AAC ACC ATC TTC TCT GCC GCC GTC                3654
Gly Ala Ala Trp Thr Pro Cys Arg Asn Thr Ile Phe Ser Ala Ala Val
                1195                1200                1205

ATG CTC ACG CTC TTC CGC GGC GTC AAG TTC GCA GCT TTC AAA GGC GAC                3702
Met Leu Thr Leu Phe Arg Gly Val Lys Phe Ala Ala Phe Lys Gly Asp
            1210                1215                1220

GAC TCG CTC CTC TGT GGT AGC CAT TAC CTC CGT TTC GAC GCT AGC CGC                3750
Asp Ser Leu Leu Cys Gly Ser His Tyr Leu Arg Phe Asp Ala Ser Arg
        1225                1230                1235

CTT CAC ATG GGC GAA CGT TAC AAG ACC AAA CAT TTG AAG GTC GAG GTG                3798
Leu His Met Gly Glu Arg Tyr Lys Thr Lys His Leu Lys Val Glu Val
    1240                1245                1250

CAG AAA ATC GTG CCG TAC ATC GGA CTC CTC GTC TCC GCT GAG CAG GTC                3846
Gln Lys Ile Val Pro Tyr Ile Gly Leu Leu Val Ser Ala Glu Gln Val
1255                1260                1265                1270

GTC CTC GAC CCT GTC AGG AGC GCT CTC AAG ATA TTT GGG CGC TGC TAC                3894
Val Leu Asp Pro Val Arg Ser Ala Leu Lys Ile Phe Gly Arg Cys Tyr
                1275                1280                1285

ACA AGC GAA CTC CTT TAC TCC AAG TAC GTG GAG GCT GTG AGA GAC ATC                3942
Thr Ser Glu Leu Leu Tyr Ser Lys Tyr Val Glu Ala Val Arg Asp Ile
            1290                1295                1300
```

```
ACC AAG GGC TGG AGT GAC GCC CGC TAC CAC AGC CTC CTG TGC CAC ATG      3990
Thr Lys Gly Trp Ser Asp Ala Arg Tyr His Ser Leu Leu Cys His Met
        1305                1310                1315

TCA GCA TGC TAC TAC AAT TAC GCG CCG GAG TCT GCG GCG TAC ATC ATC      4038
Ser Ala Cys Tyr Tyr Asn Tyr Ala Pro Glu Ser Ala Ala Tyr Ile Ile
1320                1325                1330

GAC GCT GTT GTT CGC TTT GGG CGC GGC GAC TTC CCG TTT GAA CAA CTG      4086
Asp Ala Val Val Arg Phe Gly Arg Gly Asp Phe Pro Phe Glu Gln Leu
1335                1340                1345                1350

CGC GTG GTG CGT GCC CAT GTG CAG GCA CCC GAC GCT TAC AGC AGC ACG      4134
Arg Val Val Arg Ala His Val Gln Ala Pro Asp Ala Tyr Ser Ser Thr
                1355                1360                1365

TAT CCG GCT AAC GTG CGC GCA TCG TGC CTT GAC CAC GTC TTC GAG CCC      4182
Tyr Pro Ala Asn Val Arg Ala Ser Cys Leu Asp His Val Phe Glu Pro
            1370                1375                1380

CGC CAG GCC GCC GCC CCG GCA GGT TTC GTT GCG ACA TGT GCG AAG CCG      4230
Arg Gln Ala Ala Ala Pro Ala Gly Phe Val Ala Thr Cys Ala Lys Pro
        1385                1390                1395

GAA ACG CCT TCT TCA CTT ACC GCG AAA GCT GGT GTT TCT GCG ACT ACA      4278
Glu Thr Pro Ser Ser Leu Thr Ala Lys Ala Gly Val Ser Ala Thr Thr
    1400                1405                1410

AGC CAC GTT GCG ACT GGG ACT GCG CCC CCG GAG TCT CCA TGG GAT GCA      4326
Ser His Val Ala Thr Gly Thr Ala Pro Pro Glu Ser Pro Trp Asp Ala
1415                1420                1425                1430

CCT GCA GCC AAC AGC TTT TCG GAG TTA TTG ACA CCG GAG ACC CCG TCC      4374
Pro Ala Ala Asn Ser Phe Ser Glu Leu Leu Thr Pro Glu Thr Pro Ser
                1435                1440                1445

ACA TCA TCC TCG CCG TCA TCG TCT TCA TCG GAC TCC TCT ACA TCG TGT      4422
Thr Ser Ser Ser Pro Ser Ser Ser Ser Ser Asp Ser Ser Thr Ser Cys
            1450                1455                1460

GGA AGG TCG CTC AGT GGT GGA GAC ACC GCA AGG ACC ACA GAA GAC TTG      4470
Gly Arg Ser Leu Ser Gly Gly Asp Thr Ala Arg Thr Thr Glu Asp Leu
        1465                1470                1475

AAC AGC AGA AAG CCG CCT TCG CAA GAC AGG CAA TCA CGC TCG TCT GAA      4518
Asn Ser Arg Lys Pro Pro Ser Gln Asp Arg Gln Ser Arg Ser Ser Glu
    1480                1485                1490

TGT CTG GAC AGA AGC GGA GAA AGG ACA GGC AGT TCG TTA ACT GCC CCC      4566
Cys Leu Asp Arg Ser Gly Glu Arg Thr Gly Ser Ser Leu Thr Ala Pro
1495                1500                1505                1510

ACT GCT CCG AGC CCC TCA TTC TCA TTT TCG GAA AGA GCT CGA CTG GCG      4614
Thr Ala Pro Ser Pro Ser Phe Ser Phe Ser Glu Arg Ala Arg Leu Ala
                1515                1520                1525

ACC GGG CCG ACT GTC GCC GCT GCG ACA TCA CCT TCG GCA ACC CCA TCC      4662
Thr Gly Pro Thr Val Ala Ala Ala Thr Ser Pro Ser Ala Thr Pro Ser
            1530                1535                1540

TGC GCC ACG GAC CAG GTT GCC GCG AGG ACC ACG CCG GAC TTT GCG CCT      4710
Cys Ala Thr Asp Gln Val Ala Ala Arg Thr Thr Pro Asp Phe Ala Pro
        1545                1550                1555

TTC CTG GGT TCC CAG TCT GCC CGT GCT GTC TCG AAG CCG TAC CGG CCC      4758
Phe Leu Gly Ser Gln Ser Ala Arg Ala Val Ser Lys Pro Tyr Arg Pro
    1560                1565                1570

CCC ACG ACT GCC CGT TGG AAA GAA GTC ACC CCG CTC CAC GCG TGG AAG      4806
Pro Thr Thr Ala Arg Trp Lys Glu Val Thr Pro Leu His Ala Trp Lys
1575                1580                1585                1590

GGC GTG ACC GGA GAC CGA CCG GAA GTC AGG GAG GAC CCG GAG ACA GCG      4854
Gly Val Thr Gly Asp Arg Pro Glu Val Arg Glu Asp Pro Glu Thr Ala
                1595                1600                1605

GCG GTC GTC CAG GCT CTG ATC AGC GGC CGT TAT CCT CAG AAG ACG AAG      4902
Ala Val Val Gln Ala Leu Ile Ser Gly Arg Tyr Pro Gln Lys Thr Lys
            1610                1615                1620
```

```
CTT TCC TCC GAC GCA TCC AAA GGC TAC TCA AGA ACT AAG GGA TGC TCA    4950
Leu Ser Ser Asp Ala Ser Lys Gly Tyr Ser Arg Thr Lys Gly Cys Ser
    1625                1630                1635

CAA TCC ACC TCT TTT CCT GCC CCG AGT GCG GAT TAC CAG GCC CGC GAC    4998
Gln Ser Thr Ser Phe Pro Ala Pro Ser Ala Asp Tyr Gln Ala Arg Asp
1640                1645                1650

TGC CAG ACA GTC CGA GTC TGC CGC GCC GCT GCA GAG ATG GCG CGC TCA    5046
Cys Gln Thr Val Arg Val Cys Arg Ala Ala Ala Glu Met Ala Arg Ser
1655                1660                1665                1670

TGT ATT CAC GAG CCG TTG GCT TCA TCT GCC GCC AGT GCC GAC TTG AAG    5094
Cys Ile His Glu Pro Leu Ala Ser Ser Ala Ala Ser Ala Asp Leu Lys
                1675                1680                1685

CGC ATA CGC TCT ACC TCG GAC TCT GTT CCC GAT GTA AAG ATC AGC AAG    5142
Arg Ile Arg Ser Thr Ser Asp Ser Val Pro Asp Val Lys Ile Ser Lys
        1690                1695                1700

AGC GCA TGAAGGAACA AAATTAGTTT CCTTGTTCGT AAACAAGGTG GTCCCTCCCA    5198
Ser Ala

TTGAGGTAAA GACTCTGGTG AGTCCTCAAC GTTACTCGTT GAGTCTGCTG CGGTTCGATT    5258

CCATTCCCAA GCAGCAAAGG GTGCGCAACT AGTACGGCGC CCCCTGGGAT ACCA          5312

(2) INFORMATION FOR SEQ ID NO: 40:

(i) SEQUENCE CHARACTERISTICS:
        (A) LENGTH: 1704 amino acids
        (B) TYPE: amino acid
        (D) TOPOLOGY: linear (ii) MOLECULE TYPE: protein (xi) SEQUENCE DESCRIPTION: SEQ ID NO: 40:

Met Tyr Ala Lys Ala Thr Asp Val Ala Arg Val Tyr Ala Ala Ala Asp
 1               5                  10                  15

Val Ala Tyr Ala Asn Val Leu Gln Gln Arg Ala Val Lys Leu Asp Phe
                20                  25                  30

Ala Pro Pro Leu Lys Ala Leu Glu Thr Leu His Arg Leu Tyr Tyr Pro
            35                  40                  45

Leu Arg Phe Lys Gly Gly Thr Leu Pro Pro Thr Gln His Pro Ile Leu
     50                  55                  60

Ala Gly His Gln Arg Val Ala Glu Glu Val Leu His Asn Phe Ala Arg
 65                  70                  75                  80

Gly Arg Ser Thr Val Leu Glu Ile Gly Pro Ser Leu His Ser Ala Leu
                 85                  90                  95

Lys Leu His Gly Ala Pro Asn Ala Pro Val Ala Asp Tyr His Gly Cys
            100                 105                 110

Thr Lys Tyr Gly Thr Arg Asp Gly Ser Arg His Ile Thr Ala Leu Glu
        115                 120                 125

Ser Arg Ser Val Ala Thr Gly Arg Pro Glu Phe Lys Ala Asp Ala Ser
    130                 135                 140

Leu Leu Ala Asn Gly Ile Ala Ser Arg Thr Phe Cys Val Asp Gly Val
145                 150                 155                 160

Gly Ser Cys Ala Phe Lys Ser Arg Val Gly Ile Ala Asn His Ser Leu
                165                 170                 175

Tyr Asp Val Thr Leu Glu Glu Leu Ala Asn Ala Phe Glu Asn His Gly
            180                 185                 190

Leu His Met Val Arg Ala Phe Met His Met Pro Glu Glu Leu Leu Tyr
        195                 200                 205
```

-continued

```
Met Asp Asn Val Val Asn Ala Glu Leu Gly Tyr Arg Phe His Val Ile
210                 215                 220

Glu Glu Pro Met Ala Val Lys Asp Cys Ala Phe Gln Gly Gly Asp Leu
225                 230                 235                 240

Arg Leu His Phe Pro Glu Leu Asp Phe Ile Asn Glu Ser Gln Glu Arg
                245                 250                 255

Arg Ile Glu Arg Leu Ala Ala Arg Gly Ser Tyr Ser Arg Arg Ala Val
            260                 265                 270

Ile Phe Ser Gly Asp Asp Trp Gly Asp Ala Tyr Leu His Asp Phe
        275                 280                 285

His Thr Trp Leu Ala Tyr Leu Leu Val Arg Asn Tyr Pro Thr Pro Phe
    290                 295                 300

Gly Phe Ser Leu His Ile Glu Val Gln Arg Arg His Gly Ser Ser Ile
305                 310                 315                 320

Glu Leu Arg Ile Thr Arg Ala Pro Pro Gly Asp Arg Met Leu Ala Val
                325                 330                 335

Val Pro Arg Thr Ser Gln Gly Leu Cys Arg Ile Pro Asn Ile Phe Tyr
            340                 345                 350

Tyr Ala Asp Ala Ser Gly Thr Glu His Lys Thr Ile Leu Thr Ser Gln
        355                 360                 365

His Lys Val Asn Met Leu Leu Asn Phe Met Gln Thr Arg Pro Glu Lys
    370                 375                 380

Glu Leu Val Asp Met Thr Val Leu Met Ser Phe Ala Arg Ala Arg Leu
385                 390                 395                 400

Arg Ala Ile Val Val Ala Ser Glu Val Thr Glu Ser Ser Trp Asn Ile
                405                 410                 415

Ser Pro Ala Asp Leu Val Arg Thr Val Val Ser Leu Tyr Val Leu His
            420                 425                 430

Ile Ile Glu Arg Arg Arg Ala Val Ala Val Lys Thr Ala Lys Asp
        435                 440                 445

Asp Val Phe Gly Glu Thr Ser Phe Trp Glu Ser Leu Lys His Val Leu
    450                 455                 460

Gly Ser Cys Cys Gly Leu Arg Asn Leu Lys Gly Thr Asp Val Val Phe
465                 470                 475                 480

Thr Lys Arg Val Val Asp Lys Tyr Arg Val His Ser Leu Gly Asp Ile
                485                 490                 495

Ile Cys Asp Val Arg Leu Ser Pro Glu Gln Val Gly Phe Leu Pro Ser
            500                 505                 510

Arg Val Pro Pro Ala Arg Val Phe His Asp Arg Glu Glu Leu Glu Val
        515                 520                 525

Leu Arg Glu Ala Gly Cys Tyr Asn Glu Arg Pro Val Pro Ser Thr Pro
    530                 535                 540

Pro Val Glu Glu Pro Gln Gly Phe Asp Ala Asp Leu Trp His Ala Thr
545                 550                 555                 560

Ala Ala Ser Leu Pro Glu Tyr Arg Ala Thr Leu Gln Ala Gly Leu Asn
                565                 570                 575

Thr Asp Val Lys Gln Leu Lys Ile Thr Leu Glu Asn Ala Leu Lys Thr
            580                 585                 590

Ile Asp Gly Leu Thr Leu Ser Pro Val Arg Gly Leu Glu Met Tyr Glu
        595                 600                 605

Gly Pro Pro Gly Ser Gly Lys Thr Gly Thr Leu Ile Ala Ala Leu Glu
    610                 615                 620

Ala Ala Gly Gly Lys Ala Leu Tyr Val Ala Pro Thr Arg Glu Leu Arg
```

```
          625                 630                 635                 640
Glu Ala Met Asp Arg Arg Ile Lys Pro Pro Ser Ala Ser Ala Thr Gln
                    645                 650                 655
His Val Ala Leu Ala Ile Leu Arg Arg Ala Thr Ala Glu Gly Ala Pro
                    660                 665                 670
Phe Ala Thr Val Val Ile Asp Glu Cys Phe Met Phe Pro Leu Val Tyr
                    675                 680                 685
Val Ala Ile Val His Ala Leu Ser Pro Ser Ser Arg Ile Val Leu Val
                    690                 695                 700
Gly Asp Val His Gln Ile Gly Phe Ile Asp Phe Gln Gly Thr Ser Ala
705                 710                 715                 720
Asn Met Pro Leu Val Arg Asp Val Val Lys Gln Cys Arg Arg Arg Thr
                    725                 730                 735
Phe Asn Gln Thr Lys Arg Cys Pro Ala Asp Val Val Ala Thr Thr Phe
                    740                 745                 750
Phe Gln Ser Leu Tyr Pro Gly Cys Thr Thr Ser Gly Cys Val Ala
                    755                 760                 765
Ser Ile Ser His Val Ala Pro Asp Tyr Arg Asn Ser Gln Ala Gln Thr
770                 775                 780
Leu Cys Phe Thr Gln Glu Lys Ser Arg His Gly Ala Glu Gly Ala
785                 790                 795                 800
Met Thr Val His Glu Ala Gln Gly Arg Thr Phe Ala Ser Val Ile Leu
                    805                 810                 815
His Tyr Asn Gly Ser Thr Ala Glu Gln Lys Leu Leu Ala Glu Lys Ser
                    820                 825                 830
His Leu Leu Val Gly Ile Thr Arg His Thr Asn His Leu Tyr Ile Arg
                    835                 840                 845
Asp Pro Thr Gly Asp Ile Glu Arg Gln Leu Asn His Ser Ala Lys Ala
                    850                 855                 860
Glu Val Phe Thr Asp Ile Pro Ala Pro Leu Glu Ile Thr Thr Val Lys
865                 870                 875                 880
Pro Ser Glu Glu Val Gln Arg Asn Glu Val Met Ala Thr Ile Pro Pro
                    885                 890                 895
Gln Ser Ala Thr Pro His Gly Ala Ile His Leu Leu Arg Lys Asn Phe
                    900                 905                 910
Gly Asp Gln Pro Asp Cys Gly Cys Val Ala Leu Ala Lys Thr Gly Tyr
                    915                 920                 925
Glu Val Phe Gly Gly Arg Ala Lys Ile Asn Val Glu Leu Ala Glu Pro
                    930                 935                 940
Asp Ala Thr Pro Lys Pro His Arg Ala Phe Gln Glu Gly Val Gln Trp
945                 950                 955                 960
Val Lys Val Thr Asn Ala Ser Asn Lys His Gln Ala Leu Gln Thr Leu
                    965                 970                 975
Leu Ser Arg Tyr Thr Lys Arg Ser Ala Asp Leu Pro Leu His Glu Ala
                    980                 985                 990
Lys Glu Asp Val Lys Arg Met Leu Asn Ser Leu Asp Arg His Trp Asp
                    995                 1000                1005
Trp Thr Val Thr Glu Asp Ala Arg Asp Arg Ala Val Phe Glu Thr Gln
                    1010                1015                1020
Leu Lys Phe Thr Gln Arg Gly Gly Thr Val Glu Asp Leu Leu Glu Pro
1025                1030                1035                1040
Asp Asp Pro Tyr Ile Arg Asp Ile Asp Phe Leu Met Lys Thr Gln Gln
                    1045                1050                1055
```

-continued

```
Lys Val Ser Pro Lys Pro Ile Asn Thr Gly Lys Val Gly Gln Gly Ile
            1060                1065                1070

Ala Ala His Ser Lys Ser Leu Asn Phe Val Leu Ala Ala Trp Ile Arg
            1075                1080                1085

Ile Leu Glu Glu Ile Leu Arg Thr Gly Ser Arg Thr Val Arg Tyr Ser
            1090                1095                1100

Asn Gly Leu Pro Asp Glu Glu Ala Met Leu Leu Glu Ala Lys Ile
1105                1110                1115                1120

Asn Gln Val Pro His Ala Thr Phe Val Ser Ala Asp Trp Thr Glu Phe
                1125                1130                1135

Asp Thr Ala His Asn Asn Thr Ser Glu Leu Leu Phe Ala Ala Leu Leu
            1140                1145                1150

Glu Arg Ile Gly Thr Pro Ala Ala Val Asn Leu Phe Arg Glu Arg
            1155                1160                1165

Cys Gly Lys Arg Thr Leu Arg Ala Lys Gly Leu Gly Ser Val Glu Val
            1170                1175                1180

Asp Gly Leu Leu Asp Ser Gly Ala Ala Trp Thr Pro Cys Arg Asn Thr
1185                1190                1195                1200

Ile Phe Ser Ala Ala Val Met Leu Thr Leu Phe Arg Gly Val Lys Phe
                1205                1210                1215

Ala Ala Phe Lys Gly Asp Asp Ser Leu Leu Cys Gly Ser His Tyr Leu
            1220                1225                1230

Arg Phe Asp Ala Ser Arg Leu His Met Gly Glu Arg Tyr Lys Thr Lys
            1235                1240                1245

His Leu Lys Val Glu Val Gln Lys Ile Val Pro Tyr Ile Gly Leu Leu
            1250                1255                1260

Val Ser Ala Glu Gln Val Val Leu Asp Pro Val Arg Ser Ala Leu Lys
1265                1270                1275                1280

Ile Phe Gly Arg Cys Tyr Thr Ser Glu Leu Leu Tyr Ser Lys Tyr Val
                1285                1290                1295

Glu Ala Val Arg Asp Ile Thr Lys Gly Trp Ser Asp Ala Arg Tyr His
            1300                1305                1310

Ser Leu Leu Cys His Met Ser Ala Cys Tyr Tyr Asn Tyr Ala Pro Glu
            1315                1320                1325

Ser Ala Ala Tyr Ile Ile Asp Ala Val Val Arg Phe Gly Arg Gly Asp
            1330                1335                1340

Phe Pro Phe Glu Gln Leu Arg Val Val Arg Ala His Val Gln Ala Pro
1345                1350                1355                1360

Asp Ala Tyr Ser Ser Thr Tyr Pro Ala Asn Val Arg Ala Ser Cys Leu
                1365                1370                1375

Asp His Val Phe Glu Pro Arg Gln Ala Ala Pro Ala Gly Phe Val
            1380                1385                1390

Ala Thr Cys Ala Lys Pro Glu Thr Pro Ser Ser Leu Thr Ala Lys Ala
            1395                1400                1405

Gly Val Ser Ala Thr Thr Ser His Val Ala Thr Gly Thr Ala Pro Pro
            1410                1415                1420

Glu Ser Pro Trp Asp Ala Pro Ala Ala Asn Ser Phe Ser Glu Leu Leu
1425                1430                1435                1440

Thr Pro Glu Thr Pro Ser Thr Ser Ser Ser Pro Ser Ser Ser Ser Ser
                1445                1450                1455

Asp Ser Ser Thr Ser Cys Gly Arg Ser Leu Ser Gly Gly Asp Thr Ala
            1460                1465                1470
```

```
Arg Thr Thr Glu Asp Leu Asn Ser Arg Lys Pro Pro Ser Gln Asp Arg
        1475                1480                1485

Gln Ser Arg Ser Ser Glu Cys Leu Asp Arg Ser Gly Glu Arg Thr Gly
        1490                1495                1500

Ser Ser Leu Thr Ala Pro Thr Ala Pro Ser Pro Ser Phe Ser Phe Ser
1505                1510                1515                1520

Glu Arg Ala Arg Leu Ala Thr Gly Pro Thr Val Ala Ala Thr Ser
        1525                1530                1535

Pro Ser Ala Thr Pro Ser Cys Ala Thr Asp Gln Val Ala Ala Arg Thr
        1540                1545                1550

Thr Pro Asp Phe Ala Pro Phe Leu Gly Ser Gln Ser Ala Arg Ala Val
        1555                1560                1565

Ser Lys Pro Tyr Arg Pro Pro Thr Thr Ala Arg Trp Lys Glu Val Thr
        1570                1575                1580

Pro Leu His Ala Trp Lys Gly Val Thr Gly Asp Arg Pro Glu Val Arg
1585                1590                1595                1600

Glu Asp Pro Glu Thr Ala Ala Val Val Gln Ala Leu Ile Ser Gly Arg
        1605                1610                1615

Tyr Pro Gln Lys Thr Lys Leu Ser Ser Asp Ala Ser Lys Gly Tyr Ser
        1620                1625                1630

Arg Thr Lys Gly Cys Ser Gln Ser Thr Ser Phe Pro Ala Pro Ser Ala
        1635                1640                1645

Asp Tyr Gln Ala Arg Asp Cys Gln Thr Val Arg Val Cys Arg Ala Ala
        1650                1655                1660

Ala Glu Met Ala Arg Ser Cys Ile His Glu Pro Leu Ala Ser Ser Ala
1665                1670                1675                1680

Ala Ser Ala Asp Leu Lys Arg Ile Arg Ser Thr Ser Asp Ser Val Pro
        1685                1690                1695

Asp Val Lys Ile Ser Lys Ser Ala
        1700

(2) INFORMATION FOR SEQ ID NO: 41:

(i) SEQUENCE CHARACTERISTICS:
        (A) LENGTH: 5312 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 4218..4514

(xi) SEQUENCE DESCRIPTION: SEQ ID NO: 41:

GTTCTGCCTC CCCCGGACGG TAAATATAGG GGAACAATGT ACGCGAAAGC GACAGACGTG      60

GCGCGTGTCT ACGCCGCGGC AGATGTCGCC TACGCGAACG TACTGCAGCA GAGAGCAGTC     120

AAGTTGGACT TCGCCCCGCC ACTGAAGGCA CTAGAAACCC TCCACAGACT GTACTATCCG     180

CTGCGCTTCA AAGGGGGCAC TTTACCCCCG ACACAACACC CGATCCTGGC CGGGCACCAA     240

CGTGTCGCAG AAGAGGTTCT GCACAATTTC GCCAGGGGAC GTAGCACAGT GCTCGAGATA     300

GGGCCGTCTC TGCACAGCGC ACTTAAGCTA CATGGGCAC CGAACGCCCC CGTCGCAGAC      360

TATCACGGGT GCACCAAGTA CGGCACCCGC GACGGCTCGC GACACATTAC GGCCTTAGAG     420

TCTAGATCCG TCGCCACAGG CCGGCCCGAG TTCAAGGCCG ACGCCTCACT GCTCGCCAAC     480

GGCATTGCCT CCCGCACCTT CTGCGTCGAC GGAGTCGGCT CTTGCGCGTT CAAATCGCGC     540
```

```
GTTGGAATTG CCAATCACTC CCTCTATGAC GTGACCCTAG AGGAGCTGGC CAATGCGTTT      600

GAGAACCACG GACTTCACAT GGTCCGCGCG TTCATGCACA TGCCAGAAGA GCTGCTCTAC      660

ATGGACAACG TGGTTAATGC CGAGCTCGGC TACCGCTTCC ACGTTATTGA AGAGCCTATG      720

GCTGTGAAGG ACTGCGCATT CCAGGGGGGG GACCTCCGTC TCCACTTCCC TGAGTTGGAC      780

TTCATCAACG AGAGCCAAGA GCGGCGCATC GAGAGGCTGG CCGCCCGCGG CTCCTACTCC      840

AGACGCGCCG TCATTTTCTC CGGCGACGAC GACTGGGGTG ATGCGTACTT ACACGACTTC      900

CACACATGGC TCGCCTACCT ACTGGTGAGG AACTACCCCA CTCCGTTTGG TTTCTCACTC      960

CATATAGAAG TCCAGAGGCG CCACGGCTCC AGCATTGAGC TGCGCATCAC TCGCGCGCCA     1020

CCTGGAGACC GCATGCTGGC CGTCGTCCCA AGGACGTCCC AAGGCCTCTG CAGAATCCCA     1080

AACATCTTTT ATTACGCCGA CGCGTCGGGC ACTGAGCATA AGACCATCCT TACGTCACAG     1140

CACAAAGTCA ACATGCTGCT CAATTTTATG CAAACGCGTC CTGAGAAGGA ACTAGTCGAC     1200

ATGACCGTCT TGATGTCGTT CGCGCGCGCT AGGCTGCGCG CGATCGTGGT CGCCTCAGAA     1260

GTCACCGAGA GCTCCTGGAA CATCTCACCG GCTGACCTGG TCCGCACTGT CGTGTCTCTT     1320

TACGTCCTCC ACATCATCGA GCGCCGAAGG GCTGCGGTCG CTGTCAAGAC CGCCAAGGAC     1380

GACGTCTTTG GAGAGACTTC GTTCTGGGAG AGTCTCAAGC ACGTCTTGGG CTCCTGTTGC     1440

GGTCTGCGCA ACCTCAAAGG CACCGACGTC GTCTTTACTA AGCGCGTCGT CGATAAGTAC     1500

CGAGTCCACT CGCTCGGAGA CATAATCTGC GACGTCCGCC TGTCCCCTGA ACAGGTCGGC     1560

TTCCTGCCGT CCCGCGTACC ACCTGCCCGC GTCTTTCACG ACAGGGAAGA GCTTGAGGTC     1620

CTTCGCGAAG CTGGCTGCTA CAACGAACGT CCGGTACCTT CCACTCCTCC TGTGGAGGAG     1680

CCCCAAGGTT TCGACGCCGA CTTGTGGCAC GCGACCGCGG CCTCACTCCC CGAGTACCGC     1740

GCCACCTTGC AGGCAGGTCT CAACACCGAC GTCAAGCAGC TCAAGATCAC CCTCGAGAAC     1800

GCCCTCAAGA CCATCGACGG GCTCACCCTC TCCCCAGTCA GAGGCCTCGA GATGTACGAG     1860

GGCCCGCCAG CAGCGGCAA GACGGGCACC CTCATCGCCG CCCTTGAGGC CGCGGGCGGT     1920

AAAGCACTTT ACGTGGCACC CACCAGAGAA CTGAGAGAGG CTATGGACCG GCGGATCAAA     1980

CCGCCGTCCG CCTCGGCTAC GCAACATGTC GCCCTTGCGA TTCTCCGTCG TGCCACCGCC     2040

GAGGGCGCCC CTTTCGCTAC CGTGGTTATC GACGAGTGCT TCATGTTCCC GCTCGTGTAC     2100

GTCGCGATCG TGCACGCCTT GTCCCCGAGC TCACGAATAG TCCTTGTAGG GACGTCCAC     2160

CAAATCGGGT TTATAGACTT CCAAGGCACA AGCGCGAACA TGCCGCTCGT TCGCGACGTC     2220

GTTAAGCAGT GCCGTCGGCG CACTTTCAAC CAAACCAAGC GCTGTCCGGC CGACGTCGTT     2280

GCCACCACGT TTTTCCAGAG CTTGTACCCC GGGTGCACAA CCACCTCAGG GTGCGTCGCA     2340

TCCATCAGCC ACGTCGCCCC AGACTACCGC AACAGCCAGG CGCAAACGCT CTGCTTCACG     2400

CAGGAGGAAA AGTCGCGCCA CGGGGCTGAG GGCGCGATGA CTGTGCACGA AGCGCAGGGA     2460

CGCACTTTTG CGTCTGTCAT TCTGCATTAC AACGGCTCCA CAGCAGAGCA GAAGCTCCTC     2520

GCTGAGAAGT CGCACCTTCT AGTCGGCATC ACGCGCCACA CCAACCACCT GTACATCCGC     2580

GACCCGACAG GTGACATTGA GAGACAACTC AACCATAGCG CGAAAGCCGA GGTGTTTACA     2640

GACATCCCTG CACCCCTGGA GATCACGACT GTCAAACCGA GTGAAGAGGT GCAGCGCAAC     2700

GAAGTGATGG CAACGATACC CCCGCAGAGT GCCACGCCGC ACGGAGCAAT CCATCTGCTC     2760

CGCAAGAACT TCGGGGACCA ACCCGACTGT GGCTGTGTCG CTTTGGCGAA GACCGGCTAC     2820

GAGGTGTTTG GCGGTCGTGC CAAAATCAAC GTAGAGCTTG CCGAACCCGA CGCGACCCCG     2880
```

```
AAGCCGCATA GGGCGTTCCA GGAAGGGGTA CAGTGGGTCA AGGTCACCAA CGCGTCTAAC      2940

AAACACCAGG CGCTCCAGAC GCTGTTGTCC CGCTACACCA AGCGAAGCGC TGACCTGCCG      3000

CTACACGAAG CTAAGGAGGA CGTCAAACGC ATGCTAAACT CGCTTGACCG ACATTGGGAC      3060

TGGACTGTCA CTGAAGACGC CCGTGACCGA GCTGTCTTCG AGACCCAGCT CAAGTTCACC      3120

CAACGCGGCG GCACCGTCGA AGACCTGCTG GAGCCAGACG ACCCCTACAT CCGTGACATA      3180

GACTTCCTTA TGAAGACTCA GCAGAAAGTG TCGCCCAAGC CGATCAATAC GGGCAAGGTC      3240

GGGCAGGGGA TCGCCGCTCA CTCAAAGTCT CTCAACTTCG TCCTCGCCGC TTGGATACGC      3300

ATACTCGAGG AGATACTCCG TACCGGGAGC CGCACGGTCC GGTACAGCAA CGGTCTCCCC      3360

GACGAAGAAG AGGCCATGCT GCTCGAAGCG AAGATCAATC AAGTCCCACA CGCCACGTTC      3420

GTCTCGGCGG ACTGGACCGA GTTTGACACC GCCCACAATA ACACGAGTGA GCTGCTCTTC      3480

GCCGCCCTTT TAGAGCGCAT CGGCACGCCT GCAGCTGCCG TTAATCTATT CAGAGAACGG      3540

TGTGGGAAAC GCACCTTGCG AGCGAAGGGT CTAGGCTCCG TTGAAGTCGA CGGTCTGCTC      3600

GACTCCGGCG CAGCTTGGAC GCCTTGCCGC AACACCATCT TCTCTGCCGC CGTCATGCTC      3660

ACGCTCTTCC GCGGCGTCAA GTTCGCAGCT TTCAAAGGCG ACGACTCGCT CCTCTGTGGT      3720

AGCCATTACC TCCGTTTCGA CGCTAGCCGC CTTCACATGG GCGAACGTTA CAAGACCAAA      3780

CATTTGAAGG TCGAGGTGCA GAAAATCGTG CCGTACATCG GACTCCTCGT CTCCGCTGAG      3840

CAGGTCGTCC TCGACCCTGT CAGGAGCGCT CTCAAGATAT TTGGGCGCTG CTACACAAGC      3900

GAACTCCTTT ACTCCAAGTA CGTGGAGGCT GTGAGAGACA TCACCAAGGG CTGGAGTGAC      3960

GCCCGCTACC ACAGCCTCCT GTGCCACATG TCAGCATGCT ACTACAATTA CGCGCCGGAG      4020

TCTGCGGCGT ACATCATCGA CGCTGTTGTT CGCTTTGGGC GCGGCGACTT CCCGTTTGAA      4080

CAACTGCGCG TGGTGCGTGC CCATGTGCAG GCACCCGACG CTTACAGCAG CACGTATCCG      4140

GCTAACGTGC GCGCATCGTG CCTTGACCAC GTCTTCGAGC CCCGCCAGGC CGCCGCCCCG      4200

GCAGGTTTCG TTGCGAC ATG TGC GAA GCC GGA AAC GCC TTC TTC ACT TAC         4250
                    Met Cys Glu Ala Gly Asn Ala Phe Phe Thr Tyr
                     1               5                  10

CGC GAA AGC TGG TGT TTC TGC GAC TAC AAG CCA CGT TGC GAC TGG GAC         4298
Arg Glu Ser Trp Cys Phe Cys Asp Tyr Lys Pro Arg Cys Asp Trp Asp
             15                  20                  25

TGC GCC CCC GGA GTC TCC ATG GGA TGC ACC TGC AGC CAA CAG CTT TTC         4346
Cys Ala Pro Gly Val Ser Met Gly Cys Thr Cys Ser Gln Gln Leu Phe
         30                  35                  40

GGA GTT ATT GAC ACC GGA GAC CCC GTC CAC ATC ATC CTC GCC GTC ATC         4394
Gly Val Ile Asp Thr Gly Asp Pro Val His Ile Ile Leu Ala Val Ile
 45                  50                  55

GTC TTC ATC GGA CTC CTC TAC ATC GTG TGG AAG GTC GCT CAG TGG TGG         4442
Val Phe Ile Gly Leu Leu Tyr Ile Val Trp Lys Val Ala Gln Trp Trp
 60                  65                  70                  75

AGA CAC CGC AAG GAC CAC AGA AGA CTT GAA CAG CAG AAA GCC GCC TTC         4490
Arg His Arg Lys Asp His Arg Arg Leu Glu Gln Gln Lys Ala Ala Phe
                 80                  85                  90

GCA AGA CAG GCA ATC ACG CTC GTC TGAATGTCTG GACAGAAGCG GAGAAAGGAC        4544
Ala Arg Gln Ala Ile Thr Leu Val
                 95

AGGCAGTTCG TTAACTGCCC CCACTGCTCC GAGCCCCTCA TTCTCATTTT CGGAAAGAGC      4604

TCGACTGGCG ACCGGGCCGA CTGTCGCCGC TGCGACATCA CCTTCGGCAA CCCCATCCTG      4664

CGCCACGGAC CAGGTTGCCG CGAGGACCAC GCCGGACTTT GCGCCTTTCC TGGGTTCCCA      4724

GTCTGCCCGT GCTGTCTCGA AGCCGTACCG GCCCCCCACG ACTGCCCGTT GGAAAGAAGT      4784
```

```
CACCCCGCTC CACGCGTGGA AGGGCGTGAC CGGAGACCGA CCGGAAGTCA GGGAGGACCC    4844

GGAGACAGCG GCGGTCGTCC AGGCTCTGAT CAGCGGCCGT TATCCTCAGA AGACGAAGCT    4904

TTCCTCCGAC GCATCCAAAG GCTACTCAAG AACTAAGGGA TGCTCACAAT CCACCTCTTT    4964

TCCTGCCCCG AGTGCGGATT ACCAGGCCCG CGACTGCCAG ACAGTCCGAG TCTGCCGCGC    5024

CGCTGCAGAG ATGGCGCGCT CATGTATTCA CGAGCCGTTG GCTTCATCTG CCGCCAGTGC    5084

CGACTTGAAG CGCATACGCT CTACCTCGGA CTCTGTTCCC GATGTAAAGA TCAGCAAGAG    5144

CGCATGAAGG AACAAAATTA GTTTCCTTGT TCGTAAACAA GGTGGTCCCT CCCATTGAGG    5204

TAAAGACTCT GGTGAGTCCT CAACGTTACT CGTTGAGTCT GCTGCGGTTC GATTCCATTC    5264

CCAAGCAGCA AAGGGTGCGC AACTAGTACG GCGCCCCTG GGATACCA                  5312
```

(2) INFORMATION FOR SEQ ID NO: 42:

(i) SEQUENCE CHARACTERISTICS:
        (A) LENGTH: 99 amino acids
        (B) TYPE: amino acid
        (D) TOPOLOGY: linear (ii) MOLECULE TYPE: protein (xi) SEQUENCE DESCRIPTION: SEQ ID NO: 42:

```
Met Cys Glu Ala Gly Asn Ala Phe Phe Thr Tyr Arg Glu Ser Trp Cys
 1               5                  10                  15

Phe Cys Asp Tyr Lys Pro Arg Cys Asp Trp Asp Cys Ala Pro Gly Val
                20                  25                  30

Ser Met Gly Cys Thr Cys Ser Gln Gln Leu Phe Gly Val Ile Asp Thr
            35                  40                  45

Gly Asp Pro Val His Ile Ile Leu Ala Val Ile Val Phe Ile Gly Leu
        50                  55                  60

Leu Tyr Ile Val Trp Lys Val Ala Gln Trp Trp Arg His Arg Lys Asp
65                  70                  75                  80

His Arg Arg Leu Glu Gln Gln Lys Ala Ala Phe Ala Arg Gln Ala Ile
                85                  90                  95

Thr Leu Val
```

(2) INFORMATION FOR SEQ ID NO: 43:

(i) SEQUENCE CHARACTERISTICS:
        (A) LENGTH: 5312 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 4518..4937

(xi) SEQUENCE DESCRIPTION: SEQ ID NO: 43:

```
GTTCTGCCTC CCCCGGACGG TAAATATAGG GGAACAATGT ACGCGAAAGC GACAGACGTG      60

GCGCGTGTCT ACGCCGCGGC AGATGTCGCC TACGCGAACG TACTGCAGCA GAGAGCAGTC     120

AAGTTGGACT TCGCCCCGCC ACTGAAGGCA CTAGAAACCC TCCACAGACT GTACTATCCG     180

CTGCGCTTCA AGGGGGCAC TTTACCCCG ACACAACACC CGATCCTGGC CGGGCACCAA      240

CGTGTCGCAG AAGAGGTTCT GCACAATTTC GCCAGGGGAC GTAGCACAGT GCTCGAGATA     300

GGGCCGTCTC TGCACAGCGC ACTTAAGCTA CATGGGGCAC CGAACGCCCC CGTCGCAGAC     360
```

```
TATCACGGGT GCACCAAGTA CGGCACCCGC GACGGCTCGC GACACATTAC GGCCTTAGAG      420

TCTAGATCCG TCGCCACAGG CCGGCCCGAG TTCAAGGCCG ACGCCTCACT GCTCGCCAAC      480

GGCATTGCCT CCCGCACCTT CTGCGTCGAC GGAGTCGGCT CTTGCGCGTT CAAATCGCGC      540

GTTGGAATTG CCAATCACTC CCTCTATGAC GTGACCCTAG AGGAGCTGGC CAATGCGTTT      600

GAGAACCACG GACTTCACAT GGTCCGCGCG TTCATGCACA TGCCAGAAGA GCTGCTCTAC      660

ATGGACAACG TGGTTAATGC CGAGCTCGGC TACCGCTTCC ACGTTATTGA AGAGCCTATG      720

GCTGTGAAGG ACTGCGCATT CCAGGGGGGG GACCTCCGTC TCCACTTCCC TGAGTTGGAC      780

TTCATCAACG AGAGCCAAGA GCGGCGCATC GAGAGGCTGG CCGCCCGCGG CTCCTACTCC      840

AGACGCGCCG TCATTTTCTC CGGCGACGAC GACTGGGGTG ATGCGTACTT ACACGACTTC      900

CACACATGGC TCGCCTACCT ACTGGTGAGG AACTACCCCA CTCCGTTTGG TTTCTCACTC      960

CATATAGAAG TCCAGAGGCG CCACGGCTCC AGCATTGAGC TGCGCATCAC TCGCGCGCCA     1020

CCTGGAGACC GCATGCTGGC CGTCGTCCCA AGGACGTCCC AAGGCCTCTG CAGAATCCCA     1080

AACATCTTTT ATTACGCCGA CGCGTCGGGC ACTGAGCATA AGACCATCCT TACGTCACAG     1140

CACAAAGTCA ACATGCTGCT CAATTTTATG CAAACGCGTC CTGAGAAGGA ACTAGTCGAC     1200

ATGACCGTCT TGATGTCGTT CGCGCGCGCT AGGCTGCGCG CGATCGTGGT CGCCTCAGAA     1260

GTCACCGAGA GCTCCTGGAA CATCTCACCG GCTGACCTGG TCCGCACTGT CGTGTCTCTT     1320

TACGTCCTCC ACATCATCGA GCGCCGAAGG GCTGCGGTCG CTGTCAAGAC CGCCAAGGAC     1380

GACGTCTTTG GAGAGACTTC GTTCTGGGAG AGTCTCAAGC ACGTCTTGGG CTCCTGTTGC     1440

GGTCTGCGCA ACCTCAAAGG CACCGACGTC GTCTTTACTA AGCGCGTCGT CGATAAGTAC     1500

CGAGTCCACT CGCTCGGAGA CATAATCTGC GACGTCCGCC TGTCCCCTGA ACAGGTCGGC     1560

TTCCTGCCGT CCCGCGTACC ACCTGCCCGC GTCTTTCACG ACAGGGAAGA GCTTGAGGTC     1620

CTTCGCGAAG CTGGCTGCTA CAACGAACGT CCGGTACCTT CCACTCCTCC TGTGGAGGAG     1680

CCCCAAGGTT TCGACGCCGA CTTGTGGCAC GCGACCGCGG CCTCACTCCC CGAGTACCGC     1740

GCCACCTTGC AGGCAGGTCT CAACACCGAC GTCAAGCAGC TCAAGATCAC CCTCGAGAAC     1800

GCCCTCAAGA CCATCGACGG GCTCACCCTC TCCCCAGTCA GAGGCCTCGA GATGTACGAG     1860

GGCCCGCCAG GCAGCGGCAA GACGGGCACC CTCATCGCCG CCCTTGAGGC CGCGGGCGGT     1920

AAAGCACTTT ACGTGGCACC CACCAGAGAA CTGAGAGAGG CTATGGACCG GCGGATCAAA     1980

CCGCCGTCCG CCTCGGCTAC GCAACATGTC GCCCTTGCGA TTCTCCGTCG TGCCACCGCC     2040

GAGGGCGCCC CTTTCGCTAC CGTGGTTATC GACGAGTGCT TCATGTTCCC GCTCGTGTAC     2100

GTCGCGATCG TGCACGCCTT GTCCCCGAGC TCACGAATAG TCCTTGTAGG GGACGTCCAC     2160

CAAATCGGGT TTATAGACTT CCAAGGCACA AGCGCGAACA TGCCGCTCGT TCGCGACGTC     2220

GTTAAGCAGT GCCGTCGGCG CACTTTCAAC CAAACCAAGC GCTGTCCGGC CGACGTCGTT     2280

GCCACCACGT TTTTCCAGAG CTTGTACCCC GGGTGCACAA CCACCTCAGG GTGCGTCGCA     2340

TCCATCAGCC ACGTCGCCCC AGACTACCGC AACAGCCAGG CGCAAACGCT CTGCTTCACG     2400

CAGGAGGAAA AGTCGCGCCA CGGGGCTGAG GGCGCGATGA CTGTGCACGA AGCGCAGGGA     2460

CGCACTTTTG CGTCTGTCAT TCTGCATTAC AACGGCTCCA CAGCAGAGCA GAAGCTCCTC     2520

GCTGAGAAGT CGCACCTTCT AGTCGGCATC ACGCGCCACA CCAACCACCT GTACATCCGC     2580

GACCCGACAG GTGACATTGA GAGACAACTC AACCATAGCG CGAAAGCCGA GGTGTTTACA     2640

GACATCCCTG CACCCCTGGA GATCACGACT GTCAAACCGA GTGAAGAGGT GCAGCGCAAC     2700
```

-continued

```
GAAGTGATGG CAACGATACC CCCGCAGAGT GCCACGCCGC ACGGAGCAAT CCATCTGCTC    2760

CGCAAGAACT TCGGGACCA ACCCGACTGT GGCTGTGTCG CTTTGGCGAA GACCGGCTAC     2820

GAGGTGTTTG GCGGTCGTGC CAAAATCAAC GTAGAGCTTG CCGAACCCGA CGCGACCCCG    2880

AAGCCGCATA GGGCGTTCCA GGAAGGGGTA CAGTGGGTCA AGGTCACCAA CGCGTCTAAC    2940

AAACACCAGG CGCTCCAGAC GCTGTTGTCC CGCTACACCA AGCGAAGCGC TGACCTGCCG    3000

CTACACGAAG CTAAGGAGGA CGTCAAACGC ATGCTAAACT CGCTTGACCG ACATTGGGAC    3060

TGGACTGTCA CTGAAGACGC CCGTGACCGA GCTGTCTTCG AGACCCAGCT CAAGTTCACC    3120

CAACGCGGCG GCACCGTCGA AGACCTGCTG GAGCCAGACG ACCCCTACAT CCGTGACATA    3180

GACTTCCTTA TGAAGACTCA GCAGAAAGTG TCGCCCAAGC CGATCAATAC GGGCAAGGTC    3240

GGGCAGGGGA TCGCCGCTCA CTCAAAGTCT CTCAACTTCG TCCTCGCCGC TTGGATACGC    3300

ATACTCGAGG AGATACTCCG TACCGGGAGC CGCACGGTCC GGTACAGCAA CGGTCTCCCC    3360

GACGAAGAAG AGGCCATGCT GCTCGAAGCG AAGATCAATC AAGTCCCACA CGCCACGTTC    3420

GTCTCGGCGG ACTGGACCGA GTTTGACACC GCCCACAATA ACACGAGTGA GCTGCTCTTC    3480

GCCGCCCTTT TAGAGCGCAT CGGCACGCCT GCAGCTGCCG TTAATCTATT CAGAGAACGG    3540

TGTGGGAAAC GCACCTTGCG AGCGAAGGGT CTAGGCTCCG TTGAAGTCGA CGGTCTGCTC    3600

GACTCCGGCG CAGCTTGGAC GCCTTGCCGC AACACCATCT TCTCTGCCGC CGTCATGCTC    3660

ACGCTCTTCC GCGGCGTCAA GTTCGCAGCT TTCAAAGGCG ACGACTCGCT CCTCTGTGGT    3720

AGCCATTACC TCCGTTTCGA CGCTAGCCGC CTTCACATGG GCGAACGTTA CAAGACCAAA    3780

CATTTGAAGG TCGAGGTGCA GAAAATCGTG CCGTACATCG GACTCCTCGT CTCCGCTGAG    3840

CAGGTCGTCC TCGACCCTGT CAGGAGCGCT CTCAAGATAT TTGGGCGCTG CTACACAAGC    3900

GAACTCCTTT ACTCCAAGTA CGTGGAGGCT GTGAGAGACA TCACCAAGGG CTGGAGTGAC    3960

GCCCGCTACC ACAGCCTCCT GTGCCACATG TCAGCATGCT ACTACAATTA CGCGCCGGAG    4020

TCTGCGGCGT ACATCATCGA CGCTGTTGTT CGCTTTGGGC GCGGCGACTT CCCGTTTGAA    4080

CAACTGCGCG TGGTGCGTGC CCATGTGCAG GCACCCGACG CTTACAGCAG CACGTATCCG    4140

GCTAACGTGC GCGCATCGTG CCTTGACCAC GTCTTCGAGC CCGCCAGGC CGCCGCCCCG     4200

GCAGGTTTCG TTGCGACATG TGCGAAGCCG GAAACGCCTT CTTCACTTAC CGCGAAAGCT    4260

GGTGTTTCTG CGACTACAAG CCACGTTGCG ACTGGGACTG CGCCCCGGA GTCTCCATGG     4320

GATGCACCTG CAGCCAACAG CTTTTCGGAG TTATTGACAC CGGAGACCCC GTCCACATCA    4380

TCCTCGCCGT CATCGTCTTC ATCGGACTCC TCTACATCGT GTGGAAGGTC GCTCAGTGGT    4440

GGAGACACCG CAAGGACCAC AGAAGACTTG AACAGCAGAA AGCCGCCTTC GCAAGACAGG    4500

CAATCACGCT CGTCTGA ATG TCT GGA CAG AAG CGG AGA AAG GAC AGG CAG       4550
                Met Ser Gly Gln Lys Arg Arg Lys Asp Arg Gln
                 1               5                  10

TTC GTT AAC TGC CCC CAC TGC TCC GAG CCC CTC ATT CTC ATT TTC GGA      4598
Phe Val Asn Cys Pro His Cys Ser Glu Pro Leu Ile Leu Ile Phe Gly
             15                  20                  25

AAG AGC TCG ACT GGC GAC CGG GCC GAC TGT CGC CGC TGC GAC ATC ACC      4646
Lys Ser Ser Thr Gly Asp Arg Ala Asp Cys Arg Arg Cys Asp Ile Thr
         30                  35                  40

TTC GGC AAC CCC ATC CTG CGC CAC GGA CCA GGT TGC CGC GAG GAC CAC      4694
Phe Gly Asn Pro Ile Leu Arg His Gly Pro Gly Cys Arg Glu Asp His
         45                  50                  55

GCC GGA CTT TGC GCC TTT CCT GGG TTC CCA GTC TGC CCG TGC TGT CTC      4742
Ala Gly Leu Cys Ala Phe Pro Gly Phe Pro Val Cys Pro Cys Cys Leu
60                  65                  70                  75
```

```
GAA GCC GTA CCG GCC CCC CAC GAC TGC CCG TTG GAA AGA AGT CAC CCC          4790
Glu Ala Val Pro Ala Pro His Asp Cys Pro Leu Glu Arg Ser His Pro
                80                  85                  90

GCT CCA CGC GTG GAA GGG CGT GAC CGG AGA CCG ACC GGA AGT CAG GGA          4838
Ala Pro Arg Val Glu Gly Arg Asp Arg Arg Pro Thr Gly Ser Gln Gly
                95                 100                 105

GGA CCC GGA GAC AGC GGC GGT CGT CCA GGC TCT GAT CAG CGG CCG TTA          4886
Gly Pro Gly Asp Ser Gly Gly Arg Pro Gly Ser Asp Gln Arg Pro Leu
            110                 115                 120

TCC TCA GAA GAC GAA GCT TTC CTC CGA CGC ATC CAA AGG CTA CTC AAG          4934
Ser Ser Glu Asp Glu Ala Phe Leu Arg Arg Ile Gln Arg Leu Leu Lys
    125                 130                 135

AAC TAAGGGATGC TCACAATCCA CCTCTTTTCC TGCCCCGAGT GCGGATTACC               4987
Asn
140

AGGCCCGCGA CTGCCAGACA GTCCGAGTCT GCCGCGCCGC TGCAGAGATG GCGCGCTCAT        5047

GTATTCACGA GCCGTTGGCT TCATCTGCCG CCAGTGCCGA CTTGAAGCGC ATACGCTCTA        5107

CCTCGGACTC TGTTCCCGAT GTAAAGATCA GCAAGAGCGC ATGAAGGAAC AAAATTAGTT        5167

TCCTTGTTCG TAAACAAGGT GGTCCCTCCC ATTGAGGTAA AGACTCTGGT GAGTCCTCAA        5227

CGTTACTCGT TGAGTCTGCT GCGGTTCGAT TCCATTCCCA AGCAGCAAAG GGTGCGCAAC        5287

TAGTACGGCG CCCCCTGGGA TACCA                                              5312

(2) INFORMATION FOR SEQ ID NO: 44:

(i) SEQUENCE CHARACTERISTICS:
        (A) LENGTH: 140 amino acids
        (B) TYPE: amino acid
        (D) TOPOLOGY: linear (ii) MOLECULE TYPE: protein (xi) SEQUENCE DESCRIPTION: SEQ ID NO: 44:

Met Ser Gly Gln Lys Arg Arg Lys Asp Arg Gln Phe Val Asn Cys Pro
1               5                  10                  15

His Cys Ser Glu Pro Leu Ile Leu Ile Phe Gly Lys Ser Ser Thr Gly
                20                  25                  30

Asp Arg Ala Asp Cys Arg Arg Cys Asp Ile Thr Phe Gly Asn Pro Ile
            35                  40                  45

Leu Arg His Gly Pro Gly Cys Arg Glu Asp His Ala Gly Leu Cys Ala
    50                  55                  60

Phe Pro Gly Phe Pro Val Cys Pro Cys Cys Leu Glu Ala Val Pro Ala
65                  70                  75                  80

Pro His Asp Cys Pro Leu Glu Arg Ser His Pro Ala Pro Arg Val Glu
                85                  90                  95

Gly Arg Asp Arg Arg Pro Thr Gly Ser Gln Gly Gly Pro Gly Asp Ser
            100                 105                 110

Gly Gly Arg Pro Gly Ser Asp Gln Arg Pro Leu Ser Ser Glu Asp Glu
    115                 120                 125

Ala Phe Leu Arg Arg Ile Gln Arg Leu Leu Lys Asn
130                 135                 140

(2) INFORMATION FOR SEQ ID NO: 45:

(i) SEQUENCE CHARACTERISTICS:
        (A) LENGTH: 5368 base pairs
        (B) TYPE: nucleic acid
        (C) STRANDEDNESS: unknown
```

(D) TOPOLOGY: unknown (ii) MOLECULE TYPE: DNA (ix) FEATURE:
         (A) NAME/KEY: CDS
         (B) LOCATION: 4944..5162

(xi) SEQUENCE DESCRIPTION: SEQ ID NO: 45:

```
GTTCTGCCTC CCCCGGACGG TAAATATAGG GGAACAATGT ACGCGAAAGC GACAGACGTG      60

GCGCGTGTCT ACGCCGCGGC AGATGTCGCC TACGCGAACG TACTGCAGCA GAGAGCAGTC     120

AAGTTGGACT TCGCCCCGCC ACTGAAGGCA CTAGAAACCC TCCACAGACT GTACTATCCG     180

CTGCGCTTCA AAGGGGGCAC TTTACCCCCG ACACAACACC CGATCCTGGC CGGGCACCAA     240

CGTGTCGCAG AAGAGGTTCT GCACAATTTC GCCAGGGGAC GTAGCACAGT GCTCGAGATA     300

GGGCCGTCTC TGCACAGCGC ACTTAAGCTA CATGGGCAC CGAACGCCCC CGTCGCAGAC      360

TATCACGGGT GCACCAAGTA CGGCACCCGC GACGGCTCGC GACACATTAC GGCCTTAGAG     420

TCTAGATCCG TCGCCACAGG CCGGCCCGAG TTCAAGGCCG ACGCCTCACT GCTCGCCAAC     480

GGCATTGCCT CCCGCACCTT CTGCGTCGAC GGAGTCGGCT CTTGCGCGTT CAAATCGCGC     540

GTTGGAATTG CCAATCACTC CCTCTATGAC GTGACCCTAG AGGAGCTGGC CAATGCGTTT     600

GAGAACCACG GACTTCACAT GGTCCGCGCG TTCATGCACA TGCCAGAAGA GCTGCTCTAC     660

ATGGACAACG TGGTTAATGC CGAGCTCGGC TACCGCTTCC ACGTTATTGA AGAGCCTATG     720

GCTGTGAAGG ACTGCGCATT CCAGGGGGGG GACCTCCGTC TCCACTTCCC TGAGTTGGAC     780

TTCATCAACG AGAGCCAAGA GCGGCGCATC GAGAGGCTGG CCGCCCGCGG CTCCTACTCC     840

AGACGCGCCG TCATTTTCTC CGGCGACGAC GACTGGGGTG ATGCGTACTT ACACGACTTC     900

CACACATGGC TCGCCTACCT ACTGGTGAGG AACTACCCCA CTCCGTTTGG TTTCTCACTC     960

CATATAGAAG TCCAGAGGCG CCACGGCTCC AGCATTGAGC TGCGCATCAC TCGCGCGCCA    1020

CCTGGAGACC GCATGCTGGC CGTCGTCCCA AGGACGTCCC AAGGCCTCTG CAGAATCCCA    1080

AACATCTTTT ATTACGCCGA CGCGTCGGGC ACTGAGCATA AGACCATCCT TACGTCACAG    1140

CACAAAGTCA ACATGCTGCT CAATTTTATG CAAACGCGTC CTGAGAAGGA ACTAGTCGAC    1200

ATGACCGTCT TGATGTCGTT CGCGCGCGCT AGGCTGCGCG CGATCGTGGT CGCCTCAGAA    1260

GTCACCGAGA GCTCCTGGAA CATCTCACCG GCTGACCTGG TCCGCACTGT CGTGTCTCTT    1320

TACGTCCTCC ACATCATCGA GCGCCGAAGG GCTGCGGTCG CTGTCAAGAC CGCCAAGGAC    1380

GACGTCTTTG GAGAGACTTC GTTCTGGGAG AGTCTCAAGC ACGTCTTGGG CTCCTGTTGC    1440

GGTCTGCGCA ACCTCAAAGG CACCGACGTC GTCTTTACTA AGCGCGTCGT CGATAAGTAC    1500

CGAGTCCACT CGCTCGGAGA CATAATCTGC GACGTCCGCC TGTCCCCTGA ACAGGTCGGC    1560

TTCCTGCCGT CCCGCGTACC ACCTGCCCGC GTCTTTCACG ACAGGGAAGA GCTTGAGGTC    1620

CTTCGCGAAG CTGGCTGCTA CAACGAACGT CCGGTACCTT CCACTCCTCC TGTGGAGGAG    1680

CCCCAAGGTT TCGACGCCGA CTTGTGGCAC GCGACCGCGG CCTCACTCCC CGAGTACCGC    1740

GCCACCTTGC AGGCAGGTCT CAACACCGAC GTCAAGCAGC TCAAGATCAC CCTCGAGAAC    1800

GCCCTCAAGA CCATCGACGG GCTCACCCTC TCCCCAGTCA GAGGCCTCGA GATGTACGAG    1860

GGCCCGCCAG GCAGCGGCAA GACGGGCACC CTCATCGCCG CCCTTGAGGC CGCGGGCGGT    1920

AAAGCACTTT ACGTGGCACC CACCAGAGAA CTGAGAGAGG CTATGGACCG GCGGATCAAA    1980

CCGCCGTCCG CCTCGGCTAC GCAACATGTC GCCCTTGCGA TTCTCCGTCG TGCCACCGCC    2040

GAGGGCGCCC CTTTCGCTAC CGTGGTTATC GACGAGTGCT TCATGTTCCC GCTCGTGTAC    2100
```

```
GTCGCGATCG TGCACGCCTT GTCCCCGAGC TCACGAATAG TCCTTGTAGG GGACGTCCAC    2160

CAAATCGGGT TTATAGACTT CCAAGGCACA AGCGCGAACA TGCCGCTCGT TCGCGACGTC    2220

GTTAAGCAGT GCCGTCGGCG CACTTTCAAC CAAACCAAGC GCTGTCCGGC CGACGTCGTT    2280

GCCACCACGT TTTTCCAGAG CTTGTACCCC GGGTGCACAA CCACCTCAGG GTGCGTCGCA    2340

TCCATCAGCC ACGTCGCCCC AGACTACCGC AACAGCCAGG CGCAAACGCT CTGCTTCACG    2400

CAGGAGGAAA AGTCGCGCCA CGGGGCTGAG GGCGCGATGA CTGTGCACGA AGCGCAGGGA    2460

CGCACTTTTG CGTCTGTCAT TCTGCATTAC AACGGCTCCA CAGCAGAGCA GAAGCTCCTC    2520

GCTGAGAAGT CGCACCTTCT AGTCGGCATC ACGCGCCACA CCAACCACCT GTACATCCGC    2580

GACCCGACAG GTGACATTGA GAGACAACTC AACCATAGCG CGAAAGCCGA GGTGTTTACA    2640

GACATCCCTG CACCCCTGGA GATCACGACT GTCAAACCGA GTGAAGAGGT GCAGCGCAAC    2700

GAAGTGATGG CAACGATACC CCCGCAGAGT GCCACGCCGC ACGGAGCAAT CCATCTGCTC    2760

CGCAAGAACT TCGGGGACCA ACCCGACTGT GGCTGTGTCG CTTTGGCGAA GACCGGCTAC    2820

GAGGTGTTTG GCGGTCGTGC CAAAATCAAC GTAGAGCTTG CCGAACCCGA CGCGACCCCG    2880

AAGCCGCATA GGGCGTTCCA GGAAGGGGTA CAGTGGGTCA AGGTCACCAA CGCGTCTAAC    2940

AAACACCAGG CGCTCCAGAC GCTGTTGTCC CGCTACACCA AGCGAAGCGC TGACCTGCCG    3000

CTACACGAAG CTAAGGAGGA CGTCAAACGC ATGCTAAACT CGCTTGACCG ACATTGGGAC    3060

TGGACTGTCA CTGAAGACGC CCGTGACCGA GCTGTCTTCG AGACCCAGCT CAAGTTCACC    3120

CAACGCGGCG GCACCGTCGA AGACCTGCTG GAGCCAGACG ACCCCTACAT CCGTGACATA    3180

GACTTCCTTA TGAAGACTCA GCAGAAAGTG TCGCCCAAGC CGATCAATAC GGGCAAGGTC    3240

GGGCAGGGGA TCGCCGCTCA CTCAAAGTCT CTCAACTTCG TCCTCGCCGC TTGGATACGC    3300

ATACTCGAGG AGATACTCCG TACCGGGAGC CGCACGGTCC GGTACAGCAA CGGTCTCCCC    3360

GACGAAGAAG AGGCCATGCT GCTCGAAGCG AAGATCAATC AAGTCCCACA CGCCACGTTC    3420

GTCTCGGCGG ACTGGACCGA GTTTGACACC GCCCACAATA ACACGAGTGA GCTGCTCTTC    3480

GCCGCCCTTT TAGAGCGCAT CGGCACGCCT GCAGCTGCCG TTAATCTATT CAGAGAACGG    3540

TGTGGGAAAC GCACCTTGCG AGCGAAGGGT CTAGGCTCCG TTGAAGTCGA CGGTCTGCTC    3600

GACTCCGGCG CAGCTTGGAC GCCTTGCCGC AACACCATCT TCTCTGCCGC CGTCATGCTC    3660

ACGCTCTTCC GCGGCGTCAA GTTCGCAGCT TTCAAAGGCG ACGACTCGCT CCTCTGTGGT    3720

AGCCATTACC TCCGTTTCGA CGCTAGCCGC CTTCACATGG GCGAACGTTA CAAGACCAAA    3780

CATTTGAAGG TCGAGGTGCA GAAAATCGTG CCGTACATCG GACTCCTCGT CTCCGCTGAG    3840

CAGGTCGTCC TCGACCCTGT CAGGAGCGCT CTCAAGATAT TTGGGCGCTG CTACACAAGC    3900

GAACTCCTTT ACTCCAAGTA CGTGGAGGCT GTGAGAGACA TCACCAAGGG CTGGAGTGAC    3960

GCCCGCTACC ACAGCCTCCT GTGCCACATG TCAGCATGCT ACTACAATTA CGCGCCGGAG    4020

TCTGCGGCGT ACATCATCGA CGCTGTTGTT CGCTTTGGGC GCGGCGACTT CCCGTTTGAA    4080

CAACTGCGCG TGGTGCGTGC CCATGTGCAG GCACCCGACG CTTACAGCAG CACGTATCCG    4140

GCTAACGTGC GCGCATCGTG CCTTGACCAC GTCTTCGAGC CCGCCAGGC CGCCGCCCCG    4200

GCAGGTTTCG TTGCGACATG TGCGAAGCCG GAAACGCCTT CTTCACTTAC CGCGAAAGCT    4260

GGTGTTTCTG CGACTACAAG CCACGTTGCG ACTGGGACTG CGCCCCCGGA GTCTCCATGG    4320

GATGCACCTG CAGCCAACAG CTTTTCGGAG TTATTGACAC CGGAGACCCC GTCCACATCA    4380

TCCTCGCCGT CATCGTCTTC ATCGGACTCC TCTACATCGT GTGGAAGGTC GCTCAGTGGT    4440
```

```
GGAGACACCG CAAGGACCAC AGAAGACTTG AACAGCAGAA AGCCGCCTTC GCAAGACAGG    4500

CAATCACGCT CGTCTGAATG TCTGGACAGA AGCGGAGAAA GGACAGGCAG TTCGTTAACT    4560

GCCCCCACTG CTCCGAGCCC CTCATTCTCA TTTTCGGAAA GAGCTCGACT GGCGACCGGG    4620

CCGACTGTCG CCGCTGCGAC ATCACCTTCG GCAACCCCAT CCTGCGCCAC GGACCAGGTT    4680

GCCGCGAGGA CCACGCCGGA CTTTGCGCCT TTCCTGGGTT CCCAGTCTGC CCGTGCTGTC    4740

TCGAAGCCGT ACCGGCCCCC CACGACTGCC CGTTGGAAAG AAGTCACCCC GCTCCACGCG    4800

TGGAAGGGCG TGACCGGAGA CCGACCGGAA GTCAGGGAGG ACCCGGAGAC AGCGGCGGTC    4860

GTCCAGGCTC TGATCAGCGG CCGTTATCCT CAGAAGACGA AGCTTTCCTC CGACGCATCC    4920

AAAGGCTACT CAAGAACTAA GGG ATG CTC ACA ATC CAC CTC TTT TCC TGC        4970
                         Met Leu Thr Ile His Leu Phe Ser Cys
                           1               5

TTC CCC GAG TGC GGA TTA CCA GGC CCG CGA CTG CCA GAC AGT CCG AGT      5018
Phe Pro Glu Cys Gly Leu Pro Gly Pro Arg Leu Pro Asp Ser Pro Ser
 10              15                  20                  25

CTG GCG GAG ACC GCG CCG CTG CAG AGA TGG CGC GCT CAT GTA TTC ACG      5066
Leu Ala Glu Thr Ala Pro Leu Gln Arg Trp Arg Ala His Val Phe Thr
                 30                  35                  40

AGC CGT TGG CAG AGC AGA GAA TTA GAA AGT TCA TCT GCC GCC AGT GCC      5114
Ser Arg Trp Gln Ser Arg Glu Leu Glu Ser Ser Ser Ala Ala Ser Ala
             45                  50                  55

GAC TTG AAG CGC ATA CGC TCT ACC TCG GAC AGG CAG GAA TTG CTC TGT      5162
Asp Leu Lys Arg Ile Arg Ser Thr Ser Asp Arg Gln Glu Leu Leu Cys
         60                  65                  70

TCCCGATGTA AAGATCAGCA AGAGCGCATG AAGGAACAAA ATCAGCAGGG AGTGGATAGT    5222

TTCCTTGTTC GTAAACAAGG TGGTCCCTCC CATTGAGGTA AAGACTCTGG TGAGTCCTCA    5282

ACGTTACTCG TTGAGTCTGC TGCGGTTCGA TTCCATTCCC AAGCAGCAAA GGGTGCGCAA    5342

CTAGTACGGC GCCCCCTGGG ATACCA                                         5368

(2) INFORMATION FOR SEQ ID NO: 46:

(i) SEQUENCE CHARACTERISTICS:
        (A) LENGTH: 73 amino acids
        (B) TYPE: amino acid
        (D) TOPOLOGY: linear (ii) MOLECULE TYPE: protein (xi) SEQUENCE DESCRIPTION: SEQ ID NO: 46:

Met Leu Thr Ile His Leu Phe Ser Cys Phe Pro Glu Cys Gly Leu Pro
 1               5                  10                  15

Gly Pro Arg Leu Pro Asp Ser Pro Ser Leu Ala Glu Thr Ala Pro Leu
             20                  25                  30

Gln Arg Trp Arg Ala His Val Phe Thr Ser Arg Trp Gln Ser Arg Glu
         35                  40                  45

Leu Glu Ser Ser Ser Ala Ala Ser Ala Asp Leu Lys Arg Ile Arg Ser
     50                  55                  60

Thr Ser Asp Arg Gln Glu Leu Leu Cys
 65                  70

(2) INFORMATION FOR SEQ ID NO: 47:

(i) SEQUENCE CHARACTERISTICS:
        (A) LENGTH: 2478 base pairs
        (B) TYPE: nucleic acid
        (C) STRANDEDNESS: unknown
        (D) TOPOLOGY: unknown
```

(ii) MOLECULE TYPE: DNA (ix) FEATURE:
    (A) NAME/KEY: CDS
    (B) LOCATION: 283..753

(xi) SEQUENCE DESCRIPTION: SEQ ID NO: 47:

```
GTTTTTCTTT CTTTACCAAG TGTGGTAAAA TTTAAACAAA GAAGAAAACC AGGACCGTAA      60

CCCGGCCCTT ACACACCTCG AGTCCGTGAC CACCGGATTA TACGTCGCCC ACCACACGGC     120

GCCTTTTCCG ACCACTCTCG AGAGTCGTTG GGAGTTTCGT CCGTGACCAC CCGGTTGGCA     180

GTCGACAGAC GCTTCCGGAC CACTAGAACC TCCTCGAGCG ACGCACACAC AGCACACACA     240

CCGCCTTAGC TGCACCTACG GCAGCGTTGA TAGCGCGGAT TT ATG AGC GAG CAC        294
                                                Met Ser Glu His
                                                  1

ACC ATC GCC CAC TCC ATC ACA TTA CCA CCC GGT TAC ACC CTT GCC CTA       342
Thr Ile Ala His Ser Ile Thr Leu Pro Pro Gly Tyr Thr Leu Ala Leu
  5              10                  15                  20

ATA CCC CCT GAA CCT GAA GCA GGA TGG GAG ATG CTG GAG TGG CGT CAC       390
Ile Pro Pro Glu Pro Glu Ala Gly Trp Glu Met Leu Glu Trp Arg His
              25                  30                  35

AGC GAC CTC ACA ACC GTC GCG GAA CCC GTA ACG TTC GGG TCA GCG CCA       438
Ser Asp Leu Thr Thr Val Ala Glu Pro Val Thr Phe Gly Ser Ala Pro
          40                  45                  50

ACA CCG TCA CCG TCA ATG GTA GAA GAA ACC AAC GGC GTC GGA CCG GAA       486
Thr Pro Ser Pro Ser Met Val Glu Glu Thr Asn Gly Val Gly Pro Glu
      55                  60                  65

GGC AAG TTT CTC CCC CTG ACA ATT TCA CCG CTG CTG CAC AAG ACC TCG       534
Gly Lys Phe Leu Pro Leu Thr Ile Ser Pro Leu Leu His Lys Thr Ser
  70                  75                  80

CGC AAA GCC TTG ACG CCA ACA CCG TCA CTT TCC CCG CTA ACA TCT CTA       582
Arg Lys Ala Leu Thr Pro Thr Pro Ser Leu Ser Pro Leu Thr Ser Leu
 85                  90                  95                 100

GCA TGC CCG AAT TCC GGA ATT GGG CCA AGG GAA AGA TCG ACC TCG ACT       630
Ala Cys Pro Asn Ser Gly Ile Gly Pro Arg Glu Arg Ser Thr Ser Thr
                105                 110                 115

CCG ATT CCA TCG GCT GGT ACT TCA AGT ACC TTG ACC CAG CGG GTG CTA       678
Pro Ile Pro Ser Ala Gly Thr Ser Ser Thr Leu Thr Gln Arg Val Leu
            120                 125                 130

CAG AGT CTG CGC GCG CCG TCG GCG AGT ACT CGA AGA TCC CTG ACG GCC       726
Gln Ser Leu Arg Ala Pro Ser Ala Ser Thr Arg Arg Ser Leu Thr Ala
        135                 140                 145

TCG TCA AGT TCT CCG TCG ACG CAG AGA TAAGAGAGAT CTATAACGAG            773
Ser Ser Ser Ser Pro Ser Thr Gln Arg
    150                 155

GAGTGCCCCG TCGTCACTGA CGTGTCCGTC CCCCTCGACG GCCGCCAGTG GAGCCTCTCG     833

ATTTTCTCCT TTCCGATGTT CAGAACCGCC TACGTCGCCG TAGCGAACGT CGAGAACAAG     893

GAGATGTCGC TCGACGTTGT CAACGACCTC ATCGAGTGGC TCAACAATCT CGCCGACTGG     953

CGTTATGTCG TTGACTCTGA ACAGTGGATT AACTTCACCA ATGACACCAC GTACTACGTC    1013

CGCATCCGCG TTCTACGTCC AACCTACGAC GTTCCAGACC CCACAGAGGG CCTTGTTCGC    1073

ACAGTCTCAG ACTACCGCCT CACTTATAAG GCGATAACAT GTGAAGCCAA CATGCCAACA    1133

CTCGTCGACC AAGGCTTTTG GATCGGCGGC CAGTACGCTC TCACCCCGAC TAGCCTACCG    1193

CAGTACGACG TCAGCGAGGC CTACGCTCTG CACACTTTGA CCTTCGCCAG ACCATCCAGC    1253

GCCGCTGCAC TCGCGTTTGT GTGGGCAGGT TTGCCACAGG GTGGCACTGC GCCTGCAGGC    1313
```

```
ACTCCAGCCT GGGAGCAGGC ATCCTCGGGT GGCTACCTCA CCTGGCGCCA CAACGGTACT     1373

ACTTTCCCAG CTGGCTCCGT TAGCTACGTT CTCCCTGAGG GTTTCGCCCT TGAGCGCTAC     1433

GACCCGAACG ACGGCTCTTG GACCGACTTC GCTTCCGCAG GAGACACCGT CACTTTCCGG     1493

CAGGTCGCCG TCGACGAGGT CGTTGTGACC AACAACCCCG CCGGCGGCGG CAGCGCCCCC     1553

ACCTTCACCG TGAGAGTGCC CCCTTCAAAC GCTTACACCA ACACCGTGTT TAGGAACACG     1613

CTCTTAGAGA CTCGACCCTC CTCTCGTAGG CTCGAACTCC CTATGCCACC TGCTGACTTT     1673

GGACAGACGG TCGCCAACAA CCCGAAGATC GAGCAGTCGC TTCTTAAAGA AACACTTGGC     1733

TGCTATTTGG TCCACTCCAA AATGCGAAAC CCCGTTTTCC AGCTCACGCC AGCCAGCTCC     1793

TTTGGCGCCG TTTCCTTCAA CAATCCGGGT TATGAGCGCA CACGCGACCT CCCGGACTAC     1853

ACTGGCATCC GTGACTCATT CGACCAGAAC ATGTCCACCG CTGTGGCCCA CTTCCGCTCA     1913

CTCTCCCACT CCTGCAGTAT CGTCACTAAG ACCTACCAGG GTTGGGAAGG CGTCACGAAC     1973

GTCAACACGC CTTTCGGCCA ATTCGCGCAC GCGGGCCTCC TCAAGAATGA GGAGATCCTC     2033

TGCCTCGCCG ACGACCTGGC CACCCGTCTC ACAGGTGTCT ACCCCGCCAC TGACAACTTC     2093

GCGGCCGCCG TTTCTGCCTT CGCCGCGAAC ATGCTGTCCT CCGTGCTGAA GTCGGAGGCA     2153

ACGTCCTCCA TCATCAAGTC CGTTGGCGAG ACTGCCGTCG GCGCGGCTCA GTCCGGCCTC     2213

GCGAAGCTAC CCGGACTGCT AATGAGTGTA CCAGGGAAGA TTGCCGCGCG TGTCCGCGCG     2273

CGCCGAGCGC GCCGCCGCGC CGCTCGTGCC AATTAGTTTG CTCGCTCCTG TTTCGCCGTT     2333

TCGTAAAACG GCGTGGTCCC GCACATTACG CGTACCCTAA AGACTCTGGT GAGTCCCCGT     2393

CGTTACACGA CGGGTCTGCC GCGGTTCGAT TCCATTCCCA AGCGGCAAGA AGGACGTAGT     2453

TAGCTCTGCG TCCCTCGGGA TACCA                                          2478
```

(2) INFORMATION FOR SEQ ID NO: 48:

(i) SEQUENCE CHARACTERISTICS:
        (A) LENGTH: 157 amino acids
        (B) TYPE: amino acid
        (D) TOPOLOGY: linear (ii) MOLECULE TYPE: protein (xi) SEQUENCE DESCRIPTION: SEQ ID NO: 48:

```
Met Ser Glu His Thr Ile Ala His Ser Ile Thr Leu Pro Pro Gly Tyr
 1               5                  10                  15

Thr Leu Ala Leu Ile Pro Pro Glu Pro Glu Ala Gly Trp Glu Met Leu
            20                  25                  30

Glu Trp Arg His Ser Asp Leu Thr Thr Val Ala Glu Pro Val Thr Phe
        35                  40                  45

Gly Ser Ala Pro Thr Pro Ser Pro Ser Met Val Glu Glu Thr Asn Gly
    50                  55                  60

Val Gly Pro Glu Gly Lys Phe Leu Pro Leu Thr Ile Ser Pro Leu Leu
65                  70                  75                  80

His Lys Thr Ser Arg Lys Ala Leu Thr Pro Thr Pro Ser Leu Ser Pro
                85                  90                  95

Leu Thr Ser Leu Ala Cys Pro Asn Ser Gly Ile Gly Pro Arg Glu Arg
            100                 105                 110

Ser Thr Ser Thr Pro Ile Pro Ser Ala Gly Thr Ser Ser Thr Leu Thr
        115                 120                 125

Gln Arg Val Leu Gln Ser Leu Arg Ala Pro Ser Ala Ser Thr Arg Arg
    130                 135                 140
```

```
Ser Leu Thr Ala Ser Ser Ser Pro Ser Thr Gln Arg
145                 150                 155
```

(2) INFORMATION FOR SEQ ID NO: 49:

(i) SEQUENCE CHARACTERISTICS:
        (A) LENGTH: 2478 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 366..2306

(xi) SEQUENCE DESCRIPTION: SEQ ID NO: 49:

```
GTTTTTCTTT CTTTACCAAG TGTGGTAAAA TTTAAACAAA GAAGAAAACC AGGACCGTAA      60

CCCGGCCCTT ACACACCTCG AGTCCGTGAC CACCGGATTA TACGTCGCCC ACCACACGGC     120

GCCTTTTCCG ACCACTCTCG AGAGTCGTTG GGAGTTTCGT CCGTGACCAC CCGGTTGGCA     180

GTCGACAGAC GCTTCCGGAC CACTAGAACC TCCTCGAGCG ACGCACACAC AGCACACACA     240

CCGCCTTAGC TGCACCTACG GCAGCGTTGA TAGCGCGGAT TTATGAGCGA GCACACCATC     300

GCCCACTCCA TCACATTACC ACCCGGTTAC ACCCTTGCCC TAATACCCCC TGAACCTGAA     360

GCAGG ATG GGA GAT GCT GGA GTG GCG TCA CAG CGA CCT CAC AAC CGT         407
      Met Gly Asp Ala Gly Val Ala Ser Gln Arg Pro His Asn Arg
        1               5                  10

CGC GGA ACC CGT AAC GTT CGG GTC AGC GCC AAC ACC GTC ACC GTC AAT       455
Arg Gly Thr Arg Asn Val Arg Val Ser Ala Asn Thr Val Thr Val Asn
 15                  20                  25                  30

GGT AGA AGA AAC CAA CGG CGT CGG ACC GGA AGG CAA GTT TCT CCC CCT       503
Gly Arg Arg Asn Gln Arg Arg Arg Thr Gly Arg Gln Val Ser Pro Pro
                 35                  40                  45

GAC AAT TTC ACC GCT GCT GCA CAA GAC CTC GCG CAA AGC CTT GAC GCC       551
Asp Asn Phe Thr Ala Ala Ala Gln Asp Leu Ala Gln Ser Leu Asp Ala
             50                  55                  60

AAC ACC GTC ACT TTC CCC GCT AAC ATC TCT AGC ATG CCC GAA TTC CGG       599
Asn Thr Val Thr Phe Pro Ala Asn Ile Ser Ser Met Pro Glu Phe Arg
         65                  70                  75

AAT TGG GCC AAG GGA AAG ATC GAC CTC GAC TCC GAT TCC ATC GGC TGG       647
Asn Trp Ala Lys Gly Lys Ile Asp Leu Asp Ser Asp Ser Ile Gly Trp
     80                  85                  90

TAC TTC AAG TAC CTT GAC CCA GCG GGT GCT ACA GAG TCT GCG CGC GCC       695
Tyr Phe Lys Tyr Leu Asp Pro Ala Gly Ala Thr Glu Ser Ala Arg Ala
 95                 100                 105                 110

GTC GGC GAG TAC TCG AAG ATC CCT GAC GGC CTC GTC AAG TTC TCC GTC       743
Val Gly Glu Tyr Ser Lys Ile Pro Asp Gly Leu Val Lys Phe Ser Val
                115                 120                 125

GAC GCA GAG ATA AGA GAG ATC TAT AAC GAG GAG TGC CCC GTC GTC ACT       791
Asp Ala Glu Ile Arg Glu Ile Tyr Asn Glu Glu Cys Pro Val Val Thr
            130                 135                 140

GAC GTG TCC GTC CCC CTC GAC GGC CGC CAG TGG AGC CTC TCG ATT TTC       839
Asp Val Ser Val Pro Leu Asp Gly Arg Gln Trp Ser Leu Ser Ile Phe
        145                 150                 155

TCC TTT CCG ATG TTC AGA ACC GCC TAC GTC GCC GTA GCG AAC GTC GAG       887
Ser Phe Pro Met Phe Arg Thr Ala Tyr Val Ala Val Ala Asn Val Glu
    160                 165                 170

AAC AAG GAG ATG TCG CTC GAC GTT GTC AAC GAC CTC ATC GAG TGG CTC       935
Asn Lys Glu Met Ser Leu Asp Val Val Asn Asp Leu Ile Glu Trp Leu
175                 180                 185                 190
```

```
AAC AAT CTC GCC GAC TGG CGT TAT GTC GTT GAC TCT GAA CAG TGG ATT      983
Asn Asn Leu Ala Asp Trp Arg Tyr Val Val Asp Ser Glu Gln Trp Ile
            195                 200                 205

AAC TTC ACC AAT GAC ACC ACG TAC TAC GTC CGC ATC CGC GTT CTA CGT     1031
Asn Phe Thr Asn Asp Thr Thr Tyr Tyr Val Arg Ile Arg Val Leu Arg
            210                 215                 220

CCA ACC TAC GAC GTT CCA GAC CCC ACA GAG GGC CTT GTT CGC ACA GTC     1079
Pro Thr Tyr Asp Val Pro Asp Pro Thr Glu Gly Leu Val Arg Thr Val
            225                 230                 235

TCA GAC TAC CGC CTC ACT TAT AAG GCG ATA ACA TGT GAA GCC AAC ATG     1127
Ser Asp Tyr Arg Leu Thr Tyr Lys Ala Ile Thr Cys Glu Ala Asn Met
            240                 245                 250

CCA ACA CTC GTC GAC CAA GGC TTT TGG ATC GGC GGC CAG TAC GCT CTC     1175
Pro Thr Leu Val Asp Gln Gly Phe Trp Ile Gly Gly Gln Tyr Ala Leu
255                 260                 265                 270

ACC CCG ACT AGC CTA CCG CAG TAC GAC GTC AGC GAG GCC TAC GCT CTG     1223
Thr Pro Thr Ser Leu Pro Gln Tyr Asp Val Ser Glu Ala Tyr Ala Leu
            275                 280                 285

CAC ACT TTG ACC TTC GCC AGA CCA TCC AGC GCC GCT GCA CTC GCG TTT     1271
His Thr Leu Thr Phe Ala Arg Pro Ser Ser Ala Ala Ala Leu Ala Phe
            290                 295                 300

GTG TGG GCA GGT TTG CCA CAG GGT GGC ACT GCG CCT GCA GGC ACT CCA     1319
Val Trp Ala Gly Leu Pro Gln Gly Gly Thr Ala Pro Ala Gly Thr Pro
            305                 310                 315

GCC TGG GAG CAG GCA TCC TCG GGT GGC TAC CTC ACC TGG CGC CAC AAC     1367
Ala Trp Glu Gln Ala Ser Ser Gly Gly Tyr Leu Thr Trp Arg His Asn
            320                 325                 330

GGT ACT ACT TTC CCA GCT GGC TCC GTT AGC TAC GTT CTC CCT GAG GGT     1415
Gly Thr Thr Phe Pro Ala Gly Ser Val Ser Tyr Val Leu Pro Glu Gly
335                 340                 345                 350

TTC GCC CTT GAG CGC TAC GAC CCG AAC GAC GGC TCT TGG ACC GAC TTC     1463
Phe Ala Leu Glu Arg Tyr Asp Pro Asn Asp Gly Ser Trp Thr Asp Phe
            355                 360                 365

GCT TCC GCA GGA GAC ACC GTC ACT TTC CGG CAG GTC GCC GTC GAC GAG     1511
Ala Ser Ala Gly Asp Thr Val Thr Phe Arg Gln Val Ala Val Asp Glu
            370                 375                 380

GTC GTT GTG ACC AAC AAC CCC GCC GGC GGC GGC AGC GCC CCC ACC TTC     1559
Val Val Val Thr Asn Asn Pro Ala Gly Gly Gly Ser Ala Pro Thr Phe
            385                 390                 395

ACC GTG AGA GTG CCC CCT TCA AAC GCT TAC ACC AAC ACC GTG TTT AGG     1607
Thr Val Arg Val Pro Pro Ser Asn Ala Tyr Thr Asn Thr Val Phe Arg
400                 405                 410

AAC ACG CTC TTA GAG ACT CGA CCC TCC TCT CGT AGG CTC GAA CTC CCT     1655
Asn Thr Leu Leu Glu Thr Arg Pro Ser Ser Arg Arg Leu Glu Leu Pro
415                 420                 425                 430

ATG CCA CCT GCT GAC TTT GGA CAG ACG GTC GCC AAC AAC CCG AAG ATC     1703
Met Pro Pro Ala Asp Phe Gly Gln Thr Val Ala Asn Asn Pro Lys Ile
            435                 440                 445

GAG CAG TCG CTT CTT AAA GAA ACA CTT GGC TGC TAT TTG GTC CAC TCC     1751
Glu Gln Ser Leu Leu Lys Glu Thr Leu Gly Cys Tyr Leu Val His Ser
            450                 455                 460

AAA ATG CGA AAC CCC GTT TTC CAG CTC ACG CCA GCC AGC TCC TTT GGC     1799
Lys Met Arg Asn Pro Val Phe Gln Leu Thr Pro Ala Ser Ser Phe Gly
            465                 470                 475

GCC GTT TCC TTC AAC AAT CCG GGT TAT GAG CGC ACA CGC GAC CTC CCG     1847
Ala Val Ser Phe Asn Asn Pro Gly Tyr Glu Arg Thr Arg Asp Leu Pro
            480                 485                 490

GAC TAC ACT GGC ATC CGT GAC TCA TTC GAC CAG AAC ATG TCC ACC GCT     1895
Asp Tyr Thr Gly Ile Arg Asp Ser Phe Asp Gln Asn Met Ser Thr Ala
```

-continued

```
495              500              505              510
GTG GCC CAC TTC CGC TCA CTC TCC CAC TCC TGC AGT ATC GTC ACT AAG    1943
Val Ala His Phe Arg Ser Leu Ser His Ser Cys Ser Ile Val Thr Lys
            515              520              525

ACC TAC CAG GGT TGG GAA GGC GTC ACG AAC GTC AAC ACG CCT TTC GGC    1991
Thr Tyr Gln Gly Trp Glu Gly Val Thr Asn Val Asn Thr Pro Phe Gly
            530              535              540

CAA TTC GCG CAC GCG GGC CTC CTC AAG AAT GAG GAG ATC CTC TGC CTC    2039
Gln Phe Ala His Ala Gly Leu Leu Lys Asn Glu Glu Ile Leu Cys Leu
            545              550              555

GCC GAC GAC CTG GCC ACC CGT CTC ACA GGT GTC TAC CCC GCC ACT GAC    2087
Ala Asp Asp Leu Ala Thr Arg Leu Thr Gly Val Tyr Pro Ala Thr Asp
        560              565              570

AAC TTC GCG GCC GCC GTT TCT GCC TTC GCC GCG AAC ATG CTG TCC TCC    2135
Asn Phe Ala Ala Ala Val Ser Ala Phe Ala Ala Asn Met Leu Ser Ser
575              580              585              590

GTG CTG AAG TCG GAG GCA ACG TCC TCC ATC ATC AAG TCC GTT GGC GAG    2183
Val Leu Lys Ser Glu Ala Thr Ser Ser Ile Ile Lys Ser Val Gly Glu
            595              600              605

ACT GCC GTC GGC GCG GCT CAG TCC GGC CTC GCG AAG CTA CCC GGA CTG    2231
Thr Ala Val Gly Ala Ala Gln Ser Gly Leu Ala Lys Leu Pro Gly Leu
            610              615              620

CTA ATG AGT GTA CCA GGG AAG ATT GCC GCG CGT GTC CGC GCG CGC CGA    2279
Leu Met Ser Val Pro Gly Lys Ile Ala Ala Arg Val Arg Ala Arg Arg
        625              630              635

GCG CGC CGC CGC GCC GCT CGT GCC AAT TAGTTTGCTC GCTCCTGTTT          2326
Ala Arg Arg Arg Ala Ala Arg Ala Asn
        640              645

CGCCGTTTCG TAAAACGGCG TGGTCCCGCA CATTACGCGT ACCCTAAAGA CTCTGGTGAG  2386

TCCCCGTCGT TACACGACGG GTCTGCCGCG GTTCGATTCC ATTCCCAAGC GGCAAGAAGG  2446

ACGTAGTTAG CTCTGCGTCC CTCGGGATAC CA                                2478
```

(2) INFORMATION FOR SEQ ID NO: 50:

(i) SEQUENCE CHARACTERISTICS:
        (A) LENGTH: 647 amino acids
        (B) TYPE: amino acid
        (D) TOPOLOGY: linear (ii) MOLECULE TYPE: protein (xi) SEQUENCE DESCRIPTION: SEQ ID NO: 50:

```
Met Gly Asp Ala Gly Val Ala Ser Gln Arg Pro His Asn Arg Arg Gly
 1               5                  10                  15

Thr Arg Asn Val Arg Val Ser Ala Asn Thr Val Thr Val Asn Gly Arg
                20                  25                  30

Arg Asn Gln Arg Arg Arg Thr Gly Arg Gln Val Ser Pro Pro Asp Asn
            35                  40                  45

Phe Thr Ala Ala Ala Gln Asp Leu Ala Gln Ser Leu Asp Ala Asn Thr
        50                  55                  60

Val Thr Phe Pro Ala Asn Ile Ser Ser Met Pro Glu Phe Arg Asn Trp
65                  70                  75                  80

Ala Lys Gly Lys Ile Asp Leu Asp Ser Asp Ser Ile Gly Trp Tyr Phe
                85                  90                  95

Lys Tyr Leu Asp Pro Ala Gly Ala Thr Glu Ser Ala Arg Ala Val Gly
            100                 105                 110

Glu Tyr Ser Lys Ile Pro Asp Gly Leu Val Lys Phe Ser Val Asp Ala
        115                 120                 125
```

```
Glu Ile Arg Glu Ile Tyr Asn Glu Cys Pro Val Val Thr Asp Val
    130                 135                 140
Ser Val Pro Leu Asp Gly Arg Gln Trp Ser Leu Ser Ile Phe Ser Phe
145                 150                 155                 160
Pro Met Phe Arg Thr Ala Tyr Val Ala Val Ala Asn Val Glu Asn Lys
                165                 170                 175
Glu Met Ser Leu Asp Val Val Asn Asp Leu Ile Glu Trp Leu Asn Asn
            180                 185                 190
Leu Ala Asp Trp Arg Tyr Val Asp Ser Glu Gln Trp Ile Asn Phe
        195                 200                 205
Thr Asn Asp Thr Thr Tyr Tyr Val Arg Ile Arg Val Leu Arg Pro Thr
    210                 215                 220
Tyr Asp Val Pro Asp Pro Thr Glu Gly Leu Val Arg Thr Val Ser Asp
225                 230                 235                 240
Tyr Arg Leu Thr Tyr Lys Ala Ile Thr Cys Glu Ala Asn Met Pro Thr
                245                 250                 255
Leu Val Asp Gln Gly Phe Trp Ile Gly Gly Gln Tyr Ala Leu Thr Pro
            260                 265                 270
Thr Ser Leu Pro Gln Tyr Asp Val Ser Glu Ala Tyr Ala Leu His Thr
        275                 280                 285
Leu Thr Phe Ala Arg Pro Ser Ala Ala Leu Ala Phe Val Trp
    290                 295                 300
Ala Gly Leu Pro Gln Gly Gly Thr Ala Pro Gly Thr Pro Ala Trp
305                 310                 315                 320
Glu Gln Ala Ser Ser Gly Gly Tyr Leu Thr Trp Arg His Asn Gly Thr
                325                 330                 335
Thr Phe Pro Ala Gly Ser Val Ser Tyr Val Leu Pro Glu Gly Phe Ala
            340                 345                 350
Leu Glu Arg Tyr Asp Pro Asn Asp Gly Ser Trp Thr Asp Phe Ala Ser
        355                 360                 365
Ala Gly Asp Thr Val Thr Phe Arg Gln Val Ala Val Asp Glu Val Val
    370                 375                 380
Val Thr Asn Asn Pro Ala Gly Gly Ser Ala Pro Thr Phe Thr Val
385                 390                 395                 400
Arg Val Pro Pro Ser Asn Ala Tyr Thr Asn Thr Val Phe Arg Asn Thr
                405                 410                 415
Leu Leu Glu Thr Arg Pro Ser Ser Arg Arg Leu Glu Leu Pro Met Pro
            420                 425                 430
Pro Ala Asp Phe Gly Gln Thr Val Ala Asn Asn Pro Lys Ile Glu Gln
        435                 440                 445
Ser Leu Leu Lys Glu Thr Leu Gly Cys Tyr Leu Val His Ser Lys Met
    450                 455                 460
Arg Asn Pro Val Phe Gln Leu Thr Pro Ala Ser Ser Phe Gly Ala Val
465                 470                 475                 480
Ser Phe Asn Asn Pro Gly Tyr Glu Arg Thr Arg Asp Leu Pro Asp Tyr
                485                 490                 495
Thr Gly Ile Arg Asp Ser Phe Asp Gln Asn Met Ser Thr Ala Val Ala
            500                 505                 510
His Phe Arg Ser Leu Ser His Ser Cys Ser Ile Val Thr Lys Thr Tyr
        515                 520                 525
Gln Gly Trp Glu Gly Val Thr Asn Val Asn Thr Pro Phe Gly Gln Phe
    530                 535                 540
```

```
Ala His Ala Gly Leu Leu Lys Asn Glu Glu Ile Leu Cys Leu Ala Asp
545                 550                 555                 560

Asp Leu Ala Thr Arg Leu Thr Gly Val Tyr Pro Ala Thr Asp Asn Phe
                565                 570                 575

Ala Ala Ala Val Ser Ala Phe Ala Ala Asn Met Leu Ser Ser Val Leu
            580                 585                 590

Lys Ser Glu Ala Thr Ser Ser Ile Ile Lys Ser Val Gly Glu Thr Ala
        595                 600                 605

Val Gly Ala Ala Gln Ser Gly Leu Ala Lys Leu Pro Gly Leu Leu Met
    610                 615                 620

Ser Val Pro Gly Lys Ile Ala Ala Arg Val Arg Ala Arg Arg Ala Arg
625                 630                 635                 640

Arg Arg Ala Ala Arg Ala Asn
                645

(2) INFORMATION FOR SEQ ID NO: 51:

(i) SEQUENCE CHARACTERISTICS:
        (A) LENGTH: 2479 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: CDS
        (B) LOCATION: 283..2307

(xi) SEQUENCE DESCRIPTION: SEQ ID NO: 51:
```

| | |
|---|---|
| GTTTTTCTTT CTTTACCAAG TGTGGTAAAA TTTAAACAAA GAAGAAAACC AGGACCGTAA | 60 |
| CCCGGCCCTT ACACACCTCG AGTCCGTGAC CACCGGATTA TACGTCGCCC ACCACACGGC | 120 |
| GCCTTTTCCG ACCACTCTCG AGAGTCGTTG GGAGTTTCGT CCGTGACCAC CCGGTTGGCA | 180 |
| GTCGACAGAC GCTTCCGGAC CACTAGAACC TCCTCGAGCG ACGCACACAC AGCACACACA | 240 |
| CCGCCTTAGC TGCACCTACG GCAGCGTTGA TAGCGCGGAT TT ATG AGC GAG CAC | 294 |
|                                                                                                                   Met Ser Glu His<br>                                                                                                                     1 | |
| ACC ATC GCC CAC TCC ATC ACA TTA CCA CCC GGT TAC ACC CTT GCC CTA<br>Thr Ile Ala His Ser Ile Thr Leu Pro Pro Gly Tyr Thr Leu Ala Leu<br>5                10                15                20 | 342 |
| ATA CCC CCT GAA CCT GAA GCA GGA TGG GAG ATG CTG GAG TGG CGT CAC<br>Ile Pro Pro Glu Pro Glu Ala Gly Trp Glu Met Leu Glu Trp Arg His<br>                25                30                35 | 390 |
| AGC GAC CTC ACA ACC GTC GCG GAA CCC GTA ACG TTC GGG TCA GCG CCA<br>Ser Asp Leu Thr Thr Val Ala Glu Pro Val Thr Phe Gly Ser Ala Pro<br>            40                45                50 | 438 |
| ACA CCG TCA CCG TCA ATG GTA GAA GAA ACC AAC GGC GTC GGA CCG GAA<br>Thr Pro Ser Pro Ser Met Val Glu Glu Thr Asn Gly Val Gly Pro Glu<br>55                60                65 | 486 |
| GGC AAG TTT CTC CCC CTG ACA ATT TCA CCG CTG CTG CAC AAG ACC TCG<br>Gly Lys Phe Leu Pro Leu Thr Ile Ser Pro Leu Leu His Lys Thr Ser<br>    70                75                80 | 534 |
| CGC AAA GCC TTG ACG CCA ACA CCG TCA CTT TCC CCC GCT AAC ATC TCT<br>Arg Lys Ala Leu Thr Pro Thr Pro Ser Leu Ser Pro Ala Asn Ile Ser<br>85                90                95                100 | 582 |
| AGC ATG CCC GAA TTC CGG AAT TGG GCC AAG GGA AAG ATC GAC CTC GAC<br>Ser Met Pro Glu Phe Arg Asn Trp Ala Lys Gly Lys Ile Asp Leu Asp<br>                105               110               115 | 630 |
| TCC GAT TCC ATC GGC TGG TAC TTC AAG TAC CTT GAC CCA GCG GGT GCT | 678 |

-continued

```
Ser Asp Ser Ile Gly Trp Tyr Phe Lys Tyr Leu Asp Pro Ala Gly Ala
            120                 125                 130

ACA GAG TCT GCG CGC GCC GTC GGC GAG TAC TCG AAG ATC CCT GAC GGC      726
Thr Glu Ser Ala Arg Ala Val Gly Glu Tyr Ser Lys Ile Pro Asp Gly
            135                 140                 145

CTC GTC AAG TTC TCC GTC GAC GCA GAG ATA AGA GAG ATC TAT AAC GAG      774
Leu Val Lys Phe Ser Val Asp Ala Glu Ile Arg Glu Ile Tyr Asn Glu
            150                 155                 160

GAG TGC CCC GTC GTC ACT GAC GTG TCC GTC CCC CTC GAC GGC CGC CAG      822
Glu Cys Pro Val Val Thr Asp Val Ser Val Pro Leu Asp Gly Arg Gln
165                 170                 175                 180

TGG AGC CTC TCG ATT TTC TCC TTT CCG ATG TTC AGA ACC GCC TAC GTC      870
Trp Ser Leu Ser Ile Phe Ser Phe Pro Met Phe Arg Thr Ala Tyr Val
                185                 190                 195

GCC GTA GCG AAC GTC GAG AAC AAG GAG ATG TCG CTC GAC GTT GTC AAC      918
Ala Val Ala Asn Val Glu Asn Lys Glu Met Ser Leu Asp Val Val Asn
            200                 205                 210

GAC CTC ATC GAG TGG CTC AAC AAT CTC GCC GAC TGG CGT TAT GTC GTT      966
Asp Leu Ile Glu Trp Leu Asn Asn Leu Ala Asp Trp Arg Tyr Val Val
            215                 220                 225

GAC TCT GAA CAG TGG ATT AAC TTC ACC AAT GAC ACC ACG TAC TAC GTC      1014
Asp Ser Glu Gln Trp Ile Asn Phe Thr Asn Asp Thr Thr Tyr Tyr Val
            230                 235                 240

CGC ATC CGC GTT CTA CGT CCA ACC TAC GAC GTT CCA GAC CCC ACA GAG      1062
Arg Ile Arg Val Leu Arg Pro Thr Tyr Asp Val Pro Asp Pro Thr Glu
245                 250                 255                 260

GGC CTT GTT CGC ACA GTC TCA GAC TAC CGC CTC ACT TAT AAG GCG ATA      1110
Gly Leu Val Arg Thr Val Ser Asp Tyr Arg Leu Thr Tyr Lys Ala Ile
                265                 270                 275

ACA TGT GAA GCC AAC ATG CCA ACA CTC GTC GAC CAA GGC TTT TGG ATC      1158
Thr Cys Glu Ala Asn Met Pro Thr Leu Val Asp Gln Gly Phe Trp Ile
            280                 285                 290

GGC GGC CAG TAC GCT CTC ACC CCG ACT AGC CTA CCG CAG TAC GAC GTC      1206
Gly Gly Gln Tyr Ala Leu Thr Pro Thr Ser Leu Pro Gln Tyr Asp Val
            295                 300                 305

AGC GAG GCC TAC GCT CTG CAC ACT TTG ACC TTC GCC AGA CCA TCC AGC      1254
Ser Glu Ala Tyr Ala Leu His Thr Leu Thr Phe Ala Arg Pro Ser Ser
310                 315                 320

GCC GCT GCA CTC GCG TTT GTG TGG GCA GGT TTG CCA CAG GGT GGC ACT      1302
Ala Ala Ala Leu Ala Phe Val Trp Ala Gly Leu Pro Gln Gly Gly Thr
325                 330                 335                 340

GCG CCT GCA GGC ACT CCA GCC TGG GAG CAG GCA TCC TCG GGT GGC TAC      1350
Ala Pro Ala Gly Thr Pro Ala Trp Glu Gln Ala Ser Ser Gly Gly Tyr
                345                 350                 355

CTC ACC TGG CGC CAC AAC GGT ACT ACT TTC CCA GCT GGC TCC GTT AGC      1398
Leu Thr Trp Arg His Asn Gly Thr Thr Phe Pro Ala Gly Ser Val Ser
            360                 365                 370

TAC GTT CTC CCT GAG GGT TTC GCC CTT GAG CGC TAC GAC CCG AAC GAC      1446
Tyr Val Leu Pro Glu Gly Phe Ala Leu Glu Arg Tyr Asp Pro Asn Asp
            375                 380                 385

GGC TCT TGG ACC GAC TTC GCT TCC GCA GGA GAC ACC GTC ACT TTC CGG      1494
Gly Ser Trp Thr Asp Phe Ala Ser Ala Gly Asp Thr Val Thr Phe Arg
390                 395                 400

CAG GTC GCC GTC GAC GAG GTC GTT GTG ACC AAC AAC CCC GCC GGC GGC      1542
Gln Val Ala Val Asp Glu Val Val Val Thr Asn Asn Pro Ala Gly Gly
405                 410                 415                 420

GGC AGC GCC CCC ACC TTC ACC GTG AGA GTG CCC CCT TCA AAC GCT TAC      1590
Gly Ser Ala Pro Thr Phe Thr Val Arg Val Pro Pro Ser Asn Ala Tyr
                425                 430                 435
```

```
ACC AAC ACC GTG TTT AGG AAC ACG CTC TTA GAG ACT CGA CCC TCC TCT      1638
Thr Asn Thr Val Phe Arg Asn Thr Leu Leu Glu Thr Arg Pro Ser Ser
            440                 445                 450

CGT AGG CTC GAA CTC CCT ATG CCA CCT GCT GAC TTT GGA CAG ACG GTC      1686
Arg Arg Leu Glu Leu Pro Met Pro Pro Ala Asp Phe Gly Gln Thr Val
            455                 460                 465

GCC AAC AAC CCG AAG ATC GAG CAG TCG CTT CTT AAA GAA ACA CTT GGC      1734
Ala Asn Asn Pro Lys Ile Glu Gln Ser Leu Leu Lys Glu Thr Leu Gly
            470                 475                 480

TGC TAT TTG GTC CAC TCC AAA ATG CGA AAC CCC GTT TTC CAG CTC ACG      1782
Cys Tyr Leu Val His Ser Lys Met Arg Asn Pro Val Phe Gln Leu Thr
485                 490                 495                 500

CCA GCC AGC TCC TTT GGC GCC GTT TCC TTC AAC AAT CCG GGT TAT GAG      1830
Pro Ala Ser Ser Phe Gly Ala Val Ser Phe Asn Asn Pro Gly Tyr Glu
                505                 510                 515

CGC ACA CGC GAC CTC CCG GAC TAC ACT GGC ATC CGT GAC TCA TTC GAC      1878
Arg Thr Arg Asp Leu Pro Asp Tyr Thr Gly Ile Arg Asp Ser Phe Asp
                520                 525                 530

CAG AAC ATG TCC ACC GCT GTG GCC CAC TTC CGC TCA CTC TCC CAC TCC      1926
Gln Asn Met Ser Thr Ala Val Ala His Phe Arg Ser Leu Ser His Ser
            535                 540                 545

TGC AGT ATC GTC ACT AAG ACC TAC CAG GGT TGG GAA GGC GTC ACG AAC      1974
Cys Ser Ile Val Thr Lys Thr Tyr Gln Gly Trp Glu Gly Val Thr Asn
550                 555                 560

GTC AAC ACG CCT TTC GGC CAA TTC GCG CAC GCG GGC CTC CTC AAG AAT      2022
Val Asn Thr Pro Phe Gly Gln Phe Ala His Ala Gly Leu Leu Lys Asn
565                 570                 575                 580

GAG GAG ATC CTC TGC CTC GCC GAC GAC CTG GCC ACC CGT CTC ACA GGT      2070
Glu Glu Ile Leu Cys Leu Ala Asp Asp Leu Ala Thr Arg Leu Thr Gly
                585                 590                 595

GTC TAC CCC GCC ACT GAC AAC TTC GCG GCC GCC GTT TCT GCC TTC GCC      2118
Val Tyr Pro Ala Thr Asp Asn Phe Ala Ala Ala Val Ser Ala Phe Ala
                600                 605                 610

GCG AAC ATG CTG TCC TCC GTG CTG AAG TCG GAG GCA ACG TCC TCC ATC      2166
Ala Asn Met Leu Ser Ser Val Leu Lys Ser Glu Ala Thr Ser Ser Ile
            615                 620                 625

ATC AAG TCC GTT GGC GAG ACT GCC GTC GGC GCG GCT CAG TCC GGC CTC      2214
Ile Lys Ser Val Gly Glu Thr Ala Val Gly Ala Ala Gln Ser Gly Leu
            630                 635                 640

GCG AAG CTA CCC GGA CTG CTA ATG AGT GTA CCA GGG AAG ATT GCC GCG      2262
Ala Lys Leu Pro Gly Leu Leu Met Ser Val Pro Gly Lys Ile Ala Ala
645                 650                 655                 660

CGT GTC CGC GCG CGC CGA GCG CGC CGC CGC GCC GCT CGT GCC AAT          2307
Arg Val Arg Ala Arg Arg Ala Arg Arg Arg Ala Ala Arg Ala Asn
            665                 670                 675

TAGTTTGCTC GCTCCTGTTT CGCCGTTTCG TAAAACGGCG TGGTCCCGCA CATTACGCGT   2367

ACCCTAAAGA CTCTGGTGAG TCCCCGTCGT TACACGACGG GTCTGCCGCG GTTCGATTCC   2427

ATTCCCAAGC GGCAAGAAGG ACGTAGTTAG CTCTGCGTCC CTCGGGATAC CA           2479
```

(2) INFORMATION FOR SEQ ID NO: 52:

(i) SEQUENCE CHARACTERISTICS:
        (A) LENGTH: 675 amino acids
        (B) TYPE: amino acid
        (D) TOPOLOGY: linear (ii) MOLECULE TYPE: protein (xi) SEQUENCE DESCRIPTION: SEQ ID NO: 52:

Met Ser Glu His Thr Ile Ala His Ser Ile Thr Leu Pro Pro Gly Tyr

-continued

```
  1               5                  10                 15
Thr Leu Ala Leu Ile Pro Pro Glu Pro Glu Ala Gly Trp Glu Met Leu
             20                 25                 30
Glu Trp Arg His Ser Asp Leu Thr Thr Val Ala Glu Pro Val Thr Phe
             35                 40                 45
Gly Ser Ala Pro Thr Pro Ser Pro Ser Met Val Glu Thr Asn Gly
             50                 55                 60
Val Gly Pro Glu Gly Lys Phe Leu Pro Leu Thr Ile Ser Pro Leu Leu
 65              70                 75                     80
His Lys Thr Ser Arg Lys Ala Leu Thr Pro Thr Pro Ser Leu Ser Pro
             85                 90                 95
Ala Asn Ile Ser Ser Met Pro Glu Phe Arg Asn Trp Ala Lys Gly Lys
            100                105                110
Ile Asp Leu Asp Ser Asp Ser Ile Gly Trp Tyr Phe Lys Tyr Leu Asp
            115                120                125
Pro Ala Gly Ala Thr Glu Ser Ala Arg Ala Val Gly Glu Tyr Ser Lys
            130                135                140
Ile Pro Asp Gly Leu Val Lys Phe Ser Val Asp Ala Glu Ile Arg Glu
145              150                155                160
Ile Tyr Asn Glu Glu Cys Pro Val Val Thr Asp Val Ser Val Pro Leu
                 165                170                175
Asp Gly Arg Gln Trp Ser Leu Ser Ile Phe Ser Phe Pro Met Phe Arg
                 180                185                190
Thr Ala Tyr Val Ala Val Ala Asn Val Glu Asn Lys Glu Met Ser Leu
             195                200                205
Asp Val Val Asn Asp Leu Ile Glu Trp Leu Asn Asn Leu Ala Asp Trp
210              215                220
Arg Tyr Val Val Asp Ser Glu Gln Trp Ile Asn Phe Thr Asn Asp Thr
225              230                235                240
Thr Tyr Tyr Val Arg Ile Arg Val Leu Arg Pro Thr Tyr Asp Val Pro
                 245                250                255
Asp Pro Thr Glu Gly Leu Val Arg Thr Val Ser Asp Tyr Arg Leu Thr
             260                265                270
Tyr Lys Ala Ile Thr Cys Glu Ala Asn Met Pro Thr Leu Val Asp Gln
             275                280                285
Gly Phe Trp Ile Gly Gly Gln Tyr Ala Leu Thr Pro Thr Ser Leu Pro
             290                295                300
Gln Tyr Asp Val Ser Glu Ala Tyr Ala Leu His Thr Leu Thr Phe Ala
305              310                315                320
Arg Pro Ser Ser Ala Ala Ala Leu Ala Phe Val Trp Ala Gly Leu Pro
                 325                330                335
Gln Gly Gly Thr Ala Pro Ala Gly Thr Pro Ala Trp Glu Gln Ala Ser
             340                345                350
Ser Gly Gly Tyr Leu Thr Trp Arg His Asn Gly Thr Thr Phe Pro Ala
             355                360                365
Gly Ser Val Ser Tyr Val Leu Pro Glu Gly Phe Ala Leu Glu Arg Tyr
             370                375                380
Asp Pro Asn Asp Gly Ser Trp Thr Asp Phe Ala Ser Ala Gly Asp Thr
385              390                395                400
Val Thr Phe Arg Gln Val Ala Asp Glu Val Val Thr Asn Asn
                 405                410                415
Pro Ala Gly Gly Gly Ser Ala Pro Thr Phe Thr Val Arg Val Pro Pro
             420                425                430
```

```
Ser Asn Ala Tyr Thr Asn Thr Val Phe Arg Asn Thr Leu Leu Glu Thr
        435                 440                 445

Arg Pro Ser Ser Arg Arg Leu Glu Leu Pro Met Pro Pro Ala Asp Phe
    450                 455                 460

Gly Gln Thr Val Ala Asn Asn Pro Lys Ile Glu Gln Ser Leu Leu Lys
465                 470                 475                 480

Glu Thr Leu Gly Cys Tyr Leu Val His Ser Lys Met Arg Asn Pro Val
                485                 490                 495

Phe Gln Leu Thr Pro Ala Ser Ser Phe Gly Ala Val Ser Phe Asn Asn
            500                 505                 510

Pro Gly Tyr Glu Arg Thr Arg Asp Leu Pro Asp Tyr Thr Gly Ile Arg
        515                 520                 525

Asp Ser Phe Asp Gln Asn Met Ser Thr Ala Val Ala His Phe Arg Ser
    530                 535                 540

Leu Ser His Ser Cys Ser Ile Val Thr Lys Thr Tyr Gln Gly Trp Glu
545                 550                 555                 560

Gly Val Thr Asn Val Asn Thr Pro Phe Gly Gln Phe Ala His Ala Gly
                565                 570                 575

Leu Leu Lys Asn Glu Glu Ile Leu Cys Leu Ala Asp Asp Leu Ala Thr
            580                 585                 590

Arg Leu Thr Gly Val Tyr Pro Ala Thr Asp Asn Phe Ala Ala Ala Val
        595                 600                 605

Ser Ala Phe Ala Ala Asn Met Leu Ser Ser Val Leu Lys Ser Glu Ala
    610                 615                 620

Thr Ser Ser Ile Ile Lys Ser Val Gly Glu Thr Ala Val Gly Ala Ala
625                 630                 635                 640

Gln Ser Gly Leu Ala Lys Leu Pro Gly Leu Leu Met Ser Val Pro Gly
                645                 650                 655

Lys Ile Ala Ala Arg Val Arg Ala Arg Arg Ala Arg Arg Ala Ala
            660                 665                 670

Arg Ala Asn
        675

(2) INFORMATION FOR SEQ ID NO: 53:

(i) SEQUENCE CHARACTERISTICS:
        (A) LENGTH: 59 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 53:

GGGGATCCAC AGTTCTGCCT CCCCCGGACG GTAAATATAG GGGAACCATG GTCTAGAGG        59

(2) INFORMATION FOR SEQ ID NO: 54:

(i) SEQUENCE CHARACTERISTICS:
        (A) LENGTH: 29 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO: 54:

GGCCGCTTAA TTAAGGATCC GGCGCGCCA        29
```

(2) INFORMATION FOR SEQ ID NO: 55:

(i) SEQUENCE CHARACTERISTICS:
       (A) LENGTH: 29 base pairs
       (B) TYPE: nucleic acid
       (C) STRANDEDNESS: unknown
       (D) TOPOLOGY: unknown (ii) MOLECULE TYPE: DNA (xi) SEQUENCE DESCRIPTION: SEQ ID NO: 55:

CGAATTAATT CCTAGGCCGC GCGGTGATC                                29

(2) INFORMATION FOR SEQ ID NO: 56:

(i) SEQUENCE CHARACTERISTICS:
       (A) LENGTH: 8 base pairs
       (B) TYPE: nucleic acid
       (C) STRANDEDNESS: unknown
       (D) TOPOLOGY: unknown (ii) MOLECULE TYPE: DNA (xi) SEQUENCE DESCRIPTION: SEQ ID NO: 56:

TTAATTAA                                                        8

(2) INFORMATION FOR SEQ ID NO: 57:

(i) SEQUENCE CHARACTERISTICS:
       (A) LENGTH: 8 base pairs
       (B) TYPE: nucleic acid
       (C) STRANDEDNESS: unknown
       (D) TOPOLOGY: unknown (ii) MOLECULE TYPE: DNA (xi) SEQUENCE DESCRIPTION: SEQ ID NO: 57:

GGCGCGCC                                                        8